(12) United States Patent
Chen et al.

(10) Patent No.: US 11,957,762 B2
(45) Date of Patent: *Apr. 16, 2024

(54) IMMUNE TOLERANT AND NON-IMMUNE TOLERANT ELASTIN-LIKE RECOMBINANT PEPTIDES AND METHODS OF USE

(71) Applicant: University of Utah Research Foundation, Salt Lake City, UT (US)

(72) Inventors: Mingnan Chen, Salt Lake City, UT (US); Hyung Jin Cho, Salt Lake City, UT (US); Peng Wang, Salt Lake City, UT (US); Shuyun Dong, Salt Lake City, UT (US); Peng Zhao, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 646 days.

This patent is subject to a terminal disclaimer.

(21) Appl. No.: 15/577,998

(22) PCT Filed: May 27, 2016

(86) PCT No.: PCT/US2016/034530
§ 371 (c)(1),
(2) Date: Nov. 29, 2017

(87) PCT Pub. No.: WO2016/196249
PCT Pub. Date: Dec. 8, 2016

(65) Prior Publication Data
US 2018/0289830 A1  Oct. 11, 2018

Related U.S. Application Data

(60) Provisional application No. 62/309,113, filed on Mar. 16, 2016, provisional application No. 62/230,160, filed on May 29, 2015.

(51) Int. Cl.
| | | |
|---|---|---|
| *A61K 47/64* | (2017.01) | |
| *A61K 31/337* | (2006.01) | |
| *A61K 31/35* | (2006.01) | |
| *A61K 38/00* | (2006.01) | |
| *A61K 39/00* | (2006.01) | |
| *A61P 35/00* | (2006.01) | |
| *A61P 35/04* | (2006.01) | |
| *C07K 14/77* | (2006.01) | |
| *C07K 14/78* | (2006.01) | |

(52) U.S. Cl.
CPC ........ *A61K 47/6435* (2017.08); *A61K 31/337* (2013.01); *A61K 31/35* (2013.01); *A61K 39/0005* (2013.01); *A61K 47/64* (2017.08); *A61P 35/00* (2018.01); *A61P 35/04* (2018.01); *C07K 14/77* (2013.01); *C07K 14/78* (2013.01); *A61K 38/00* (2013.01); *A61K 2039/6031* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,703,004 A | 10/1987 | Hopp et al. | |
| 4,851,341 A | 7/1989 | Hopp et al. | |
| 5,587,455 A | 12/1996 | Berger et al. | |
| 5,767,260 A | 6/1998 | Whitlow et al. | |
| 5,856,456 A | 1/1999 | Whitlow et al. | |
| 5,914,254 A | 6/1999 | Mascarenhas et al. | |
| 5,981,177 A | 11/1999 | Demirjian et al. | |
| 5,994,104 A | 11/1999 | Anderson et al. | |
| 2007/0105195 A1* | 5/2007 | Dunker .................. | C07K 14/47 435/456 |
| 2012/0121709 A1 | 5/2012 | Chilkoti et al. | |
| 2013/0164340 A1* | 6/2013 | Ensley .................... | A61L 27/26 424/400 |

FOREIGN PATENT DOCUMENTS

| | | |
|---|---|---|
| WO | WO-1998/022577 A1 | 5/1998 |
| WO | WO-1998/036087 A1 | 8/1998 |
| WO | WO-2015/051001 A2 | 4/2015 |

OTHER PUBLICATIONS

Crombie et al. (Biochem Biophys Res Commun. Jun. 19, 1973;52(4):1228-33) (Year: 1973).*
Chung et al. (Matrix Biology 25 (2006) 492-504) (Year: 2006).*
Otto et al. (The genome sequences of chimpanzee malaria parasites reveal the path to human adaptation; submitted May 22, 2014) (Year: 2014).*
Zhao et al. (Mol. Pharmaceutics 2014, 11, 2703-2712) (Year: 2014).*
Pierce et al. (Biochemistry 1990, 29, 9677-9683) (Year: 1990).*
Yuzawa et al. (FEMS Immunol Med Microbiol 64 (2012) 265-272) (Year: 2012).*
Alexander, J. et al., A decaepitope polypeptide primes for multiple CD8+ IFN-γ and Th lymphocyte responses: evaluation of multiepitope polypeptides as a mode for vaccine delivery. J Immunol. 2002; 168(12):6189-98.
Bachmann, M.F. and Zinkernagel, R.M., Neutralizing Antiviral B Cell Responses. Annu Rev Immunol. 1997; 15:235-70.
Bastianello et al., A Chronic Cardiomyopathy in Feedlot Cattle Attributed to Toxic Levels of Salinomycin in the Feed. J S Afr Vet Accos. 1996; 67(1):38-41.

(Continued)

*Primary Examiner* — Sergio Coffa
(74) *Attorney, Agent, or Firm* — Ballard Spahr LLP

(57) ABSTRACT

Disclosed herein, are recombinant polypeptides comprising one or more homologous amino acid repeats; and, non-immunogenic bioconjugates comprising recombinant polypeptides comprising one or more homologous amino acid repeats and one or more therapeutic agents. Also, disclosed herein are pharmaceutical compositions including the recombinant polypeptides; and methods of administering the recombinant polypeptides to patients for the treatment of cancer or infections.

5 Claims, 48 Drawing Sheets
Specification includes a Sequence Listing.

(56) References Cited

OTHER PUBLICATIONS

Benitez, P.L. et al., Sequence-specific crosslinking of electrospun, elastin-like protein preserves bioactivity and native-like mechanics. Adv Healthc Mater. 2013; 2(1):114-8 (10 pages).
Bernard, A. et al., T and B cell cooperation: a dance of life and death. Transplantation. 2005; 79(3 Suppl):S8-11.
Bidwell, G.L. 3rd et al., Thermally targeted delivery of a c-Myc inhibitory polypeptide inhibits tumor progression and extends survival in a rat glioma model. PLoS one. 2013; 8(1):e55104 (12 pages).
Brooks, P. et al., Subcellular Localoization of Proteasomes and Their Regulatory Complexes in Mammalian Cells. Biochem J. 2000; 346(Pt 1):155-61.
Cantin, A.M. et al., Normal Alveolar Epithelial Lining Fluid Contains High Levels of Glutathione. J Appl Physiol. 1987; 63(1):152-7.
Cappello. J., in Handbook of Biodegradable Polymers, A. J. Domb;, J. Kost; D. M. Wiseman, Eds. (Harwood Academic Publishers, Amsterdam, 1997), pp. 387-416.
Chen et al., Abstract 2816: Immune-Tolerant Elastin-like Polypeptide (iTEP) Particles Promote Peptide Vaccine Presentation by Dendritic Cells. Cancer Res. 2014; 74(19). Abstract only (2 pages).
Chilkoti, A. et al., Targeted drug delivery by thermally responsive polymers. Adv Drug Deliv Rev. 2002; 54(5):613-30.
Cho et al., Immune-Tolerant Elastin-like Polypeptides (iTEPs) and Their Application as CTL Vaccine Carriers. J Drug Target. 2015; early online:1-12.
Christiansen, M. et al., Weekly Subcutaneous Doses of Glymera (PB1023) a Novel GLP-1 Analogue Reduce Glucose Exposure Dose-Dependently. (Philadelphia, Pennsylvania, 2012) (1 page).
Da Silva, D.M. et al., Effect of preexisting neutralizing antibodies on the anti-tumor immune response induced by chimeric human papillomavirus virus-like particle vaccines. Virology. 2001; 290(2):350-60.
De Groot, A.S. and Scott, D.W., Immunogenicity of protein therapeutics. Trends Immunol. 2007; 28(11):482-90.
Dong et al., A Comparison Study of iTEP Nanoparticle-Based CTL Vaccine Carriers Revealed a Surprise Relationship Between the Stability and Efficiency of the Carriers. Theranostics. 2016; 6(5):666-78.
Dreher, M.R. et al., Temperature Triggered Self-Assembly of Polypeptides into Multivalent Spherical Micelles. J Am Chem Soc. 2008; 130(2):687-94 (22 pages).
Epstein, J.E. et al., Live Attenuated Malaria Vaccine Designed to Protect Through Hepatic CD8+ T Cell Immunity. Science. 2011; 334:475-80.
Fang, J. et al., The EPR Effect: Unique Features of Tumor Blood Vessels for Drug Delivery, Factors Involved, and Limitations and Augmentation of the Effect. Adv Drug Deliv Rev. 2011; 63(3):136-51.
Feldmann, M. and Easten, A., The Relationship Between Antigenic Structure and the Requirement for Thymus-Derived Cells in the Immune Response. J Exp Med. 1971; 134(1):103- 19.
Frey, A. et al., A statistically defined endpoint titer determination method for immunoassays. J Immunol Methods. 1998; 221(1-2):35-41.
García-Arévalo, C. et al., Immunomodulatory nanoparticles from elastin-like recombinamers: single-molecules for tuberculosis vaccine development. Mol Pharm. 2013; 10(2):586-97.
Goldberg, M.S., Immunoengineering: How Nanotechnology Can Enhance Cancer Immunotherapy. Cell. 2015; 161(2):201-4.
Hassouneh, W. et al., Elastin-like polypeptides as a purification tag for recombinant proteins. Curr Protoc Protein. 2010; Chapter 6:Unit 6.11 (20 pages).
Hassouneh, W. et al., Unexpected multivalent display of proteins by temperature triggered self-assembly of elastin-like polypeptide block copolymers. Biomacromolecules. 2012; 13(5):1598-605 (17 pages).
Jefferis, R., Aggregation, immune complexes and immunogenicity MAbs. 2010; 3(6):503-4.
Jones, D.P. et al., Glutathione Measurement in Human Plasma. Evaluation of Sample Collection, Storage and Derivatization Conditions for Analysis of Dansyl Derivatives by HPLC. Clin Chim Acta. 1998; 275(2):175-84.
Karttunen, J. et al., Detection of Rare Antigen-Presenting Cells by the lacZ T-Cell Activation Assay Suggests an Expression Cloning Strategy for T-Cell Antigens. Proc Natl Acad Sci USA. 1992; 89(13):6020-4.
Kaspar, A.A. and Reichert, J.M., Future directions for peptide therapeutics development. Drug discovery today. 2013; 18(17-18):807-17.
Klebanoff, C.A. et al., Therapeutic Cancer Vaccines: Are We There Yet? Immunol Rev. 2011; 239(1):27-44.
Kloetzel, P.-M. and Ossendorp, F., Proteasome and Peptidase Function in MHC-Class-I-Mediated Antigen Presentation. Curr Opin Immunol. 2004; 16(1):76-81.
Kontos, S. and Hubbell, J.A., Drug development: longer-lived proteins. Chem Soc Rev. 2012; 41(7):2686-95.
Kovacs-Nolan, J. and Mine, Y., Tandem copies of a human rotavirus VP8 epitope can induce specific neutralizing antibodies in BALB/c mice Biochim BiophysActa. 2006; 1760(12):1884-93.
Krüger, E. and Kloetzel, P.-M., Immunoproteasesomes at the Interface of Innate and Adaptive Immune Responses: Two Faces of One Enzyme. Curr Opin Immunol. 2012; 24(1):77-83.
Le, D.H. et al., Self-assembly of elastin-mimetic double hydrophobic polypeptides. Biomacromolecules. 2013; 14(4):1028-34.
Lee, C. et al., Copper staining: a five-minute protein stain for sodium dodecyl sulfate-polyacrylamide gels. Anal Biochem. 1987; 166(2):308-12 (7 pages).
Liu, J. et al., Endocytic uptake of a large array of HPMA copolymers: Elucidation into the dependence on the physicochemical characteristics. J Control Release. 2010; 143(1):71-9 (24 pages).
Liu, W. et al., High epitope density in a single recombinant protein molecule of the extracellular domain of influenza A virus M2 protein significantly enhances protective immunity. Vaccine. 2004; 23(3):366-71.
Liu, X.S. et al., IL-10 mediates suppression of the CD8 T cell IFN-γ response to a novel viral epitope in a primed host. J Immunol. 2003; 171:4765-72.
Livingston, B.D. et al., Optimization of epitope processing enhances immunogenicity of multiepitope DNA vaccines. Vaccine. 2001; 19(32):4652-60.
Macewan, S.R. and Chilkoti, A., Elastin-like polypeptides: biomedical applications of tunable biopolymers. Biopolymers. 2010; 94(1):60-77.
MacKay, J.A. et al., Self-assembling chimeric polypeptide-doxorubicin conjugate nanoparticles that abolish tumours after a single injection. Nat Mater. 2009; 8(12):993-9 (18 pages).
Matsumura et al., A New Concept for Macromolecular Therapeutics in Cancer Chemotherapy: Mechanism of Tumoritropic Accumulation of Proteins and the Antitumor Agent Smancs. Cancer Res. 1986; 46(12 part 1):6387-92.
McCaniel, J.R. et al., Recursive directional ligation by plasmid reconstruction allows rapid and seamless cloning of oligomeric genes. Biomacromolecules. 2010; 11(4):944-52 (20 pages).
Moreland, L.W. et al., Phase I/II trial of recombinant methionyl human tumor necrosis factor binding protein PEGylated dimer in patients with active refractory rheumatoid arthritis. J Rheumatol. 2000; 27:601-9.
Nouri, F.S. et al., Reducing the Visibility of the Vector/DNA Nanocomplexes to the Immune System by Elastin-Like Peptides. Pharm Res. 2015; 32(9):3018-28.
Ohyanagi, F. et al., Safety of BLP25 Liposome Vaccine (L-BLP25) in Japanese Patients with Unresectable Stage III NSCLC After Primary Chemoradiotherapy: Preliminary Resuls from a Phase I/II Study. Jpn J clin Oncol. 2011; 41(5):718-22.
Onda, M. et al., An immunotoxin with greatly reduced immunogenicity by identification and removal of B cell epitopes. Proc Natl Acad Sci USA. 2008; 105(32):11311-6.
Onda, M. et al., Characterization of the B cell epitopes associated with a truncated form of Pseudomonas exotoxin (PE38) used to make immunotoxins for the treatment of cancer patients. J Immunol. 2006; 177(12):8822-34.

(56) References Cited

OTHER PUBLICATIONS

Parker, D.C., T cell-dependent B cell activation. Annu Rev Immunol. 1993; 11:331-60.
Partidos, C. et al., The influence of orientation and 5 number of copies of T and B cell epitopes on the specificity and affinity of antibodies induced by chimeric peptides. Eur J Immunol. 1992; 22(10):2675-80.
Petros, R.A. and DeSimone, J.M., Strategies in the Design of Nanoparticles for Therapeutic Applications. Nat Rev Drug Discov. 2010; 9(8):615-27.
Plummer, E.M. and Manchester, M., Viral Nanoparticles and Virus-like Particles: Platforms for Contemporary Vaccine Design. WIREs Nanomed Nanobiotechnol. 2011; 3(2):174-96.
Rau, R. et al., Intravenous human recombinant tumor necrosis factor receptor p55-Fe IgG1 fusion protein Ro 45-2081 (Lenercept): a double blind, placebo controlled dose-finding study in rheumatoid arthritis. J Rheumatol. 2003; 30(4):680-90.
Robinson, H.L. and Amara, R.R., T Cell Vaccines for Microbial Infections. Nat Med. 2005; 11(4 Suppl):s25-32.
Rock, K L. et al., Peptide-priming of cytolytic T cell immunity in vivo using $\beta_2$-microglobulin as an adjuvant. J Immunol. 1993; 150(4):1244-52.
Rosenberg, A.S., Effects of protein aggregates: an immunologic perspective. AAPS J. 2006; 8(3):E501-7.
Ruedl, C. et al., Virus-like particles as carriers for T-cell epitopes: limited inhibition of T-cell priming by carrier-specific antibodies. J Virol. 2005; 79(2):717-24.
Sahdev, P. et al., Biomaterials for Nanoparticle Vaccine Delivery Systems. Pharm Res. 2014; 31(10):2563-82 (35 pages).
Scheller, J. et al., Forcing single-chain variable fragment production in tobacco seeds by fusion to elastin-like polypeptides. Plant Biotechnol J. 2006; 4(2):243-9.
Schumacher, R. et al., Efficient Induction of Tumoricidal Cytotoxic T Lymphocytes by HLA-A0201 Restricted, Melanoma Associated, $L_{27}$Melan-A/MART-$1_{26-35}$ Peptide Encapsulated into Virosomes In Vitro. Vaccine. 2005; 23(48-49):5572-82.
Sela, M., Antigenicity: some molecular aspects. Science. 1969; 166(3911):1365-74.
Shankar, G. et al., Scientific and regulatory considerations on the immunogenicity of biologics. Trends Biotechnol. 2006; 24(6):274-80.
Shen, Z. et al., Cloned dendritic cells can present exogenous antigens on both MHC class I and class II molecules. J Immunol. 1997; 158(6):2723-30.
Shi, P. et al., Elastin-based protein polymer nanoparticles carrying drug at both corona and core suppress tumor growth in vivo. J Control Release. 2013; 171(3):330-8 (21 pages).
Smejkal, G.B., The Coomassie chronicles: past, present and future perspectives in polyacrylamide gel staining. Expert Rev Proteomics. 2004; 1(4):381-7.
Smith, C.V. et al., Compartmentation of Glutathione: Implications for the Study of Toxicity and Disease. Toxicol Appl Pharmacol. 1996; 140(1):1-12.
Tao, K. et al., Imagable 4T1 Model for the Study of Late Stage Breast Cancer. BMC Cancer. 2008; 8(1):228 (20 pages).
Thomson, S.A. et al., Minimal epitopes expressed in a recombinant polyepitope protein are processed and presented to CD8+ cytotoxic T cells: implications for vaccine design. Proc Natl Acad Sci USA. 1995; 92(13):5845-9.
Urry, D.W. and Parker, T.M., Biocompatibility of the Bioelastic Materials, Poly(GVGVP) and Its γ-Irradiation Cross-Linked Matrix: Summary of Generic Biological Test Results. J Bioactiv Compatible Polymers. 1991; 6(3):263-82.
Urry, D.W. et al., Temperature of Polypeptide Inverse Temperature Transition Depends on Mean Residue Hydrophobicity. J Am Chem Soc. 1991; 113:4346-8.
Urry, D.W., Free energy transduction in polypeptides and proteins based on inverse temperature transitions. Prog Biophys Mol Biol. 1992; 57(1):23-57 (split into 2 parts).
Urry, D.W., Physical Chemistry, of Biological Free Energy Transduction as Demonstrated by Elastic Protein-Based Polymers. J Phys Chem B. 1997; 101:11007-28.
Van Regenmortel, M. H., Chapter 1: Molecular Dissection of Protein Antigens. Structure of Antigens. M. H. Van Regenmortel, Ed. CRC Press, 1992. pp. 1-28.
Wu, G. et al., Glutathione Metabolism and Its Implications for Health. J Nutr. 2004; 134(3):489-92.
Yewdell, J.W. and Bennink, J.R., Cut and Trim: Generating MHC Class I Peptide Ligands. Curr Opin Immunol. 2001; 13(1):13-8.
Zhang, Y. et al., The Eradication of Breast Cancer Stem Cells Using Octreotide Modified Paclitaxel Active Targeting Micelles and Salinomycin Passive Targeting Micelles. Biomaterials. 2012; 33(2):679-91.
Zhang, Z. et al., Paclitaxel Drug Delivery Systems. Expert Opin Drug Deliv. 2013; 10(3):325-40.
Zhao et al., An ITEP-Salinomycin Nanoparticle that Specifically and Effectively Inhibits Metastases of 4T1 Orthotopic Breast Tumors. Biomaterials. 2016; 93:1-9.
Zhao et al., iTEP Nanoparticle-Delivered Salinomycin Displays an Enhanced Toxicity to Cancer Stem Cells in Orthotopic Breast Tumors. Mol Pharm. 2014; 11:2703-12 (27 pages).
Zhou, L. et al., Stratification of Antibody-Positive Subjects by Antibody Level Reveals an Impact of Immunogenicity on Pharmacokinetics. AAPS J. 2013; 15(1):30-40.
International Search Report and Written Opinion dated Oct. 31, 2016 by the International Searching Authority for Patent Application No. PCT/US2016/034530, which was filed on May 27, 2016 and published as WO 2016/196249 dated Dec. 8, 2016 (Inventor—Chen et al.; Applicant—University of Utah Research Foundation) (13 pages).
International Preliminary Report on Patentability dated Dec. 5, 2017 by the International Searching Authority for Patent Application No. PCT/US2016/034530, which was filed on May 27, 2016 and published as WO 2016/196249 dated Dec. 8, 2016 (Inventor—Chen et al.; Applicant—University of Utah Research Foundation) (7 pages).
Moroy, G. et al., Structural Characterization of Human Elastin Derived Peptides Containing the GXXP Sequence. Biopolymers. 2005; 78(4):206-20.
Supplementary European Search Report dated Jan. 21, 2019 by the European Patent Office for Patent Application No. 16804094.7, which was filed on May 27, 2016 and published as EP 3302531 dated Apr. 11, 2018 (Inventor—Chen et al.; Applicant—University of Utah Research Foundation) (8 pages).
U.S. Appl. No. 62/568,880, filed Oct. 6, 2017, Mingnan Chen (University of Utah Research Foundation).
U.S. Appl. No. 16/152,825, filed Oct. 5, 2018, (2019-0106479), (Apr. 11, 2019), Mingnan Chen (University of Utah Research Foundation).
U.S. Appl. No. 62/568,949, filed Oct. 6, 2017, Mingnan Chen (University of Utah Research Foundation).
U.S. Appl. No. 16/652,629, filed Mar. 31, 2020, (2020-0239575), (Jul. 30, 2020), Mingnan Chen (University of Utah Research Foundation).
U.S. Appl. No. 62/890,936, filed Aug. 23, 2018, Mingnan Chen (University of Utah Research Foundation).
EP, 2018864755, May 6, 2020, Mingnan Chen (Univ. Of Utah Res. Found.).
PCT, PCT/US2018/054645, Oct. 5, 2018, (WO 2019/071150), (Apr. 11, 2019), Mingnan Chen (Univ. Of Utah Res. Found.).
PCT, PCT/US20/040230, Jun. 30, 2020, Mingnan Chen (Univ. Of Utah Res. Found.).
Office Action dated Jun. 22, 2020 for Japanese Application No. 2017-561974, which claims priority to PCT/US2016/034530, filed on May 27, 2016 (Applicant—University Of Utah Research Foundation; Inventor—Chen et al.) (3 pages).
Zhao et al., Itep Nanoparticle-Delivered Salinomycin Displays an Enhanced Toxicity to Cancer Stem Cells in Orthotropic Breast Tumors. Molecular pharmaceutics. 2014; 11:2703-2712.

* cited by examiner (A)

(B)

(D)

(E)

(A)

(B)

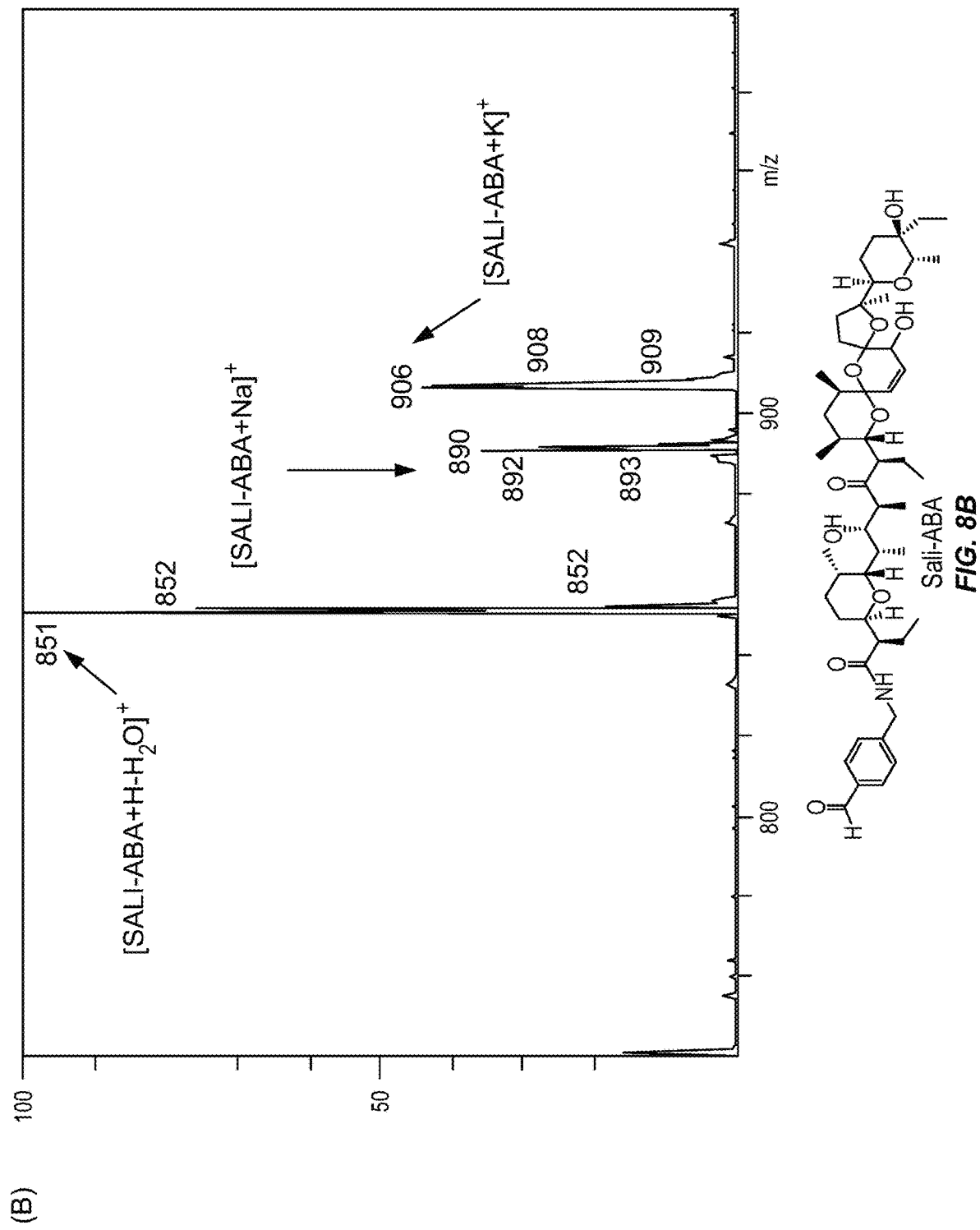

C

D

A iTEP$_{B70}$-iTEP$_{A28}$-(G$_8$C)$_4$-pOVA fusion (RED-NP)

B

G

H

C

D

IMMUNE TOLERANT AND NON-IMMUNE TOLERANT ELASTIN-LIKE RECOMBINANT PEPTIDES AND METHODS OF USE

CROSS REFERENCE TO RELATED APPLICATIONS

This application claims the benefit of priority under 35 U.S.C. § 371 of International Application No. PCT/US2016/034530, filed on May 27, 2016, which claims the benefit of the filing dates of U.S. Provisional Application No. 62/230,160, which was filed on May 29, 2015; and U.S. Provisional Application No. 62/309,113, which was filed on Mar. 16, 2016. The contents of these earlier filed applications are hereby incorporated by reference herein in their entirety.

STATEMENT REGARDING FEDERALLY FUNDED RESEARCH

This invention was made with government support under grant number CA153929 awarded by National Institutes of Health. The government has certain rights in the invention.

SEQUENCE LISTING

The sequence listing submitted herewith as a text filed named "21101_0314U3_SL," created on Nov. 13, 2017, and having a size of 85,448 bytes is herein incorporated by reference in its entirety pursuant to 37 C.F.R. § 1.52(e)(5).

FIELD OF THE INVENTION

The present invention relates to elastin-derived recombinant peptides and more particularly to recombinant elastin-derived peptides that have immune tolerant and that are useful as, for example, a delivery system of therapeutics for a variety of diseases and conditions including infections and cancer.

BACKGROUND

Cancer patients with metastases still face a poor prognosis due to a lack of effective treatments directed to the metastasis. Metastases and cancer stem cells (CSCs) are known to have a close relationship and CSCs have been shown to be resistant to conventional chemotherapeutics and radiotherapeutics. One strategy to generate an effective anti-metastasis therapy has been to target CSCs because these cells play important roles in initiating and promoting metastases including those of breast tumors. Vaccines have been developed as a prophylactic and therapeutic treatment for cancer and infectious diseases. The efficacy of the vaccines especially cancer vaccines, however, need to be improved. An alternative therapeutic approach for effective anti-metastasis therapies and prophylactic or therapeutic modules against cancer and infectious disease is needed.

SUMMARY

Effective methods to reduce cancer stem cells (CSC) rely on the identification of new drugs that can be particularly toxic to CSCs. Herein, a new elastin-like polypeptide (ELP) design and engineering practice emphasizing physicochemical properties as well as immunogenicity of the ELPs from the very beginning of ELP design is disclosed. To this end, ELPs, referred to as iTEPs herein have been designed and generated. The iTEPs disclosed herein are humorally tolerant and also possess a phase transition property. Further, the Examples demonstrate that an amphiphilic iTEP copolymer can self-assemble into a nanoparticle. The nanoparticle, when used to deliver a model cytotoxic T lymphocyte (CTL) peptide vaccine, improved the potency of the vaccine in comparison to CTL vaccines in free peptide or protein forms.

Described herein are recombinant polypeptides comprising an homologous amino acid repeat, wherein the homologous amino acid repeat comprises four or more amino acid residues, wherein one of the amino acid residues is proline and one or more of the amino acid residues is valine, having at least 75% amino acid sequence identity to the homologous amino acid repeat, and wherein the homologous amino acid repeat is: Gly-Val-Leu-Pro-Gly-Val-Gly (SEQ ID NO: 1; iTEP$_A$); Gly-Ala-Gly-Val-Pro-Gly (SEQ ID NO: 2; iTEP$_B$); Val-Pro-Gly-Phe-Gly-Ala-Gly-Ala-Gly (SEQ ID NO: 3; iTEP$_C$); Val-Pro-Gly-Leu-Gly-Ala-Gly-Ala-Gly (SEQ ID NO: 4; iTEP$_D$); Val-Pro-Gly-Leu-Gly-Val-Gly-Ala-Gly (SEQ ID NO: 5; iTEP$_E$); Gly-Val-Leu-Pro-Gly-Val-Gly-Gly (SEQ ID NO: 6); Gly-Val-Leu-Pro-Gly (SEQ ID NO: 7); Gly-Leu-Val-Pro-Gly-Gly (SEQ ID NO: 8); Gly-Leu-Val-Pro-Gly (SEQ ID NO: 9); Gly-Val-Pro-Leu-Gly (SEQ ID NO: 10); Gly-Ile-Pro-Gly-Val-Gly (SEQ ID NO: 11); Gly-Gly-Val-Leu-Pro-Gly (SEQ ID NO: 12); Gly-Val-Leu-Pro-Gly (SEQ ID NO: 13); Gly-Val-Gly-Val-Leu-Pro-Gly (SEQ ID NO: 14); or Gly-Val-Pro-Gly (SEQ ID NO: 15).

Described herein are recombinant polypeptides comprising an amino acid sequence conforming to the formula: Val-Pro-Gly-Xaa$_1$-Gly-Xaa$_2$-Gly-Ala-Gly, wherein Xaa$_1$ is Leu or Phe and Xaa$_2$ is Ala or Val (SEQ ID NOs: 16-19); wherein the amino acid sequence is repeated.

Described here are non-immunogenic bioconjugates comprising a recombinant polypeptide comprising an homologous amino acid repeat, wherein the homologous amino acid repeat comprises four or more amino acid residues, wherein one of the amino acid residues is a proline, and one or more of the amino acid residues is a valine, and the homologous amino acid repeat is: Gly-Val-Leu-Pro-Gly-Val-Gly (SEQ ID NO: 1; iTEP$_A$); Gly-Ala-Gly-Val-Pro-Gly (SEQ ID NO: 2; iTEP$_B$); Val-Pro-Gly-Phe-Gly-Ala-Gly-Ala-Gly (SEQ ID NO: 3; iTEP$_C$); Val-Pro-Gly-Leu-Gly-Ala-Gly-Ala-Gly (SEQ ID NO: 4; iTEP$_D$); Val-Pro-Gly-Leu-Gly-Val-Gly-Ala-Gly (SEQ ID NO: 5; iTEP$_E$); Gly-Val-Leu-Pro-Gly-Val-Gly-Gly (SEQ ID NO: 6); Gly-Val-Leu-Pro-Gly (SEQ ID NO: 7); Gly-Leu-Val-Pro-Gly-Gly (SEQ ID NO: 8); Gly-Leu-Val-Pro-Gly (SEQ ID NO: 9); Gly-Val-Pro-Leu-Gly (SEQ ID NO: 10); Gly-Ile-Pro-Gly-Val-Gly (SEQ ID NO: 11); Gly-Gly-Val-Leu-Pro-Gly (SEQ ID NO: 12); Gly-Val-Leu-Pro-Gly (SEQ ID NO: 13); Gly-Val-Gly-Val-Leu-Pro-Gly (SEQ ID NO: 14); or Gly-Val-Pro-Gly (SEQ ID NO: 15), and one or more therapeutic agents.

Described herein are recombinant polypeptides comprising an homologous amino acid repeat, wherein the homologous amino acid repeat comprises four or more amino acid residues, wherein one of the amino acid residues is proline and one or more of the amino acid residues is valine, having at least 75% amino acid sequence identity to the homologous amino acid repeat, and wherein the homologous amino acid repeat is: Leu-Val-Val-Gly-Gly-Gly-Pro (SEQ ID NO: 20; iMEPA); or Ala-Gly-Gly-Pro-Gly-Val-Val-Ala-Gly-Gly-Pro-Gly-Val-Ala-Gly-Gly-Pro-Gly (SEQ ID NO: 21; iMEPB).

BRIEF DESCRIPTION OF THE DRAWINGS

FIGS. 2A-C show the cloning and expression of iTEPs. FIG. 2A is an illustration of schematics showing the approach to double the length of the coding genes of iTEPs. FIG. 2B shows iTEP coding genes on agarose gel after they were cleaved from pET25b(+) vector by XbaI and BamHI. FIG. 2C shows SDS-PAGE gel showing MWs and purity of individual iTEPs.

FIG. 3A-D shows turbidity profiles (OD350) of $iTEP_A$, $iTEP_B$, $iTEP_C$, and $iTEP_D$ as they were heated and then cooled between 20° C. and 80° C. FIG. 3E shows the turbidity profiles of $iTEP_B$ in 2.5M NaCl as a function of temperature. Each curve represented an average of three measurements.

FIG. 4A shows the immunization schedule and the time point of the assessment of humoral responses. FIG. 4B shows the summary of IgG titers of OVA, MSA, and iTEP-immunized mice. Each dot represents one mouse's result. The medians and interquartile ranges of the titers are shown. FIG. 4C-F shows the absorbance (OD450) of sera that were collected from $iTEP_A$ (C), $iTEP_B$ (D), $iTEP_C$ (E), and $iTEP_D$ (F) immunized mice after they were diluted and assayed by ELISA. Each data point corresponds to the mean value of three absorbance measurements per serum dilution. The data of each mouse were linked together with a line. The cut-off ranges for positive absorbance values were shown as a blue shade.

FIG. 5A is an illustration of schematics showing that the $iTEP_B$-$iTEP_A$-pOVA fusion (SEQ ID NO: 56) self-assembles into a nanoparticle (NP). FIG. 5B is an SDS-PAGE gel showing MWs and purity of two fusions, $iTEP_B$-pOVA (SEQ ID NO: 57) and $iTEP_B$-$iTEP_A$-pOVA (SEQ ID NO: 56). FIG. 5C shows the turbidity profile of the $iTEP_1$-$iTEP_A$-pOVA fusion (SEQ ID NO: 56) as a function of temperature. FIG. 5D shows size distributions of the $iTEP_B$-pOVA (SEQ ID NO: 57) and $iTEP_B$-$iTEP_A$-pOVA fusions (SEQ ID NO: 56) (25 µM) obtained from DLS measurement. FIG. 5E is a representative micrograph of a negatively stained $iTEP_B$-$iTEP_A$-pOVA fusion (SEQ ID NO: 56) confirming the NP size of the fusion.

FIG. 6A shows the presentation of SIINFEKL (SEQ ID NO: 22) by DC 2.4 cells after the SIINFEKL (SEQ ID NO: 22) was delivered by OVA, soluble $iTEP_B$-pOVA fusion (SEQ ID NO: 57), or iTEP-pOVA NP. Data are presented as means of normalized MFI±SD of the entire DC population used in the experiments (n>4 independent experiments). FIG. 6B shows the activation of B3Z cells after they were incubated with DCs that presented SIINFEKL (SEQ ID NO: 22). The DCs were pre-incubated with different forms of antigens as noted in the picture. Data are presented as mean±SD 3 independent experiments). FIG. 6C shows the ex vivo analysis of active, SIINFEKL-restricted splenocytes cells from mice (n=3-5) immunized with OVA, free SIINFEKL peptide (SEQ ID NO: 22), or iTEP-pOVA NP. The activation of the cells was characterized by using an INF-γ-based ELISPOT assay. Data were presented as Spot Forming Units (SFU)/million cells±SD. For all panels, ★ indicates $p<0.05$, t-test between the paired treatments.

FIGS. 8A-C illustrates the synthesis scheme and characterization of Sali-ABA and Sali-ABA-MPBH. FIG. 8A shows the synthesis scheme of Sali-ABA and Sali-ABA-MPBH. FIG. 8B is ESI-MS spectrum of a purified reaction product between ABA and Sali. FIG. 8C is an ESI-MS spectrum of purified reaction product between Sali-ABA and MPBH.

FIG. 9A shows the viability profile of regular 4T1-luc cells after they were exposed to different concentrations of Sali or Sali-ABA for 72 hours. FIG. 9B shows the viability profile of regular 4T1-luc cells versus mammosphere 4T1-luc cells after they were exposed to different concentrations of Sali-ABA for 72 hours.

FIG. 10A shows a copper-stained SDS-PAGE photo of purified iTEPs after 10 rounds of purification. The loading amount was 50 µg/well. The band is highlighted with a red arrow. FIG. 10B shows the in vitro release profile of iTEP-MPBH-ABA-Sali NP at pH=5.0 (0.1 M acetate buffer) and pH=7.0 (PBS). FIG. 10C shows the viability profile of regular 4T1-luc cells after they were exposed to different concentrations of iTEP-MPBH-ABA-Sali NP or Sali-ABA for 72 hours. FIG. 10D shows the viability profile of regular 4T1-luc cells versus mammosphere 4T1-luc cells after they were exposed to different concentrations of iTEP-MPBH-ABA-Sali NP for 72 hours.

FIG. 11A shows the plasma concentration of Sali-ABA after it was administered in its free form or iTEP-MPBH-ABA-Sali NP. FIG. 11B shows the tumor accumulation of Sali-ABA after it was administered at 20 mg/kg dose. FIG. 11C shows the heart accumulation of Sali-ABA. FIG. 11D shows the accumulation of Sali-ABA in livers, spleens, lungs, and kidneys.

FIGS. 12 A-C show the inhibition of primary tumor growth and metastasis by iTEP-MPBH-ABA-Sali-NP.

FIG. 13A shows the viability profile of regular 4T1-luc cells and mammosphere 4T1-luc cells after they were treated by PTX NP for 72 hours. FIG. 13B shows the volume changes of 4T1-luc orthotopic tumors after they were treated by iTEP-MPBH-ABA-Sali NP, PTX NP, or a combinational regimen of PTX NP and iTEP-MPBH-ABA-Sali NP. FIG. 13C shows the metastasis-free survival of mice bearing 4T1-luc orthotopic tumors after they were treated as described in FIG. 13B. * indicates the time points when some mice were censored because they reached humane endpoints. FIG. 13D shows the overall survival profile of mice described in FIG. 13B.

FIG. 16A is a schematic illustration showing that the iTEP$_{B}$70-iTEP$_{A28}$-pOVA (SEQ ID NO: 64) and iTEP$_{B70}$-iTEP$_{A56}$-pOVA (SEQ ID NO: 60) fusions self-assemble in MS-NP and ST-NP. FIG. 16B shows the hydrodynamic diameters by number distribution of two NPs before and after 16 h incubations at 37° C. Green line was for MS-NP and blue line was for ST-NP. FIG. 16C is a representative TEM micrograph of a negatively stained sample of iTEP$_{B70}$-iTEP$_{A56}$-pOVA (ST-NP) (SEQ ID NO: 60) confirmed NP structure of the sample. Three particles are pointed out by arrows. FIG. 16D shows $I_1/I_3$, the ratio between two peaks [peak1 ($I_{370-373nm}$); peak3 ($I_{381-384nm}$)] of pyrene fluorescence emissions plotted as a function of log 10 concentrations of iTEP-vaccine fusions. The error bars indicated the standard deviation of each data point (n=3). The inflection point of the sigmoid fit of one fusion was defined as the CMC of that fusion.

FIG. 17A shows the hydrodynamic diameters by intensity of MS-NP and ST-NP. The data were collected by DLS before (0 h) and after (16 h) the NPs were incubated at 37° C. for 16 h. The green line represents size distribution of MS-NP. The blue line is for ST-NP. Before the incubation, the diameters for MS-NP and ST-NP were 111.90±35.02 nm and 78.56±21.60 nm, respectively. After the incubation, ST-NP had a diameter of 74.45±18.99 nm; the MS-NP had two peaks: 75.47±9.75 nm (92.2%) and 8.86±0.90 nm (7.8%). FIG. 17B shows the hydrodynamic diameters by intensity of RED-NP were 75.55±15.32 nm and 70.99±17.52 nm before and after 16-h incubation, respectively. The red broken line and the red solid line represent size distribution for RED-NP before and after the incubation, respectively.

FIG. 18A shows the presentation of pOVA by DC 2.4 cells after the cells were incubated with pOVA delivered in different NPs. The data are presented as MFI means±SD of DC cells in each treatment; each treatment had three repeats (N=3). ★ $p<0.05$ (t-test). The graph represents data collected from four independent experiments. FIG. 18B shows the activation of B3Z cells by DC 2.4 cells which were pre-incubated with different NPs. The shown values are mean ODs±SD of samples of each treatment (N=3). The OD values of these treatments had been normalized to the mean OD of the NP-free treatment. ★ $p<0.05$ (t-test). The graph represents data collected from three independent experiments. FIG. 18C shows the ex vivo analysis of active, SIINFEKL-restricted splenocytes cells from mice (N=5) immunized with MS-NP and ST-NP. Data are presented as Spot Forming Units (SFU)/million cells±SD. ★ $p<0.05$ (t-test). FIG. 18D shows the comparison of uptake of ST-NP and MS-NP by DCs and various control cells. The ratio data are presented as ratio mean±SD (N=3). ★ $p<0.05$ (1-test).

FIG. 19A is a schematic showing that the iTEP$_{B70}$-iTEP$_{A28}$-($G_8C)_4$-pOVA (SEQ ID NO: 61) fusion self-assembles in RED-NP. FIG. 19B shows the hydrodynamic diameters by number distribution of two NPs before and after 16 h incubations at 37° C. FIG. 19C is a representative TEM micrograph of RED-NP. Three particles were pointed out by arrows. FIGS. 19D-F shows fluorescence microscopy of MS-NP (D), ST-NP (E) and RED-NP (F) that were internalized by DC2.4 cells. FIG. 19G shows the uptake of MS-NPs, ST-NPs and RED-NPs by DC2.4 cells as normalized MFI of the cells. Data are presented as mean MFI±SD (N=3). ★ $p<0.05$ (t-test). FIG. 19H shows the comparison of uptake of RED-NP to MS-NP by DCs and various control cells. The data were processed and presented as FIG. 18D (N=3). ★ $p<0.05$ (t-test).

FIG. 22A is a Presentation of pOVA by DC 2.4 cells after the cells were incubated with three NPs. The data are presented as MFI means±SD of DC cells in each treatment; each treatment had three repeats (N=3). ★ $p<0.05$ (t-test). The graph represents data collected from three independent experiments. FIG. 22B shows the results of the activation of B3Z cells by DC 2.4 cells after the DCs were pre-incubated with different NPs. The shown values are mean ODs±SD of samples of each treatment (N=3). ★ $p<0.05$ (t-test). The graph represents data collected from three independent experiments. FIG. 22C shows the xx vivo analysis of active, SIINFEKL-restricted splenocytes cells from mice (N=5) immunized with MS-NP and RED-NP. Data are presented as Spot Forming Units (SFU)/million cells±SD. ★ $p<0.05$ (t-test).

FIG. 23A shows the presentation of pOVA by DC 2.4 cells after the cells were incubated with empty iTEP carriers. The data are presented as MFI means±SD of DC cells in each treatment. Each treatment had three repeats (N=3). FIG. 23B shows the results of the activation of B3Z cells by DC 2.4 cells which were pre-incubated with empty iTEP carriers. The shown values are mean ODs±SD of samples of each treatment (N=3).

FIG. 24A shows hydrodynamic diameter distributions by numbers (upper panel) and by intensity (lower panel) of RED-NP2 before and after 16 h incubations at 37° C. FIG. 24B shows the presentation of pOVA by DC 2.4 cells after the cells were incubated with MS-NP and RED-NP2. The data are presented as MFI means±SD of DC cells in each treatment. Each treatment had three repeats (N=3). ★ $p<0.05$ (t-test). The graph represents data collected from three independent experiments. FIG. 24C shows the activation of B3Z cells by DC 2.4 cells which were pre-incubated with MS-NP and RED-NP2. The shown values are mean ODs±SD of samples of each treatment (N=3). ★ $p<0.05$ (t-test). The graph represents data collected from three independent experiments. FIG. 24D shows the ex vivo analysis of active, SIINFEKL-restricted splenocytes from mice (N=5) immunized with MS-NP and REDNP2. Data were presented as Spot Forming Units (SFU)/million cells±SD. ★$p<0.05$ (t-test).

FIG. 25A shows the viability of DC 2.4 cells after they were treated with various iTEP-vaccine fusions. FIG. 25B shows the viability of EA.hy926 cells after they were treated with various iTEP-vaccine fusions. Green dots: MS-NP; blue squares: ST-NP; red triangles: RED-NP. The data are presented as mean±SD. Each of the graphs represents results from 3 independent experiments.

FIG. 26A shows the intracellular distribution of RED-NP in DC 2.4 cells revealed by differential interference contrast (DIC) microscopy. The red dye stains low pH lysosome compartments in DCs. The green dye was used to label RED-NP. Yellow staining in the merged image indicated the co-localization of RED-NPs and lysosomes. FIG. 26B is an SDS-PAGE picture of DC 2.4 cell lysate after the cells was incubated with Alexa-488 labeled RED-NP for 1 h and washed away.

FIG. 27A shows the viability profile of regular MDA-MB-231 cells versus mammosphere MDA-MB-231 cells after the cells were exposed to different concentrations of Sali-ABA for 72 hours. FIG. 27B shows the viability profile of regular HCT-15 cells versus mammosphere HCT-15 cells after the cells were exposed to different concentrations of Sali-ABA for 72 hours. FIG. 27C shows the viability profile of regular PC-3 cells versus mammosphere PC-3 cells after the cells were exposed to different concentrations of Sali-ABA for 72 hours.

DETAILED DESCRIPTION

Figure 1:
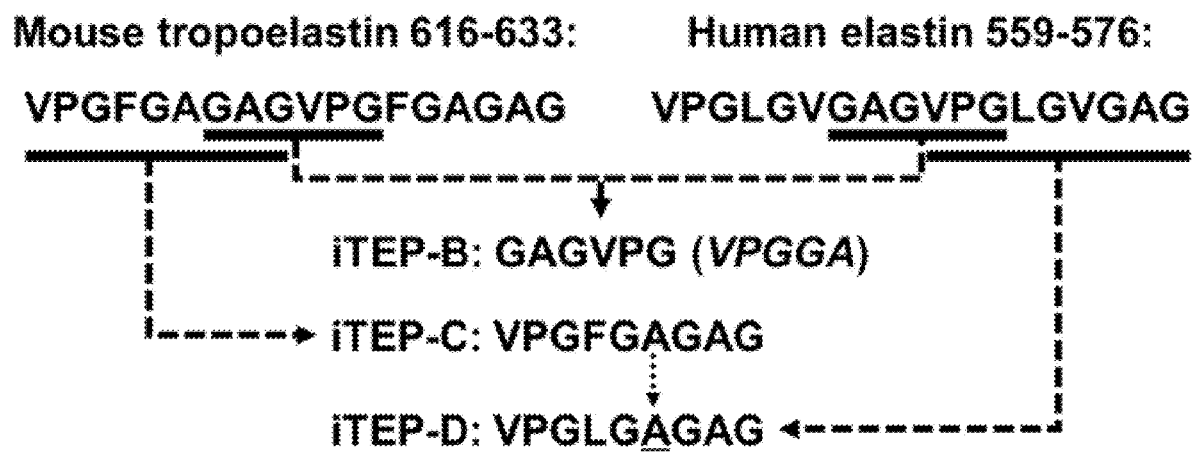
FIG. 1 is an outline of iTEP monomers obtained from a homology analysis between mouse tropoelastin and human elastin. Blue and red letters indicate amino acids from mouse and human elastins, respectively. Green letters indicate the same amino acids across both species. The numbers indicate the positions of these building blocks in their parent elastin proteins.

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "comprising" can include the aspects "consisting of" and "consisting essentially of."

As used herein, the term "iTEP" refers to an immune-tolerant, elastin-like polypeptide differing from previous disclosed elastin-like polypeptides (referred to as ELPs) as they have the phase transition property and are immune-tolerant.

Introduction

Vaccines that induce cytotoxic T lymphocyte (CTL) responses are important prophylactic or therapeutic modules against cancer and infectious diseases.[1-3] Using carriers to promote the delivery of these vaccines to antigen presenting cells is a strategy to enhance the potency of the vaccines.[4,5] While various natural and synthetic materials have been tested as building materials of CTL vaccine carriers,[6,7] it is the virus-like particles (VLPs) that have been approved for clinical use to facilitate CTL responses,[5] highlighting the need to identify other suitable vaccine carrier materials.

Elastin-like polypeptides (ELPs) and VLPs are both proteins. Like VLPs, ELPs can also self-assemble into nanoparticles (NPs) of a similar size.[8] Besides these similarities to VLPs, ELPs have several additional features appealing to vaccine delivery: (1) the protein- or peptide-based CTL vaccines, potentially, can be fused together with ELPs using a genetic engineering approach, resultanting in fusion proteins that can be easily reproduced in *E. coli* or other expression system similar to existing ELP fusions;[9,10] (2) when the vaccines are loaded to the carriers using the genetic engineering approach described herein, the copy numbers of the vaccines and their cleavage sites from the carriers are well defined and precisely adjusted to improve the potency of vaccines;[11-13] and (3) the signature property of ELP—the reversible, thermally (or ion)-induced, inverse phase transition—can be transferable to ELP-protein fusions and possibly to iTEP-vaccine fusions.[14] The fusions can, thus, be simply purified by cycling the transition. Despite having these appealing features, ELPs have not been reported as CTL vaccine carriers to date. Disclosed here are compositions and methods using ELP (referred to as iTEP) nanoparticles as CTL vaccine carriers. Previous reports have shown that humorally immunogenic carriers jeopardize the potency of their CTL vaccine payloads.[15-17] Described herein is the use of humorally tolerant ELPs as CTL vaccine carriers. Among reported ELPs, a few have been confirmed as immune tolerant while others have been proven immunogenic.[18-22] These immune tolerant ELPs, however, do not offer the required hydrophobicity and length to form NPs. This limitation lead to the design and production of new immune tolerant ELPs described herein to meet the vaccine delivery need.

Polypeptide materials, including ELPs, have typically been invented and optimized for physicochemical properties such as their phase transition property, while their immunogenicity was considered after their physicochemical properties were established. Such practice, however, bears the risk that an ELP with a well-characterized function may indeed become valueless due to its later-discovered adverse immunogenicity.[23,24] Thus, as described herein, a new ELP development practice was employed that places equal weight on ELP's phase transition feature as well as immunogenicity from the beginning of development.

Using this new practice, ELPs (e.g., iTEPs) are described herein. The sequences of each are non-canonical to the typical ELP "V-P-G-X-G" (SEQ ID NO: 29) motif.[25,26] As used herein, these novel ELPs are referred to as iTEPs to underscore this new ELP engineering practice. The iTEPs disclosed herein possess the desired transition property and were also tolerated by mouse humoral immunity. Also described herein, are two paired iTEPs that were opposite in hydrophobicity to make an amphiphilic diblock copolymer or fusion protein. A fusion protein can be generated by fusing two or more proteins together. A diblock copolymer can used to describe the fusion of two proteins. The copolymer (e.g., fusion protein), when fused with a model CTL peptide vaccine, SIINFEKL (SEQ ID NO: 22), self-assembled into a NP. The NP enhanced the presentation of the vaccine by dendritic cells (DCs) and increased the strength of the vaccine-induced CTL response. The results disclosed herein suggest that iTEPs developed, using this new practice, are suitable for CTL peptide vaccine carriers.

Compositions

Recombinant polypeptides. As used herein, the term "recombinant polypeptide" refers to a polypeptide generated by a variety of methods including recombinant techniques.

In an aspect, the recombinant polypeptide comprises amino acid sequence Gly-(Gly-Val-Leu-Pro-Gly-Val-Gly)$_{28}$-Gly-Gly (SEQ ID NO: 23); Gly-(Gly-Ala-Gly-Val-Pro-Gly)$_{70}$-Gly-Gly (SEQ ID NO: 24); Gly-(Val-Pro-Gly-Phe-Gly-Ala-Gly-Ala-Gly)$_{21}$-Gly-Gly (SEQ ID NO: 25); or Gly-(Val-Pro-Gly-Leu-Gly-Ala-Gly-Ala-Gly)$_{96}$-Gly-Gly (SEQ ID NO: 26).

The recombinant polypeptide can further comprise two or more homologous amino acid repeats. In an aspect, the recombinant polypeptide comprises a diblock copolymer or a fusion protein. Diblock copolymers or fusion proteins comprise two or three homologous amino acid repeats linked together by covalent bonds. One or more cysteine residues can be inserted between the diblock copolymer or fusion protein and a therapeutic (e.g., a vaccine) or a plasmid (e.g., pOVA). The number of cysteine residues can be 1, 2, 3, 4, 5, 10, 15, 20, 30, 40 or more or any number in between. In an aspect, the number of cysteine residues is four. The cysteine residues can be separated by one or more glycine residues. The number of glycine residues can vary and depend on the number of cysteine residues inserted between the diblock copolymer and pOVA. The number of glycine residues can be 1, 2, 3, 4, 5, 10, 15, 20, 30, 40 or more or any number in between. In an aspect, the number of glycine residues can be eight. For example, when four cysteine residues are inserted between the diblock copolymer and pOVA, eight glycine residues can be inserted to separate the adjacent cysteine residues. In an aspect, the diblock copolymers or fusion proteins can be amphiphilic. In some aspects, the diblock copolymers or fusion proteins can be fused with a therapeutic agent (e.g., a vaccine).

Also described herein, are recombinant polypeptides comprising an amino acid sequence conforming to the formula: Val-Pro-Gly-Xaa$_1$-Gly-Xaa$_2$-Gly-Ala-Gly wherein Xaa$_1$ is Leu or Phe and Xaa$_2$ is Ala or Val (SEQ ID NOs: 16-19), wherein the amino acid sequence is repeated. The recombinant polypeptide can further comprise one or more residues positioned at the N-terminus, C-terminus, or both the N-terminus and C-terminus of the recombinant polypeptide. In an aspect, the one or more residues are glycine, alanine or serine or a combination thereof. In an aspect, the recombinant polypeptide comprises the amino acid sequence Gly-(Val-Pro-Gly-Phe-Gly-Ala-Gly-Ala-Gly)$_{21}$-Gly-Gly (SEQ ID NO: 25); or Gly-(Val-Pro-Gly-Leu-Gly-Ala-Gly-Ala-Gly)$_{96}$-Gly-Gly (SEQ ID NO: 26); or XX-(Val-Pro-Gly-Leu-Gly-Val-Gly-Ala-Gly)$_x$-XX (SEQ ID NO: 27). As described below, "XX" can be one or more glycine residues at both the C-terminus and the N-terminus ends; and "x" can be 2, 3, 4, 5, 10, 15, 20, 30, 40, 50, 100, 150, 200 or any number in between.

In an aspect, the identified molecular weight of the recombinant polypeptide can be between 10 and 100 kDa.

Homologous amino acid repeat. As used herein, the term "homologous amino acid repeat" or "monomer" refers to an amino acid sequence comprising any of the 20 protein amino acids and is reiterated or duplicated linearly. The homologous amino acid repeat sequence can be repeated 2, 3, 4, 5, 10, 15, 20, 30, 40, 50, 100, 150, 200 times or more or any number of times in between. In an aspect, the homologous amino acid repeat comprises no more than 100 repeats. In another aspect, the homologous amino acid repeat comprises at least 20 repeats.

In an aspect, the homologous amino acid repeat can be the sequence Gly-Val-Leu-Pro-Gly-Val-Gly (SEQ ID NO: 1; iTEP$_A$); Gly-Ala-Gly-Val-Pro-Gly (SEQ ID NO: 2; iTEP$_B$); Val-Pro-Gly-Phe-Gly-Ala-Gly-Ala-Gly (SEQ ID NO: 3; iTEP$_C$); Val-Pro-Gly-Leu-Gly-Ala-Gly-Ala-Gly (SEQ ID NO: 4; iTEP$_D$); Val-Pro-Gly-Leu-Gly-Val-Gly-Ala-Gly (SEQ ID NO: 5; iTEP$_E$); Gly-Val-Leu-Pro-Gly-Val-Gly-Gly (SEQ ID NO: 6); Gly-Val-Leu-Pro-Gly (SEQ ID NO: 7); Gly-Leu-Val-Pro-Gly-Gly (SEQ ID NO: 8); Gly-Leu-Val-Pro-Gly (SEQ ID NO: 9); Gly-Val-Pro-Leu-Gly (SEQ ID NO: 10); Gly-Ile-Pro-Gly-Val-Gly (SEQ ID NO: 11); Gly-Gly-Val-Leu-Pro-Gly (SEQ ID NO: 12); Gly-Val-Leu-Pro-Gly (SEQ ID NO: 13); Gly-Val-Gly-Val-Leu-Pro-Gly (SEQ ID NO: 14); or Gly-Val-Pro-Gly (SEQ ID NO: 15). Table 1 lists homologous amino acid repeat sequences.

TABLE 1

Homologous Amino Acid Repeat Sequences

| SEQ ID NO: | Homologous Amino Acid Repeat |
|---|---|
| 1 | Gly-Val-Leu-Pro-Gly-Val-Gly |
| 2 | Gly-Ala-Gly-Val-Pro-Gly |
| 3 | Val-Pro-Gly-Phe-Gly-Ala-Gly-Ala-Gly |
| 4 | Val-Pro-Gly-Leu-Gly-Ala-Gly-Ala-Gly |
| 5 | Val-Pro-Gly-Leu-Gly-Val-Gly-Ala-Gly |
| 6 | Gly-Val-Leu-Pro-Gly-Val-Gly-Gly |
| 7 | Gly-Val-Leu-Pro-Gly |
| 8 | Gly-Leu-Val-Pro-Gly-Gly |
| 9 | Gly-Leu-Val-Pro-Gly |
| 10 | Gly-Val-Pro-Leu-Gly |
| 11 | Gly-Ile-Pro-Gly-Val-Gly |
| 12 | Gly-Gly-Val-Leu-Pro-Gly |
| 13 | Gly-Val-Leu-Pro-Gly |
| 14 | Gly-Val-Gly-Val-Leu-Pro-Gly |
| 15 | Gly-Val-Pro-Gly |

In another aspect, the homologous amino acid repeat is not the amino acid sequence: Gly-Gly-Val-Pro-Gly (SEQ ID NO: 28).

In an aspect, the homologous amino acid repeat sequence comprises four or more amino acid residues. In an aspect, the one of the amino acids residues is proline, and one or more of the amino acid residues is a valine. The proline and valine residues can be adjacent to each other. Alternatively, the proline and valine residues are not adjacent to each other. In some aspects, no more than one proline is present in the homologous amino acid repeat. The homologous amino acid repeat sequence can exist as a naturally occurring sequence in an elastin. The homologous amino acid repeat sequence can also be naturally flanked by one or more glycine residues at both the N-terminus and C-terminus ends.

In an aspect, the homologous amino acid repeat can be elastin-derived. The homologous amino acid repeat sequence can be derived from a mouse and/or human elastin. The homologous amino acid repeat sequence can be derived from a mouse and/or human elastin that can be further flanked by one or more glycine residues at both the C-terminus and the N-terminus ends. In an aspect, the homologous amino acid repeat can exhibit a certain degree of identity or homology to the homologous amino acid repeat, and wherein the homologous amino acid repeat is one or more of SEQ ID NOs: 1-15, etc. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The homologous amino acid repeat of a recombinant polypeptide described herein can have at least or about 25%, 50%, 65%, 75%, 80%, 85%, 90%, 95%, 96%, 97%, 98%, or 99% identity or homology to the homologous amino acid repeat, and wherein the homologous amino acid repeat is one or more of SEQ ID NOs: 1-15, etc.

In an aspect, the recombinant polypeptide described herein can further comprise one or more residues positioned at the N-terminus, C-terminus, or both the N-terminus and C-terminus of the recombinant polypeptide. The one or more residues can be glycine, alanine or serine or a combination thereof. The one or more residues described herein can be any residue that reduces immunogenicity.

In an aspect, the recombinant polypeptides can be immunogenic. For example, the recombinant polypeptides can be immunogenic to mouse and possess heat- and ion-induced, reversible, inverse phase transition between soluble single molecule phase and insoluble aggregate phase. This group of polypeptides is referred to herein as immunogenic elastin-like polypeptides (iMEPs).

In an aspect, the homologous amino acid repeat is Leu-Val-Val-Gly-Gly-Gly-Pro (SEQ ID NO: 20; iMEPA) and Ala-Gly-Gly-Pro-Gly-Val-Val-Ala-Gly-Gly-Pro-Gly-Val-Ala-Gly-Gly-Pro-Gly (SEQ ID NO: 21; iMEPB).

In an aspect, the iMEPs disclosed herein can be used as control materials, for example, for one or more iTEPs. They can also be used as drug carriers when an immunogenic carrier is desired. In many aspects, the iMEPs disclosed herein can be made and used as provided for the iTEPs herein. In addition, in many aspects, the disclosures regarding iTEPs can also apply to iMEPs.

Methods of Making Non-Immunogenic Bioconjugates

As used herein, the term "non-immunogenic bioconjugates" refers to a protein comprising a recombinant polypeptide as described herein and one or more therapeutic agents.

Disclosed herein are techniques that can be used to produce non-immunogenic bioconjugates described herein.

Design. In an aspect, the recombinant polypeptides (e.g., iTEPs) described herein can be designed as polymers of peptides derived from elastin. The recombinant polypeptide should be humorally tolerant in mice and humans, containing one or more epitopes to bind to B cell receptor, and one or more epitopes to bind to the MHC class II complex followed by binding with T cell receptors (e.g., CD4+ T cells). The recombinant polypeptide sequences selected should not intrinsically induce an autoimmune response (i.e., the sequences should not intrinsically bind to B cell or T cell receptors).

To reduce the possibility of generating recombinant polypeptides that are immunogenic, two strategies can be employed. First, common, existing peptide repeats within human and mouse elastins can be used as a component of the homologous amino acid repeat to limit generating extrinsic junction sequences. Second, when one or more extrinsic junction sequences were produced, the homologous amino acid repeats should be four residues or longer and from elastins; and be flanked by one or more glycine residues at the N- and C-terminuses. By using homologous amino acid repeats that are longer rather than shorter, the number of extrinsic junction sequences can be reduced. Reducing or eliminating extrinsic junction sequences may reduce the immunogenicity of the recombinant polypeptide or homologous amino acid repeat.

In some aspects, for the homologous amino acid repeats to have the phase transition property, they can be designed to have one proline residue and one or more valine residues.

The polypeptides useful as non-immunogenic conjugates can be produced by synthetic methods and recombinant techniques used routinely to produce protein from nucleic acids. The polypeptides can be stored in an unpurified or in an isolated or substantially purified form until later use.

Non-immunogenic bioconjugates. In some aspects, the recombinant polypeptide disclosed herein is a recombinant fusion protein or diblock polymer. It can be expressed in a variety of expression systems (e.g., *E. coli*, yeast, insect cell, and mammalian cell cultures; and plants). Briefly, a plasmid DNA encoding the recombinant fusion protein can be transfected into cells of any of the expression systems described above. After the fusion protein (e.g., iTEP$_B$-iTEP$_A$) is produced in any one of these systems, they can then also be purified, lyophilized and stored until use.

Therapeutic agent. A wide variety of therapeutic agents can be incorporated, associated, or linked to the non-immunogenic bioconjugate. The therapeutic agents can be a chemical compound, a protein, a peptide, a small molecule or a cell. Examples of therapeutic agents include peptide vaccines, antibodies, nucleic acids (e.g., siRNA) and cell-based agents (e.g., stem cells, CAR-T cells). In some aspects, one or more of the therapeutic agents can be an anti-cancer agent. The anti-cancer agent can be an agent, vaccine or drug that has anti-cancer properties. In an aspect, the anti-cancer agent has anti-microbial or anti-viral properties. In an aspect, the anti-cancer agent can be a cancer stem cell inhibitor. Examples of anti-cancer agents are salinomycin and paclitaxel or any analogues thereof.

The recombinant polypeptides as described herein can also be used as a carrier for scaffolding materials, for example, for cell adherence and growth, and, thus, can be used in tissue repair or cell-based therapy. The recombinant polypeptides can also be used as a matrix gel, for example, to facilitate cell growth in vitro and in vivo; and as an adjuvant.

Linkers. The non-immunogenic bioconjugates described herein can further comprise a one or more linkers. A given linker within the compositions disclosed herein can provide a cleavable linkage (e.g., a thioester linkage). Sites available for linking can be found on the recombinant polypeptides described herein. Useful linkers in the present non-immunogenic bioconjugates can comprise a group that is reactive with a primary amine on the recombinant polypeptide to which a therapeutic agent or vaccine is conjugated. Useful linkers are available from commercial sources. In an aspect the linker can be 4-(4-N-maleimidophenyl)butyric acid hydrazide hydrochloride (MPBH). One of ordinary skill in the art is capable of selecting the appropriate linker.

The linker can be a covalent bond. To form covalent bonds, a chemically reactive group can be used, for instance, that has a wide variety of active carboxyl groups (e.g., esters) where the hydroxyl moiety is physiologically acceptable at the levels required to modify the recombinant polypeptide.

Any of the recombinant polypeptides described herein and incorporated into the non-immunogenic conjugates can be modified to chemically interact with, or to include, a linker as described herein. These modified recombinant polypeptides and peptide-linker constructs are within the scope of the present disclosure and can be packaged as a component of a kit with instructions for completing the process of conjugation to a therapeutic agent. The recombinant polypeptides can be modified to include a cysteine residue or other thio-bearing moiety (e.g., C—SH) at the N-terminus, C-terminus, or both.

In an aspect, the therapeutic agent (e.g., paclitaxel) can be encapsulated or loaded onto the recombinant polypeptide using methods known to one of ordinary skill in the art. The encapsulated therapeutic agent can be determined by high performance liquid chromatography.

Configurations. Each part of the non-immunogenic bioconjugate, including the recombinant polypeptide, therapeutic agent, and linker, can be selected independently. One of ordinary skill in the art would understand that the component parts need to be associated in a compatible manner. The non-immunogenic bioconjugates can be used to deliver therapeutic agents to a patient for the treatment of cancer and infections. The number of therapeutic agents per non-immunogenic bioconjugate can be controlled by adding more iTEPs (e.g., diblock polymers, fusion proteins). One or more cysteines residues can be added at one of end of an iTEP and be used as conjugation sites for one or more therapeutic agents. For example, eight cysteine residues can be added and provide eight conjugation sites for eight therapeutic agents. The therapeutic agents can be the same, different or any combination thereof. When two or cysteine residues are added to the end of a recombinant polypeptide as described herein (e.g., an iTEP), one or more spacers (e.g., glycine residues) can be inserted between, for example, two cysteine residues. The number of spacers can be adjusted according to the number of cysteine residues added or to the number of therapeutic molecules desired. The spacers serve to provide ample space to accommodate two or more therapeutic agents. Spacers can be one or more glycines or serines or a combination thereof.

Accordingly, in some aspects, the therapeutic agents can be two or more. In other embodiments, the recombinant polypeptide as described herein (e.g., an iTEP) and the therapeutic agent are present in a ratio of 1:1 (recombinant polypeptide:therapeutic agent). The recombinant polypeptide:therapeutic agent ratio can also be 1:2, 1:3, 1:4, 1:5, 1:6, 1:7, 1:8, 1:9, 1:10 or any other combinations thereof. The number of therapeutic agents that can be conjugated to the recombinant polypeptides described herein can be determined by the number of conjugation sites (e.g., cysteine residues) that are added in a given polypeptide.

One or more cysteine residues can be added between to recombinant polypeptides described herein (e.g., between two iTEP molecules). The cysteine residues can further be separated by adding two or more spacers (e.g., glycine residues). For example, four cysteine residues can be inserted between a diblock polymer (or copolymer or fusion protein) and a plasmid (e.g., pOVA). These cysteine residues, for instance, can be further separated by the addition of eight glycine residues.

Labels. The recombinant polypeptides described herein can further comprise one or more labels or detection tags. (e.g., FLAG™ tag, epitope or protein tags, such as myc tag, 6 His, and fluorescent fusion protein). In an aspect, the label (e.g., FLAG™ tag) is fused to the recombinant polypeptide. In an aspect, the disclosed methods and compositions further comprise a fusion protein, or a polynucleotide encoding the same. In various aspects, the fusion protein comprises at least one epitope-providing amino acid sequence (e.g., "epitope-tag"), wherein the epitope-tag is selected from i) an epitope-tag added to the N- and/or C-terminus of the protein (e.g., recombinant polypeptide); or ii) an epitope-tag inserted into a region of the protein (e.g., recombinant polypeptide), and an epitope-tag replacing a number of amino acids in the protein (e.g., recombinant polypeptide).

Epitope tags are short stretches of amino acids to which a specific antibody can be raised, which in some aspects allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western blotting"), and affinity chromatography. Epitope tags add a known epitope (e.g., antibody binding site) on the subject protein, to provide binding of a known and often high-affinity antibody, and thereby allowing one to specifically identify and track the tagged protein that has been added to a living organism or to cultured cells. Examples of epitope tags include, but are not limited to, myc, T7, GST, GFP, HA (hemagglutinin), V5 and FLAG tags. The first four examples are epitopes derived from existing molecules. In contrast, FLAG is a synthetic epitope tag designed for high antigenicity (see, e.g., U.S. Pat. Nos. 4,703,004 and 4,851,341). Epitope tags can have one or more additional functions, beyond recognition by an antibody.

In an aspect, the disclosed methods and compositions comprise an epitope-tag wherein the epitope-tag has a length of between 6 to 15 amino acids. In an alternative aspect, the epitope-tag has a length of 9 to 11 amino acids. The disclose methods and compositions can also comprise a fusion protein comprising two or more epitope-tags, either spaced apart or directly in tandem. Further, the disclosed methods and composition can comprise 2, 3, 4, 5 or even more epitope-tags, as long as the fusion protein maintains its biological activity/activities (e.g., "functional").

In an aspect, the epitope-tag is a VSV-G tag, CD tag, calmodulin-binding peptide tag, S-tag, Avitag, SF-TAP-tag, strep-tag, myc-tag, FLAG-tag, T7-tag, HA (hemagglutinin)-tag, His-tag, S-tag, GST-tag, or GFP-tag. The sequences of these tags are described in the literature and well known to the person of skill in art.

As described herein, the term "immunologically binding" is a non-covalent form of attachment between an epitope of an antigen (e.g., the epitope-tag) and the antigen-specific part of an antibody or fragment thereof. Antibodies are preferably monoclonal and must be specific for the respective epitope tag(s) as used. Antibodies include murine, human and humanized antibodies. Antibody fragments are known to the person of skill and include, amongst others, single chain Fv antibody fragments (scFv fragments) and Fab-fragments. The antibodies can be produced by regular hybridoma and/or other recombinant techniques. Many antibodies are commercially available.

The construction of fusion proteins from domains of known proteins, or from whole proteins or proteins and peptides, is well known. Generally, a nucleic acid molecule that encodes the desired protein and/or peptide portions are joined using genetic engineering techniques to create a single, operably linked fusion oligonucleotide. Appropriate molecular biological techniques can be found in Sambrook et al. (Molecular Cloning: A laboratory manual Second Edition Cold Spring Harbor Laboratory Press, Cold spring harbor, NY, USA, 1989). Examples of genetically engineered multi-domain proteins, including those joined by various linkers, and those containing peptide tags, can be found in the following patent documents: U.S. Pat. No. 5,994,104 ("Interleukin-12 fusion protein"); U.S. Pat. No. 5,981,177 ("Protein fusion method and construction"); U.S. Pat. No. 5,914,254 ("Expression of fusion polypeptides transported out of the cytoplasm without leader sequences"); U.S. Pat. No. 5,856,456 ("Linker for linked fusion polypeptides"); U.S. Pat. No. 5,767,260 ("Antigen-binding fusion proteins"); U.S. Pat. No. 5,696,237 ("Recombinant antibody-toxin fusion protein"); U.S. Pat. No. 5,587,455 ("Cytotoxic agent against specific virus infection"); U.S. Pat. No. 4,851,341 ("Immunoaffinity purification system"); U.S. Pat. No. 4,703,004 ("Synthesis of protein with an identification peptide"); and WO 98/36087 ("Immunological tolerance to HIV epitopes").

The placement of the functionalizing peptide portion (epitope-tag) within the subject fusion proteins can be influenced by the activity of the functionalizing peptide portion and the need to maintain at least substantial fusion protein, such as TCR, biological activity in the fusion. Two methods for placement of a functionalizing peptide are: N-terminal, and at a location within a protein portion that exhibits amenability to insertions. Though these are not the only locations in which functionalizing peptides can be inserted, they serve as good examples, and will be used as illustrations. Other appropriate insertion locations can be identified by inserting test peptide encoding sequences (e.g., a sequence encoding the FLAG peptide) into a construct at different locations, then assaying the resultant fusion for the appropriate biological activity and functionalizing peptide activity, using assays that are appropriate for the specific portions used to construct the fusion. The activity of the subject proteins can be measured using any of various known techniques, including those described herein.

The methods disclosed herein related to the process of producing the non-immunogenic bioconjugates as disclosed herein can be readily modified to produce a pharmaceutically acceptable salt of the non-immunogenic bioconjugates.

Pharmaceutical compositions including such salts and methods of administering them are within the scope of the present disclosure.

Pharmaceutical Compositions

As disclosed herein, are pharmaceutical compositions, comprising the non-immunogenic bioconjugates (and the recombinant polypeptides) and a pharmaceutical acceptable carrier described above. In some aspects, the therapeutic agent is an anti-cancer agent or an anti-microbial agent or anti-viral agent and the pharmaceutical composition is formulated for intravenous administration. The compositions of the present disclosure also contain a therapeutically effective amount of a non-immunogenic bioconjugate as described herein. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the non-immunogenic bioconjugate. Thus, compositions can be prepared for parenteral administration that includes non-immunogenic bioconjugates dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein, are methods of treating a patient with cancer, the method comprising: (a) identifying a patient in need of treatment; and (b) administering to the patient a therapeutically effective amount of the pharmaceutical composition comprising the non-immunogenic bioconjugate comprising a recombinant polypeptide comprising an homologous amino acid repeat, wherein the homologous amino acid repeat comprises four or more amino acid residues, wherein one of the amino acid residues is a proline, and one or more of the amino acid residues is a valine; and a therapeutic agent, and a pharmaceutically acceptable carrier.

Disclosed herein, are methods of treating a patient with an infection, the method comprising: (a) identifying a patient in need of treatment; and (b) administering to the patient a therapeutically effective amount of the pharmaceutical composition comprising the non-immunogenic bioconjugate comprising a recombinant polypeptide comprising an homologous amino acid repeat, wherein the homologous amino acid repeat comprises four or more amino acid residues, wherein one of the amino acid residues is a proline, and one or more of the amino acid residues is a valine; and a therapeutic agent, and a pharmaceutically acceptable carrier.

The pharmaceutical compositions described above can be formulated to include a therapeutically effective amount of a non-immunogenic bioconjugate. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of cancer or infection.

The pharmaceutical compositions described herein can be administered to the subject (e.g., a human patient) in an amount sufficient to delay, reduce, or preferably prevent the onset of clinical disease. Accordingly, in some aspects, the patient is a human patient. In therapeutic applications, compositions are administered to a subject (e.g., a human patient) already with or diagnosed with cancer (or an infection) in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effect amount includes amounts that provide a treatment in which the onset or progression of the cancer (or an infection) is delayed, hindered, or prevented, or the cancer (or the infection) or a symptom of the cancer (or the infection) is ameliorated. One or more of the symptoms can be less severe. Recovery can be accelerated in an individual who has been treated.

In some aspects, the cancer is a primary or secondary tumor. In other aspects, the primary or secondary tumor is within the patient's breast, lung, colon or ovaries.

Disclosed herein, are methods of treating a patient with cancer. The cancer can be any cancer. In some aspects, the cancer is breast cancer, ovarian cancer, lung cancer, colon cancer, or gastric cancer. In an aspect, the cancer is metastatic. In some aspects, the cancer is associated with cancer stem cells.

Amounts effective for this use can depend on the severity of the cancer and the weight and general state and health of the subject, but generally range from about 0.05 µg to about 1000 µg (e.g., 0.5-100 µg) of an equivalent amount of the immunogenic bioconjugate per dose per subject. Suitable regimes for initial administration and booster administrations are typified by an initial administration followed by repeated doses at one or more hourly, daily, weekly, or monthly intervals by a subsequent administration. For example, a subject can receive an immunogenic bioconjugate (or recombinant polypeptide) in the range of about 0.05 to 1,000 μg equivalent dose as compared to unbound or free therapeutic agent(s) per dose one or more times per week (e.g., 2, 3, 4, 5, 6, or 7 or more times per week). For example, a subject can receive 0.1 to 2,500 μg (e.g., 2,000, 1,500, 1,000, 500, 100, 10, 1, 0.5, or 0.1 μg) dose per week. A subject can also receive an immunogenic bioconjugate (or recombinant polypeptide) in the range of 0.1 to 3,000 μg per dose once every two or three weeks. A subject can also receive 2 mg/kg every week (with the weight calculated based on the weight of the immunogenic bioconjugate or any part or component of the immunogenic bioconjugate).

The total effective amount of an immunogenic bioconjugate (or recombinant polypeptide) in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of one or more of the therapeutic agents present within the compositions described herein and used in the methods as disclosed herein applied to mammals (e.g., humans) can be determined by one of ordinary skill in the art with consideration of individual differences in age, weight, and other general conditions (as mentioned above).

Because the immunogenic bioconjugates of the present disclosure can be stable in serum and the bloodstream and in some cases more specific, the dosage of the immunogenic bioconjugates including any individual component can be lower (or higher) than an effective dose of any of the individual components when unbound. Accordingly, in some aspects, the anti-cancer agent administered has increased efficacy or reduced side effects when administered as part of a immunogenic bioconjugates as compared to when the anti-cancer agent is administered alone or not as part of a immunogenic bioconjugates.

EXAMPLES

Example 1: Design of Immune-Tolerant Elastin-Like Polypeptides (iTEPs)

Construction of iTEP expression plasmids. The genes encoding iTEPs were synthesized on a modified pET25b(+) vector using a reported method with some modifications.[27] First, a pET25b(+) vector was modified by inserting a double-stranded DNA at the vector's XbaI and BamHI endonuclease restriction sites. The inserted DNA was assembled by annealing together two complementary oligonucleotides, pET25-F and pET25-R (Table 2) (Eurofins Genomics, USA). The insertion of this DNA introduced two new restriction sites for BseRI and AcuI, and an in-frame stop codon to the pET25b(+) vector. Second, genes that encoded subunits of iTEP$_A$: (GVLPGVG)$_4$ (SEQ ID NO: 30), iTEP$_B$: (GAGVPG)$_5$ (SEQ ID NO: 31), iTEP$_C$: (VPGFGAGAG)$_3$ (SEQ ID NO: 32), and iTEP$_D$: (VPGLGAGAG)$_3$ (SEQ ID NO: 33) were generated by annealing the sense and antisense oligonucleotides of these genes together (Table 2). Third, these iTEP genes were inserted to the modified pET25b(+) vector at its BseRI site. Finally, iTEP genes were extended to desired lengths through the following method. Specifically, the modified vector harbouring iTEP genes was digested by two sets of enzymes, respectively. The first set includes AcuI, ApaI, and BglI; the second set includes BseRI and ApaI. Then, two DNA fragments that were from the two sets of digestions and contained iTEP genes were isolated and ligated together using T4 DNA ligase to create a new iTEP expression vector. The vector was transformed into DH5a for its amplification. The lengths of iTEP genes which dictated repeat numbers of iTEP building blocks were confirmed by an XbaI and BamH I double digestion and the followed agarose gel analysis. This PRe-RDL process was repeated as desired to generate iTEP genes with designed lengths. The final iTEP genes were verified by DNA sequencing in combination with an endonuclease digestion approach (Genewiz, USA).

TABLE 2

Sequences of primers for cloning

| | Name | Sequence 5'-3' | SEQ ID NO: |
|---|---|---|---|
| SDO84 | pET25-F | CTAGaaataattttgtttaactttaagaaggaggagtacatatgg gcggttgataatgatcttcag | 34 |
| SDO85 | pET25-R | GATCctgaagatcattatcaaccgcccatatgtactcctccttctt aaagttaaacaaaattattt | 35 |
| SDO86 | ITEP$_B$-F | Cgcgggtgtgccgggcggcgccggtgttccaggggggcgcgg gtgtgccgggaggcgcaggtgtccctgggggcgctggtgtacc gggaGG | 36 |
| SDO87 | ITEP$_B$-R | tcccggtacaccagcgccccagggacacctgcgcctcccgc acacccgcgcccctggaacaccggcgccgcccggcacaccc gcGCC | 37 |
| SDO88 | ITEP$_C$-F | Cgtgccgggctttggtgcgggcgccggggttccaggcttcggtg caggcgcgggagtcccgggttttggcgccggggctGG | 38 |

TABLE 2-continued

Sequences of primers for cloning

| Name | | Sequence 5'-3' | SEQ ID NO: |
|---|---|---|---|
| SD089 | ITEP$_C$-R | agccccggcgccaaaacccgggactcccgcgcctgcaccgaa gcctggaacccggcgcccgcaccaaagcccggcacGCC | 39 |
| SD092 | ITEP$_D$-F | Cgtgccgggcctgggtgcgggcgccggggttccaggcttaggt gcaggcgcgggagtcccgggictgggcgccggggctGG | 40 |
| SD093 | ITEP$_D$-R | agccccggcgcccagacccgggactcccgcgcctgcacctaag cctggaacccggcgcccgcacccaggcccggcacGCC | 41 |
| SD094 | ITEP$_A$-F | Cgtgctgccgggtgttggcggtgtgttaccaggcgtcggggtg tgctgccgggcgttggtggtgtcttgcctggcgtaggaGG | 42 |
| SD095 | ITEP$_A$-R | tcctacgccaggcaagacaccaccaacgcccggcagcacccc ccgacgcctggtaacacaccgccaacacccggcagcacGCC | 43 |
| SD072 | pOVA-1F (2C) (pOVA-F) | Ggagagtataatcaactttgaaaaactgactgaaagcatcataaat ttcgaaaagctgaccGG | 44 |
| SD073 | pOVA-1R (2C) (pOVA-R) | ggtcagcttttcgaaatttatgatgctttcagtcagttttcaaagttga ttatactctcCCC | 45 |
| | (G$_1$C)$_4$-F | CTGTGGTTGCGGCTGCGGGTGTGG | 46 |
| | (G$_1$C)$_4$-R | ACACCCGCAGCCGCAACCACAGCC | 47 |
| | (G$_8$C)$_4$-F | CGGTGGAGGTGGGTGTGGTGGCGGCGG AGGTGGCGGTGGCTGCGGTGGTGGCGG CGGGGGCGGCGGTTGCGGCGGCGGTGG CGGTGGGGGAGGATGTGGTGGGGGTGG | 48 |
| | (G$_8$C)$_4$-R | ACCCCCACCACATCCTCCCCCACCGCCA CCGCCGCCGCAACCGCCGCCCCCGCCGC CACCACCGCAGCCACCGCCACCTCCGCC GCCACCACACCCACCTCCACCGCC | 49 |

The iTEPs used as representatives were: iTEP$_A$ having 28 repeats of GVLPGVG (SEQ ID NO: 50), iTEP$_B$ having 70 repeats of GAGVPG (SEQ ID NO: 51), iTEP$_C$ having 21 repeats of VPGFGAGAG (SEQ ID NO: 52), and iTEP$_D$ having 96 repeats of VPGLGAGAG (SEQ ID NO: 53). iTEP$_C$ which has an odd number of repeat was generated unexpectedly. iTEPs with the above lengths were used for this study because they can be expressed from *E. coli* and their transition temperature, with or without salt, are between ambient temperature and 60° C. so that it is operationally possible to purify them by cycling the transition. In addition, these sizes of iTEP are in the range of natural proteins permitting the study and analysis of the immunogenicity of the iTEPs as proteins instead of peptides.

The gene encoding an amphiphilic fusion, iTEP$_B$-iTEP$_A$ (SEQ ID NO: 54), was generated by linking iTEP$_B$ and iTEP$_A$ genes together using the PRe-RDL method.[27] The gene encoding a fusion, iTEP$_B$-iTEP$_A$-pOVA (SEQ ID NO: 56) was generated in a similar manner using a gene of pOVA (Table 2). It is noteworthy that pOVA has two copies of a CTL epitope, SIINFEKL (SEQ ID NO: 22).[28] One natural flanking residue was on the each side of SIINFEKL (SEQ ID NO: 22). The actual amino acid sequence of pOVA is ESIINFEKLTESIINFEKLT (SEQ ID NO: 55).

Results. The iTEPs were designed as polymers of peptides derived from elastin. One criteria of these iTEPs is that they be humorally tolerant in both mice and humans, a feature that can facilitate their preclinical and clinical applications. For a polypeptide to be humorally immunogenic, it can contain at least one epitope to bind with B cell receptors (BCRs) and another epitope to bind first with the MHC class II complex, and then with a cognate T cell receptor (TCRs) on CD4+ T cells.[34-36] By the same token, a humorally tolerant polypeptide should not contain TCR or BCR epitopes. Homologous peptide sequences between human and mouse elastins were chosen as the monomers (e.g., homologous amino acid repeats) of iTEPs. These homologous sequences should intrinsically not bind with BCRs and TCRs of human and mouse; otherwise they would induce autoimmune responses (FIG. 1).

Because iTEPs are polymers of elastin-derived peptides, the polymerization may introduce junction sequences that are exogenous to humans and mice, and these junction sequences can be potentially humorally immunogenic. To diminish the possible immunogenicity, two strategies were utilized. First, the homologous peptides that repeat themselves within human and mouse elastins as the monomers (e.g., homologous amino acid repeats) of iTEPs (see iTEP$_C$ and iTEP$_D$, FIG. 1) were used, such that no extrinsic junction sequences were in iTEPs. Further, the repeats have 18 residues and are longer than the typical length of MHC class II-restricted TCR epitopes (13-17 residues) and linear BCR epitopes (4-6 residue).[33, 38] Thus, the repeats (e.g., homologous amino acid repeats) are long enough to be used naturally to negatively select and deplete the BCRs and TCRs binding with them during lymphocyte development.[39] Consequently, no human and mouse BCRs or TCRs should bind with these repeats (e.g., homologous amino acid repeats). iTEPs that are polymerized from these repeats (e.g., homologous amino acid repeats), therefore, can be low- or non-immunogenic.

The second strategy was applied when exogenous junction sequences were unavoidable. In this case, the two criteria for monomers of iTEPs were: one, that they be long homologous peptides from the elastins; two, they be flanked by Glys at both ends (iTEP$_A$ and iTEP$_B$; FIG. 1). By using the longer monomers (e.g., homologous amino acid repeats) rather than shorter ones, the number of junction sequences in iTEPs was lower. This change could potentially reduce the immunogenicity of the iTEPs because the epitope density is an important factor for the strength of immune responses.[40-42] The Gly-flanked monomers resulted in a high frequency of Glys inside the junction sequences, which can mitigate the immunogenicity of the junction sequences as Gly had been shown to silence BCR epitopes.[43, 44] Using the second strategy, the iTEPs are expected to have a low immunogenicity.

In order for the iTEPs described herein to have the phase transition property of ELPs, all monomers (e.g., homologous amino acid repeats) of iTEPs were designed to contain one proline and at least one valine (FIG. 1). Based on previous work of published ELP sequences,[21] it was hypothesized that this criterion can be sufficient to render iTEPs the transition property. None of the iTEP monomers (e.g., homologous amino acid repeats) disclosed herein can have the canonical motif, VPGXG (SEQ ID NO: 29), of ELPs,[45] which is not unexpected since the canonical motif was not a part of the iTEP design criteria described above.

Described herein, a new ELP design and engineering practice that emphasizes physicochemical properties as well as immunogenicity of the ELPs from the very beginning of ELP design was tested. Novel ELPs, termed as iTEPs were designed and generated. The iTEPs described herein are humorally tolerant and possess a phase transition property. The results disclosed herein demonstrate that an amphiphilic iTEP copolymer self-assembles into a nanoparticle (see Examples below). The nanoparticle, when used to deliver a model CTL peptide vaccine, improved the potency of the vaccine in comparison to CTL vaccines in free peptide or protein forms.

Adverse immunogenicity of the peptide and protein materials could compromise their functionality by blocking the materials' interactions with their targets, shortening their half-lives,[52, 53] and decreasing their bioavailability.[54] Immunogenicity can also be life-threating.[54] In the case of CTL vaccine delivery, it was suggested that humoral responses against vaccine carriers impede the effectiveness of their vaccine payloads.[55, 56] Since our motivation in this study is to explore ELPs' potential as CTL vaccine carriers, iTEPs were created so that immunogenicity of these polypeptides would not be a hurdle for their usage as the carriers. The need for creating iTEPs was substantiated by a very recent report showing that ELPs having distinct sequences displayed very different humoral immunogenicity when they were complexed with plasmid DNAs.[22] To create iTEPs, an unconventional polypeptide design and engineering practice was used that incorporates both functionality and immunogenicity criteria in the design. This practice was employed to minimize the risk that a material with a well characterized function may become valueless due to its afterward discovered adverse immunogenicity. This practice, indeed, has proven fruitful. As disclosed herein iTEPs with the desired low immunogenicity were generated.

Besides as a proof-of-principle for the new ELP development practice, the success of generating these iTEPs has a practical significance. These iTEPs are different and uncommon, and likely more valuable in preclinical and clinical applications than other reported ELPs because they were designed as immune tolerant materials to both mice and humans, which is unprecedented.[18-21] iTEPs' immune tolerance in mice has been confirmed. Because the underlying idea to render the iTEPs immune tolerated by mice and humans is the same, it is plausible that these iTEPs can be tolerated by human immunity when they are tested.

Example 2: Cloning and Expression of iTEPs

Production and purification of iTEPs and iTEP fusions. Competent BL21(DE3) E. coli cells (EMD Chemicals, Inc. USA) were transformed with the pET25b(+) expression vector bearing iTEP or iTEP fusion genes. The single colony transformant was grown in TB media containing 100 μg/ml ampicillin for 24 hours at 37° C. After the growth, E. coli cells were collected as a pellet by centrifugation for 25 minutes at 4,816×g and 4° C. The cell pellet was then resuspended in phosphate buffered saline (PBS) and lysed by sonication for 3 minutes/L couture (sonication pulse rate: 10 seconds on and 30 seconds off). Later, 10% of polyethylenimine (PEI) was added to the cell lysate to precipitate E. coli DNA, and the precipitant was removed by centrifugation for 15 minutes at 21,000×g and 4° C. Lastly, iTEPs or iTEP fusions were purified from the supernatant via inverse transition cycling (ITC) as described previously.[29] The purity of iTEP was assessed by SDS-PAGE using copper staining.[30]

Endotoxin removal for iTEPs and iTEP fusions. Endotoxin of iTEPs or iTEP fusions was removed using Pierce High Capacity Endotoxin Removal Resin (Thermo Scientific, USA) following the manufacturer's instruction. The endotoxin level was determined by Limulus Amebocyte Lysate (LAL) PYROGENT Single Test Vials (Lonza, USA). Final endotoxin levels in these samples were below 0.25 EU per mg protein.

Figure 2B:
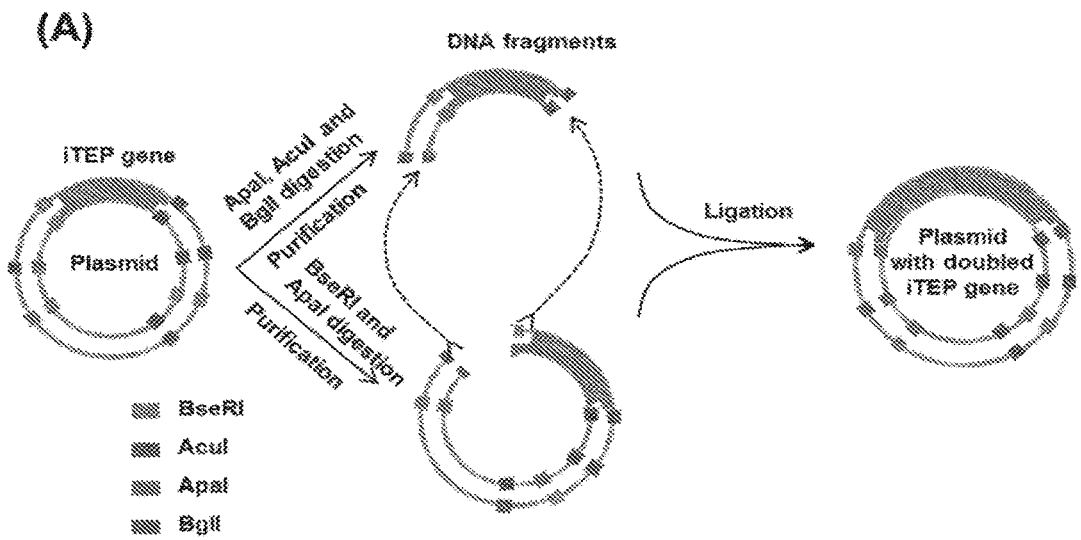
Figure 2B:
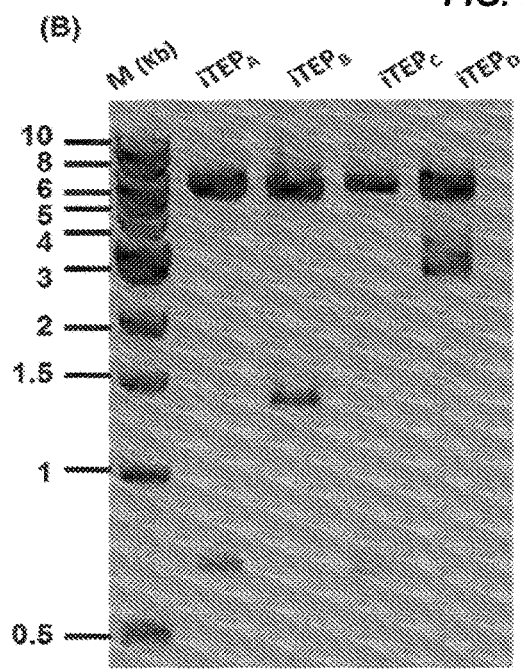
Figure 2C:
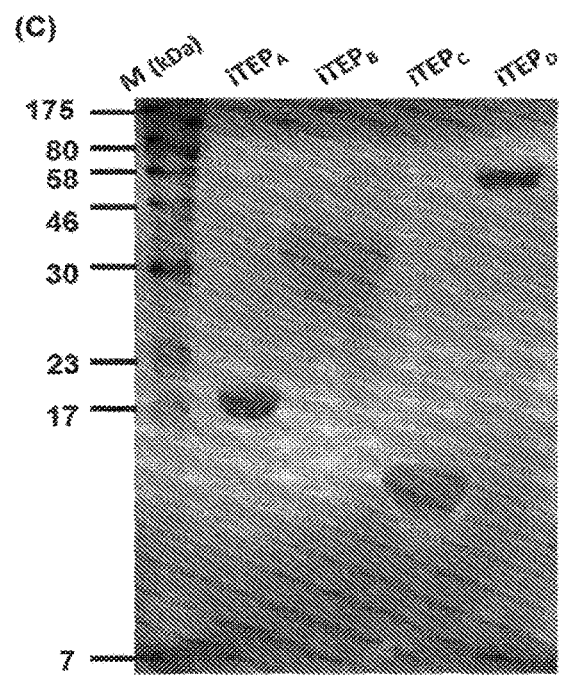

Results. iTEPs were produced and purified as recombinant proteins from E. coli. The coding genes for iTEPs were constructed and elongated using a modified Pre-RDL method (FIG. 2A).[27] The coding genes were confirmed by DNA sequencing in combination with endonuclease digestion approach. The agarose gel results (FIG. 2B) confirmed the sizes of the coding genes: iTEP$_A$ (600 bps), iTEP$_B$ (1272 bps), iTEP$_C$ (579 bps), and iTEP$_D$ (2604 bps). Sizes of these iTEP genes confirmed they have the right lengths, suggesting these genes would code iTEPs of expected lengths. Purity and sizes of the iTEPs after purification were confirmed by SDS-PAGE (FIG. 2C). It is noteworthy that iTEP$_B$ did not negatively stain as well as other iTEPs, probably due to its hydrophilic yet uncharged nature (below), which may hinder the emulsification of SDS around the iTEP, thus the iTEP can neither focus well on the gel nor have enough SDS to prevent formation of copper complex in situ.[46, 47] As a result, this iTEP appears as a smear on a copper-stained SDS-PAGE.

Example 3: Thermally-Induced, Reversible Phase Transition of iTEPs

Characterization of thermally-induced, reversible, inverse phase transition of iTEPs and the iTEP$_B$-iTEP$_A$-pOVA fusion. The phase transitions of iTEP or iTEP fusions were characterized by turbidity changes of sample solutions as a function of temperature. Specifically, the optical density at 350 nm (OD$_{350}$) of a sample solution was monitored using an UV-visible spectrophotometer equipped with a multi-cell thermoelectric temperature controller (Cary 300, Varian Instruments, Walnut Creek, CA) while the solution was heated from 20° C. to 80° C. and then cooled to 20° C. at a rate of 1° C./min. The maximum first derivative of the turbidity curve of a sample was identified. The transition temperature (Tt) of the sample is the temperature that corresponds to the maximum derivative.

Figure 3A:
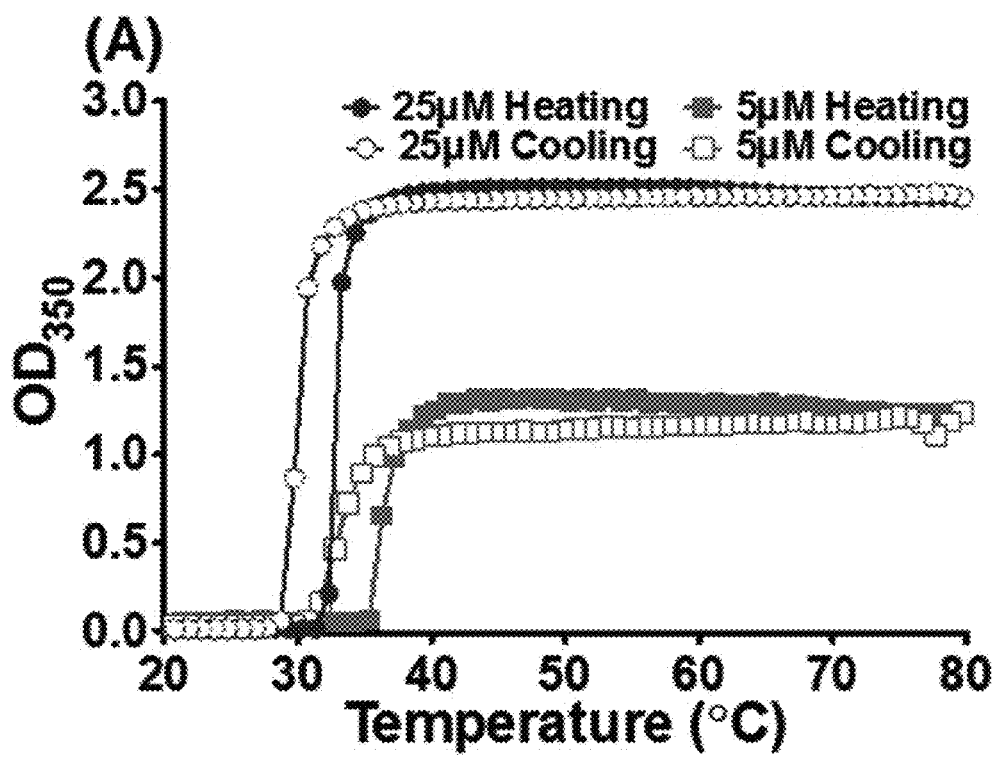
FIG. 3A-E illustrates the reversible phase transition of iTEPs.
Figure 3B:
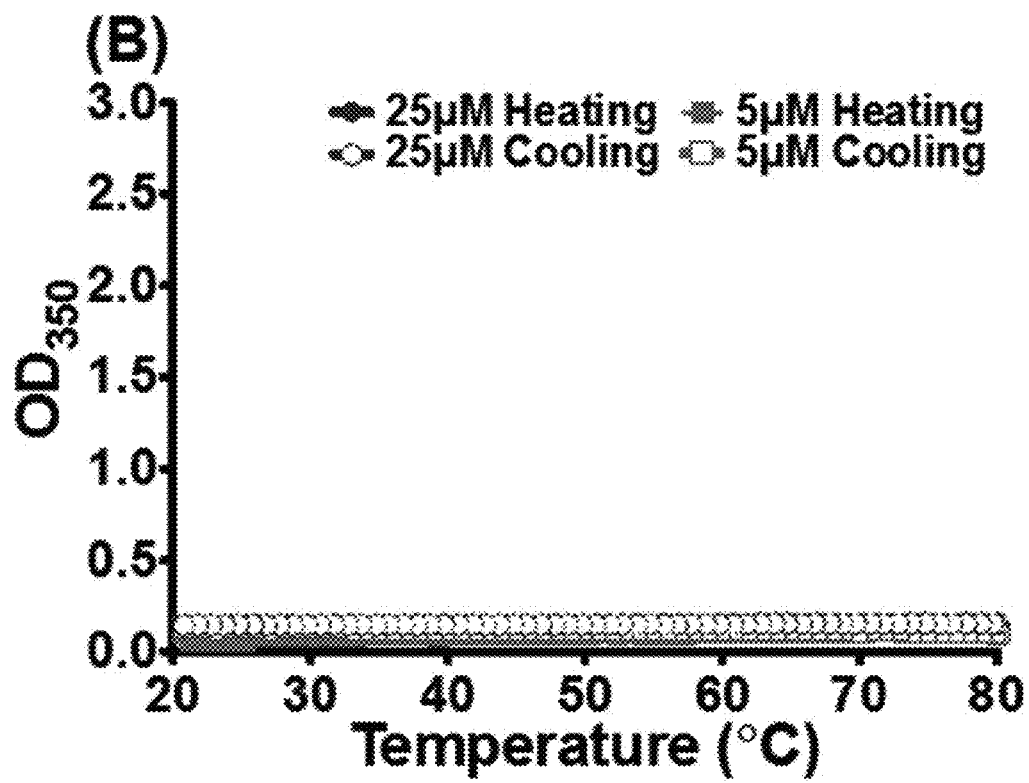
Figure 3C:
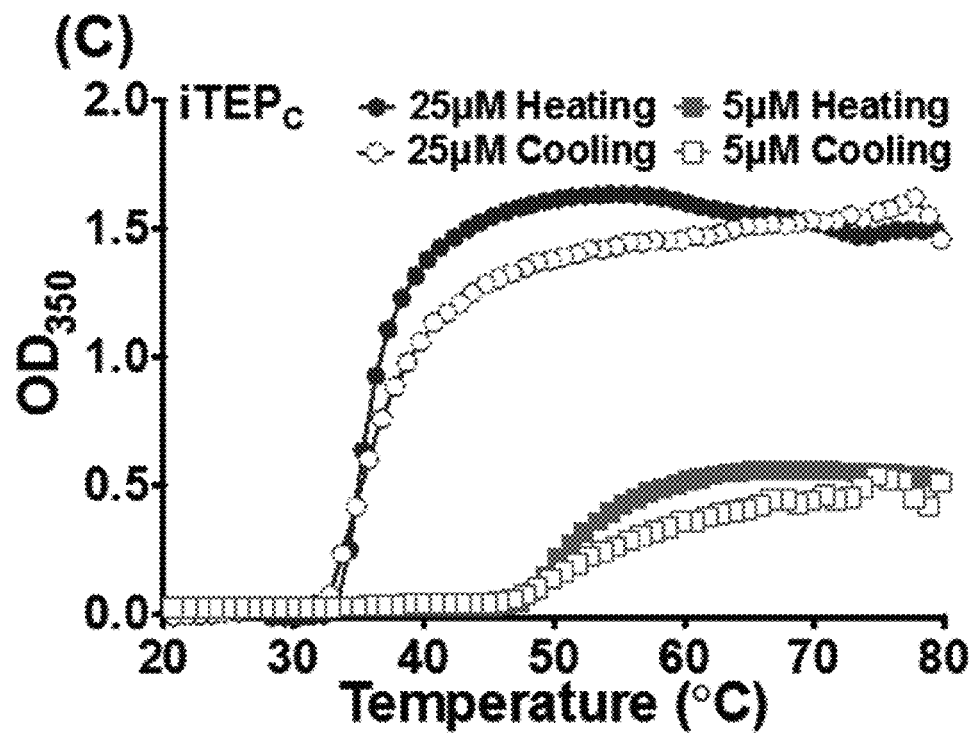
Figure 3D:
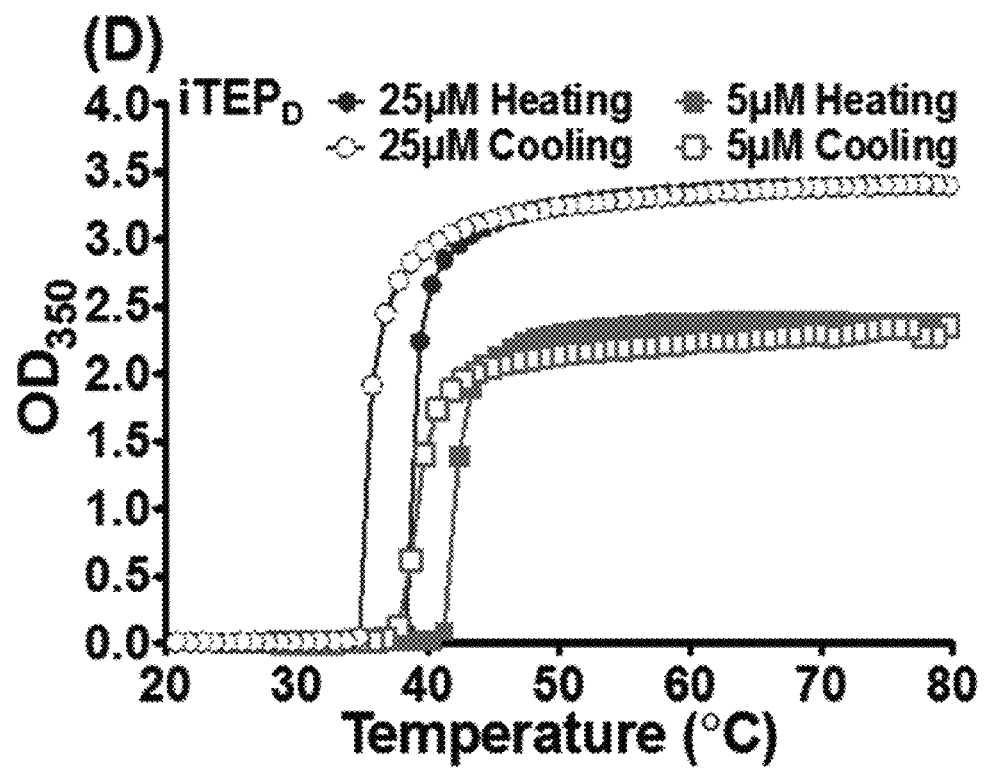
Figure 3E:
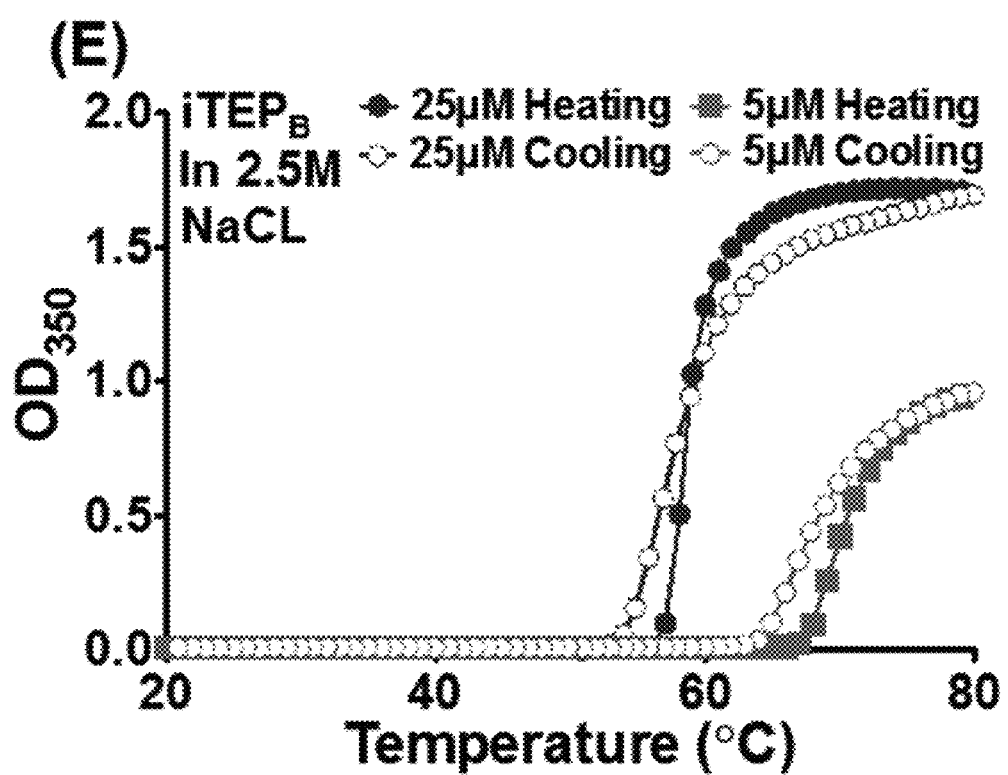

Results. All iTEP sets tested have variants displaying the phase transition feature (FIG. 3A-E). The associated inverse transition temperatures (Tts) of these iTEPs are summarized together with their sequences and molecular weights in Table 3. iTEP$_B$ displayed much higher Tts than the other three iTEPs. Specifically, iTEP$_B$ did not form coacervates in the tested temperature range (20-80° C.) in H$_2$O, while the others formed coacervates between 29-38° C. (FIG. 3B versus FIG. 3A, C, D). To achieve a thermally-induced phase transition of iTEP$_B$, an experiment was carried out in a solution containing 2.5M NaCl (FIG. 3F). The high Tt of iTEP$_B$ suggests it is much more hydrophilic than the other three iTEPs. Thus, among the four sets of iTEPs, both hydrophilic and hydrophobic ones were attained (Table 3).

lead to a shift of the paradigm on the relationship between the VPGXG (SEQ ID NO: 29) motif and the phase transition.[59] Because using the design strategy described herein, new ELPs were generated outside of the conventional VPGXG (SEQ ID NO: 29) motif, permitting greater freedom and power to create novel and functional ELPs.

Example 4: Humoral Immunogenicity of iTEPs

Immunization of iTEPs and collection of immune sera. C57BL/6 mice were immunized twice at their right hocks with iTEPs at a dose of 100 µg/mouse. The two immunizations had a 2 week interval. At 1 week after the second immunization, 100 µL blood was collected from each immunized mouse. The blood samples were allowed to sit for 30 minutes to one hour at room temperature to clot. Sera were

TABLE 3

The sequences, MW, transition temperatures of iTEPs

| iTEP | Construct sequence | MW | Tt (heating) | Tt (cooling) | Relative Hydrophobicity |
|---|---|---|---|---|---|
| iTEP$_A$ | G(GVLPGVG)$_{28}$GG<br>SEQ ID NO: 23 | 16.6 kDa | 33.30 ± 0.09° C. | 29.70 ± 0.05° C. | High |
| iTEP$_B$ | G(GAGVPG)$_{70}$GG<br>SEQ ID NO: 24 | 32.1 kDa | 65.45* ± 0.15° C. | 60.85* ± 0.44° C. | Low |
| iTEP$_C$ | G(VPGFGAGAG)$_{21}$GG<br>SEQ ID NO: 25 | 15.3 kDa | 35.70 ± 0.58° C. | 34.00 ± 0.58° C. | High |
| iTEP$_D$ | G(VPGLGAGAG)$_{96}$GG<br>SEQ ID NO: 26 | 65.6 kDa | 38.60 ± 1.20° C. | 35.20 ± 0.57° C. | High |
| iTEP$_B$-iTEP$_A$-pOVA | G(GAGVPG)$_{70}$G(GVLPGVG)$_{28}$G(ESIINFEKLT)$_2$GG<br>SEQ ID NO: 56 | 49.7 kDa | 75.40 ± 0.14° C. | 73.70 ± 0.23° C. | (N/A) |

The Tt data presented in the table were obtained from experiments with sample's concentrations at 25 µM in H$_2$O except for iTEP$_B$.
*The Tts of iTEP$_B$ was measured in the presence of 2.5 M NaCl.

An interesting observation was made when Tts of iTEP$_C$ and iTEP$_D$ (FIGS. 3C and D) were compared at two different concentrations, 5 and 25 µM. At 25 PAM, iTEP$_C$ had a lower (heating) Tt than iTEP$_D$, 35.7° C. versus 38.6° C.; at 5 µM, iTEP$_C$, however, displayed a higher Tt than iTEP$_D$. 50.5° C. versus 42.3° C. These two iTEPs are similar to each other with two differences: (1) the fourth residue of their repeat units, Phe for iTEP$_C$ versus Leu for iTEP$_D$ (FIG. 1), and (2) the number of repeat units, 21 for iTEP$_C$ versus 96 for iTEP$_D$ (Table 1). While the first difference predisposes iTEP$_C$ to a lower Tt than iTEP$_D$, the second difference predisposes iTEP$_C$ to a higher Tt than iTEP$_D$.[48, 49] At 25 µM, the impact of the fourth residue difference apparently prevailed over the impact of the repeat number difference; at 5M, vice versa. Thus, these data show that concentration changes of iTEPs can alter the impact of the two differentiating factors but at different scales.

The iTEPs described herein possess the characteristic phase transition of ELPs without having their typical VPGXG (SEQ ID NO: 29) motif. On the one hand, it is reasonable because the iTEP design was not limited to the motif. Generating an immune tolerant ELP for both humans and mice was more important than generating an ELP fitting in with the motif, although these two needs are not necessarily mutually exclusive. On the other hand, this result may collected from the blood samples after the samples were spun for 10 min at 14,000 rpm at 4° C. The sera were kept at −80° C. before an analysis of the titers of iTEP-specific IgG.

Determination of IgG titers by ELISA. 96-well ELISA plates were coated overnight at 4° C. with 100 µl/well of capture antigens (20 µg/ml corresponding iTEPs, ovalbumin (OVA) or MSA). Plates were washed with PBS-0.02% Tween 20 (PBST) buffer and blocked with 200 µL/well of PBST buffer containing 1% BSA for 1 hour at room temperature. Mouse sera were serially diluted in the PBST-1% BSA buffer and added at 100 µL/well into the 96-well plate. The plates were incubated at 4° C. overnight. After thoroughly washing with PBST, 100 µL/well of 1 µg/mL detection antibody (horseradish peroxidase-conjugated anti-mouse IgG) was added, and plates were incubated for 1 hour at room temperature under continuous shaking. After washing with PBST, 100 µl/well of tetramethylbenzidine (TMB) substrate solution was added for 15-30 minutes with continual shaking. The reaction was stopped with 100 µL/well of 1 M H$_2$SO$_4$. Plates were read at OD 450 nm (minus 570 nm for wavelength correction).

The end point titer of a serum IgG was defined as the reciprocal of the higher serum dilution which OD value from the ELISA assay is higher than a statistically valid cutoff.

The titer results were expressed as IgG titers (Log 10) for each sample. The cutoff was established for individual ELISA assays that utilize a given capture antigen, so the cutoffs can be different for distinct capture antigens. Specifically, the cutoff was obtained by using PBS-(negative control) immunized serum to perform ELISA in the corresponding antigen-coated wells. The value of the cutoff was calculated using the following equation:[31]

$$\text{Cutoff} = \bar{X} + SD\sqrt{1+(1/n)}$$

where $\bar{X}$ is the mean absorbance readings of independent PBS control sera, SD is the standard deviation of the readings, n is the number of independent PBS controls (mouse samples), t is the $(1-\alpha)$th percentile of the one-tailed t-distribution with $v=n-1$ degrees of freedom.

Figure 4A:
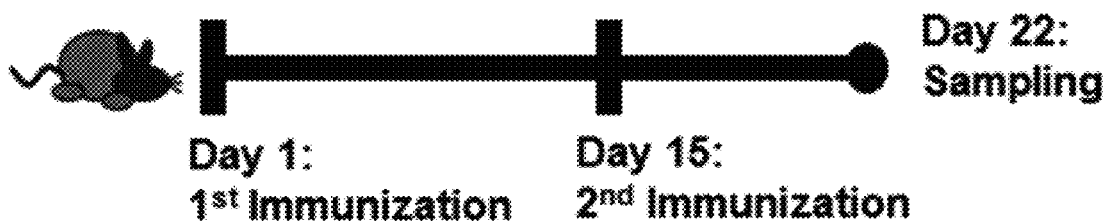
FIGS. 4A-E demonstrate the humoral immunogenicity of iTEPs.
Figure 4B:
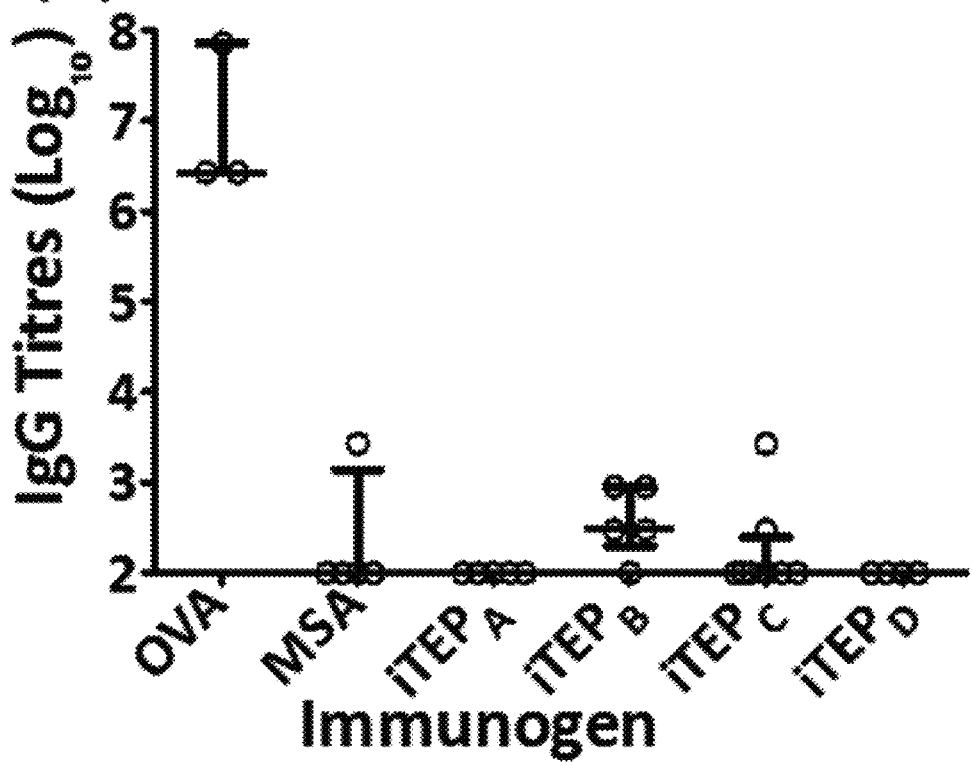
Figure 4C:
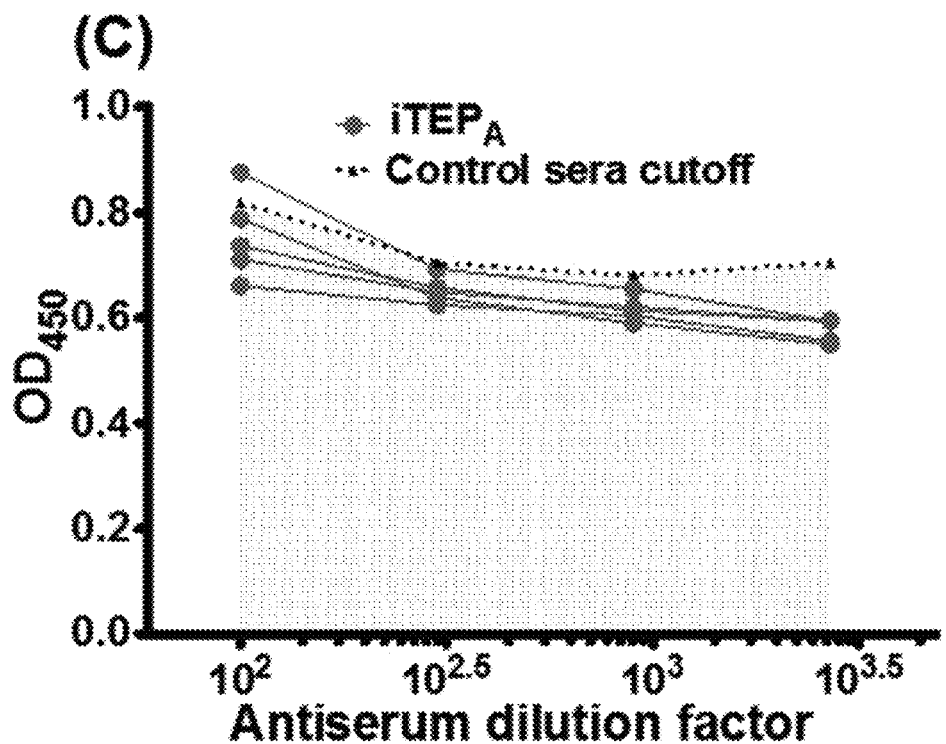
Figure 4D:
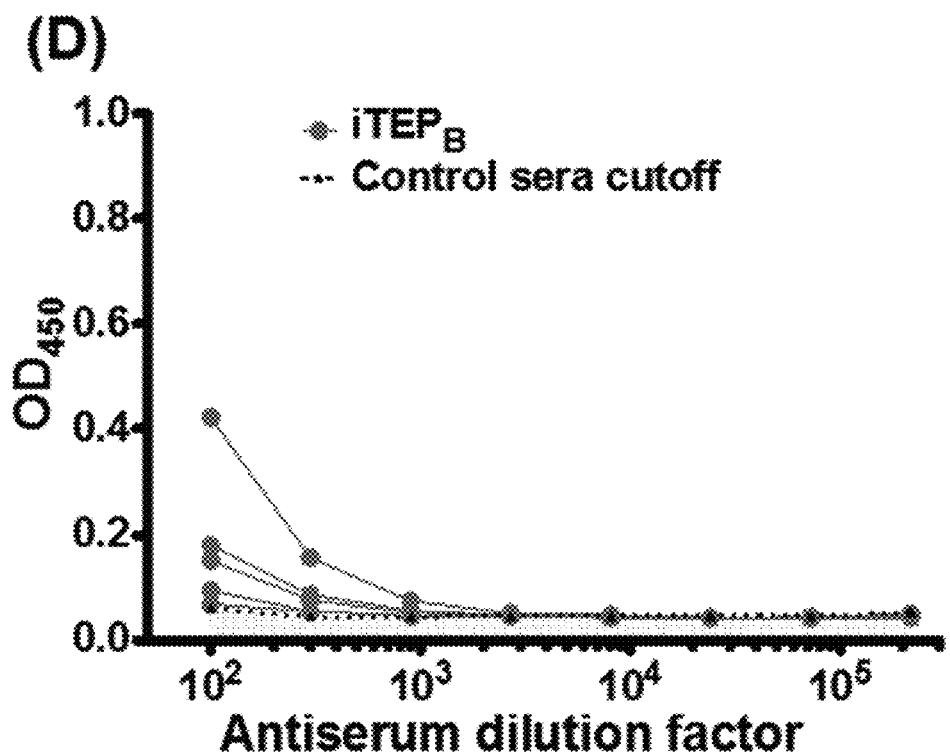
Figure 4E:
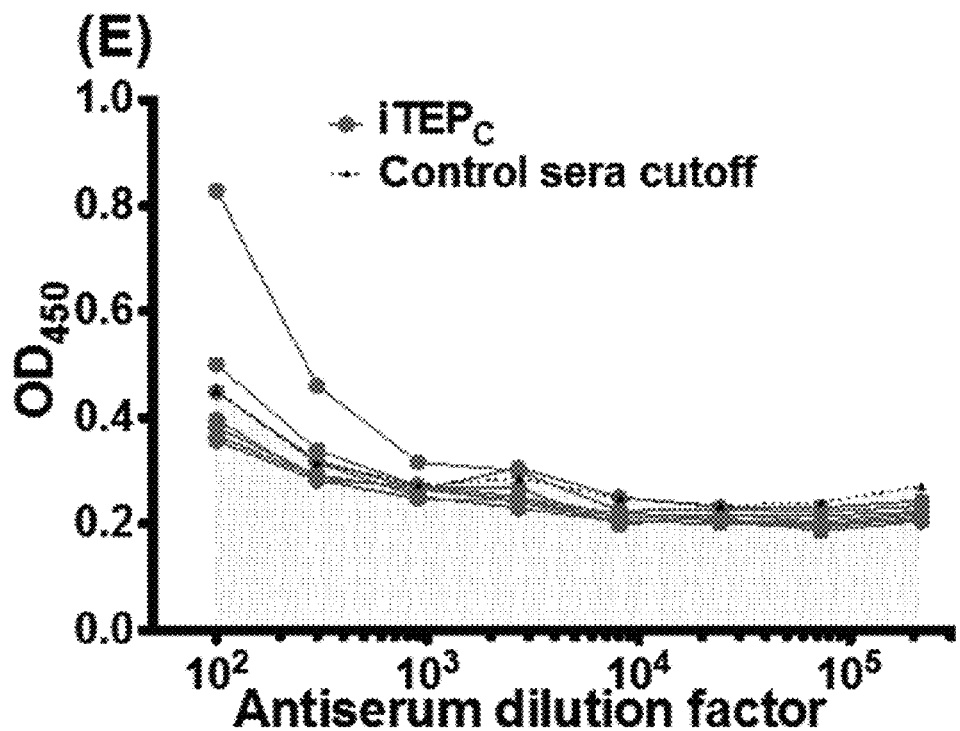
Figure 4F:
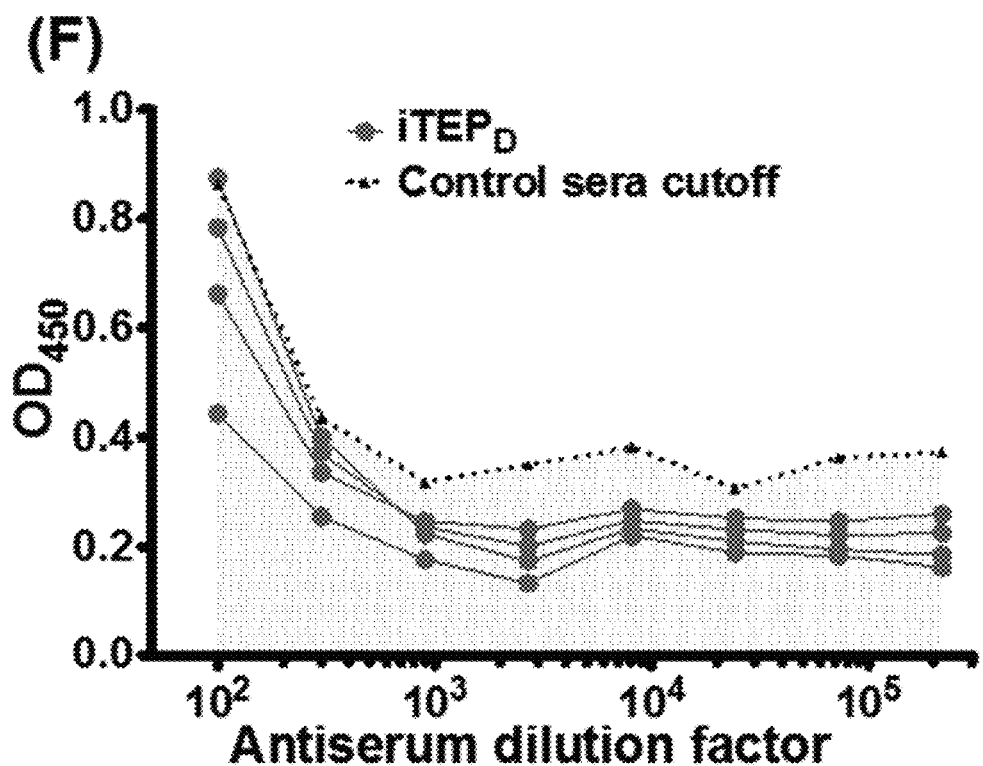

Results. Mice were immunized with the four iTEPs, a positive control (OVA), and a negative control (mouse serum albumin, MSA) (FIG. 4A). As expected, the OVA-immunized mice displayed a strong humoral response to OVA with a median antibody titer of $2.6 \times 10^7$; MSA-treated mice showed a very low humoral response, evidenced by a median antibody titer of $6.2 \times 10^2$ (FIG. 4B). Among the four iTEPs, the plasma of $iTEP_A$-, $iTEP_C$-, and $iTEP_D$-treated mice were negative for any iTEP-specific antibody after the plasmas were diluted by 100 times and up (FIG. 4C, 4E, 4F), so their median titers should be less than or equal to 100 (FIG. 4B). The plasma of $iTEP_B$-treated mice had a median antibody titer of $4.5 \times 10^2$ (FIG. 4B, 4D). Because all of the iTEPs' titers are indifferent to that of MSA, but significantly different to the titer of OVA, it was concluded that all iTEPs are humorally immune-tolerated by mice as MSA.

Figure 7A:
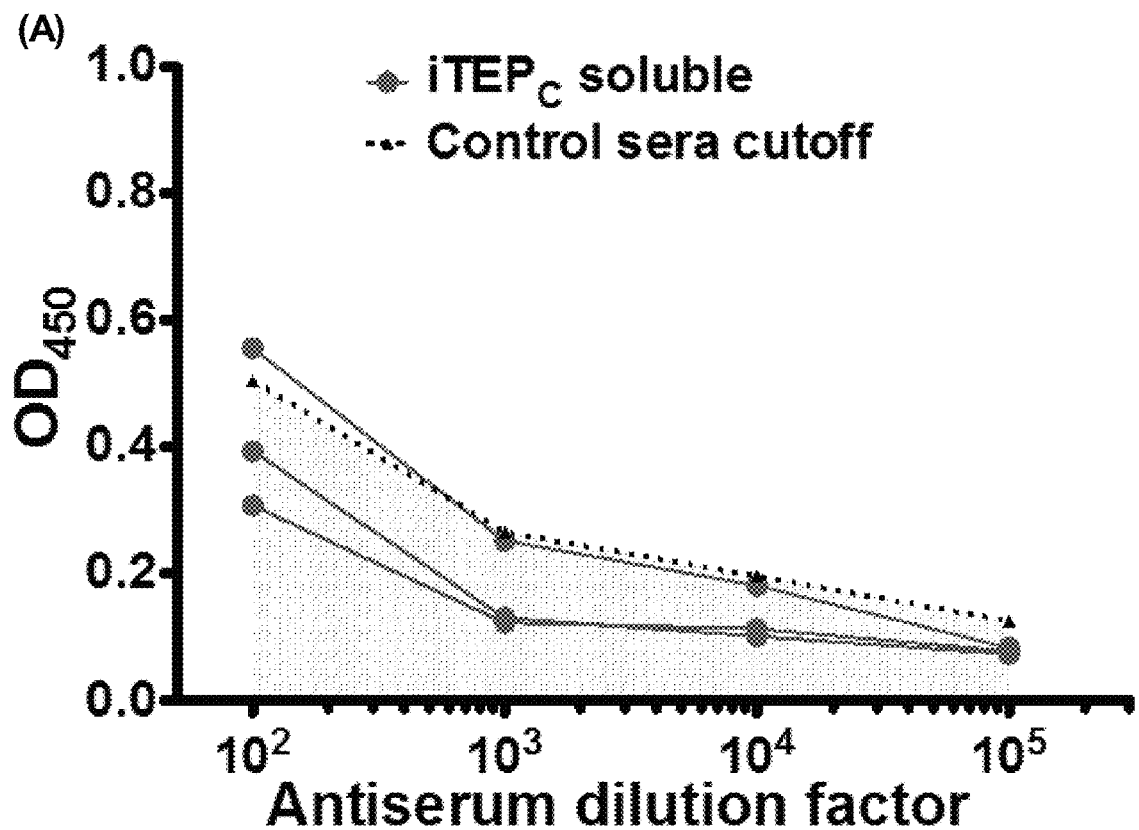
FIGS. 7A-B show the absorbance (OD450) of insoluble (A) and soluble (B) $iTEP_C$ immunized mouse sera after they were diluted and assayed by ELISA. Each data point corresponds to the mean of absorbance values of three repetitive measurements per mouse per serum dilution. The data of each mouse were linked together with a line. The cut-off ranges for positive absorbance values were shown as a blue shade.
Figure 7B:
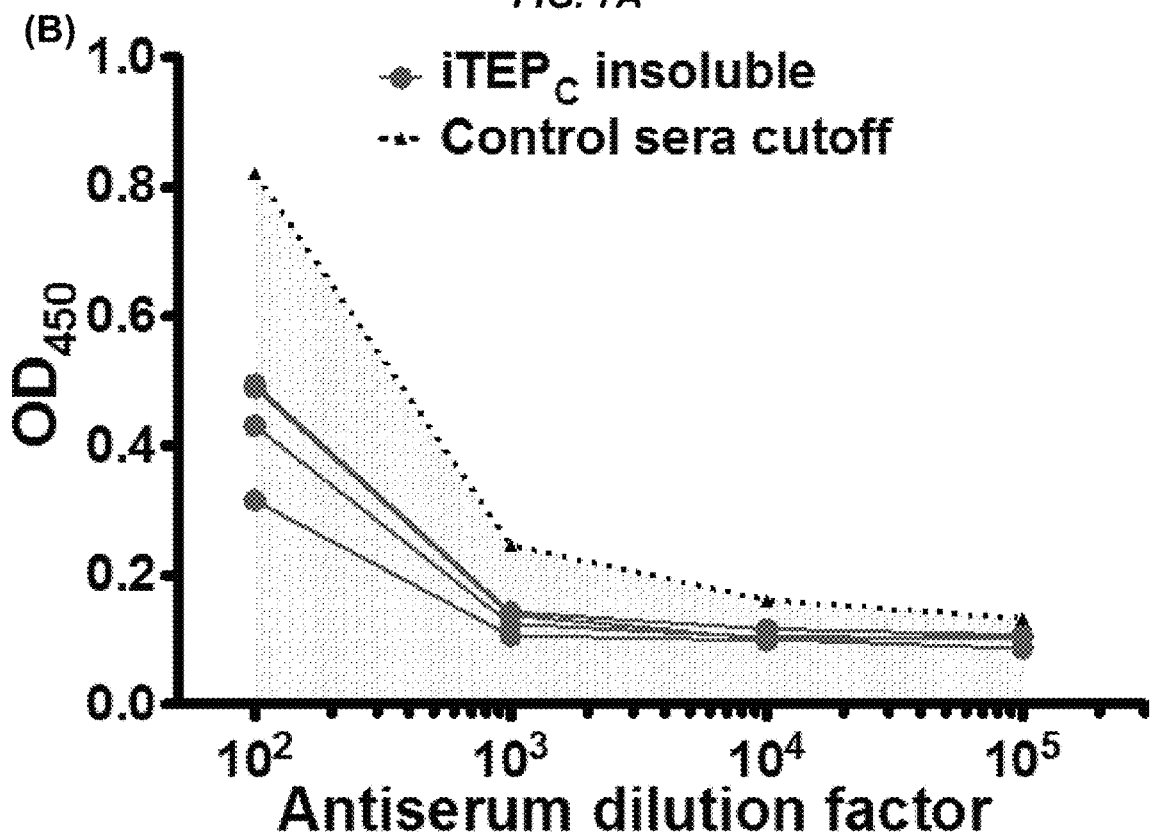

It has been reported that the aggregation of peptide and proteins could drastically increase their humoral immunogenicity.[50, 51] The aggregation statuses of the iTEPs, however, did not appear to affect their immunogenicity. First, soluble and aggregate forms of $iTEP_C$ did not show different immunogenicity (FIG. 7). Second, all tested iTEPs are non-immunogenic despite the fact that $iTEP_A$, $iTEP_C$, and $iTEP_D$ were injected as aggregates, while $iTEP_B$ was injected as a soluble molecule for the immunization.

Example 5: NPs Self-Assembled from iTEP-CTL Vaccine Fusions

Characterization of the size of $iTEP_B$-pOVA and $iTEP_B$-$iTEP_A$-pOVA fusions. The particle size distribution of the iTEP fusions was determined by dynamic light scattering (DLS) using a Zetasizer Nano-ZS instrument (Malvern Instruments, Malvern, UK) as previously described.[29] The fusions were prepared at 5 µM and 25 µM in PBS and equilibrated at 37° C. for the measurement. The reported results represented the average particle size by number.

Negative-stain, transmission electron microscopy of the $iTEP_B$-$iTEP_A$-pOVA fusion. Small, 3.5 µL aliquots of assembled particles (50 µM) were applied to a continuous carbon support film (Ted Pella, Redding, CA). The sample was briefly washed with distilled water and then stained with 1% aqueous uranyl acetate. Micrographs were recorded on a DE-20 camera (Direct Electron, LP, San Diego, CA) equipped with a 5120×3840 Direct Detection Device (DDD®) sensor in a JEOL 2200FS microscope at a nominal magnification of 30,000 (1.72 Å per pixel) at an acceleration voltage of 200 kcV.

Figure 5A:
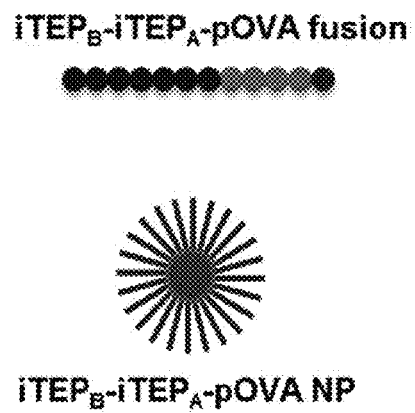
FIGS. 5A-E show nanoparticles self-assembled from iTEP-CTL vaccine fusions.
Figure 5B:
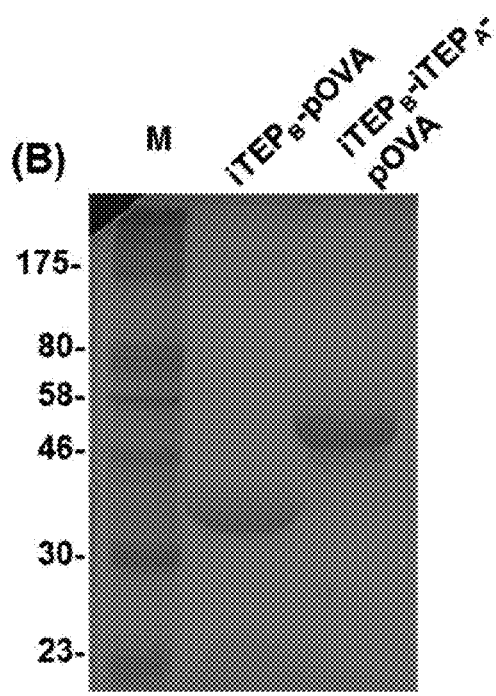
Figure 5C:
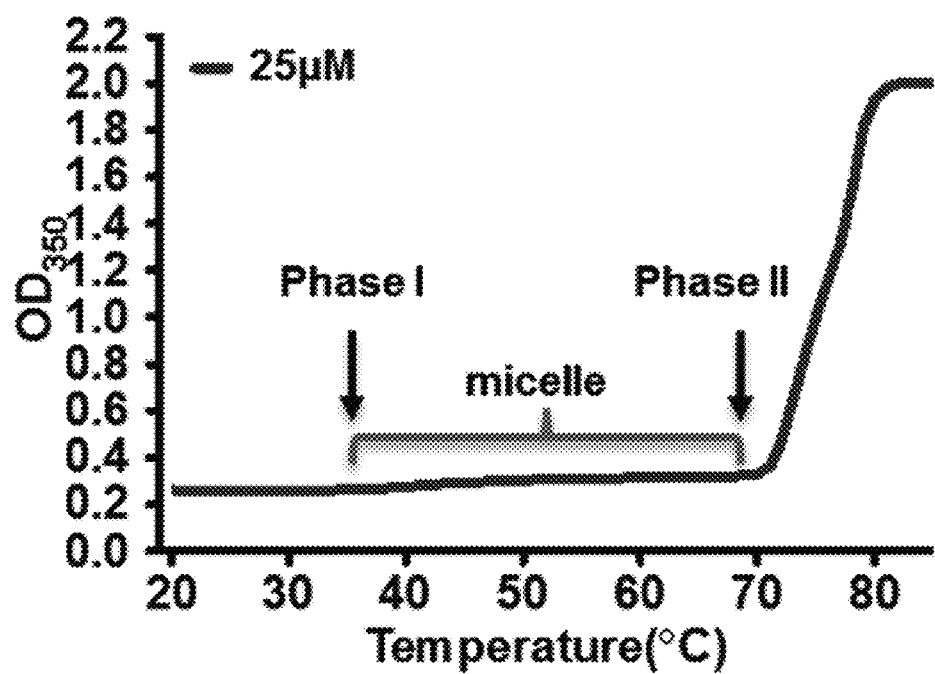
Figure 5D:
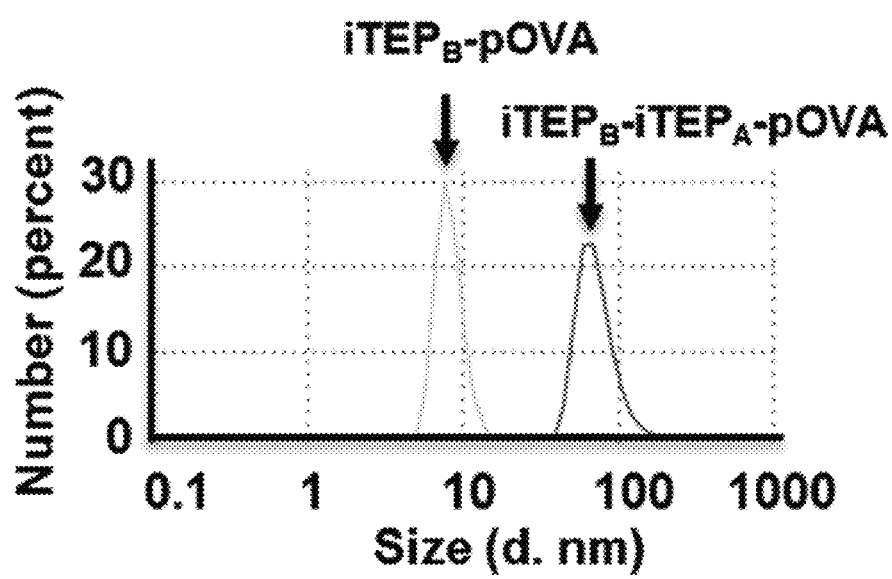
Figure 5E:
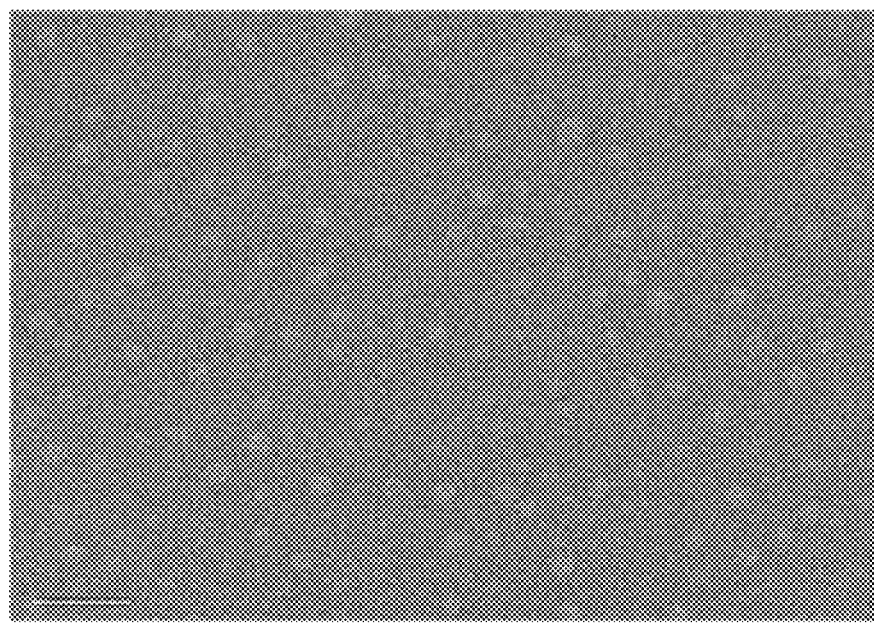

Results. The hydrophobic $iTEP_A$, hydrophilic $iTEP_B$, and pOVA were fused together to form an amphiphilic iTEP copolymer or fusion: $iTEP_B$-$iTEP_A$-pOVA (SEQ ID NO: 56) (FIG. 5A). This pair of iTEPs was used to construct the amphiphile because both iTEPs gave good yields, and so it was expected that the amphiphile would also have a good yield. Indeed, about 200 mg of amphiphilic fusion from one liter of culture was purified (FIG. 5B). The solution has a sharp increase of the turbidity at 70° C. indicating the formation of aggregates at that temperature. Before that, there is a slow, mild increase of turbidity suggesting the formation of micelles[8]. The fusion displayed a micelle-like NP structure, evidenced by its two-step phase transition profile (FIG. 5C).[8] The NP structure of the fusion was also confirmed by DLS (FIG. 5D), as well as electron microscopy (FIG. 5E). According to DLS data, the NPs have a mean diameter of $81.2 \pm 14.2$ nm at 5 µM and $71.9 \pm 20.8$ nm at 25 µM (FIG. 5D). Contrariwise, $iTEP_B$-pOVA, a fusion of the hydrophilic $iTEP_B$ and the vaccine, is soluble and does not form particles. The size of this fusion is less than 10 nm as measured by DLS (FIG. 5D).

Example 6: Immune Responses Induced by the iTEP-pOVA NP

Presentation of the CTL epitope, SIINFEKL, by DCs. Cells of a murine DC line (DC2.4, a gift from K. Rock)[32] were plated at $2.5 \times 10^5/500$ µL/well in 24-well plates. 500 µL of OVA, SIINFEKL peptide (SEQ ID NO: 22), or $iTEP_B$-$iTEP_A$-pOVA NP (SEQ ID NO: 56) (iTEP-pOVA NP hereafter) were dissolved in cell culture media and added to the wells containing DCs. The cells were further cultured for 16 hrs. at 37° C. with 5% $CO_2$ before they were collected and washed with PBS. The MHC class I complex, H-2kb/SIINFEKL presented on DC surface was stained with a PE-tagged monoclonal antibody 25-D1.16 (Biolegend, 1:100 dilution) and quantified with flow cytometry ($5 \times 10^4$ events collected per sample). The data are presented as MFI normalized to the MFI of untreated DC2.4 cells.

B3Z CD8+ T cell hybridoma activation assay. B3Z cells (a gift from N. Shastri) are a CD8+ T-cell hybridoma engineered to secrete β-galactosidase when their T-cell receptors are engaged with an SIINFEKL:H2K$^b$ complex.[33] To do this assay, $1 \times 10^5$ DC2.4 cells/well were set in 96-well plates. OVA, SIINFEKL peptide (SEQ ID NO: 22), and iTEP-pOVA NP (SEQ ID NO: 56) at indicated concentrations were loaded into the cell culture for 16 hours and then washed away. $1 \times 10^5$ B3Z cells/well were added to the DC2.4 cell culture and co-cultured with DC2.4 cells for 24 hours. The cells were washed with PBS before 100 µL of lysis buffer (PBS with 100 mM 2-mercaptoethanol, 9 mM $MgCl_2$, 0.125% NP-40) together with 0.15 mM chlorophenol red β-galactoside were added into the wells. After the plates were incubated at 37° C. for 4 hours, the reaction was stopped with 50 µL/well of 15 mM EDTA and 300 mM glycine. The OD at 570 nm was measured and the OD at 630 nm was used as reference. The OD was used as an indicator as activation status of B3Z cells.

in vivo CTL response by ELISPOT IFN-γ assay. C57BL/6 mice were immunized subcutaneously with each immunogen (2 nmol SIINFEKL equivalents per mouse) together with incomplete Freunds Adjuvants (IFA; Sigma, USA) at their left flanks. The immunization was repeated at their right flanks 1 week later. At 10 days after the second immunization, mice were sacrificed, and the spleens were harvested. The spleens of the sacrificed mice were teased into single-cell suspensions and filtered through nylon mesh (40 m). Red blood cells were lysed by Ammonium-Chloride-Potassium (ACK) lysing buffer. The washed and resuspended single cells were counted using Contess™ Automated Cell Counter (Invitrogen, USA). Splenocytes ($8 \times 10^6$/ mL) were incubated in RPMI-1640 medium supplemented with 10% heat inactivated fetal calf serum, 2 mM glutamine, 100 units/mL penicillin and 100 μg/mL streptomycin (Invitrogen, USA), in a 14 mL polypropylene tissue culture tube for 48 hours, with or without SIINFEKL peptide (SEQ ID NO: 22) (2.5 μg/mL). The cells were then washed and recounted. $2\times10^5$ live cells in 100 μL medium were then loaded into wells of 96-well Filtration plates (Millipore, USA) coated with 5 mg/mL of capture anti-mouse IFN-γ mAb (Clone: R4-6A2, Biolegend, USA). Triplicates were set up for each condition. Cells were discarded after 24 hours of culture and the wells were incubated with 2 mg/mL of detectionbiotinylated, anti-mouse IFN-γ mAb overnight (Clone: XMG1.2-Biotin, Biolegend, USA). After the unbound antibodies were washed away from the wells, the bound antibodies were detected using horseradish peroxidase (HRP Avidin, Biolegend, USA) together with 3-amino-9-ethyl-carbazole (AEC) substrate (Sigma, USA). The membranes on the bottom of the wells were peeled off, and color spots on the membrane were scanned. The spots were automatically counted using ImageJ software.

Figure 6A:
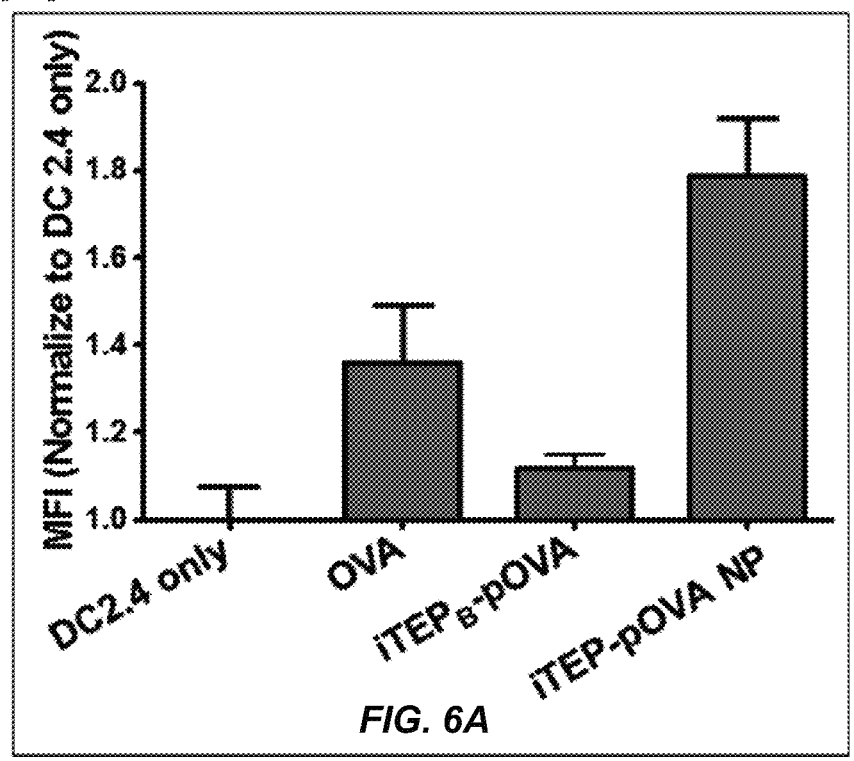
FIGS. 6A-C show immune responses induced by the iTEP-pOVA nanoparticle (NP).

Results. First, experiments were carried out to test whether the iTEP-pOVA NP promotes processing and presentation of SIINFEKL (SEQ ID NO: 22) by DCs. The NP, soluble iTEP$_B$-pOVA fusion (SEQ ID NO: 57), as well as OVA was incubated with DCs, respectively. The surface presentation of SIINFEKL (SEQ ID NO: 22) by DCs was detected by an antibody that can recognize the SIINFEKL/H-2K$^b$ complex. Although all of the above incubations led to presentations of the epitope on the DCs' surface, DCs incubated with the NP presented significantly more SIINFEKL (SEQ ID NO: 22) epitopes than DCs with OVA or iTEP$_B$-pOVA (SEQ ID NO: 57) (FIG. 6A). Free SIINFEKL peptide (SEQ ID NO: 22) resulted in much stronger SIINFEKL (SEQ ID NO: 22) presentation by DCs than the NP, OVA, or iTEP$_B$-pOVA fusion (SEQ ID NO: 57) (data not shown). This result was likely caused by a direct exchange between SIINFEKL (SEQ ID NO: 22) with those epitopes that were originally present on the DCs' surface. Thus, the presentation of free SIINFEKL peptide (SEQ ID NO: 22) by DCs does not need an antigen processing by the cells. Consequently, the result of free SIINFEKL peptide (SEQ ID NO: 22) is not comparable with the results of other forms SIINFEKL-containing antigens which require antigen processing before SIINFEKL (SEQ ID NO: 22) is presented.

Figure 6B:
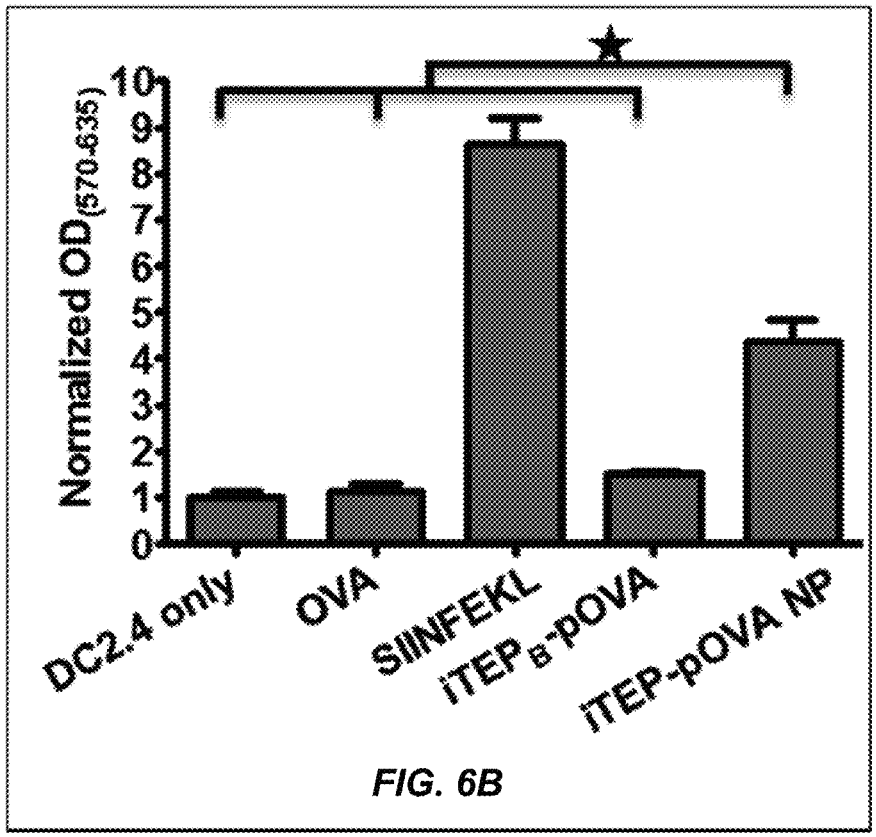

The next set of experiments examined whether the improved presentation of SIINFEKL (SEQ ID NO: 22) by iTEP-pOVA NP-treated DCs can lead to a more efficient activation of SIINFEKL-restricted CD8 cells. B3Z cells were used as target cells to perform a CD8+ T cell activation assay. The B3Z cells that were co-cultured with the NP-pretreated DC2.4 cells were several fold more active than the B3Z cells co-cultured with the DC2.4 cells pre-treated with other antigens. Specifically, NP/DC-treated B3Z cells were 4.38, 3.81, or 2.9 fold more active than DC-treated B3Z cells, OVA/DC-treated B3Z cells, and iTEP$_B$-pOVA/DC-treated B3Z cells, respectively (FIG. 6B). As a positive control, B3Z cells co-cultured with DC2.4 cells pre-pulsed with free SIINFEKL peptide (SEQ ID NO: 22) showed the highest activity among all treatments (FIG. 6B). This result is consistent with the observation that DCs are much more efficiently presented SIINFEKL (SEQ ID NO: 22) when the peptide was incubated with DCs as a free form.

Figure 6C:
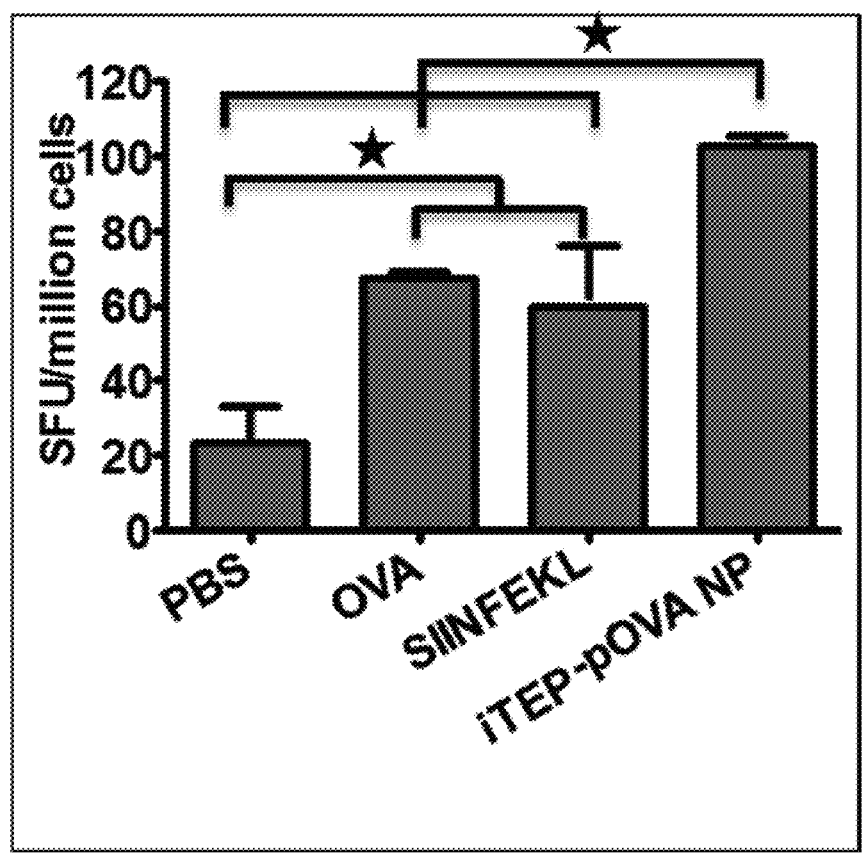

Next, experiments were performed to examine whether the enhanced vaccine presentation and CTL activation caused by the iTEP-pOVA NP (SEQ ID NO: 56) can translate into elevated CTL responses in vivo. To this end, C57BL/6J mice were subcutaneously immunized twice with PBS, OVA, SIINFEKL (SEQ ID NO: 22) peptide, or the NP and splenocytes were collected from these mice. Next, SIINFEKL-restricted, activated splenocytes were quantified using an INF-γ-based ELISPOT assay; those splenocytes released INF-7 should be SIINFEKL-restricted CTLs. Both OVA and the free peptide immunization lead to a boost of the number of CTLs compared to the PBS control. The NP-immunized mice, however, had a much higher number of the CTLs (averagely 105 spots per million seeded splenocytes) than both OVA- and SIINFEKL peptide-immunized mice (averaging 61 and 60 spots per million seeded splenocytes, respectively) (FIG. 6C). The activation of the cells was characterized by using an INF-γ-based ELISPOT assay. It is interesting that the free peptide did not induce the strongest SIINFEKL-specific CTL response in vivo even though it had the highest response in vitro, suggesting that the CTL peptide vaccines need a supportive carrier. The deficiency of the free peptide vaccine might be due to a fast clearance of the peptide after its immunization; thus the vaccine had very limited access to dendritic cells and other antigen presenting cells.

As described herein, the criteria of designing non-immunogenic polypeptides is affirmed. The iTEPs described herein and tested were found to be non-immunogenic regardless of their aggregation statues or their nature as repetitive sequences, two auxiliary factors that were reported to possibly boost immunogenicity of polypeptides and proteins.[51, 57, 58] This result is consistent with the notion that iTEPs likely do not contain BCR or TCR epitopes, or both. If a polypeptide doesn't consist of BCR or TCR epitopes, it should not induce humoral responses even when those auxiliary factors favor such. More significantly, because two different strategies were utilized to diminish potential immunogenicity of iTEPs' junction sequences, these results regarding the immunogenicity of iTEPs also suggest that both strategies are valid and can be useful to generate other immune tolerant polypeptides.

ELPs have been widely tested in biomedical applications, and they can assemble into nanostructures that can be good carriers for vaccines.[26, 60-67] ELPs, however, have not been used as CTL vaccine carriers. These results show that an iTEP NP in fact boosted the potency of the vaccines it delivered, suggesting a new role for utilizing ELPs in vaccines and immunotherapy. This reasoning may be further substantiated if the immunogenicity of ELPs could be established depending on their potential applications. For example, if both immunogenic and nonimmunogenic ELPs and their corresponding carriers were generated, these pairs of otherwise very similar carriers could be used to elucidate how the immunogenicity of carriers affect the potency of their vaccines or other immunotherapeutics payloads, which has not been clarified. In summary, an ability to precisely control the immunogenicity and functionality of ELPs is important to using the materials in delivering immunotherapeutics, which is still at its infancy.[68]

In conclusion, non-canonical ELPs (iTEPs) that possess the inverse phase transition property and are immune-tolerated by mice have been successfully created. The success validates the mechanistic understanding with respect to the phase transition and immunogenicity of ELPs. These iTEPs can be used for many reported biomedical applications of ELPs and possess the advantage of being non-immunogenic. Importantly, these results also demonstrate, for the first time, that ELPs can be used as CTL vaccine carriers. Most significantly, using the novel polypeptide development practice as described herein, which places an equal design emphasis on functionality and immunogenicity, can help to avoid squandering efforts on developing functional ELPs that turn out to be immunogenic.

Example 7: Synthesis and Characterization of Sali-ABA and Sali-ABA-MPBH Conjugates Materials. All chemicals, unless otherwise described, were purchased from Thermo Fisher Scientific Inc. (MA, USA) at biological grade. Organic solvents including acetonitrile (ACN), dichloromethane (DCM), dimethylformamide (DMF), isopropanol, and methanol were purchased from Thermo Fisher Scientific Inc. (MA, USA) at HPLC grade. The LB and TB media were prepared in our lab using the standard formula. All the cell culture plates were purchased from Corning Inc. (NY, USA). The cell culture media and supplements including RPMI-1640 (with 2 mM L-Glutamine), and fetal bovine serum (FBS) were purchased from Life Technologies, Inc. (CA, USA).

4T1, a highly metastatic murine cell line derived from a spontaneous syngeneic breast cancer of Balb/c mice were purchased from American Type Culture Collection (MD, USA). 4T1-luc, a 4T1 cell line that stably expressed firefly luciferase was generated in-house using a published method (Tao et al., BMC Cancer, 2008; 8(1):228). Both 4T1 and 4T1-luc cells were maintained in monolayer cultures in an RPMI 1640 medium supplemented with 10% FBS. Cells were maintained at 37° C. humidified atmosphere with 5% $CO_2$.

Female Balb/c mice that were 24-28 days old (18-19 g) were purchased from Charles River Laboratories International, Inc. (USA). All the animal experiment protocols were approved by the Institutional Animal Care and Use Committee at the University of Utah.

Synthesis of Sali-ABA. Salinomycin (Sali; 9.50 g, 12.67 mmol), (4-(1, 3-dioxolan-2-yl)phenyl)methanamine (the chemical name of ABA before conjugation to Sali; (4-(1, 3-dioxolan-2-yl)phenyl)methanamine is the chemical of ABA after conjugation to Sali) (3.40 g, 18.97 mmol), and 1,3-diisopropylcarbodiimide (2.39 g, 18.97 mmol) were dissolved together in 150 mL dry DCM. To this stirred mixture, 1-hydroxybenzotriazole (2.05 g, 15.17 mmol) solubilized in 10 mL of dry DMF was added at 0° C. The resulting mixture was further stirred for 24 h before allowed to warm to room temperature. Then, the mixture was stirred for additional 24 h. The mixture was then quenched with 200 mL brine, and reaction products and unused reactant were extracted three times with 100 mL DCM. The combined DCM solution was dried over anhydrous $Na_2SO_4$, concentrated under vacuum, and the residue was purified by flash chromatography on silica gel (200-300 mesh). The purified conjugation product was a white solid.

To de-protect the aldehyde group of the conjugation product (Sali-ABA), the product was dissolved in 22 mL THF to which 2 N HCl (22.72 mL) was added. The mixture was stirred at room temperature for 6 h. Then the reaction was quenched with aqueous $NaHCO_3$ (200 mL) and extracted with DCM (100 mL, two times). The combined DCM solution was dried over anhydrous $Na_2SO_4$, concentrated under vacuum. The residue was purified by flash chromatography on silica gel (200-300 mesh). The purified, de-protected Sali-ABA was a white solid (6.68 g, 61% yield). The presence of Sali-ABA was confirmed by the $^1H$ NMR. The $^1H$ NMR was performed in $CDCl_3$ and measured on a Bruker 400 MHz. The chemical shift was analyzed and integrated. $^1H$ NMR ($CDCl_3$, 400 MHz) δ 0.75-0.81 (m, 4H), 0.81-0.86 (m, 5H), 0.86-0.91 (m, 6H), 0.91-0.99 (m, 8H), 1.14 (s, 3H), 1.19-1.27 (m, 8H), 1.46-1.55 (m, 4H), 1.80-1.88 (m, 5H), 2.02-2.06 (m, 1H), 2.18-2.45 (m, 2H), 2.62-2.73 (m, 1H), 2.74-3.13 (m, 8H), 3.37-3.47 (m, 1H), 3.53 (s, 1H), 3.60-3.84 (m, 6H), 3.85-3.95 (m, 1H), 4.03-4.20 (m, 3H), 4.43-4.59 (m, 1H), 4.63-4.78 (m, 1H), 6.23-6.29 (m, 1H), 6.63-6.77 (m, 1H), 7.14 (d, J=4.0 Hz, 1H), 7.52 (d, J=8.0 Hz, 2H), 7.81 (d, J=8.0 Hz, 2H), 9.95 (s, 1H). For ESI-MS analysis, purified reaction product was dissolved in a 50% acetonitrile aqueous solution containing 0.1% TFA, loaded onto a sinapinic acid matrix, and examined using a QTOF 2 Mass Spectrometer (Waters, MA, USA) equipped with a nitrogen laser (337 nm).

Synthesis of Sali-ABA-MPBH. Under the atmosphere of argon, a mixture of Sali-ABA (1.70 g, 1.96 mmol), MPBH-HCl (0.91 g, 2.97 mmol), and 4 Å molecular sieve (1 g) in dry isopropanol/methanol (20 mL/20 mL) was prepared and stirred at 40° C. overnight. After the mixture was filtered and the solvent was evaporated, the residue was purified by flash chromatography on silica gel (200-300 mesh). The purified conjugation product was a light yellow solid. The yield was 41%. The purity of the collected conjugation product was confirmed by HPLC. The presence of Sali-ABA-MPBH conjugates was confirmed by the $^1H$ NMR. The $^1H$ NMR was performed in $CDCl_3$ and measured on a Bruker 400 MHz. The chemical shift was analyzed and integrated. $^1H$ NMR ($CDCl_3$, 400 MHz) δ 0.76-0.82 (m, 4H), 0.82-0.87 (m, 6H), 0.87-0.93 (m, 8H), 0.93-1.00 (m, 7H), 1.14 (s, 3H), 1.19-1.27 (m, 11H), 2.01-2.07 (m, 5H), 2.17-2.36 (m, 3H), 2.63-2.77 (m, 6H), 2.77-3.13 (m, 8H), 3.37-3.53 (m, 2H), 3.53-3.63 (m, 1H), 3.64-3.74 (m, 2H), 3.75-3.84 (m, 2H), 3.86-3.97 (m, 1H), 4.05-4.19 (m, 3H), 4.22-4.32 (m, 1H), 4.36-4.51 (m, 1H), 4.56-4.73 (m, 1H), 6.20-6.32 (m, 1H), 6.45-6.60 (m, 1H), 6.81-6.90 (m, 2H), 7.05-7.13 (m, 1H), 7.20-7.28 (m, 2H), 7.30-7.41 (m, 4H), 7.45-7.54 (m, 2H), 7.69 (s, 1H), 9.38-9.62 (m, 1H). The reaction product was analyzed by ESI-MS as described above.

The formation of the hydrazone bond between Sali-ABA and MPBH-HCl is slow at room temperature. A trace of the product can be detected after 48 h of reaction at this temperature. To address this issue, the reaction temperature was raised to 40° C. and molecular sieves were added to promote this reaction.

Expression and purification of iTEP. The gene that codes the iTEP was generated as previously described. The production and purification of the iTEP were same as previously described (Zhao, et al; Mol. Pharm, 2014; 11(8):2703-12).

Synthesis of iTEP-MPBH-ABA-Sali. iTEP-ABA-Sali was synthesized as previously described (Zhao, et al; Mol. Pharm, 2014; 11(8):2703-12). TCEP-reduced iTEP was reacted with Sali-ABA-MPBH in phosphate buffer (pH=7.00, 1 M NaPO4, 1 mM EDTA). After purification, the purity of iTEP-MPBH-ABA-Sali conjugate was confirmed by HPLC. After the purification, iTEP-MPBH-ABA-Sali conjugate was lyophilized and stored at −20° C. The conjugation efficiency of Sali-ABA-MPBH to iTEP was determined by the Ellman's reagent method. To this end, 5,5'-Dithiobis-(2-Nitrobenzoic Acid) (DTNB; Ellman's Reagent, Thermo Fisher Scientific Inc., Massachusetts, USA) was used to quantify the conjugation ratio by measuring the number of thiol groups. The quantification was done following the manufacturer's protocol, and the concentration of thiol groups was determined by fitting data to a standard curve of a series of cysteine solutions at different concentrations. The absorption was measured at 410 nm.

Figure 8A:
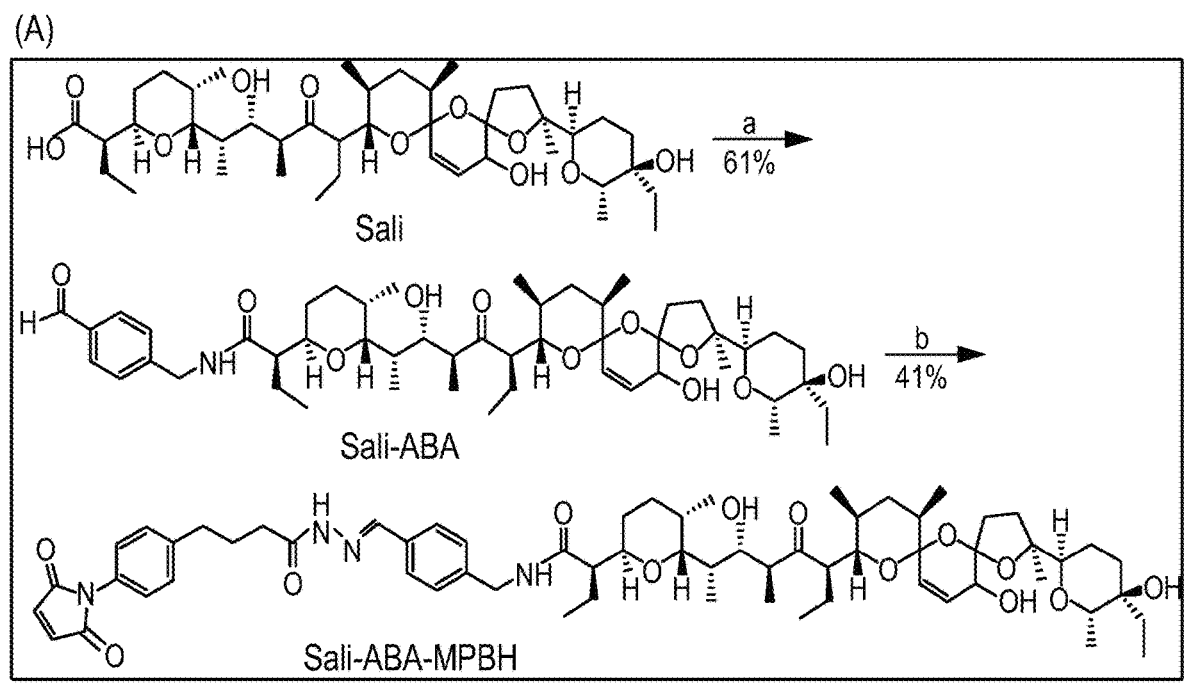

Results. In order to link Sali to the iTEPs through a cleavable chemical bond, modified Sali was first modified by attaching a small molecule, ABA, to it; the resulting Sali-ABA was then linked to the iTEPs through a bifunctional linker, MPBH. The linkage between Sali-ABA and MPBH is a cleavable hydrazone bond (FIG. 8A). After the Sali-ABA conjugation product was purified, HCl was used to remove a protecting group of ABA and generate an active aldehyde group on the product. The MS spectrum of the purified, de-protected product confirmed that the product was the expected conjugate, Sali-ABA, showing several major molecular ion peaks (labeled) (FIG. 8B). The yield for the de-protected Sali-ABA was 61%.

Figure 8C:
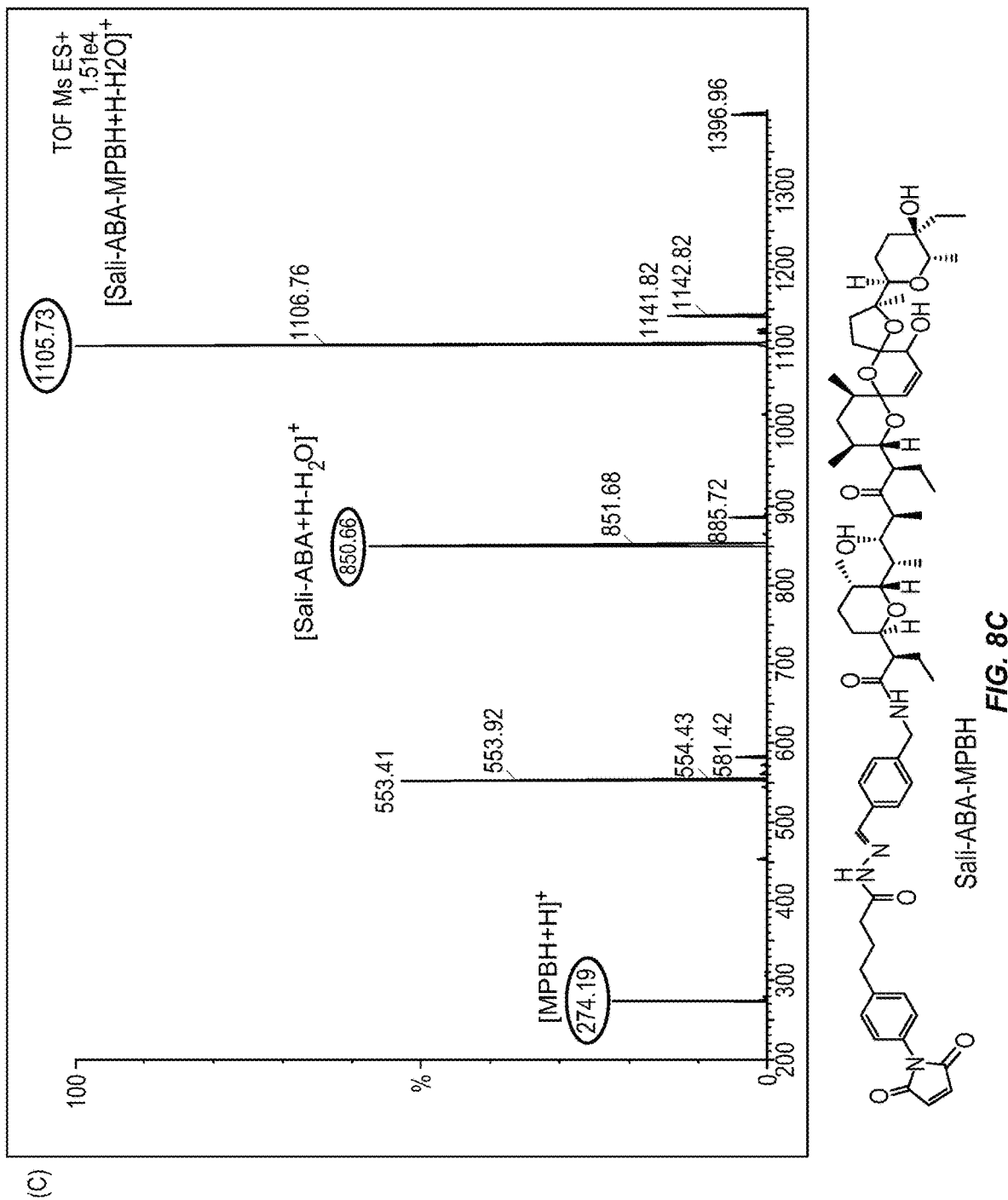

Sali-ABA and MPBH were linked together through an aldehyde group and a hydrazide group on the two molecules (FIG. 8A). MS spectrum (FIG. 8C) and $^1$HNMR peak data of the purified conjugation product indicated that the Sali-ABA-MPBH formed in the reaction. The insert is the expected chemical structure of the Sali-ABA-MPBH conjugate. The peak that matches the MW of Sali-ABA-MPBH is evident. The presence of peaks of MPBH and Sali-ABA of this purified conjugate suggests that the hydrazone bond inside the conjugate is not stable under the ESI-MS experimental conditions. The yield of Sali-ABA-MPBH was 41%.

Figure 9A:
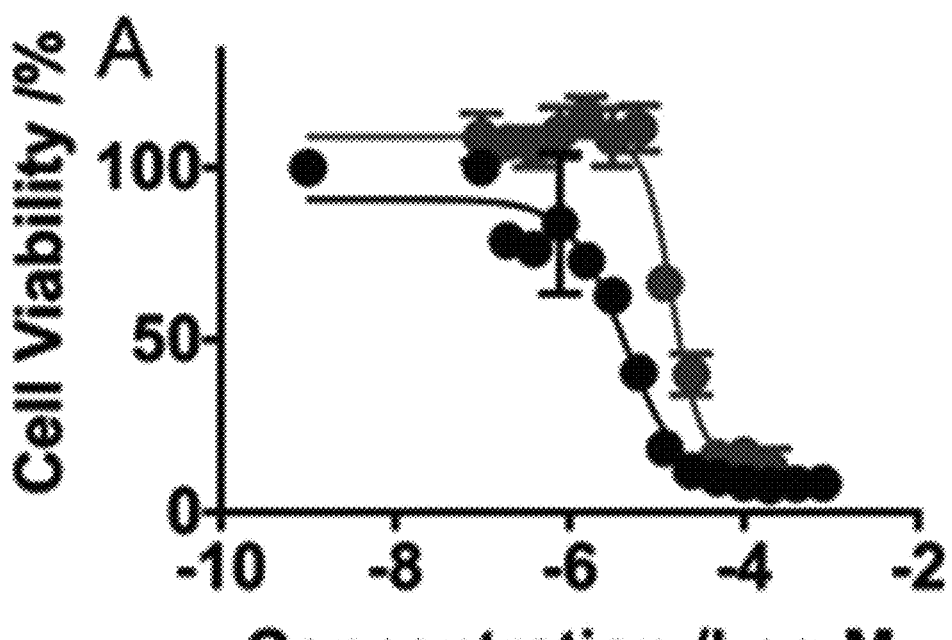
FIGS. 9A-B show the viability profiles of regular 4T1-luc cells under different conditions.
Figure 9B:
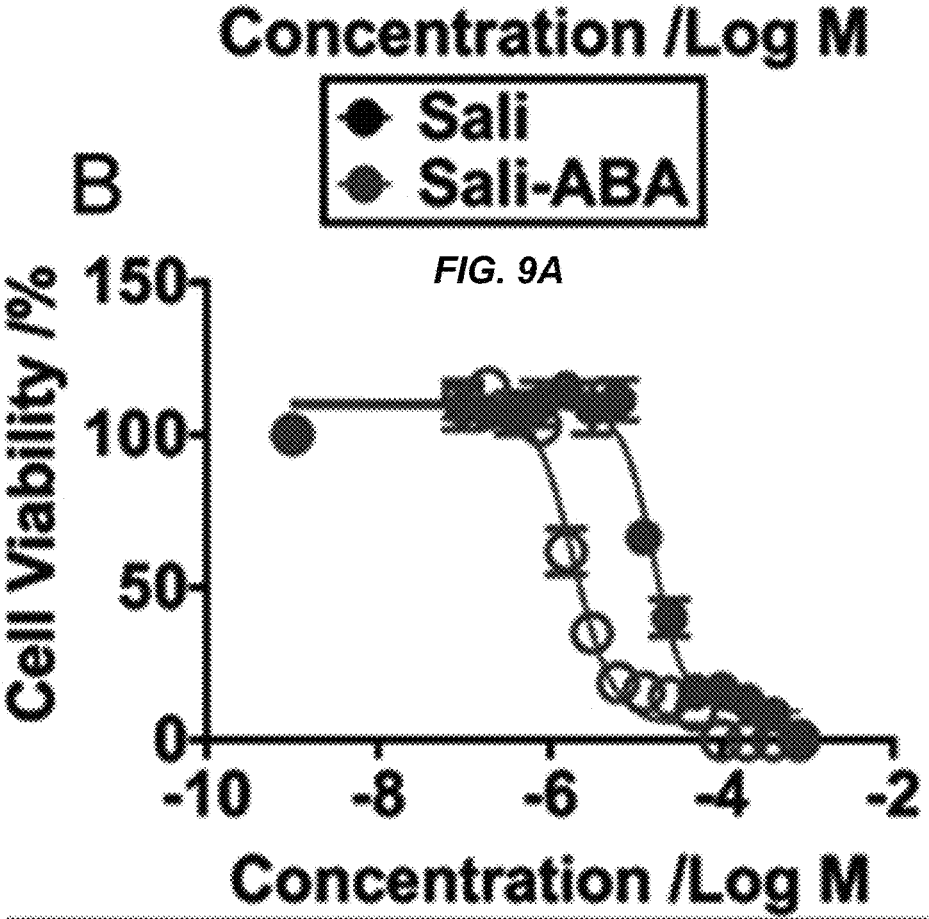
Figure 9B:

Next, the toxicity of Sali-ABA and Sali was compared to regular 4T1-luc cells (FIG. 9A). The $IC_{50}$ of Sali-ABA was 16.4 µM (95% CI=14.3~18.8 µM); the $IC_{50}$ of Sali was 4.4 µM (95% CI=2.3~11.2 µM); the $IC_{50s}$ of Sali and the Sali-ABA are statistically different (P<0.0001, t-test). Therefore, toxicity of Sali-ABA was significantly lower than Sali. The lower toxicity of Sali-ABA agreed with its higher tolerated dose in mice as compared to Sali alone (data not shown). Then, Sali-ABA's toxicity was compared to regular 4T1-luc cells and the cells collected from 4T1-luc mammospheres, a cell population that is commonly used as CSCs of 4T1 tumors (Gupta, et al., Cell, 2009; 138(4):645). The $IC_{50}$ of Sali-ABA to mammosphere 4T1-luc cells was 1.9 µM (95% CI=1.7~2.2 µM) (FIG. 9B), which was significantly less than that of regular 4T1-luc cells; the $IC_{50}$, of Sali-ABA to regular 4T1-luc and mammosphere 4T1-luc are statistically different (P<0.0001 t-test). Thus, Sali-ABA maintained the selective toxicity of Sali to CSCs.

Example 8: Generation and Characterization of iTEP and iTEP-MPBH-ABA-Sali Conjugates Dynamic light scattering (DLS) measurement. The measurement was carried out as previously described. iTEP, iTEP-MPBH-ABA-Sali conjugate, or PTX NP were measured at 25 µM in PBS at 37° C. using a Malvern Zetasizer Nano system (Malvern, Chester County, PA, USA).

Figure 10A:
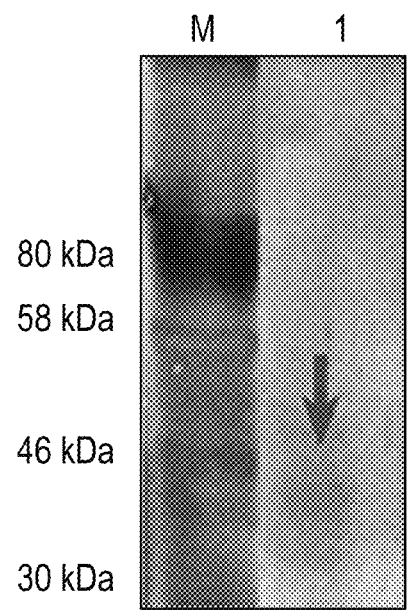
FIGS. 10A-D show the characteristics of iTEP and iTEP-MPBH-ABA-Sali conjugates.

Results. Since nanocarriers facilitate tumor accumulation of their drug payloads through the EPR effect (Matsumura et al., 1986: 46 (12 Part 1):6387-6392; Fang et al., Adv. Drug Deliv. Rev., 2011; 63(3):136-51), the next set of experiments aimed to generate a nanocarrier and use it to deliver Sali-ABA to tumors. Previous results showed an amphiphilic conjugate consisting of a hydrophilic iTEP and hydrophobic Sali (Log D 3.24 at pH 7.4, by MarvinSketch) self-assembled into NPs driven by its segmented amphiphilicity (Zhao, et al; Mol. Pharm, 2014; 11(8):2703-12). To test whether a conjugate between a hydrophilic iTEP and Sali-ABA-MPBH would also possess sufficiently segmented amphiphilicity and assume an NP structure since Sali-ABA (Log D 7.34, pH 7.4) is more hydrophobic than Sali, a previously established iTEP was modified resulting in a new hydrophilic iTEP having a sequence as NH2-(GAGVPG)$_{70}$-(CGGGGGGGG)$_8$-COOH (SEQ ID NO: 58). The eight cysteines offered eight conjugation sites for Sali-ABA-MPBH at one end of the iTEP. Eight-glycine spacers were inserted in between two adjacent cysteines so that each cysteine had ample space to accommodate a Sali-ABA-MPBH molecule. The new iTEP was generated as a recombinant protein from E. coli cells. Purified new iTEP migrated as a band between the 30 kDa and 46 kDa markers on SDS-PAGE, which was consistent with the theoretical molecular weight of the iTEP, 35.2 KDa (FIG. 10A).

Figure 10B:
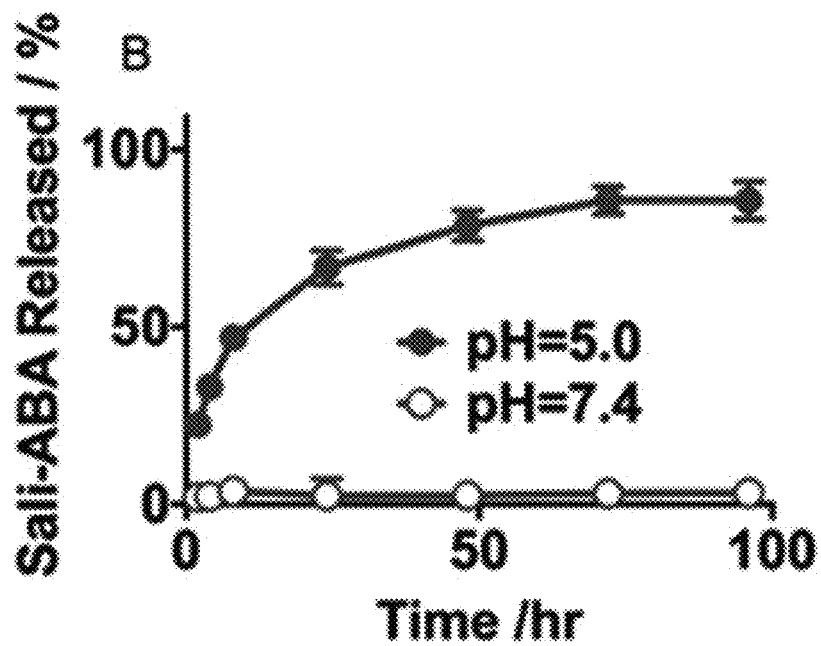
Figure 10C:
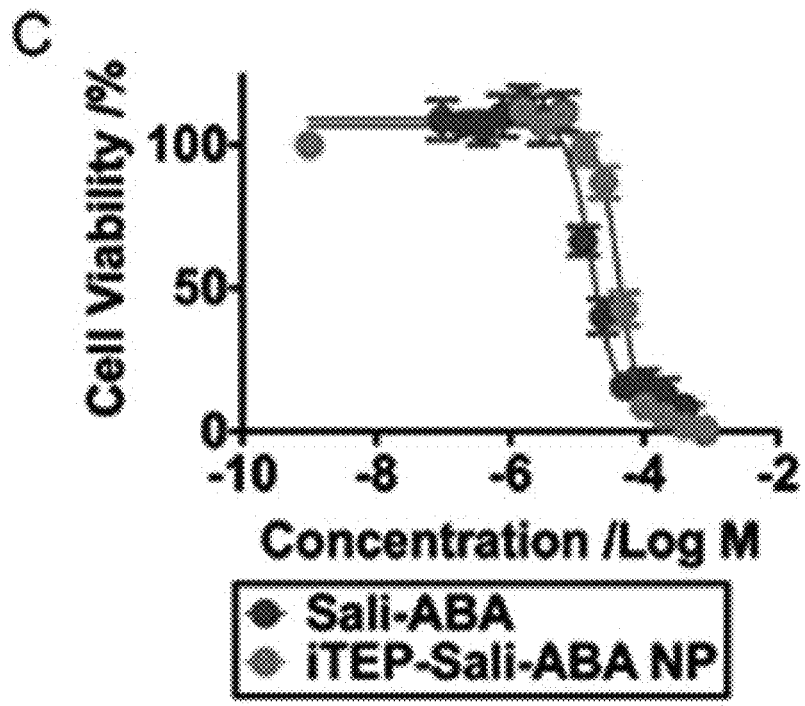
Figure 10D:
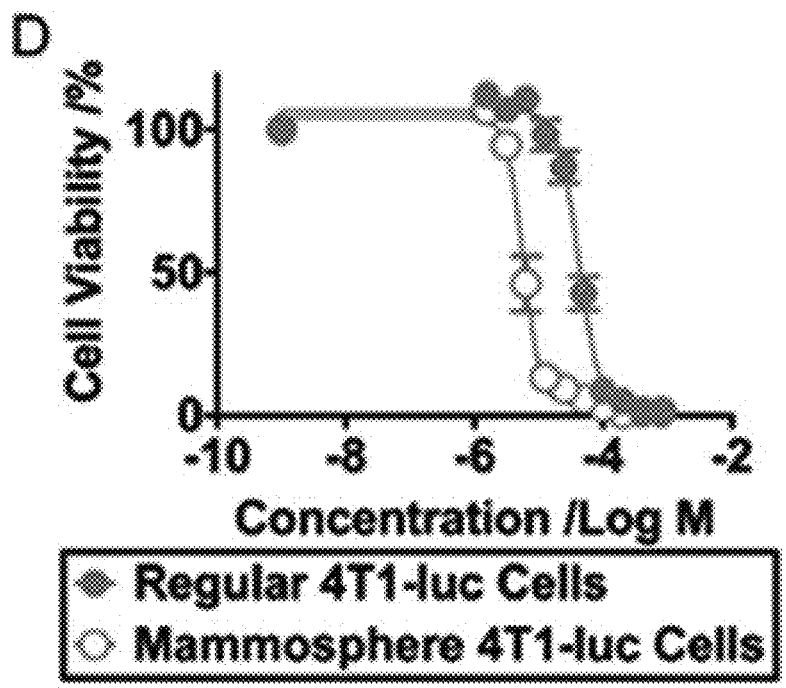

The new iTEP was linked with Sali-ABA through MPBH. The ratio between Sali-ABA-MBPH and iTEP in the purified iTEP-MPBH-ABA-Sali conjugate was estimated to be 3:1. The release half-life of Sali-ABA from the conjugate was 12.15 hours (95% CI=9.98~15.52 hours) at pH 5.0 (FIG. 10B). In contrast, there was no detectable release of Sali-ABA-MPBH at the neutral pH during up to 100-hour monitoring. The different release rates at different pH indicated that the hydrazone bond between Sali-ABA and MPBH-iTEP allowed a pH-dependent, controlled release of Sali-ABA from the conjugate.

iTEP-MPBH-ABA-Sali possessed a cytotoxicity 2.6 times lower than Sali-ABA-MPBH alone when they were used to treat regular 4T1-luc cells (FIG. 10C). The $IC_{50}$s of iTEP-MPBH-ABA-Sali and Sali-ABA were 42.2 µM (95% CI 39.0-45.6 µM) and 16.4 µM (95% CI=14.3~18.8), respectively; the $IC_{50s}$ of iTEP-MPBH-ABA-Sali NP and Sali-ABA to regular 4T1-luc cells are statistically different (P<0.0001, t-test). iTEP-MPBH-ABA-Sali, however, was about eight times more toxic to mammosphere 4T1-luc cells (CSCs) than to regular 4T1-luc cells, resembling the selective toxicity of Sali-ABA and Sali (FIG. 10D). The two types of cells have statistically different $IC_{50}$s (P<0.0001, t-test). The $IC_{50}$ of the iTEP-MPBH-ABA-Sali to mammosphere 4T1-luc cells was 5.8 µM (95% CI=5.4~6.2 µM), and the value for the regular 4T1-luc cells was 42.2 µM.

Figure 10E:
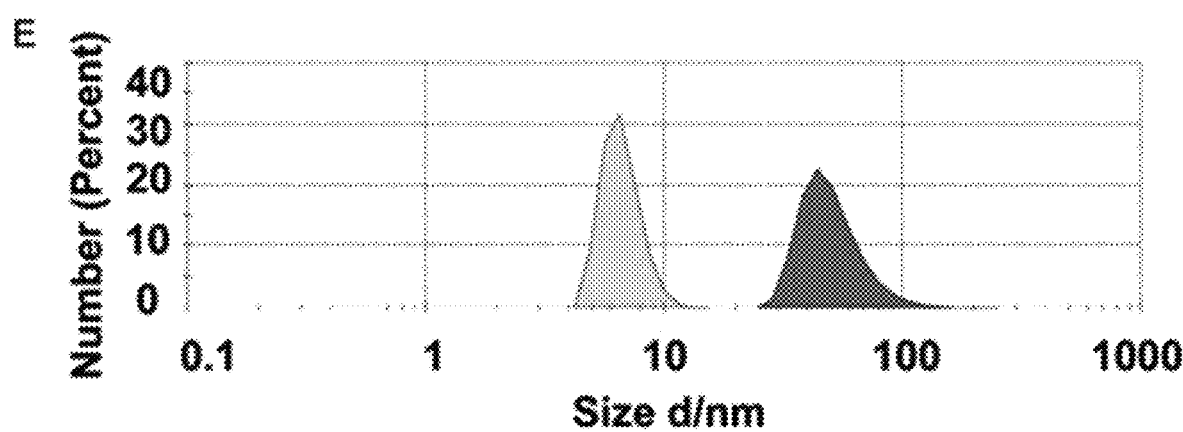
FIG. 10E shows the hydrodynamic diameters of the unconjugated iTEP (green filled area) and iTEP-MPBH-ABA-Sali NP (red filled area). The sample concentrations were 25 µM.

The unmodified iTEP had a hydrodynamic diameter of 6.63±1.25 nm at 37° C. according to DLS analysis (FIG. 10E), which was consistent with the expectation that the iTEP remained a monomer in aqueous solution. iTEP-MPBH-ABA-Sali, on the other hand, displayed a diameter of 51.2±18.2 nm, suggesting that the conjugate assumed a NP structure, as designed. The unconjugated iTEP was reduced in 100 mM TCEP solution overnight before the measurement. The size of iTEP-MPBH-ABA-Sali is also suitable for accumulation in tumors through the EPR effect (Petros et al., Nat. Rev. Drug Discov., 2010; 9(8):615-27).

Example 9: Pharmacokinetics and Tissue Distribution of iTEP-MPBH-ABA-Sali

In vitro Sali-ABA release assay. The release of Sali-ABA from iTEP-MPBH-ABA-Sali NP was measured after the NP was incubated in PBS (pH=7.4) or 0.1M sodium acetate/acetic acid buffer (pH=5) at 37° C. Multiple repeats of each mixture were kept in separate Eppendorf tubes and shaken at 100 rpms at 37° C. At predetermined time points, free Sali-ABA in one tube of sample was determined by HPLC based on a standard curve of Sali-ABA. The standard curve was established at 280 nm. The HPLC setup was the same as the described herein.

The relationship of the percentage of Sali-ABA release (F) with time (t) was fitted using the following equation and GraphPad V5.0.

$$F_{\%, released} = 100[1 e^{Kt}]$$

K is the release rate constant:

$$K = \frac{\ln 2}{t_{1/2}}.$$

Pharmacokinetics and biodistribution study. Sali-ABA concentrations in blood and tissues were analyzed, and the concentrations were analyzed as previously described (Zhao, et al; Mol. Pharm, 2014; 11(8):2703-12).

Cytotoxicity studies. The cytotoxicity was measured as previously described (Zhao, et al; Mol. Pharm, 2014; 11(8): 2703-12). The incubation time was 72 hours. 4T1-lu mammosphere cells were generated as the previously described (Zhao, et al; Mol. Pharm, 2014; 11(8):2703-12).

Figure 11A:
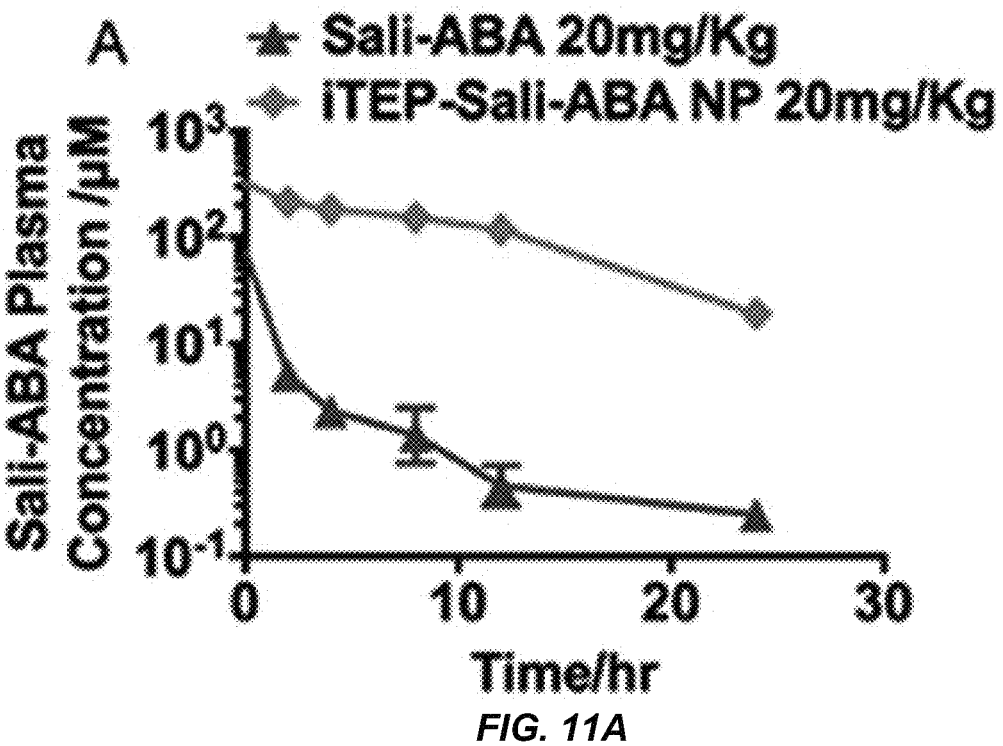
FIGS. 11A-D show the pharmacokinetics and tissue distribution of iTEP-MPBH-ABA-Sali.

Results. The pharmacokinetics of Sali-ABA and iTEP-MPBH-ABA-Sali were compared after they were administered intravenously to mice at a dose of 20 mg/Kg Sali-ABA equivalent. Plasma concentrations of Sali-ABA after the administration of either formulation were monitored for up to 24 hours (FIG. 11A). The temporal changes of the concentrations were fitted into a two-compartment pharmacokinetics model. According to the fitting results, the AUC of Sali-ABA resulted from the iTEP-MPBH-ABA-Sali administration was 2967.0 µM/hour (95% CI=2244.0~3509.0 µM/hour), which was approximately 30 times greater than the AUC resulted from the free Sali-ABA-MPBH administration (99.9 µM/hour (95% CI=47.1~132.2 µM/hour). Similarly, the elimination half-life of Sali-ABA after the iTEP-MPBH-ABA-Sali administration was 35 times longer than free Sali-ABA administration (13.9 hours, 95% CI=9.9~24.8 vs. 0.4 hours, 95% CI=0.2~4.1). In summary, these comparative results support the notion that iTEP-MPBH-ABA-Sali significantly retarded the systematic clearance of Sali-ABA.

Figure 11B:
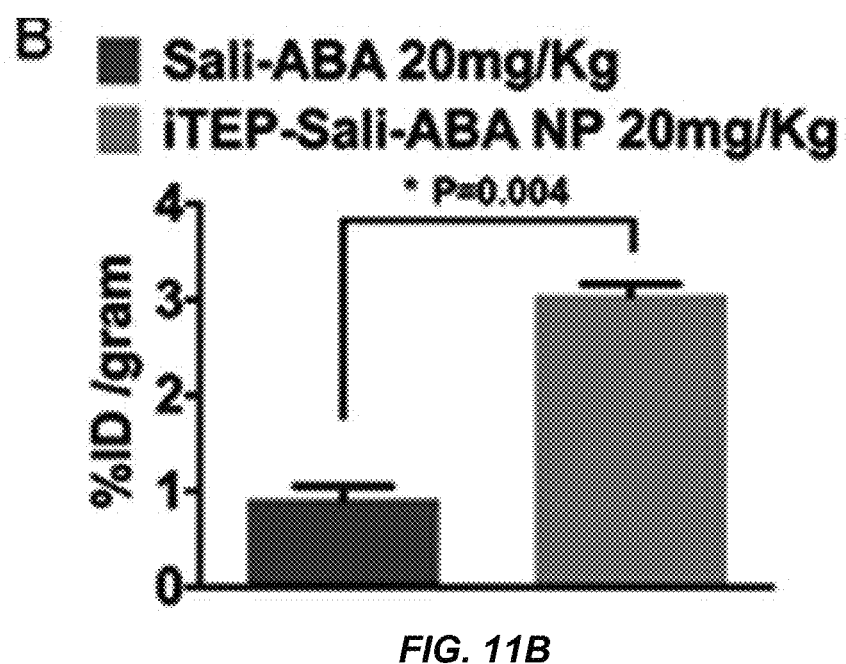
Figure 11C:
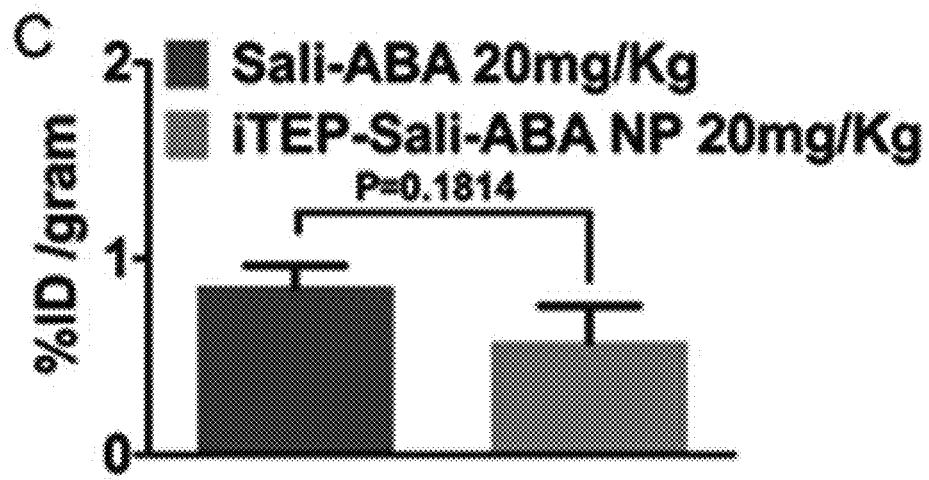
Figure 11D:
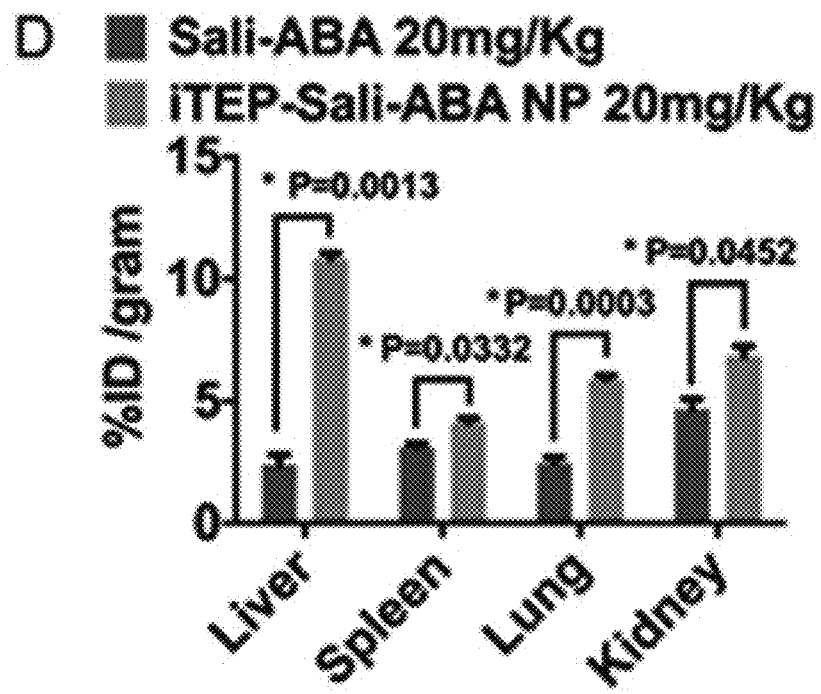

The aforementioned slow clearance and particle size of iTEP-MPBH-ABA-Sali could enable the conjugate to leverage the EPR effect and, therefore, more efficiently accumulate in tumors. Indeed, at 24 hours after administration of free Sali-ABA or iTEP-MPBH-ABA-Sali NP to 4T1-luc tumored mice, the NP resulted in 3.4 fold more Sali-ABA accumulation in the tumors than free Sali-ABA (3.1±0.1 ID %/gram vs 0.9±0.1 ID %/gram, FIG. 11B). Tumors and all following organ samples were collected at 24 hours post administration. The quantities of Sali-ABA were expressed as percentage of initial dose normalized by weight of organs, ID %/gram. The data were analyzed by one-way ANOVA. P-value is shown in the figure and * indicates a significant difference. At the same time, there was a reduction of Sali-ABA accumulation in the heart when iTEP-MPBH-ABA-Sali NP was compared with free Sali, although the difference was not statistically significant (0.57±0.18 ID %/gram vs 0.86±0.11 ID %/gram, FIG. 11C). The data were analyzed by one-way ANOVA. P-value is shown in the figure. The reduction may benefit the toxicity profile of the NP as the heart is an organ sensitive to Sali (Bastianello, et al., J S Afr Vet Assoc, 1996; 67(1):38-41). The Sali-ABA accumulations in the liver, spleen, lung and kidneys have varied increases due to iTEP-MPBH-ABA-Sali-ABA NP (FIG. 11D). The data were analyzed by one-way ANOVA. P-values are shown in the figure and * indicates a significant difference.

Example 10: Inhibition of Primary Tumor Growth and Metastasis by iTEP-MPBH-ABA-Sali NP Tumor growth study. Balb/c mice were inoculated subcutaneously with $10^6$ 4T1-luc cells in 50 µL PBS at the #9 mammary glands. At the seventh day after inoculation when the volumes of all tumors reached or exceeded 100 mm$^3$, the mice were randomly assigned into groups as described in FIGS. 12 and 13. The dosing and dosing schedules are as following:
1. PBS control (three day interval); Sali-ABA (20 mg/Kg BW, three-day interval),
2. iTEP-MPBH-ABA-Sali NP (20 mg/Kg BW, three-day interval),
3. PTX NP (10 mg/Kg BW, three-day interval),
4. PTX NP and iTEP-MPBH-ABA-Sali combination, iTEP-MPBH-ABA-Sali NP on the first day (20 mg/Kg BW), PTX NP on the second day (10 mg/Kg BW), then two-day interval.

Seven total doses were administered intravenously. The length and width dimensions of tumors were measured with a caliper every other day. Tumor volumes were estimated using the formula: Tumor Volume=(length×width$^2$/2) (Zhang et al., Biomaterials, 2012; 33(2):679-91). Also, mouse body weight was recorded the same day when the tumor size was measured. The treatments of PTX NP and the combinational therapy were done after the results of the first three treatment groups were obtained.

Moreover, in order to monitor metastasis, bioluminescence signals released from 4T1-luc cells were monitored as previously described (Tao et al., BMC Cancer, 2008; 8(1): 228). Specifically, experimental mice were injected intraperitoneally with 100 µl of D-luciferin (15 mg/ml) at predetermined time points (twice each week, 3-4 days interval). At 15 minutes after luciferin injection, the mice were imaged under anesthesia in a Xenogen IVIS 200 biophotonic imager (PerkinElmer, Inc., MA, USA). The bioluminescence intensity was denoted using photon emission from the subject or radiance in the unit of photons/sec/cm$^2$/sr (steradian). The intensity scale for all bioluminescence images was set between $1\times10^6$ photons/sec/cm$^2$/sr and $\sim 1\times10^7$ photons/sec/cm$^2$/sr. Metastasis was defined as an area with a pre-defined size and outside the area of primary tumors with an average radiance exceeding $1\times10^6$ photons/sec/cm$^2$/sr. The number of days between tumor inoculation and the first day that metastasis was observed on a mouse was designated as the metastasis-free survival time. The overall survival time was counted as days between tumor inoculation and mouse sacrifice. Metastasis-free survival and overall survival were analyzed by the Kaplan-Meier method, and the median survival of each groups were compared using the Log-rank test with GraphPad V5.0.

Figure 12A:
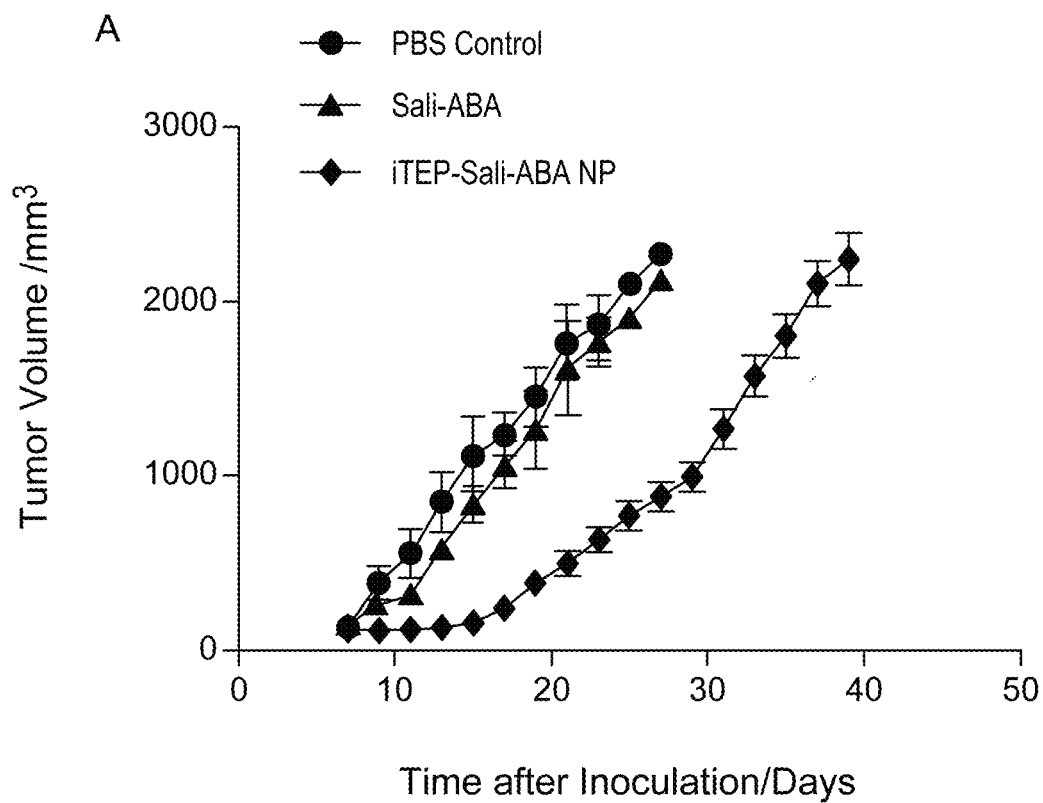
FIG. 12A shows the volume change of 4T1-luc orthotopic tumors after they were treated by PBS, free Sali-ABA, or iTEP-MPBH-ABA-Sali NP.

Results. When iTEP-MPBH-ABA-Sali NPs were assessed for their inhibition of the growth and metastasis of 4T1-luc orthotopic tumors, the results showed that the NP slowed primary tumor growth. The tumors treated by the NP were always smaller than the PBS-treated tumors from day 2 after the treatments (day 9 after tumor inoculation) (FIG. 12A, P<0.05, t-test). Free Sali-ABA (20 mg/KG), on the other hand, failed to slow tumor growth.

Figure 12B:
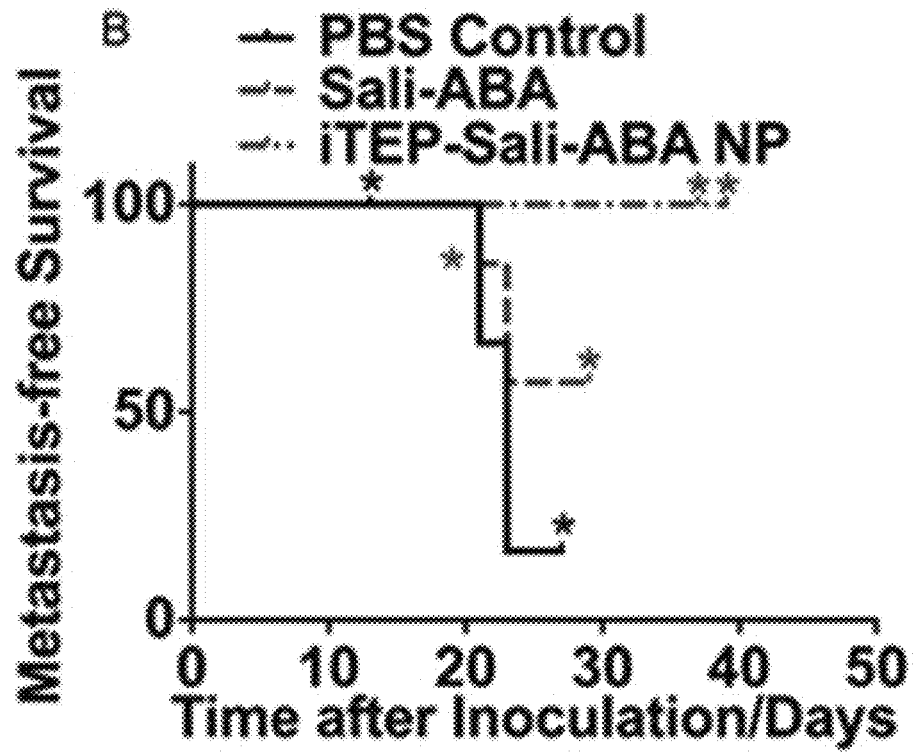
FIG. 12B shows the metastasis-free survival of mice bearing 4T1-luc orthotopic tumors after they were treated as described in FIG. 12A. * indicates the time points when some mice were censored because they reached humane endpoints.
Figure 12C:
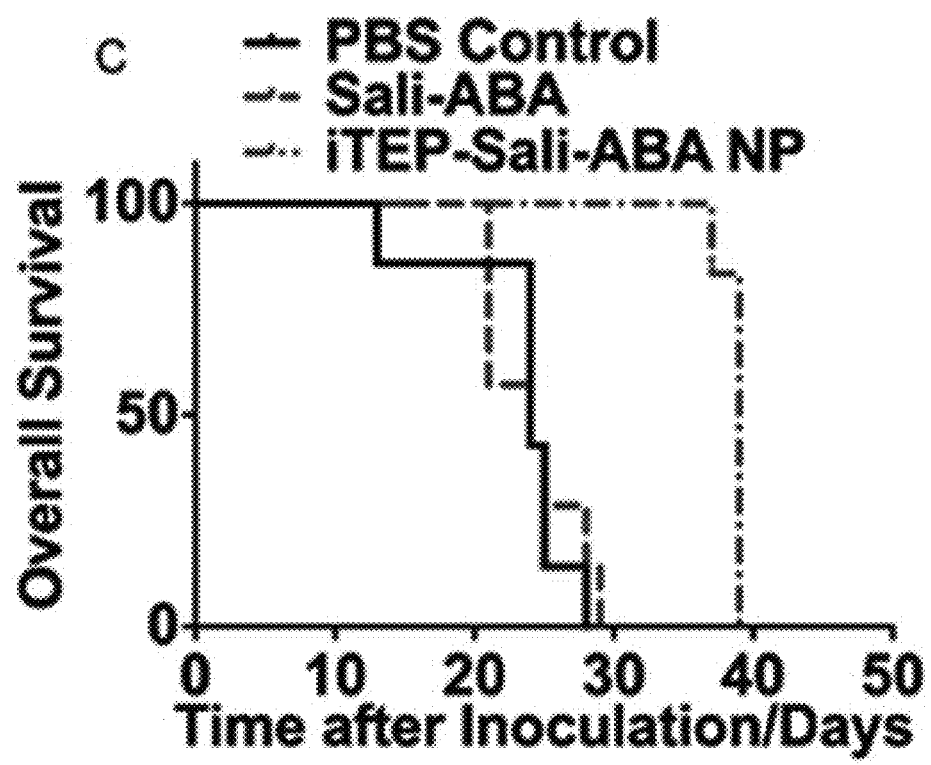
FIG. 12C shows the overall survival profile of mice described in FIG. 12A.

The NP effectively inhibited metastasis of 4T1-luc tumors evidenced by its drastic improvement of metastasis-free survival in comparison to PBS treatment (P=0.007, Log-rank; FIG. 12B). No mice in the NP-treated group developed metastasis before they were sacrificed. In contrast, the median metastasis-free survival for the PBS-treated mice was only 23 days. Free Sali-ABA also inhibited metastasis, as less than half of the mice in this group developed metastasis, and the median metastasis-free survival of this group was not reached before the mice were sacrificed. The inhibition effect of Sali-ABA, however, was weaker than that of the NP because some Sali-ABA-treated mice developed metastasis. In addition, the survival of the PBS control group and the Sali-ABA group were not statistically different (P=0.252).

The overall survival of PBS- and Sali-ABA-treated mice was not different from each other; both had a median survival of 24 days (FIG. 12C). iTEP-MPBH-ABA-Sali, however, significantly improved overall survival with a median survival of 39 days (iTEP-MPBH-ABA-Sali vs PBS, P=0.0012; iTEP-MPBH-ABA-Sali vs PBS p=0.0011).

Although iTEP-MPBH-ABA-Sali NP inhibited both primary tumor growth and metastasis, the inhibition was not enough to lead to stabilization or shrinking of the primary tumors. Indeed, NP-treated mice were sacrificed because of large primary tumor burdens. To overcome this effect of iTEP-MPBH-ABA-Sali NP, a combinational therapy that incorporates Sali and paclitaxel (PTX) together was developed.

Example 11: Inhibition of Primary Tumor Growth and Metastasis by a Combinational Therapy of iTEP-MPBH-ABA-Sali NPs and PTX NPs Loading of PTX into iTEP-MPBH-ABA-Sali NP. PTX was loaded into iTEP-MPBH-ABA-Sali NP as previously described (Zhao, et al; Mol. Pharm, 2014; 11(8):2703-12). 10 mg iTEP-MPBH-ABA-Sali, 5 mg PTX, and 2.5 mg a-Tocopherol (Sigma-Aldrich, MO, USA) were co-dissolved in 125 µL DMF. The encapsulated PTX was determined by HPLC based on its absorbance at 280 nm and a standard curve of PTX. The standard curve was generated by measuring the absorbance of serially diluted PTX on HPLC. The column for HPLC was Symmetry C18 column (100 Å, 3.5 µm, 4.6 mm×150 mm, Waters, MA, USA) which was connected to an Agilent Infinity-1260 LC system (CA, USA). The analysis was performed using water (solvent A) and Acetonitrile (solvent B) (0.05% TFA) at a flow rate of 1.0 mL/min. The gradient was gradually increased from 80% B to 100% B from 0 to 20 minutes. The loading efficiency was defined by the following equation:

Loading efficiency (%)=100×(PTX encapsulated)/(PTX feed).

In vitro PTX release assay. The in vitro release profile of PTX from the PTX NP was measured by a previously described dialysis method with minor modifications (Zhang et al., Biomaterials, 2012; 33(2):679-91). The PTX NP was diluted in 0.5 mL MiliQ water containing 4% BSA and kept in a bag (Spectrum Laboratories, Inc. CA, USA, MW cutoff=8,000 Da). The bag was dialyzed in 100 mL PBS solution (pH=7.4) and shaken at 100 rpms at 37° C. At predetermined time points, 10 µL of the sample was collected form the bag after the sample was well mixed. PTX in the 10 µL sample was determined by HPLC as described herein and assumed to be un-released PTX. The release kinetics was determined as described herein.

Figure 13A:
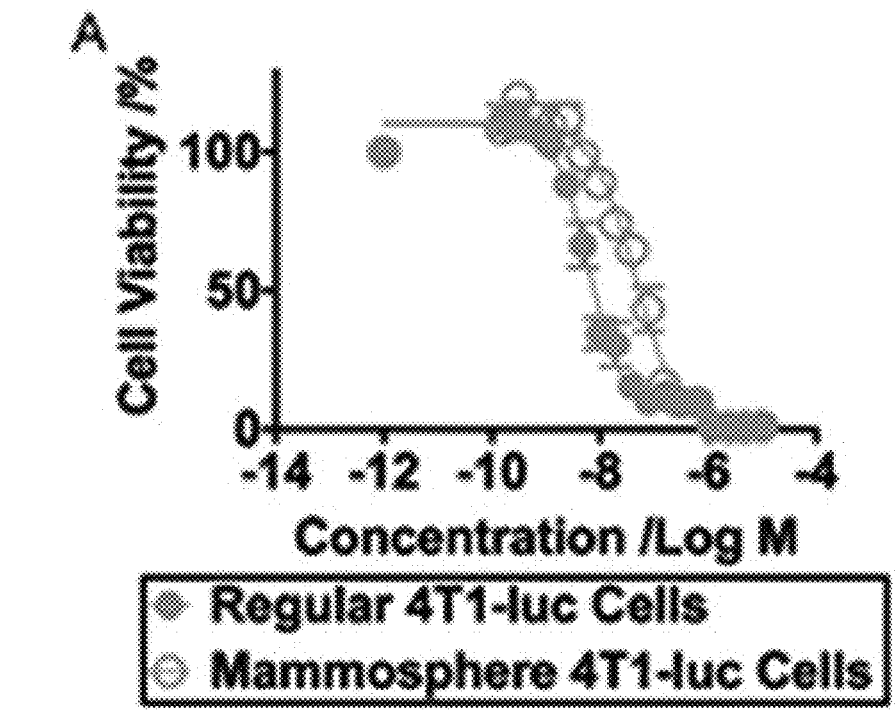
FIGS. 13A-D show that combinational therapy of iTEP-MPBH-ABA-Sali NPs and PTX NPs inhibit primary tumor growth and metastasis.
Figures 26A, 26B:
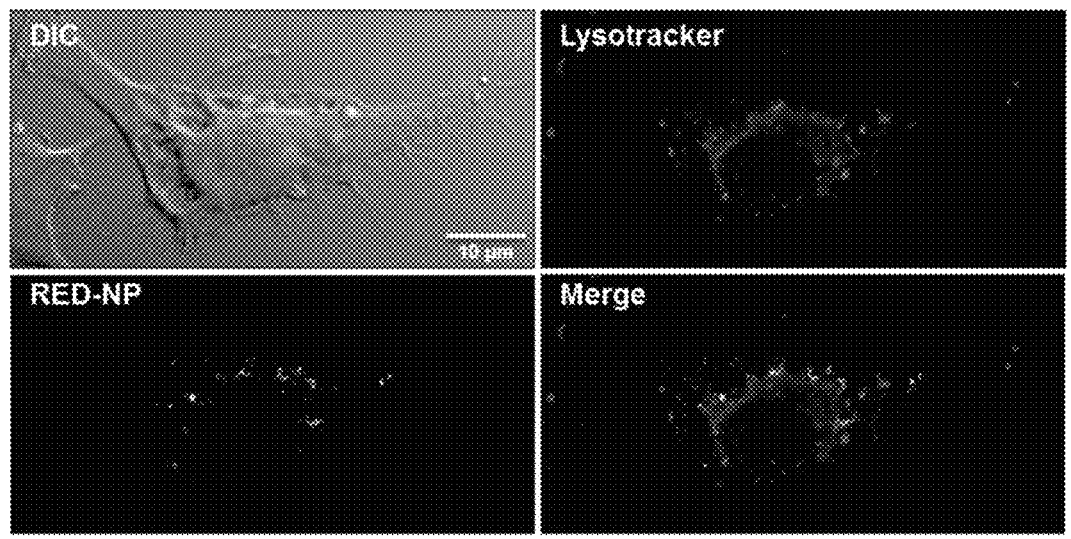
FIGS. 26A-B show that NPs reach the cytosol.
Figure 26C:
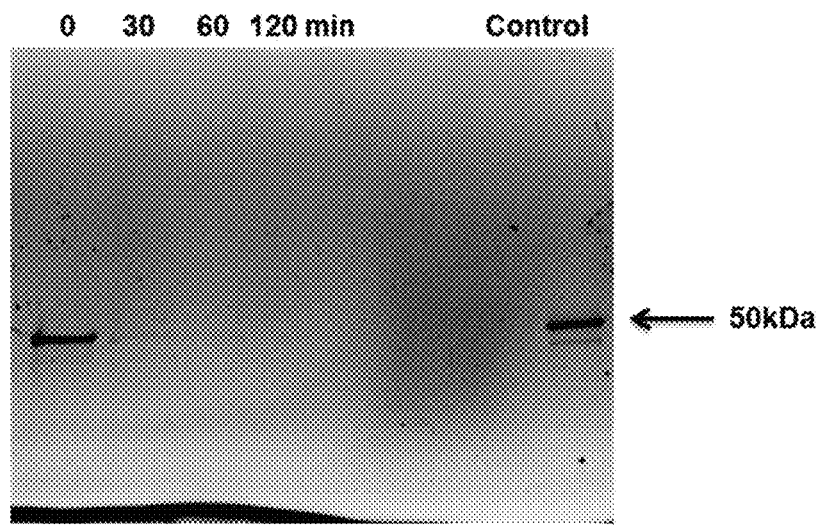
Figure 27A:
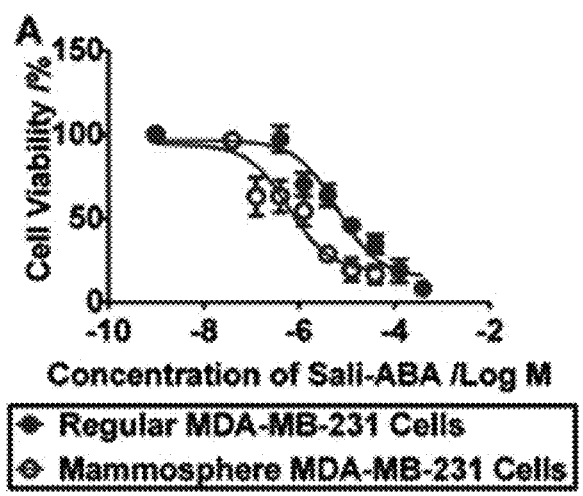
FIGS. 27A-C show viability profiles.
Figure 27B:
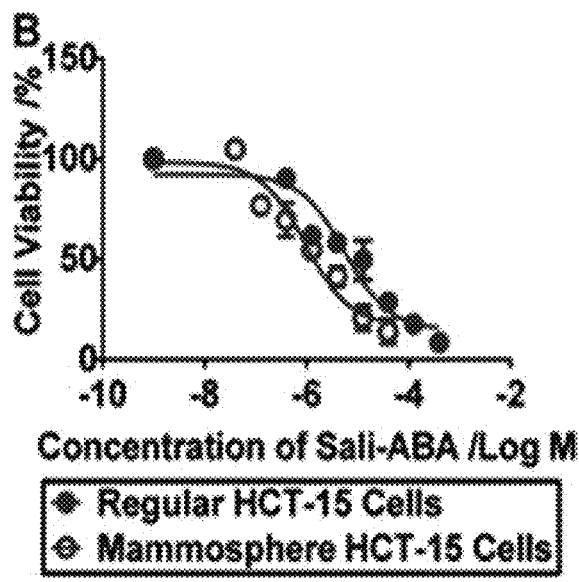
Figure 27C:
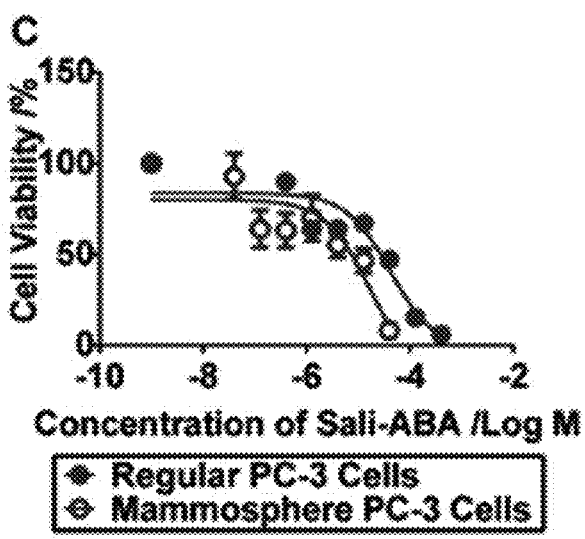
Figure 28:
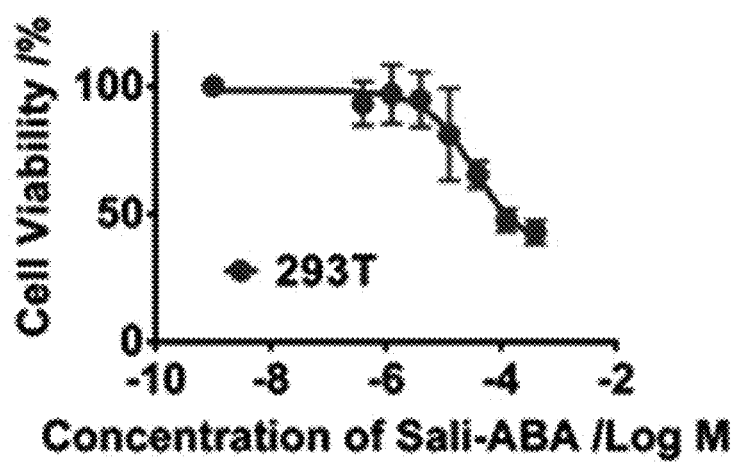
FIG. 28 shows the viability profile of 293T cells after they were exposed to different concentrations of Sali-ABA for 72 hours.

Results. Since PTX delivered by a nanocarrier has better efficacy than free PTX (Zhang et al., Expert Opin Drug Deliv, 2013; 10(3):325-40), iTEP-MPBH-ABA-Sali NPs were to deliver PTX in an encapsulated form. The resulting NP, termed PTX NP, had PTX and Sali-ABA at a ratio of 6.6 to 1. Given Sali-ABA was much less toxic than PTX to regular 4T1 cells ($IC_{50s}$: 16.4 µM versus 6.3 nM), the toxicity of iTEP-MPBH-ABA-Sali NP as the carrier was negligible in comparison to PTX. PTX was load in the NP at an efficiency of 84.6±1.25% (n=3). The PTX NP had a mean diameter of 85.09±31.64 nm (FIG. 27) and released PTX at a half-life of 4.67 hours, (95% CI=4.03~5.55 hours, FIG. 28). For instance, FIG. 26 shows the following: that the $IC_{50}$ value of Sali-ABA in the regular cells was significantly greater than that in the mammosphere cells (6.4 µM, 95% CI=3.8~10.9 µM versus 0.6 µM, 95% CI=0.3~1.2 µM, P<0.0001, t-test); that the $IC_{50}$ value of Sali-ABA in the regular cells was significantly greater than that in the mammosphere cells (5.6 µM, 95% CI=3.1~10.4 µM versus 1.0 µM, 95% CI=0.6~1.6 µM, P<0.0001, t-test); and that the $IC_{50}$ value of Sali-ABA in the regular cells is significantly greater than that in the mammosphere cells (42.6 µM, 95% CI=19.7~91.8 µM versus 17.0 µM 95% CI=3.8~76.6 µM, P<0.0001, t-test). FIG. 28 shows that the $IC_{50}$ value of Sali-ABA was 34.3 µM (95% CI=16.1~73.3 µM), which was greater than the value in 4T1-luc cells. In addition, PTX NP treated-mice had less body weight loss when compared with free PTX treated mice (data not shown). Lastly, results of the in vitro cytotoxicity study showed that the PTX NP possessed greater cytotoxicity to regular 4T1-luc cells than to mammosphere 4T1-luc cells (FIG. 13A). The $IC_{50}$, of the PTX NP to the two types of cells were 6.32 nM (%95 CI=5.5~7.3 nM) and 44.6 nM (%95 CI=37.8~52.6 nM), respectively. The two $IC_{50}$, are statistically different (P<0.0001, t-test).

PTX NP and iTEP-MPBH-ABA-Sali NP exert the same level of inhibition to primary tumor growth. The mean tumor sizes of mice receiving these two treatments were not significantly different from each other except between the day 15 to day 25 after tumor inoculation (P<0.05, t-test, FIG. 13B). The median metastasis-free survival of the PTX NP treated mice was 37 days, suggesting the metastasis-inhibition effect of PTX NP was not as effective as iTEP-MPBH-ABA-Sali NP since the latter treatment resulted in zero metastasis during the 39-day observation period (FIG. 13C). Indeed, the metastasis-free survival of the two treatment groups were statistically different (P=0.002).

Figure 13B:
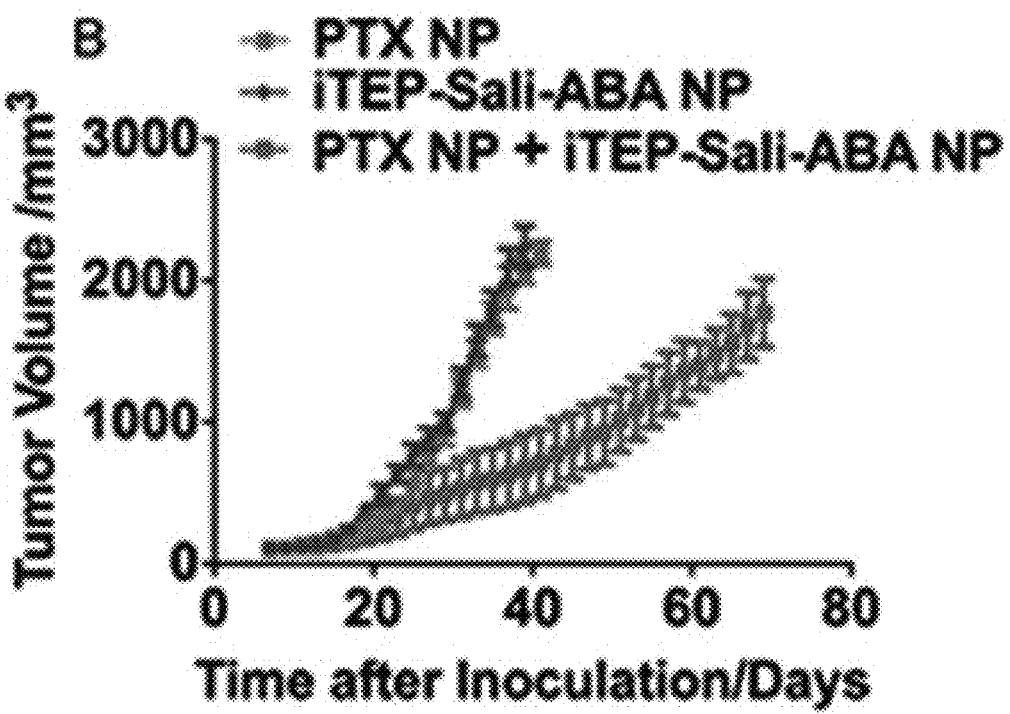
Figure 13C:
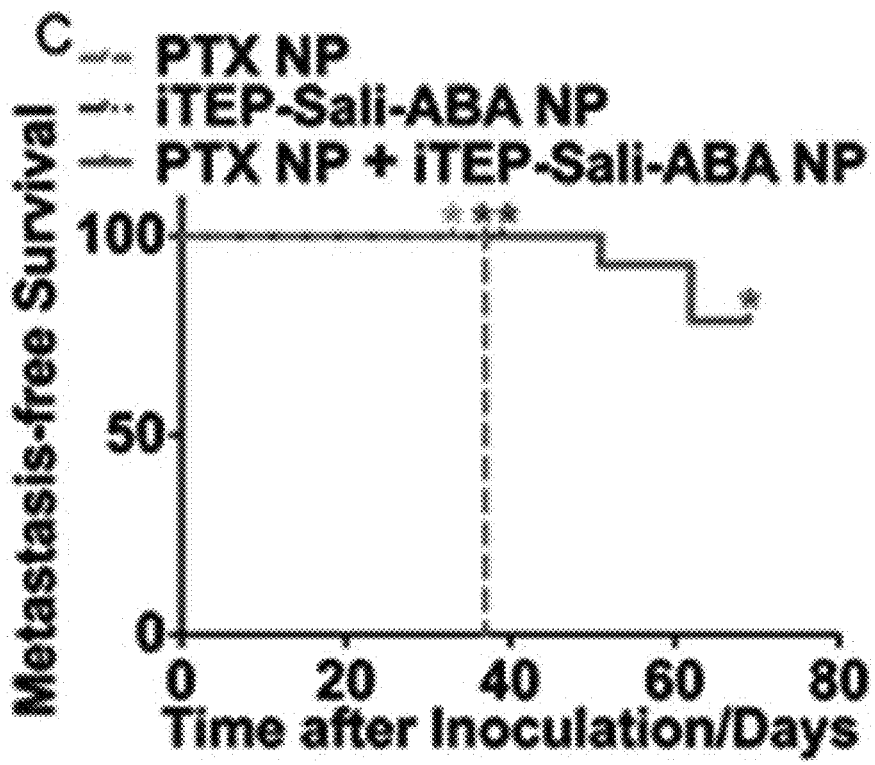

A combinational therapy consisting of both the iTEP-MPBH-ABA-Sali NP and the PTX NP showed a superior inhibition to primary tumors than the PTX NP or the iTEP-MPBH-ABA-Sali NP monotherapies from the 29th day after tumor inoculation (FIG. 13B). The combinational therapy is more effective to inhibit metastasis than the PTX NP monotherapy (P=0.001). Eleven of fourteen mice treated by the combinational therapy remained metastasis free even at the end of the study, 69 days post tumor inoculation. The combinational therapy, however, was not superior to the iTEP-MPBH-ABA-Sali NP in inhibiting metastasis.

Figure 13D:
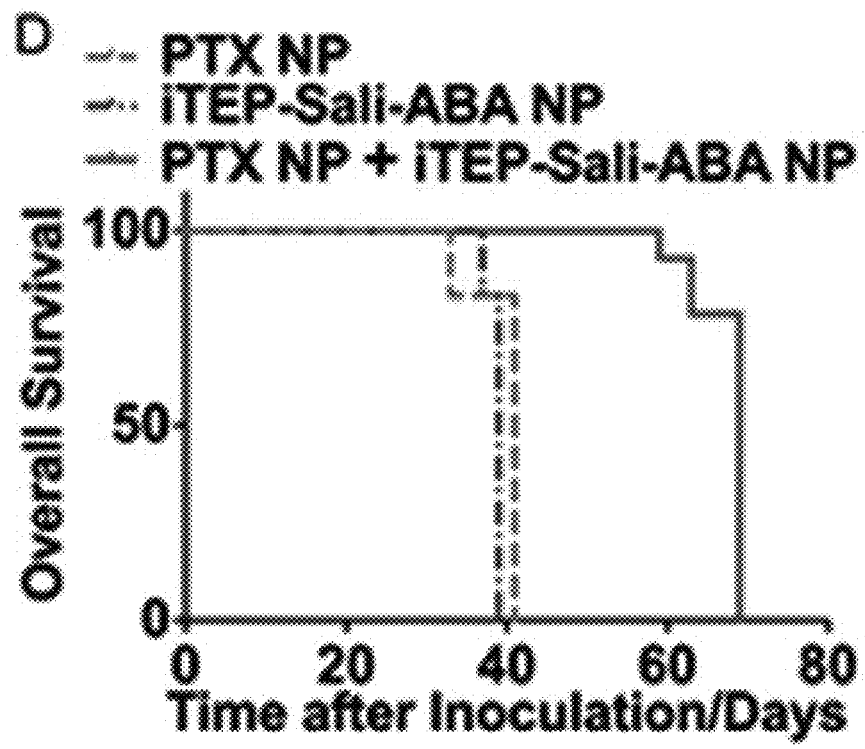

The combinational therapy was able to further prolong the overall survival of treated mice as compared to the PTX NP monotherapy and the iTEP-MPBH-ABA-Sali NP monotherapy. The median overall survival of the combinational therapy group was 69 days, while survival for PTX NP and iTEP-MPBH-ABA-Sali NP therapy groups were only 41 days and 39 days (FIG. 13D, P<0.001 in either comparison).

Example 12: Design and Generation of a Stable iTEP NP

Cell lines and mice. The DC2.4 DC line (H-2K$^b$) was kindly provided by Dr. Kenneth Rock (University of Massachusetts, USA). The DC2.4 cells were cultured in RPMI-1640 medium supplemented with 10% heat inactivated fetal calf serum, 2 mM glutamine, 1% non-essential amino acids, 1% Hepes, 50 µM P-Mercaptoethanol, 100 units/ml penicillin and 100 µg/mL streptomycin (Invitrogen, USA). The B3Z T-cell hybridoma specific for H-2K$^b$: OVA$_{257-264}$ (SIIFEKL; SEQ ID NO: 22) was kindly provided by Dr. Nilabh Shastri (University of California, USA). The B3Z cells were cultured in RPMI-1640 medium supplemented with 10% heat inactivated fetal calf serum, 2 mM glutamine, 1 mM pyruvate, 50 μM β-Mercaptoethanol, 100 units/mL penicillin and 100 μg/mL streptomycin (Invitrogen, USA). EA.hy926, bEnd.3 and 3T3 cells were obtained from ATCC and were maintained in in DMEM medium supplemented with 10% heat inactivated fetal calf serum. C57BL/6 female mice, 6-8 weeks of age, were obtained from Jackson Laboratories.

Figure 14:
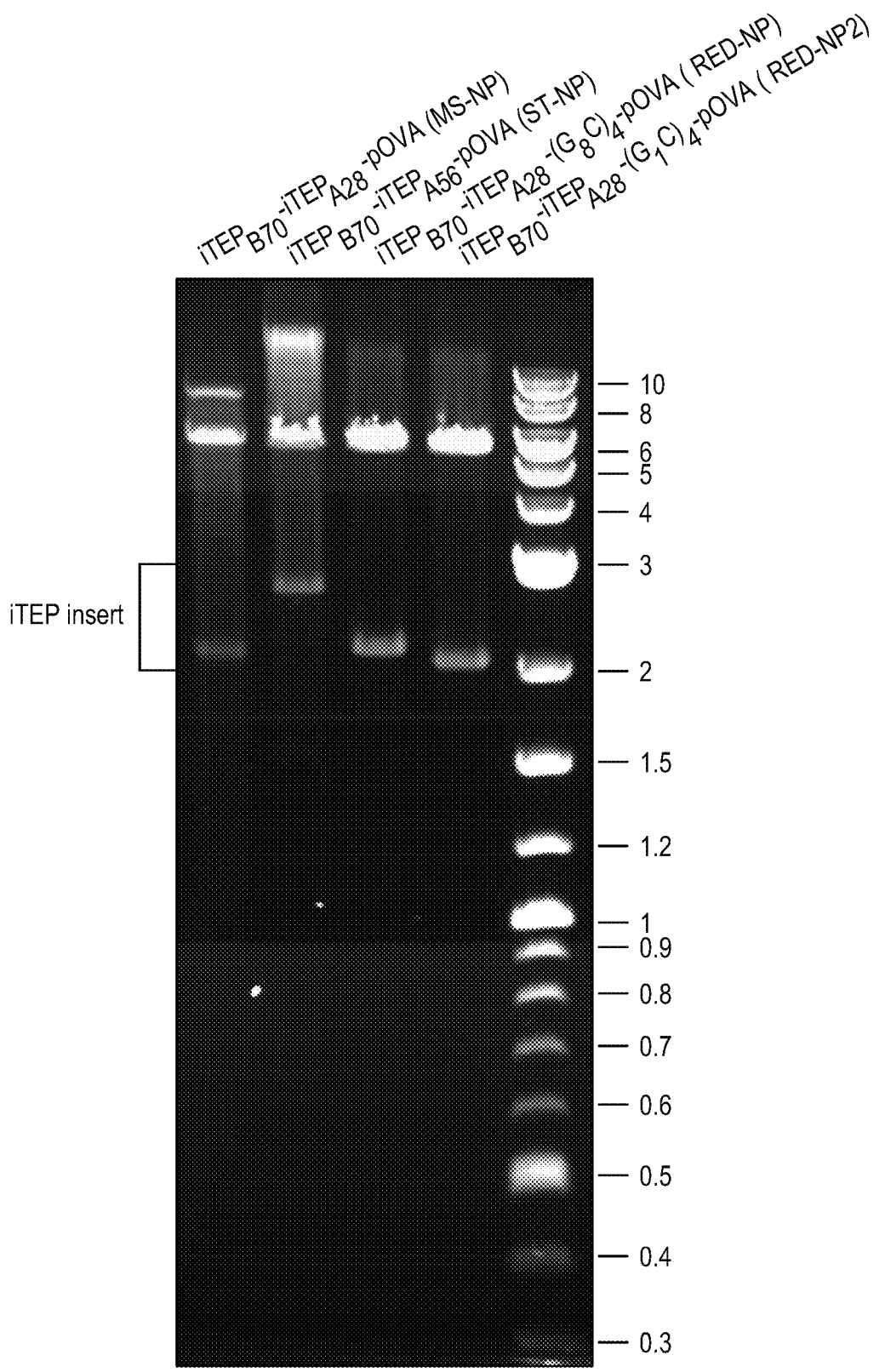
FIG. 14 shows the bands of coding genes of iTEP-vaccine fusions on agarose gel after these genes were cleaved from pET25b(+) vector by XbaI and BamHI. The bands confirmed that the sizes of the genes agree with the expected sizes of the iTEP fusions.

Construction of the expression plasmids of iTEP-vaccine fusions. The genes encoding iTEP vaccines were synthesized on a modified pET25b(+) vector using a previously described method (Cho et al., J Drug Target, 2015, p. 1-12). Specifically, genes that encoded subunits of $iTEP_A$ $(GVLPGVG)_4$ (SEQ ID NO: 30) and $iTEP_B$ $(GAGVPG)_5$ (SEQ ID NO: 31) were generated by annealing the sense and antisense oligonucleotides of these genes together (see Table 2). Then these annealed iTEP genes were inserted to the vector at its BseRI site. Lastly, iTEP genes were polymerized by the PRe-RDL method until a desired length of iTEP genes were achieved. $iTEP_A$ contained 28 repeats of GVLPGVG (SEQ ID NO: 1) and was named $iTEP_{A28}$ (SEQ ID NO: 50). $iTEP_B$ had 70 repeats of GAGVPG (SEQ ID NO: 2) and was named $iTEP_{B70}$ (SEQ ID NO: 31). The genes encoding the fusions of $iTEP_{B70}$-$iTEP_{A28}$ (SEQ ID NO: 54), $iTEP_{B70}$-$iTEP_{A56}$ (SEQ ID NO: 59), $iTEP_{B70}$-$iTEP_{A28}$-pOVA (SEQ ID NO: 56), $iTEP_{B70}$-$iTEP_{A56}$-pOVA (SEQ ID NO: 60), $iTEP_{B70}$-$iTEP_{A28}$-$(G_8C)_4$-pOVA (SEQ ID NO: 61) and $iTEP_{B70}$-$iTEP_{A28}$-$(G_1C)_4$-pOVA (SEQ ID NO: 62) were generated in a similar manner. The sequences of the oligonucleotides used for constructing these genes are listed in Table 2. The sequences for the pOVA fusion had two copies of the CTL epitope, SIINFEKL (SEQ ID NO: 22), and one natural flanking residue on the each side of SIINFEKL (SEQ ID NO: 22). After the resulting expression vectors were transformed into DH5α for their amplification, the lengths of the coding genes were confirmed by an Xba I and BamH I double digestion and followed agarose gel analysis (FIG. 14). The sizes of these genes agree with the expected residue numbers of the fusions. The coding genes were also verified by DNA sequencing (Genewiz, USA).

Figure 15:
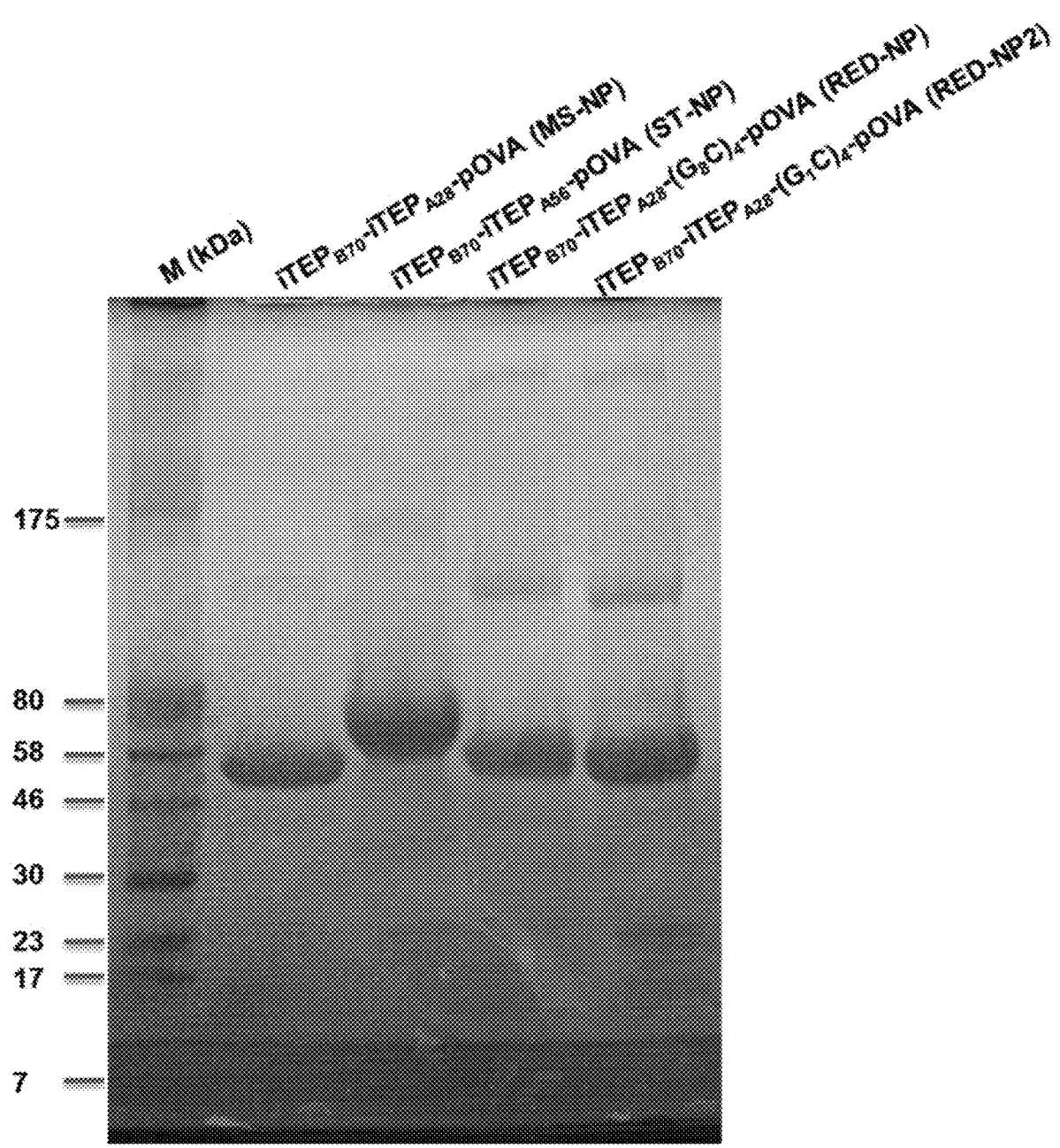
FIG. 15 is an SDS-PAGE analysis confirming molecular weights and purity of iTEP-vaccine fusions after they were purified from $E.$ $coli$ cells.

Production and purification of iTEP-vaccine fusions and iTEPs. The fusions and iTEPs were produced and purified as previously described (Cho et al., J Drug Target, 2015, p. 1-12). The sonication was done with Sonic Dismembrator Model 500 (Fisher Scientific). The endotoxin was also removed as previously described (Cho et al., J Drug Target, 2015, p. 1-12). The purity of the fusions and iTEPs was assessed by SDS-PAGE (FIG. 15).

Preparation of reductive environment-responsive iTEP-vaccine fusions. The protein purification of $iTEP_{B70}$-$iTEP_{A28}$-$(G_1C)_4$-pOVA (SEQ ID NO: 62) and $iTEP_{B70}$-$iTEP_{A28}$-$(G_8C)_4$-pOVA (SEQ ID NO: 61) was carried out in PBS with 10 mM TCEP-HCl, pH 7.0 to keep the reductive condition. The final purified protein was dissolved in water before lyophilization. The purified proteins were then treated with 0.3% $H_2O_2$ at 37° C. for 15 min for oxidization to generate disulfide bond stabilized particles. The $H_2O_2$ was then removed by Amicon centrifugal filter devices (Millipore, USA).

Characterization of hydrodynamic diameters of iTEP-vaccine fusions. Hydrodynamic diameters of iTEP-vaccine fusions were determined by dynamic light scattering (DLS) using a Zetasizer Nano-ZS instrument (Malvern Instruments, Malvern, UK) as previously described (Zhao et al., Mol Pharm, 2014; 11(8):2703-12). The samples were resuspended at concentrations of 5, 25, 50, and 100 μM in PBS and sat at room temperature overnight before measurement. Some samples were kept in 5% C02 at 37° C. for 16 h before DLS measurement. Hydrodynamic diameter results of the sample of 5 μM concentration were reported because they were not affected by the used sample concentrations. Hydrodynamic diameters were presented using the size-by-number distribution approach. Z-average values and sizes-by-intensity data, however, were also reported.

Negative-stain, transmission electron microscopy (TEM) of iTEP-vaccine fusions. TEM was done as previously described (Cho et al., J Drug Target, 2015; p 1-12).

Measurement of critical micelle concentrations (CMCs) of iTEP-vaccine fusions by pyrene assay. The CMCs of iTEP-vaccine fusions (NPs) were measured through fluorescence spectra by using pyrene as a hydrophobic fluorescent probe as described previously with some adjustments (Ohyanagi et al., Jpn J Clin Oncol, 2011; 41(5); 718-22; Dreher et al., J Am Chem Soc, 2008; 130(2):687-94). Briefly, the fusions were serially 2×time diluted in PBS starting from 250 μM in 96-well black clear-bottom plates. The final volume for each dilution was 150 μL. Three μL of a stock solution of 30 μM pyrene in ethanol was added to each well and mixed well. Fluorescence of these samples were scanned using an Infinite M1000 PRO plate reader (Tecan Trading AG, Switzerland) with the setting: Ex: 334 nm with a slit of 10 nm, Em: ranging 360-400 nm with a slit of 2.5 nm. Four peaks were recorded for pyrene between 360-400 nm. The ratio of emission peak number 1 ($I_1$; 370-373 nm) and emission peak number 3 ($I_3$; 381-384 nm) of pyrene ($I_1/I_3$) was plotted as a function of iTEP concentration. The data points were fitted to a sigmoidal-dose response curve, and the CMC was defined as the inflection point of the curve.

Figure 16A:
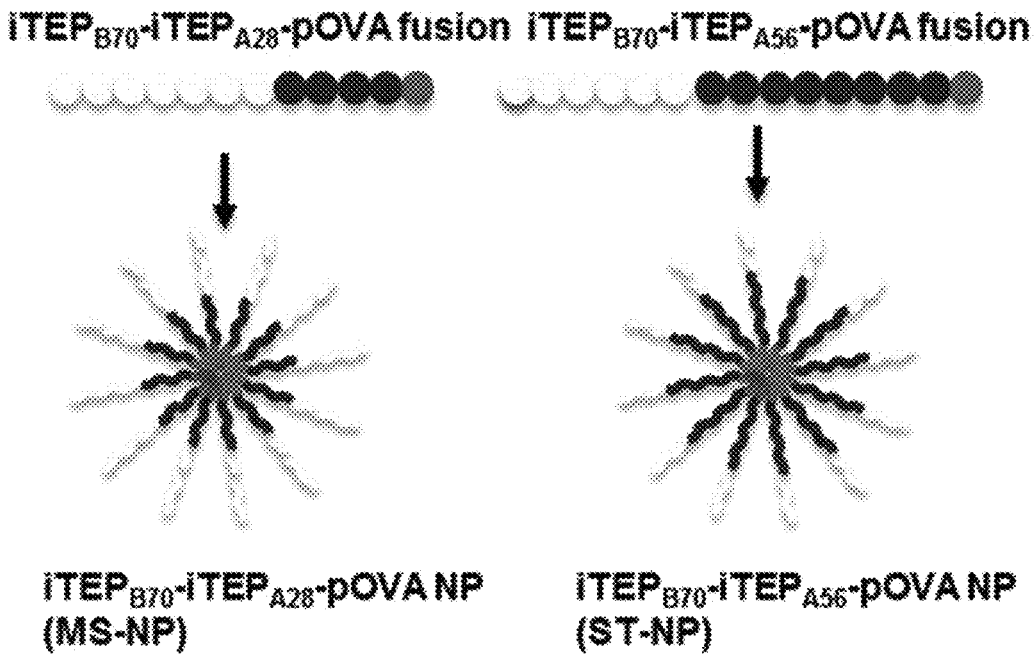
FIGS. 16A-D show the design and generation of a stable iTEP NP.

Results. Previously, an iTEP NP, $iTEP_{B70}$-$iTEP_{A28}$-pOVA (SEQ ID NO: 64) (schematic in FIG. 16A) was generated that enhanced the potency of a CTL peptide vaccine, SIINFEKL (SEQ ID NO: 22), when compared with a free vaccine peptide or the vaccines delivered as soluble ovalbumin protein (Cho et al., J Drug Target, 2015; p 1-12). This NP, however, was not stable. The NP structure dissolved after it was kept in 5% $CO_2$ at 37° C. for 16 h. At 0 h, the hydrodynamic diameter of the NP sample was 71.94±20.81 nm according to DLS measurement (the major peak by number distribution); after 16 h of incubation, the hydrodynamic diameter of the sample became 8.39±1.20 nm, which was similar to the diameters of soluble iTEPs (FIG. 16B) (Cho et al., J Drug Target, 2015; p 1-12). This NP is referred to as the marginally stable NP (MS-NP).

Figure 16B:
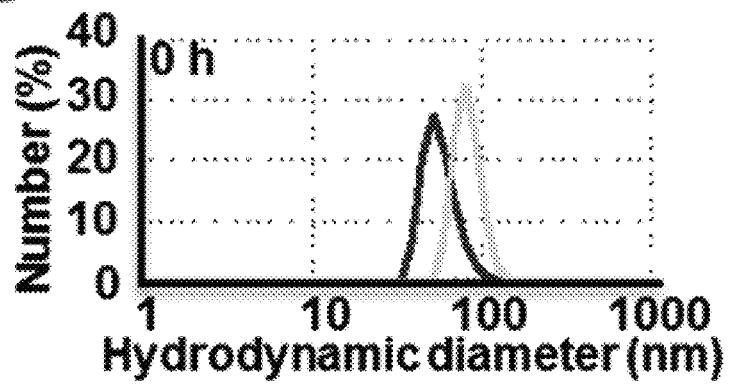
Figure 16B:
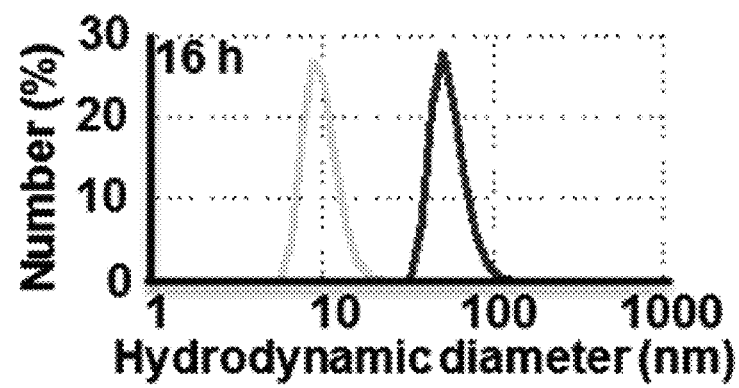
Figure 16C:
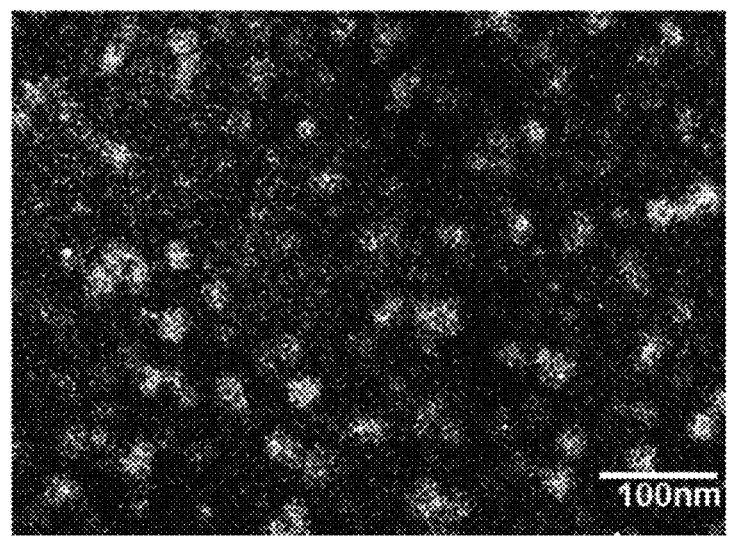
Figure 16D:
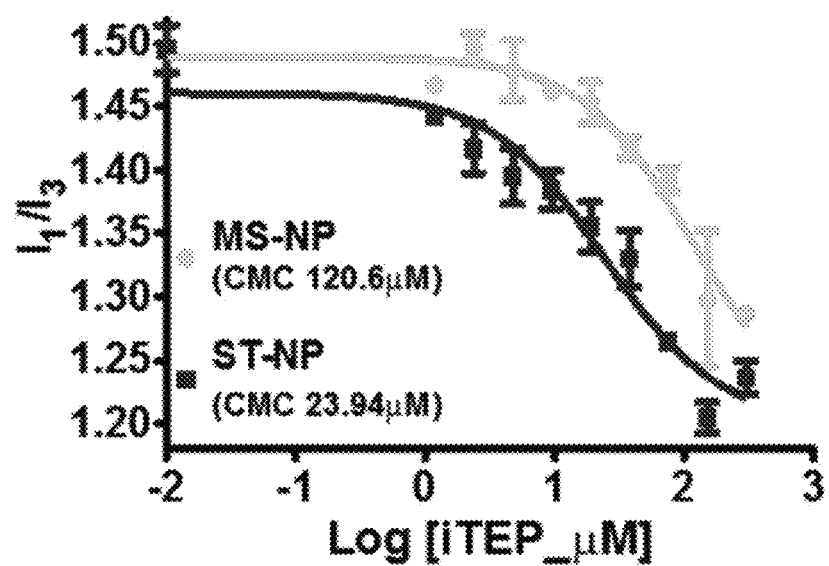
Figure 17A:
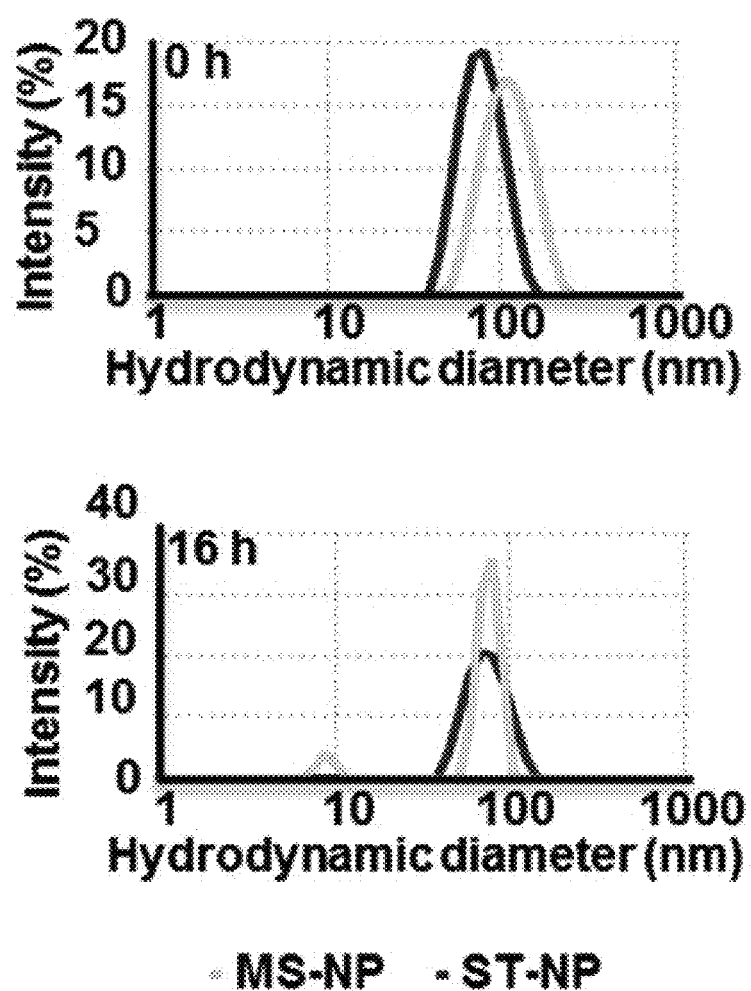
FIGS. 17A-B show the difference between the MS-NP and the ST-NP using sizes-by-intensity data from DLS measurements.

To test whether the benefit of the MS-NP could be expanded, if a more stable NP was used, a new amphiphilic iTEP diblock copolymer fused with the SIINFEKL (SEQ ID NO: 22) vaccine, $iTEP_{B70}$-$iTEP_{A56}$-pOVA (SEQ ID NO: 60) (FIG. 16A) was generated. This new fusion had a longer hydrophobic block than the fusion used for the MS-NP, $iTEP_{A56}$ versus $iTEP_{A28}$. According to DLS analysis, $iTEP_{B70}$-$iTEP_{A56}$-pOVA (SEQ ID NO: 60) formed a NP with a hydrodynamic diameter of 56.01±13.54 nm (the major peak by number distribution) (FIG. 16B). The size of this NP is comparable to the MS-NP. The TEM images of this new fusion also confirmed its particle structure (FIG. 16C). The new fusion kept its particle structure after incubation in cell culture medium in 5% $CO_2$ at 37° C. for 16 h (diameter, 55.36±12.88 nm) (FIG. 16B), indicating the particle of the new fusion is more stable than the MS-NP. The NP of this new fusion referred to as the stable NP or ST-NP. The measurements were obtained by DLS. Z-averages for MS-NP and ST-NP were 101.00 nm and 74.59 nm before the incubation. Z-averages for MS-NP and ST-NP were 422.90 nm and 70.42 nm after the incubation. The difference between the MS-NP and the ST-NP was confirmed when sizes-by-intensity data from DLS measurement were used for analysis (FIG. 17). The data were collected by DLS before (0 h) and after (16 h) the NPs were incubated at 37° C. for 16 h. Before the incubation, the diameters for MS-NP and ST-NP were 111.90±35.02 nm and 78.56±21.60 nm, respectively. After the incubation, ST-NP had a diameter of 74.45±18.99 nm; the MS-NP had two peaks: 75.47±9.75 nm (92.2%) and 8.86±0.90 nm (7.8%). To further compare the stability of the MS-NP and the ST-NP, their critical micelle concentrations (CMCs) were measured by a pyrene assay. Results of the assay revealed that the CMC of the MS-NP was 120.6 µM and the CMC of the ST-NP was 23.94 µM (FIG. 16D). The CMC results also suggested that the ST-NP was more stable than the MS-NP.

Example 13: The ST-NP Fails to Expand the Benefit of the MS-NP to CTL Vaccines and DCs Internalize the ST-NP Fluorescent labeling of iTEP-vaccine fusions. For the flow cytometry study, the fusions were labeled with the amine-reactive coumarin, 7-diethylaminocoumarin-3-carboxylic acid, through succinimidyl ester to form blue-fluorescent bioconjugates. For the microscopy-based cellular uptake study and the cellular degradation study, the fusions were labeled with Alexa Fluo 488 5-SDP ester (Alexa-488) to form green-fluorescent bioconjugates. The reactions were performed based on the manufacturer's instructions (Molecular Probes by Life Technologies). Briefly, 10 mg of iTEPs were reacted with 1 mg of coumarin or 0.2 mg of Alexa-488 in 0.1 M sodium bicarbonate buffer, pH 8.3 at a final volume of 1 mL. The reaction was carried out with continuous stirring in the dark and at room temperature for 1.5 h. The protein-dye conjugates were purified using Amicon Ultra1-5 (10k) centrifugal filters (Millipore). The coumarin conjugate was measured for their absorbances of at 205 nm ($A_{205}$) and 433 nm ($A_{433}$, λmax for coumarin); the Alexa-488 conjugate was measured at 205 nm and 495 nm ($A_{495}$, λmax for Alexa-488). The iTEP-vaccine fusion concentrations and the degree of labeling (DOL) were calculated based on these equations:

$$iTEP\text{-vaccine concentration (mg/mL)} = \frac{A205}{31(\varepsilon \text{ of } iTEP \text{ vaccine at } A205) \times 1(\text{path length})}$$

$$DOL_{coumarin} = \frac{A433 \times MW \text{ of } iTEP \text{ vaccine}}{iTEP\text{-vaccine concentration (mg/mL)} \times 59000(\varepsilon \text{ of dye})}$$

$$DOL_{Alexa-488} = \frac{A495 \times MW \text{ of } iTEP \text{ vaccine}}{iTEP\text{-vaccine concentration (mg/mL)} \times 71000(\varepsilon \text{ of dye})}$$

where $\varepsilon$ is the extinction coefficient in $cm^{-1} M^{-1}$. $DOL_{coumarins}$ for the coumarin conjugate were between 8-10% and adjusted to 3% by adding the corresponding, unlabeled iTEP-vaccines fusions before usage. $DOL_{Alexa-488s}$ for Alexa-488 conjugate were between 0.02-0.03% and adjusted to 0.02% before usage.

Presentation of SIINFEKL epitope vaccine by DCs. The presentation was studied as previously described (Cho et al., J Drug Target, 2015; p 1-12). The concentration of iTEP-vaccine fusions (NPs) used in this experiment was 5 µM. The results of presentation were shown as mean fluorescence intensity (MFI) of 5000 treated, live cells in a given treatment, which were normalized to the MFI value of untreated DC2.4 cells.

Activation of B3Z hybridoma (CD8+T) cells. This assay was done with a protocol described previously (Cho et al., J Drug Target, 2015; p 1-12).

Cellular uptake of iTEP-vaccine fusions. DC2.4, EA.hy926, bEnd.3, 3T3 cells were plated at $1.5 \times 10^5/500$ µL/well in 24-well plates. When the cells attached to the bottom of the plate (4 h or overnight), the media was replaced with 500 µL of fresh media with or without 5 µM of coumarine labeled iTEP-vaccine fusions. After being cultured for 4 h at 37° C. in 5% $CO_2$, the cells were collected and washed twice with PBS. The fluorescence of the cells was measured by flow cytometry (collecting $5 \times 10^4$ events per sample).

For the florescent microscopy, DC 2.4 cells were seeded onto a 12 mm glass coverslip-bottomed 24-well plate at 250,000 per well in complete RPMI-1640 medium. When the cells reached 80% confluence, they were washed with warm medium followed by incubation with 5 M of iTEP-vaccine fusions at 37° C. for 1 to 4 h. Then the cells were rinsed twice with warm medium, and incubated with 75 nM of LysoTracker Red DND-99 (Invitrogen, USA). Afterwards, the cells were washed twice with PBS and fixed with 4% of paraformaldehyde. The cells were mounted on a glass slide and imaged using a Nikon ECLIPSE Ti (Nikon Instruments Inc., USA).

Animal immunization. C57BL/6 mice were immunized by the subcutaneous injection of 2 nmol iTEP NP vaccines and incomplete Freunds Adjuvants (IFA; Sigma, USA) at their left flanks. Immunization was repeated at their right flanks after 1 week. On day 10 after the second immunization, mice were sacrificed, and the spleens were harvested.

Figure 18A:
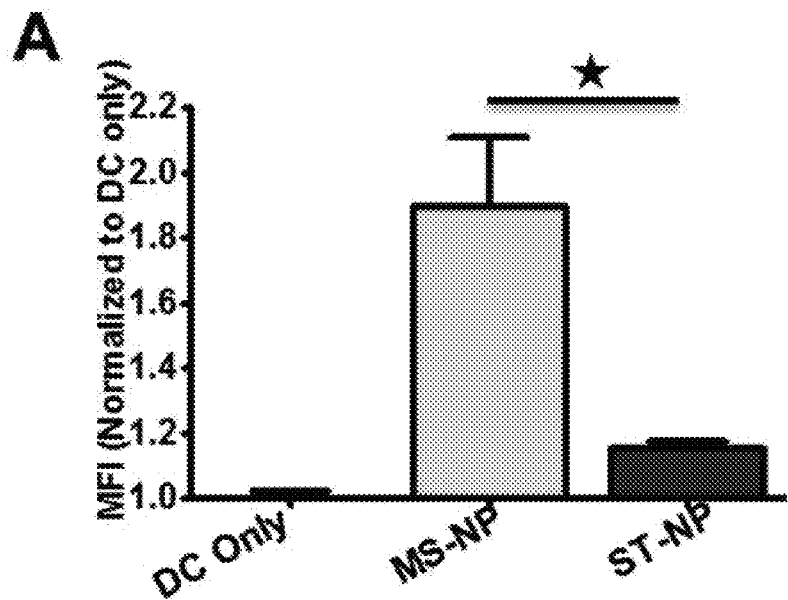
FIGS. 18A-D show that the ST-NP fails to expand the benefit of the MS-NP to CTL vaccines and DCs internalize the ST-NP.
Figure 18B:
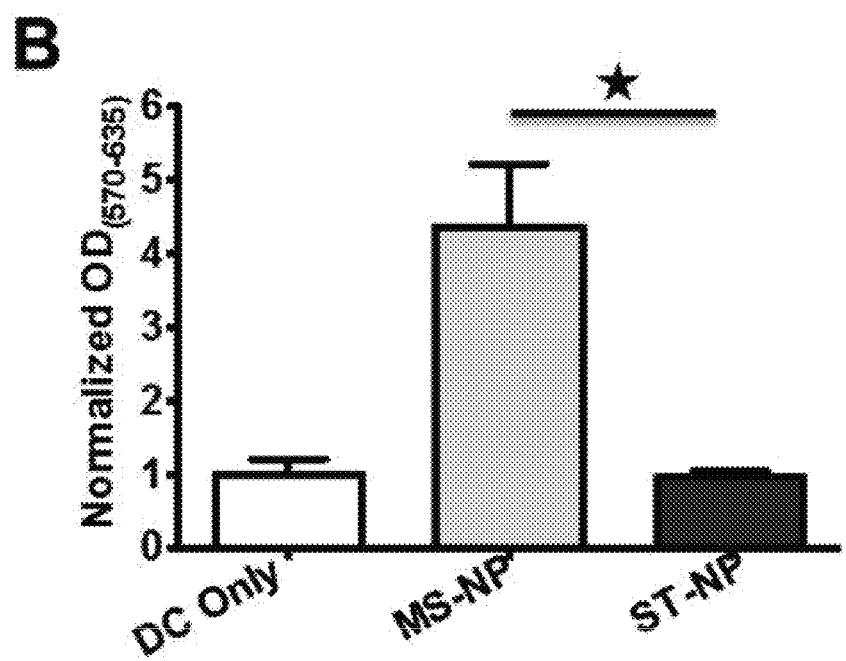
Figure 18C:
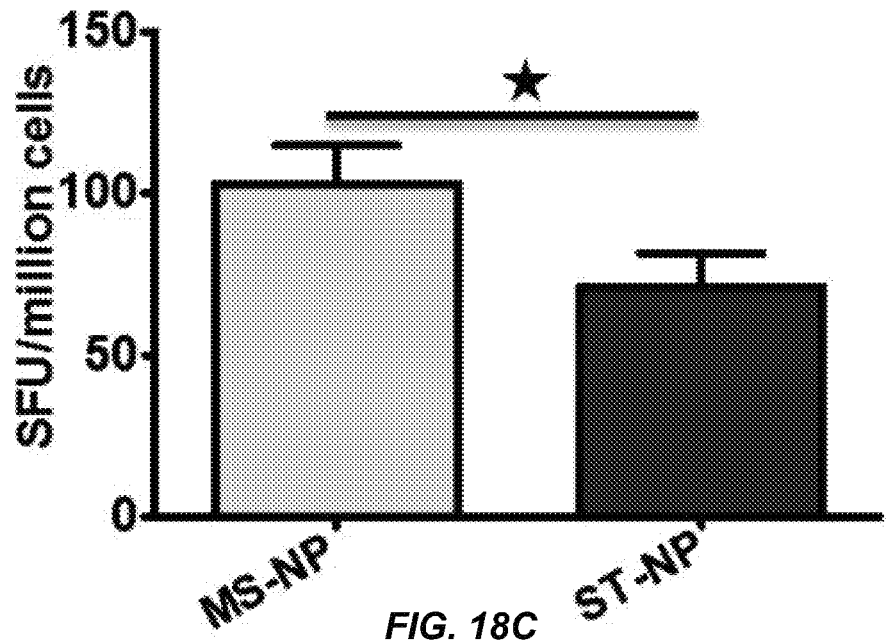

Results. In vitro and in vivo activity of the SIINFEKL (SEQ ID NO: 22) vaccine that was delivered by the ST-NP and the MS-NP was compared. First, the SIINFEKL (SEQ ID NO: 22) epitope presentation by DCs was assessed after the cells were treated with the ST-NP or the MS-NP. The results of the assessment showed that the ST-NP led to a significantly weaker presentation than the MS-NP (FIG. 18A). Second, the activation of B3Z cells after the cells were incubated with the DCs that were pretreated with either the ST-NP or the MS-NP was compared. B3Z cells are a genetically engineered CD8+ T cell hybridoma line restricted to the H-2K$^b$/SIINFEKL complex (Karttunen et al., Proc Natl Acad Sci USA, 1992; 89(13):6020-4). The results show that the ST-NP was much less robust in activating B3Z cells than the MS-NP (FIG. 18B). Last, C57BL/6 mice were immunized using either the ST-NP or the MS-NP and then the SIINFELKL-specific CTL response the NPs induced was examined. The ST-NP did elicite the response. The response, however, was significantly weaker than the one elicited by the MS-NP (FIG. 18C). The activation of the cells was evaluated by an IFNγ-based ELISPOT assay.

Figure 18D:
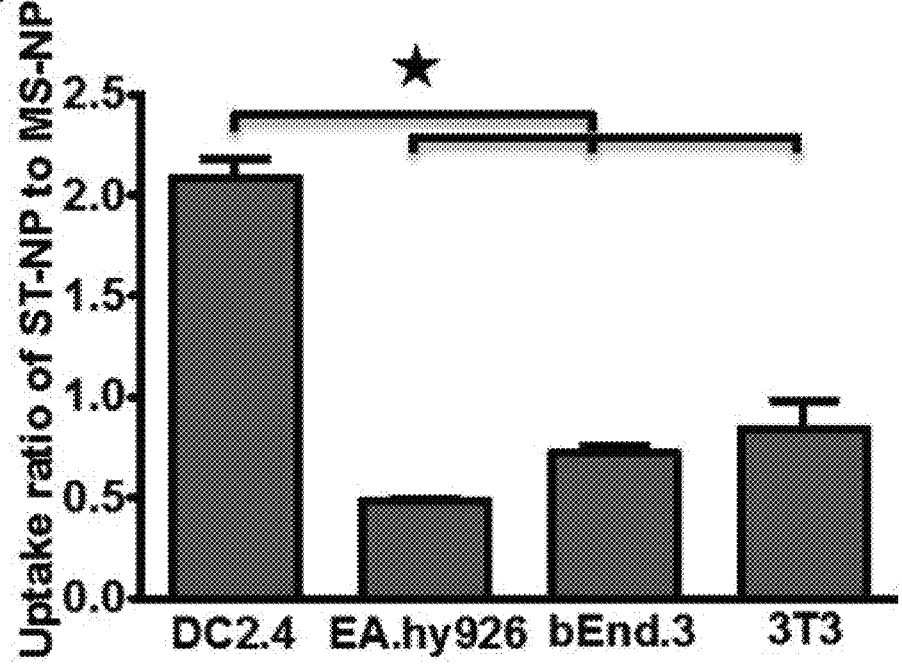

Although the MS-NP is better than the ST-NP in promoting SIINFEKL (SEQ ID NO: 22) presentation, B3Z activation, and in vivo CTL responses, it was observed that the superiority was much weaker in the CTL responses than the presentation and the B3Z activation (FIG. 18C versus FIG. 18A or 18B). The discrepancy between the in vitro and in vivo results suggested that the ST-NP might have certain unrevealed advantages over the MS-NP in vivo. It was hypothesized that one advantage of the ST-NP is that DCs uptake the ST-NP over the MS-NP. The uptake of the MS-NP and the ST-NP by DCs and other cells were compared. The results show that DCs internalized two times more of the ST-NP than the MS-NP (FIG. 18D). The uptake ratios between ST-NP and MS-NP by a given cell type are presented as MFI ratios of the cells after they were incubated with fluorescence-labeled ST-NPs and MS-NPs, respectively. In contrast, endothelial cells (EA.hy926 and bEnd.3) and fibroblasts (3T3) internalized either the same amount or less of the ST-NP than the MS-NP. These observations suggested that DCs but not other common cells in the body favored the uptake of particles. The ST-NP is more stable that the MS-NP, therefore, the ST-NP sample should have more iTEP-vaccine fusion molecules in NP structure than the MS-NP sample during above uptake study, resulting in more uptake of the ST-NP sample over the MS-NP sample. Practically, the NP structure exerts a passive DC-targeting effect.

Since the ST-NP was better than the MS-NP for DC uptake, the low SIINFEKL (SEQ ID NO: 22) presentation and B3Z activation associated with the ST-NP must be due to inefficient processing of the NP in DCs. Because the stability is the major difference between the ST-NP and the MS-NP, it is plausible to link the impeded intracellular processing of the ST-NP with the high stability of the NP. It is possible that the high stability prevents the dissociation of the NP inside DCs. Without the dissociation, the linkage between pOVA and iTEP will not be exposed to s-proteasomes and immunoproteasomes in DCs since pOVA is in the hydrophobic core of the ST-NP. Thus, the SIINFEKL (SEQ ID NO: 22) epitope cannot be effectively released from the ST-NP.

Example 14: Generation of an iTEP NP Carrier Having a Reductive Environment-Responsive Stability Quantification of free sulfhydryl groups of RED-NP after reducing treatments. Twenty mg of RED-NP were dissolved in 2 mL of $H_2O$ and treated with 1 mM of GSH for 16 h. The solution was then dialyzed (membrane cutoff MW: 3,500 Dalton) in deionized water at 4° C. for 24 h. Then the sample was concentrated to 0.5 mL using Amicon centrifugal filter devices (Millipore, USA). Numbers of free sulfhydryl groups of RED-NP were determined by Ellman's method. Briefly, 250 µL of sample and 50 µL of Ellman's reagent (Thermo Scientific, USA) were added to 2.5 mL of reaction buffer (0.1 M sodium phosphate, pH 8.0, 1 mM EDTA). After 15 min of incubation at room temperature, the $OD_{412}$ was measured. To generate a standard curve of free sulfhydryl groups, $OD_{412}$ of serial dilutions of cysteine hydrochloride monohydrate was measured. The serial $OD_{412}$ values were plotted against concentrations of cysteine hydrochloride monohydrate to generate a standard curve. Concentrations of free sulfhydryl groups in the RED-NP samples were determined from the standard curve and used to calculate numbers of free sulfhydryl groups per iTEP-vaccine fusion molecules.

Figure 17B:
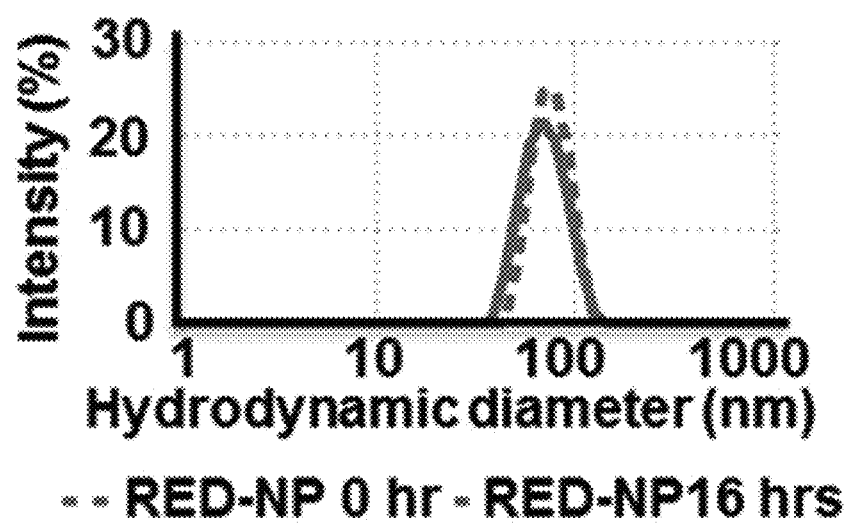
Figure 19A:
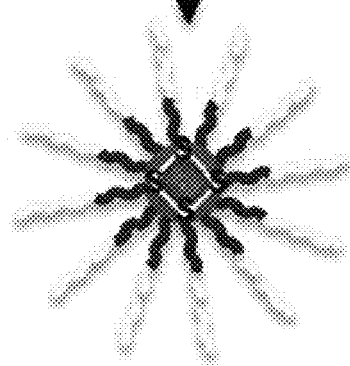
FIGS. 19A-H show the results of generating an iTEP NP carrier having a reductive environment-responsive stability.
Figure 19B:
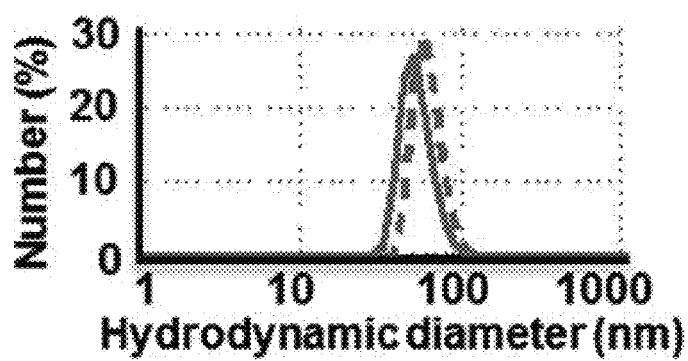
Figure 19C:
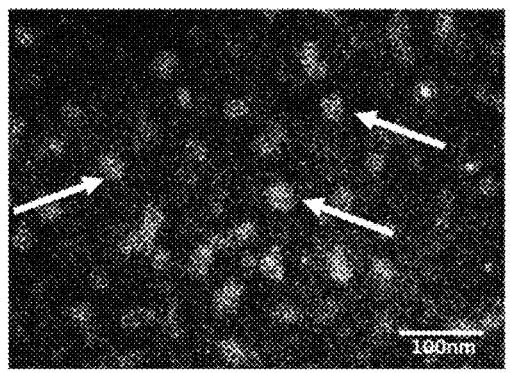

Results. Based on comparisons between the ST-NP and the MS-NP, it was thought that a more effective carrier of CTL peptide vaccines should be the one that is as stable as the ST-NP during its systematic circulation in the body but becomes as unstable as the MS-NP after its internalization by DCs. To generate such a carrier, the MS-NP was modified by forming disulfide bonds inside the NP and using the bonds to stabilize the NP (FIG. 19A). The new NP was expect to behave as a stable NP unless its disulfide bonds were reduced in a reductive environment such as cytosol (Smith et al., Toxicol Appl Pharmacol, 1996; 140(1):1-12; Wu et al., J Nutr, 2004; 134(3):489-92). Specifically, four cysteines were inserted between the amphiphilic copolymer $iTEP_{B70}$-$iTEP_{A28}$ (SEQ ID NO: 54) and pOVA and separated the adjacent cysteines by eight glycines. The resultant iTEP fusion, $iTEP_{B70}$-$iTEP_{A28}$-$(G_8C)_4$-pOVA (SEQ ID NO: 61), self-assembled in a NP according to a DLS measurement of the fusion (FIG. 19B). The NP had a hydrodynamic diameter of 61.94±12.71 nm (the major peak by number distribution) and maintained its particle structure after an overnight incubation in cell culture medium in 5% $CO_2$ at 37° C. The hydrodynamic diameter after the incubation was 53.05±12.38 nm (FIG. 19B). Z-averages for RED-NP before and after the incubation were 87.59 nm and 76.89 nm, respectively. The same conclusion was reached when sizes-by-intensity data were used for the analysis (FIG. 17B). The TEM image of the $iTEP_{B70}$-$iTEP_{A28}$-$(G_8C)_4$-pOVA fusion (SEQ ID NO: 61) also confirmed the particle structure of the fusion (FIG. 19C).

The next set of experiments tested whether disulfide bonds inside the new NP were reducible and if the NP structure was dissolvable in a reductive environment like cytosol (glutathione, GSH 1-10 mM) (Smith et al., Toxicol Appl Pharmacol, 1996; 140(1):1-12; Wu et al., J Nutr, 2004; 134(3):489-92). The new NP and the ST-NP were treated using two concentrations of GSH, at 37° C. overnight and then analyzed particle structure changes of both NPs by DLS. These concentrations mimic GSH concentrations in either cytoplasm (GSH 1-10 mM) or the extracellular (GSH 1-10 µM) environment (Smith et al., Toxicol Appl Pharmacol, 1996; 140(1):1-12; Cantin et al., Appl Physiol (1985), 1987, 63(1):152-7; Jones et al., Clin Chim Acta, 1998; 275(2):175-84). Both NPs were stable at 10 µM of GSH. The new NP lost its particle structure after being treated with 1 mM of GSH (Table 4). Consistent with this result, free sulfhydryl groups increased, on average, from zero per iTEP molecule to two per iTEP molecule after the treatment of 1 mM of GSH. In contrast, the ST-NP, as a control, maintained its particle structure regardless of its incubation with any concentration of GSH. Similar results emerged when dithiothreitol (DTT) was used as the reductant except that the new iTEP-NP was not stable in 10 µM of DTT (Table 4). The drastic difference between the new NP and the ST-NP suggested that the new NP had stability responsive to the reductive environment. The new NP was named the reductive-environment dependable NP or RED-NP.

TABLE 4

Comparison of ST-NP and RED-NP for their response to reductants.

| Reductant concentration (µM) | ST-NP | RED-NP |
|---|---|---|
| | Hydrodynamic diameter (nm) | |
| 0 | 54.82 ± 12.89 (NP) | 47.11 ± 13.18 (NP) |
| GSH 10 | 52.23 ± 13.59 (NP) | 37.98 ± 6.72 (NP) |
| 1000 | 50 ± 13.62 (NP) | 8.35 ± 1.04 |
| DTT 10 | 52.56 ± 13.67 (NP) | 8.75 ± 2.03 |
| 1000 | 53.10 ± 13.56 (NP) | 6.43 ± 2.01 |

ST-NP and RED-NP were treated with or without reductants for 16 hours.
Hydrodynamic diameters by number distribution of these two NPs were compared.

Figure 20A:
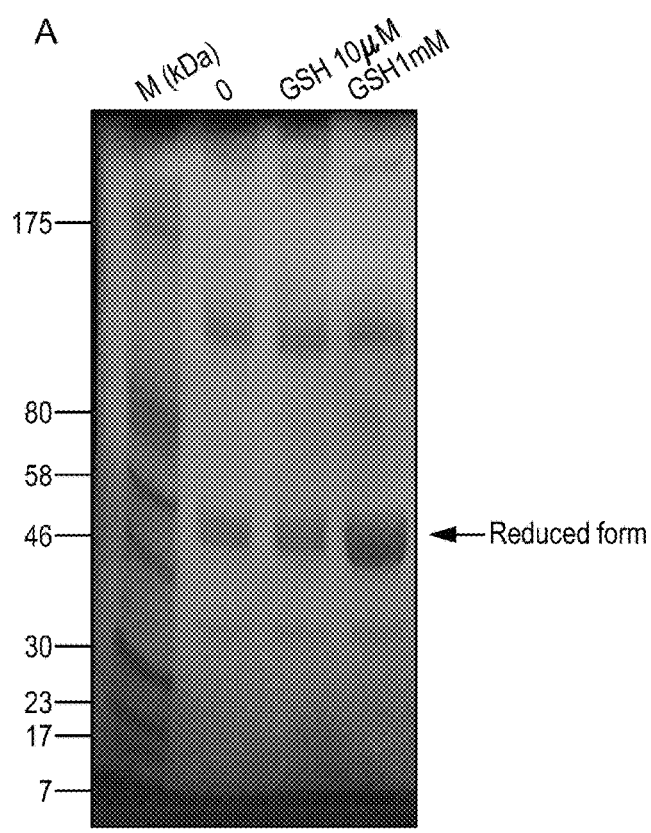
FIG. 20A-B shows SDS-PAGE analyses of RED-NP (A) as well as MS-NP and ST-NP (B) after these NPs were treated with different concentrations of GSH overnight.
Figure 20B:
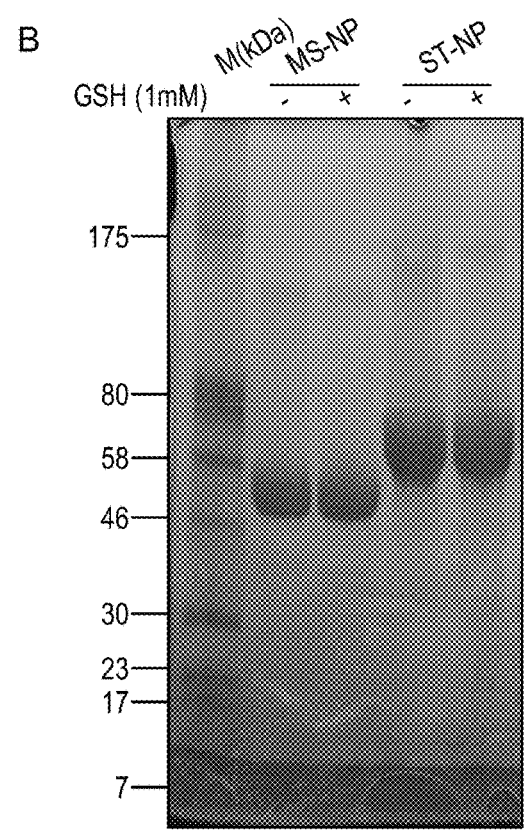

SDS-PAGE was used to analyze responses of the RED-NP, the MS-NP, and the ST-NP to the treatment of 1 mM GSH. 1 mM but not 10 µM of GSH reduced disulfide bonds inside RED-NP. A large fraction of polymers of the RED-NP fusion ($iTEP_{B70}$-$iTEP_{A28}$-$(G_8C)_4$-pOVA; (SEQ ID NO: 61)) became monomers due to the treatment of 1 mM GSH, showing as a 50-kDa band on the gel. In contrast, GSH had no effect on polymerization status of the fusions of MS-NP and ST-NP. Non-reducing gels and 25 μg of each fusion were used for the analysis. The results show that the RED-NP can be reduced by 1 mM but not by 10 μM of GSH (FIG. 20). In contrast, the MS-NP and the ST-NP did not respond to the treatment (FIG. 20). This result reinforced the aforementioned conclusion.

Figure 19D:
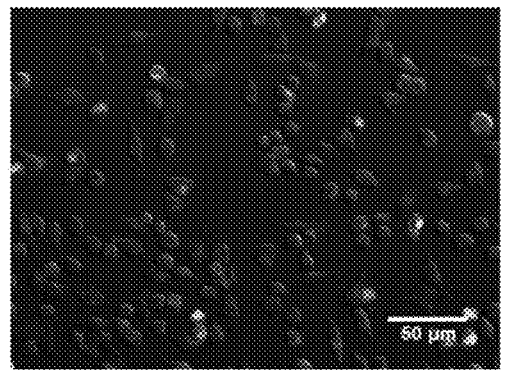
Figure 19E:
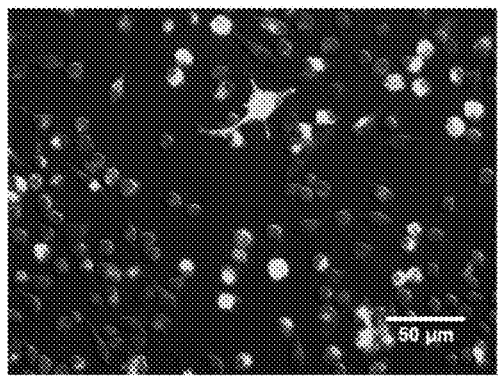
Figure 19F:
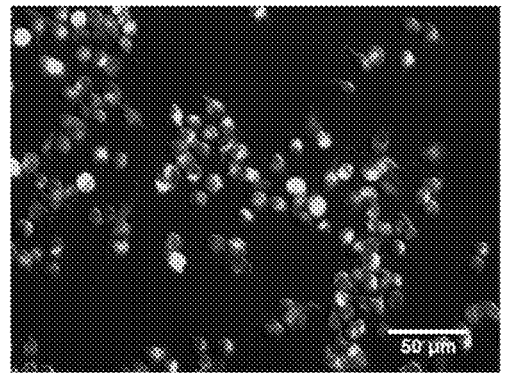
Figure 19G:
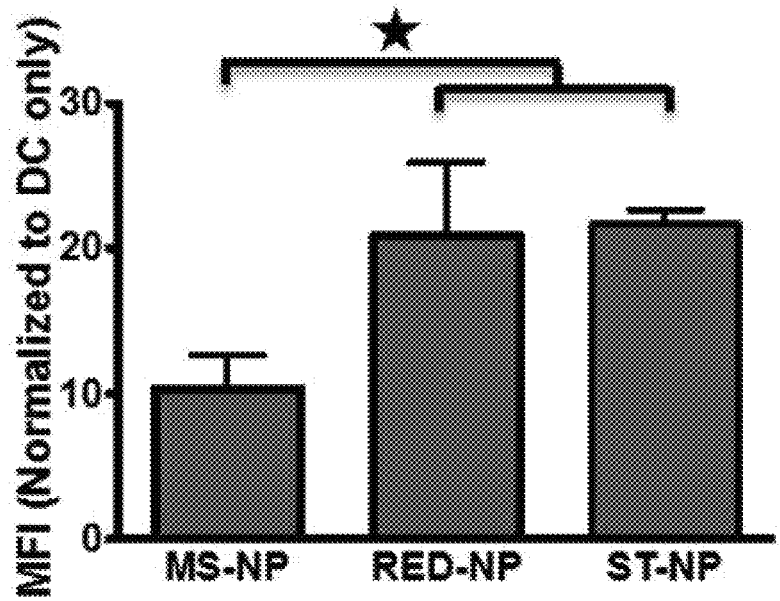
Figure 19H:
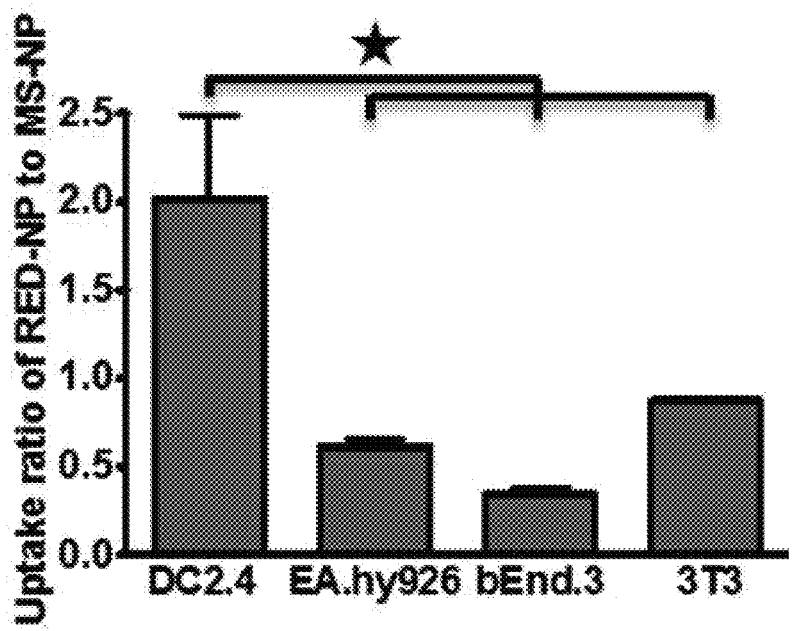
Figure 21A:
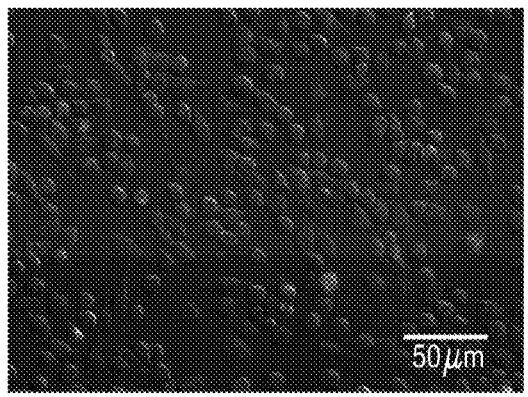
FIGS. 21A-C show the fluorescence microscopy of MS-NP (A), ST-NP (B) and RED-NP (C) that were internalized by DC2.4 cells.
Figure 21B:
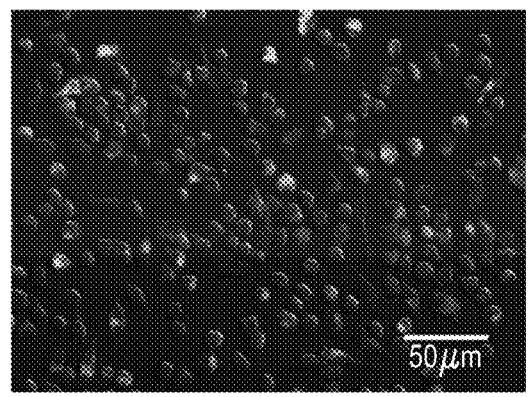
Figure 21C:
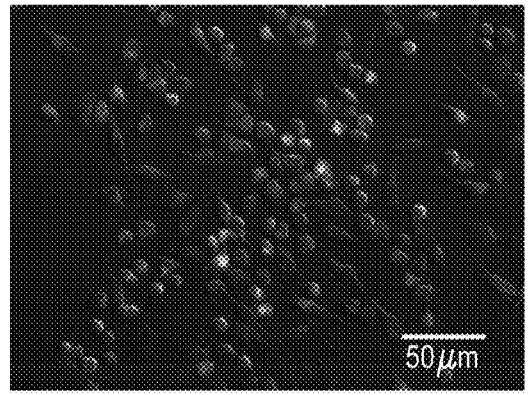

Lastly, the next set of experiments investigated whether DCs would internalize the RED-NP as efficiently as the ST-NP, or as inefficiently as the MS-NP. The results show that the internalization of the RED-NP to DCs was as efficient as the ST-NP and more robust than the MS-NP according to both fluorescence microscopy results (FIG. 19D-F for 4 h of uptake and FIG. 21 for 1 h of uptake; Alexa-488 labeled NPs were incubated with DCs for 4 h before imaging) and flow cytometry results (FIG. 19G). In addition, DCs, but not endothelial and fibroblasts, preferentially internalized the RED-NP over the MS-NP (FIG. 19H), which was similar to the ST-NP (FIG. 18D). Therefore, the RED-NP has a passive DC-targeting capability, just as the ST-NP.

Example 15: The RED-NP is a More Effective Vaccine Carrier than Both the ST-NP and the MS-NP The methods used to generate the results described below are described herein.

Figure 22A:
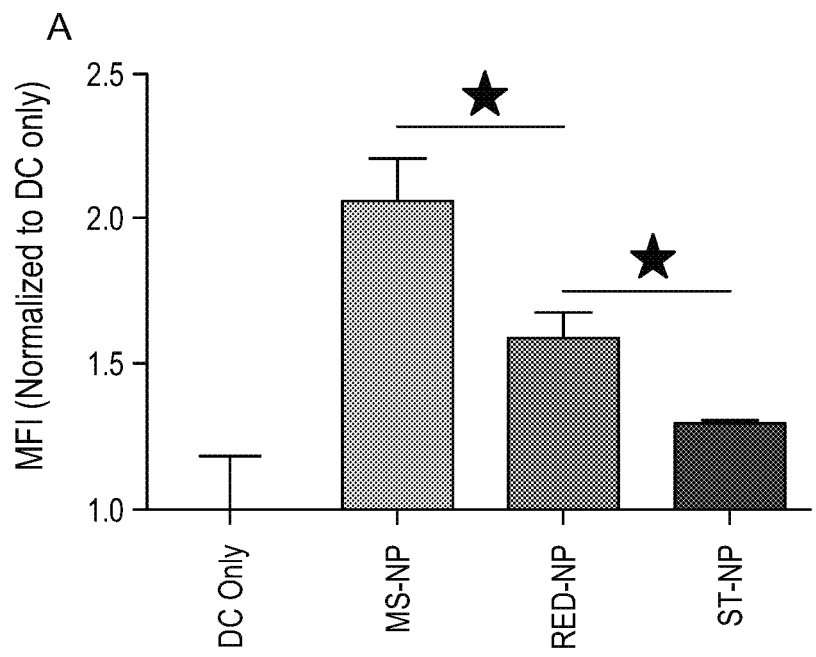
FIGS. 22A-C show that the RED-NP is a more effective vaccine carrier than ST-NP or MS-NP.
Figure 22B:
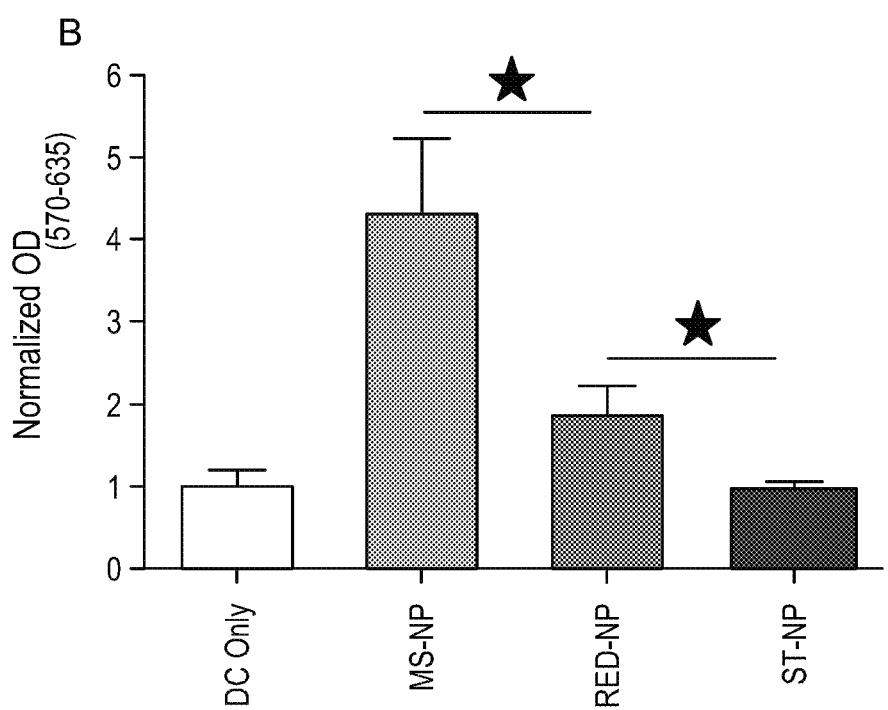
Figure 23A:
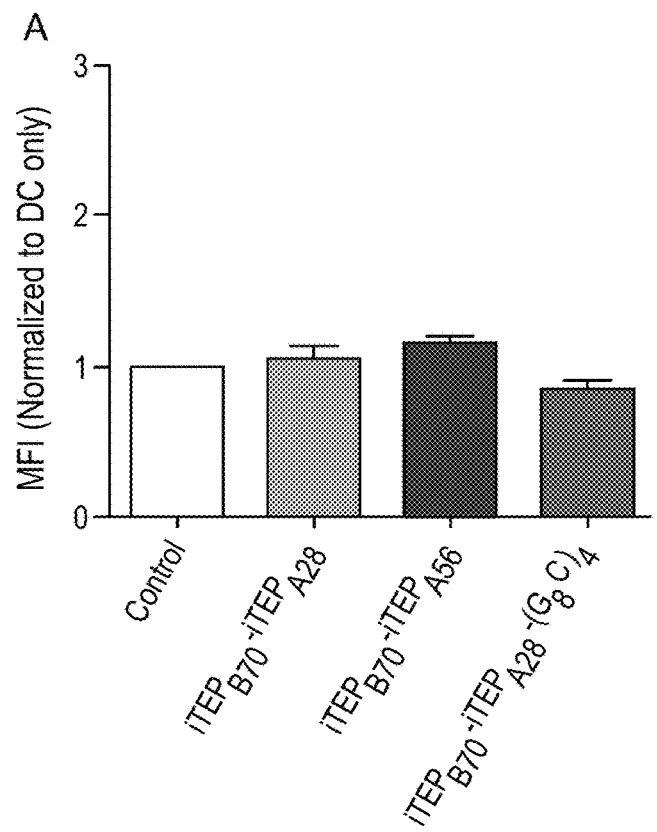
FIGS. 23A-B show the results of incubations with empty carriers.
Figure 23B:
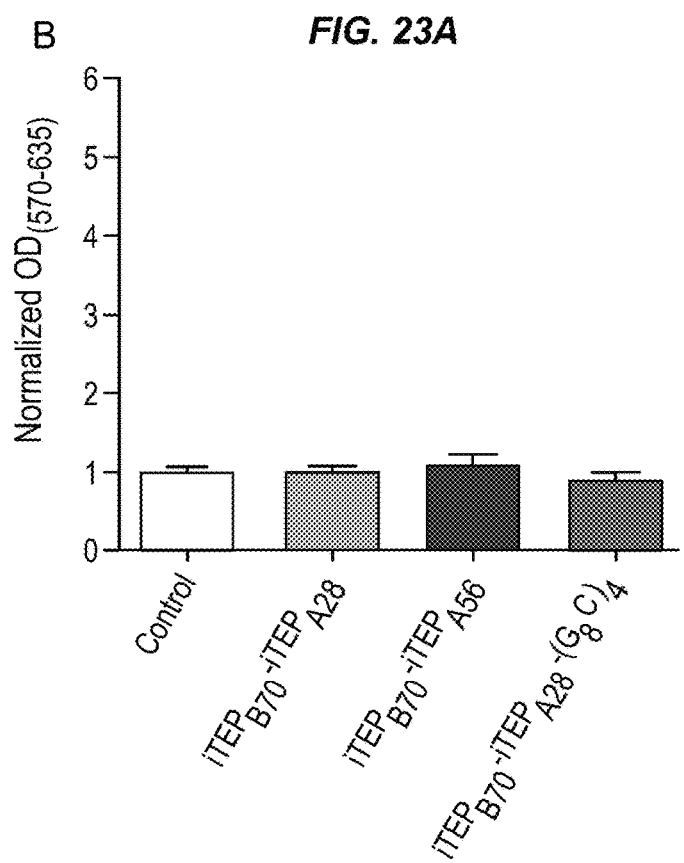
Figure 24A:
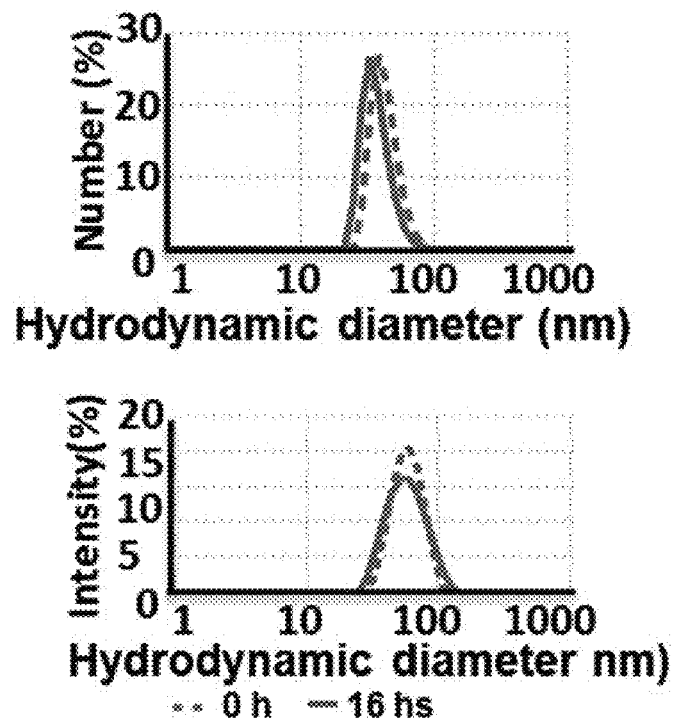
FIGS. 24A-D show that RED-NP2 is similar to RED-NP and superior to MS-NP in vivo.
Figure 24B:
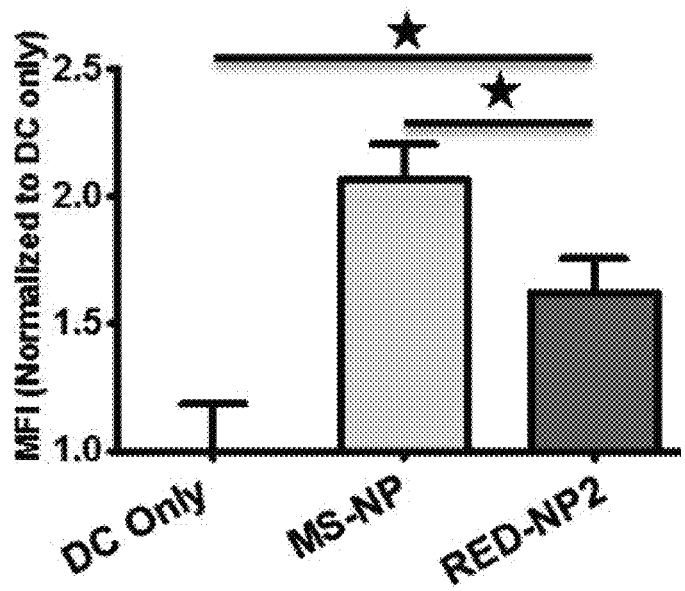
Figure 24C:
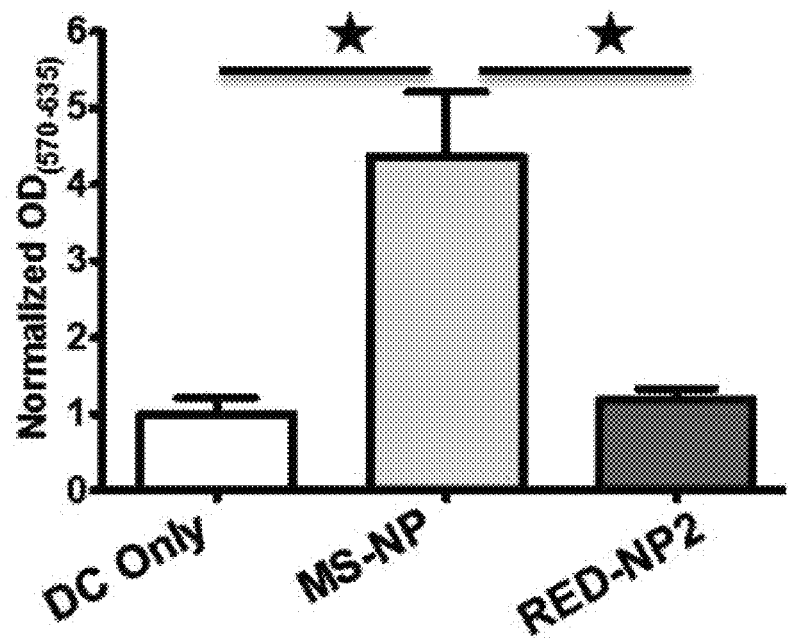
Figure 24D:
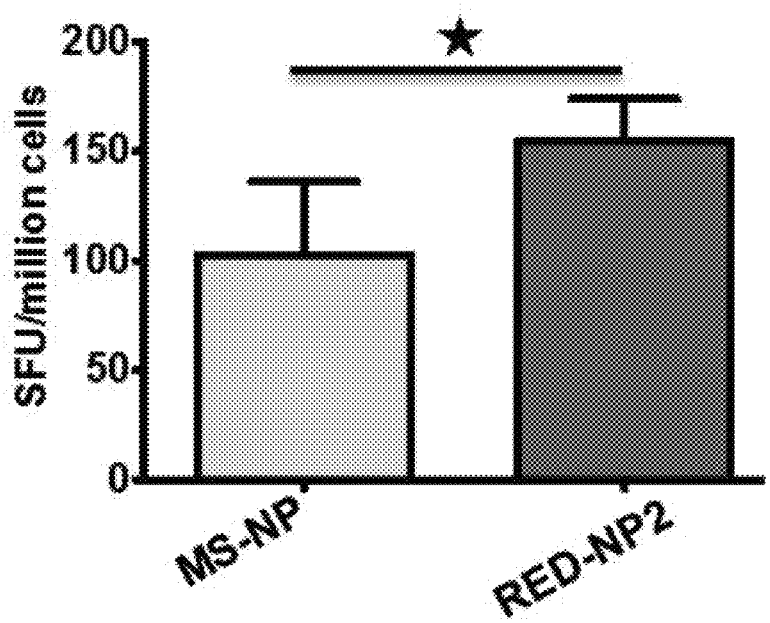

Results. The effects of the RED-NP, the MS-NP, and the ST-NP on CTL epitope presentation by DCs were compared. Although the SIINFEKL (SEQ ID NO: 22) epitope delivered by the RED-NP was not presented as well as when it was delivered by the MS-NP, the presentation that resulted from the RED-NP was significantly better than that of the ST-NP (FIG. 22A). The comparative results implied that the environment-dependent stability of the RED-NP facilitated processing and presentation of its vaccine payloads by DCs. On the other hand, there was a gap between the presentation results of the RED-NP and the MS-NP, indicating the reduction of the disulfide bonds inside the RED-NP may not be complete so that not all the RED-NP behaved like the MS-NP. Consistent with the presentation results, the RED-NP failed to activate B3Z cells as effectively as the MS-NP but, again, fared better than the ST-NP (FIG. 22B). It is worth noting that all these DC presentation and B3Z activation results were SIINFEKL vaccine-specific since incubations of empty carrier NPs with DCs and B3Z cells did not lead to any antigen presentation or T cell activation (FIG. 23).

Figure 22C:
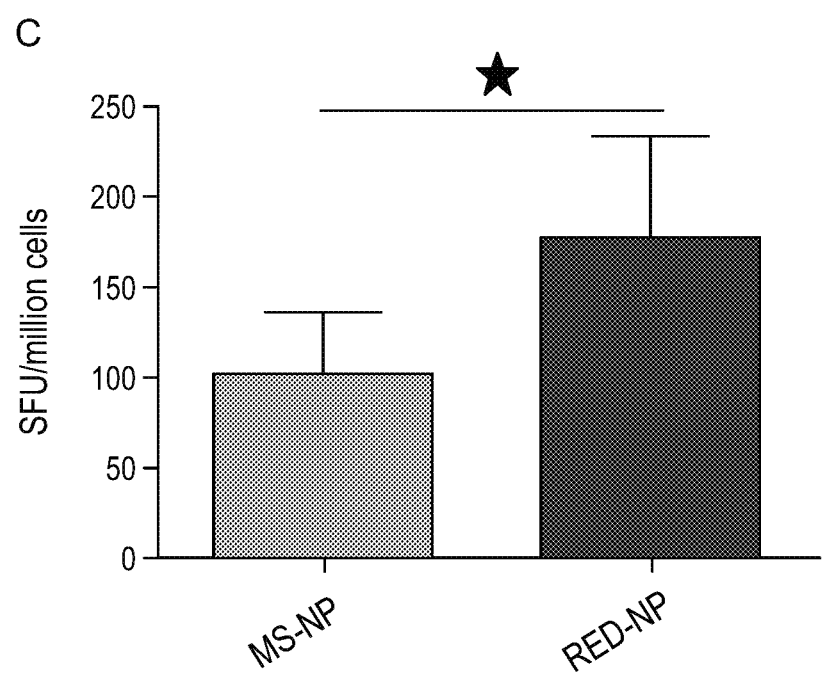

When the mice were immunized with either the RED-NP or the MS-NP and their induced CTL responses were compared, it was found that the RED-NP outperformed the MS-NP and induced stronger CTL responses to the SIINFEKL epitope (SEQ ID NO: 22) (FIG. 22C). It was noteworthy that another reductive environment-dependent NP, RED-NP2 (assembled from the fusion, iTEP$_{B70}$-iTEP$_{A28}$-(G$_1$C)$_4$-pOVA) (SEQ ID NO: 62) brought about similar results as RED-NP and was also superior than the MS-NP in vivo (FIG. 24). For instance, the hydrodynamic diameter values were 42.49±10.23 nm (by number), 59.15±15.32 nm (by intensity), and 89.25 (Z-average) before the incubation; the values were 36.75±9.56 nm (by number), 58.95±19.53 nm (by intensity), and 54.81 (Z-average) after the incubation.

Figure 25A:
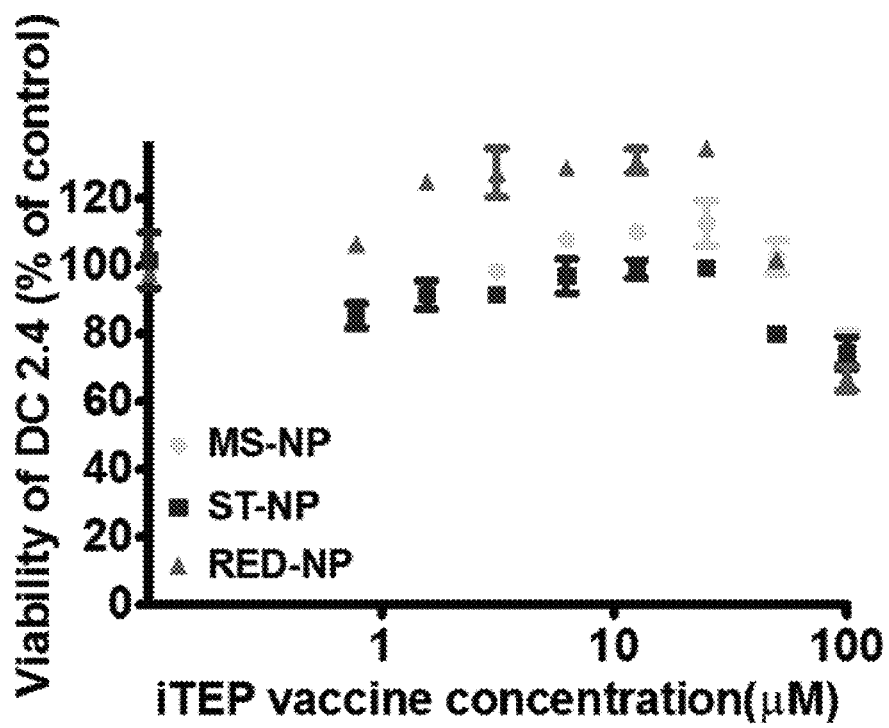
FIGS. 25A-B show that iTEP-vaccine fusions are not cytotoxic.
Figure 25B:
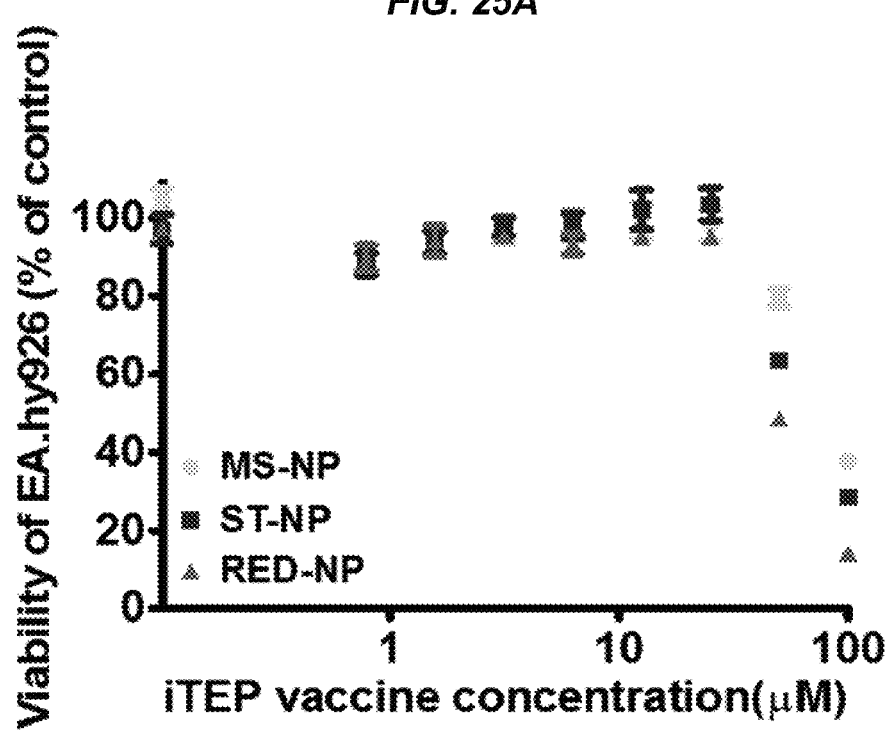

Table 5 summarizes the stability, uptake, and CTL responses of the three iTEP NPs. Among the NPs, RED-NP, the one that had a changeable stability between the extracellular non-reductive and the cytosolic reductive environments was the most effective in delivering CTL peptide vaccines. It was noted that all three NPs together with their vaccines were safe. They were not toxic to DC 2.4 cells or EA.hy926 cells even at 50 μM (FIG. 25). They did not cause any adverse response during the lengthy vaccination study.

TABLE 5

Summary of stability, uptake and CTL responses of three different iTEPs

| | Fusion design | Stability | Uptake by DC 2.4 cells | CTL response (in vitro) | CTL response (in vivo) |
|---|---|---|---|---|---|
| MS-NP SEQ ID NO: 56 | iTEP$_{870}$-iTEP$_{A28}$-pOVA | + | + | +++ | ++ |
| ST-NP SEQ ID NO: 60 | iTEP$_{870}$-iTEP$_{A56}$-pOVA | ++ | ++ | + | + |
| RED-NP SEQ ID NO: 61 | iTEP$_{870}$-iTEP$_{A28}$-(G$_8$C)$_4$-pOVA | ++ (unstable under reductive environment) | ++ | ++ | +++ |

Example 16: The RED-NP is Trafficked to Cytosol and Degraded

Since the RED-NP has a stable response to a reductive environment and performed better than the ST-NP in vaccine delivery, it is very likely that the RED-NP reached the reductive the cytosol during the intracellular trafficking and leveraged the reductive environment of cytosol. The next set of experiments tested whether the RED-NP was trafficked to the cytosol and degraded. To carry out this study, the intracellular partition of RED-NP was assessed after it was internalized by DCs.

Results. After 1 h incubation of RED-NP with DCs, a sizeable fraction of the internalized NPs had reached the cytosol while the remaining NPs were in the phagolysosomes (FIG. 26A). This observation suggests a fairly fast escape of the NP from the phagolysosomes to the cytosol of DCs. It was also found that processing and degradation of RED-NP happened quickly inside DCs. The integrity of intracellular RED-NP by SDS-PAGE was analyzed after the NP was incubated with DCs for 1 h (FIG. 26B). Cell lysate was collected at different time points after the incubation. iTEP-vaccine fusions of RED-NP showed a ~50 kDa band on the SDS-PAGE gel immediately after the incubation. This band, however, mostly faded away within 30 min after the incubation. At 1 h after incubation, this band disappeared completely. The fast degradation is consistent with the fast trafficking from phagolysosomes to the cytosol as s-proteasomes and immunoproteasomes for peptide degradation are in cytosol (Yewdell and Bennink, Curr Opin Immunol, 2001; 13(1):13-8; Kloetzel and Ossendorp, Curr Opin Immunol 2004; 16(1):76-81; and Brooks et al., Biochemical Journal, 2000; 346 (Pt 1):155-61). Meanwhile, an efficient biodegradation of the epitope-containing proteins facilitates the MHC class I antigen presentation pathway (Kruger and Kloetzel, Curr Opin Immunol, 2012; 24(1):77-83; Yewdell and Bennink, Curr Opin Immunol, 2001; and Amigorena and Savina, Curr Opin Immunol, 2010; 22(1):109-17).

REFERENCES

1. Robinson, H. L., Amara, R. R., T cell vaccines for microbial infections Nat Med (2005); 11, s25-s32.

2. Epstein, J. E., Tewari, K., Lyke, K. E., Sim, B. K. L., Billingsley, P. F., Laurens, M. B. et al., Live Attenuated Malaria Vaccine Designed to Protect Through Hepatic CD8+ T Cell Immunity Science (2011); 334, 475-480.
3. Klebanoff, C. A., Acquavella, N., Yu, Z., Restifo, N. P., Therapeutic cancer vaccines: are we there yet? Immunological Reviews (2011); 239, 27-44.
4. Schumacher, R., Amacker, M., Neuhaus, D., Rosenthal, R., Groeper, C., Heberer, M. et al., Efficient induction of tumoricidal cytotoxic T lymphocytes by HLA-A0201 restricted, melanoma associated, L(27)Melan-A/MART-1 (26-35) peptide encapsulated into virosomes in vitro Vaccine (2005); 23, 5572-5582.
5. Plummer, E. M., Manchester, M., Viral nanoparticles and virus-like particles: platforms for contemporary vaccine design WIREs Nanomed Nanobiotechnol (2011); 3, 174-196.
6. Goldberg, Michael S., Immunoengineering: How Nanotechnology Can Enhance Cancer Immunotherapy Cell (2015); 161, 201-204.
7. Sahdev, P., Ochyl, L., Moon, J., Biomaterials for Nanoparticle Vaccine Delivery Systems Pharm Res (2014); 31, 2563-2582.
8. Dreher, M. R., Simnick, A. J., Fischer, K., Smith, R. J., Patel, A., Schmidt, M. et al., Temperature triggered self-assembly of polypeptides into multivalent spherical micelles J Am Chem Soc (2008); 130, 687-694.
9. Hassouneh, W., Fischer, K., MacEwan, S. R., Branscheid, R., Fu, C. L., Liu, R. et al., Unexpected multivalent display of proteins by temperature triggered self-assembly of elastin-like polypeptide block copolymers Biomacromolecules (2012); 13, 1598-1605.
10. Scheller, J., Leps, M., Conrad, U., Forcing single-chain variable fragment production in tobacco seeds by fusion to elastin-like polypeptides Plant biotechnology journal (2006); 4, 243-249.
11. Alexander, J., Oseroff, C., Dahlberg, C., Qin, M., Ishioka, G., Beebe, M. et al., A decaepitope polypeptide primes for multiple CD8+ IFN-gamma and Th lymphocyte responses: evaluation of multiepitope polypeptides as a mode for vaccine delivery J Immunol (2002); 168, 6189-6198.
12. Livingston, B. D., Newman, M., Crimi, C., McKinney, D., Chesnut, R., Sette, A., Optimization of epitope processing enhances immunogenicity of multiepitope DNA vaccines Vaccine (2001); 19, 4652-4660.
13. Thomson, S. A., Khanna, R., Gardner, J., Burrows, S. R., Coupar, B., Moss, D. J. et al., Minimal epitopes expressed in a recombinant polyepitope protein are processed and presented to CD8+ cytotoxic T cells: implications for vaccine design Proceedings of the National Academy of Sciences of the United States of America (1995); 92, 5845-5849.
14. Hassounh, W., Christensen, T., Chilkoti, A., Elastin-like polypeptides as a purification tag for recombinant proteins Current protocols in protein science/editorial board, John E. Coligan . . . [et al.] (2010); Chapter 6, Unit 6 11.
15. Da Silva, D. M., Pastrana, D. V., Schiller, J. T., Kast, W. M., Effect of preexisting neutralizing antibodies on the anti-tumor immune response induced by chimeric human papillomavirus virus-like particle vaccines Virology (2001); 290, 350-360.
16. Ruedl, C., Schwarz, K., Jegerlehner, A., Storni, T., Manolova, V., Bachmann, M. F., Virus-like particles as carriers for T-cell epitopes: limited inhibition of T-cell priming by carrier-specific antibodies J Virol (2005); 79, 717-724.
17. Liu, X. S., Xu, Y., Hardy, L., Khammanivong, V., Zhao, W., Fernando, G. J. et al., IL-10 mediates suppression of the CD8 T cell IFN-gamma response to a novel viral epitope in a primed host J Immunol (2003); 171, 4765-4772.
18. Urry, D. W., Parker, T. M., Reid, M. C., Gowda, D. C., Biocompatibility of the Bioelastic Materials, Poly (GVGVP) and Its y-Irradiation Cross-Linked Matrix: Summary of Generic Biological Test Results Journal of Bioactive and Compatible Polymers (1991); 6, 263-282.
19. Urry, D. W., Pattanaik, A., Accavitti, M. A., Luan, C., McPherson, D. T., Xu, J. et al., in *Handbook of Biodegradable Polymers*, A. J. Domb, J. Kost, D. M. Wiseman, Eds. (CRC Press, 1998).
20. CHRISTIANSEN, M., MATSON, M., BRAZG, R. L., GEORGOPOULOS, L., ARNOLD, S., KRAMER, W. et al., Weekly Subcutaneous Doses of Glymera (PB 1023) a Novel GLP-1 Analogue Reduce Glucose Exposure Dose-Dependently. (Philadelphia, Pennsylvania, 2012),
21. Cappello, J., in *Handbook of Biodegradable Polymers*, A. J. Domb; J. Kost; D. M. Wiseman, Eds. (Harwood Academic Publishers, Amsterdam, 1997), pp. 387-416.
22. Nouri, F., Wang, X., Chen, X., Hatefi, A., Reducing the Visibility of the Vector/DNA Nanocomplexes to the Immune System by Elastin-Like Peptides Pharm Res (2015), 1-11.
23. Moreland, L. W., McCabe, D. P., Caldwell, J. R., Sack, M., Weisman, M., Henry, G. et al., Phase I/II trial of recombinant methionyl human tumor necrosis factor binding protein PEGylated dimer in patients with active refractory rheumatoid arthritis The Journal of rheumatology (2000); 27, 601-609.
24. Rau, R., Sander, O., van Riel, P., van de Putte, L., Hasler, F., Zaug, M. et al., Intravenous human recombinant tumor necrosis factor receptor p55-Fc IgG1 fusion protein Ro 45-2081 (lenercept): a double blind, placebo controlled dose-finding study in rheumatoid arthritis The Journal of rheumatology (2003); 30, 680-690.
25. Urry, D. W., Free energy transduction in polypeptides and proteins based on inverse temperature transitions Progress in biophysics and molecular biology (1992); 57, 23-57.
26. MacEwan, S. R., Chilkoti, A., Elastin-like polypeptides: Biomedical applications of tunable biopolymers Peptide Science (2010); 94, 60-77.
27. McDaniel, J. R., Mackay, J. A., Quiroz, F. G., Chilkoti, A., Recursive directional ligation by plasmid reconstruction allows rapid and seamless cloning of oligomeric genes Biomacromolecules (2010); 11, 944-952.
28. Rock, K. L., Fleischacker, C., Gamble, S., Peptide-priming of cytolytic T cell immunity in vivo using beta 2-microglobulin as an adjuvant The Journal of Immunology (1993); 150, 1244-1252.
29. Zhao, P., Dong, S., Bhattacharyya, J., Chen, M., iTEP Nanoparticle-Delivered Salinomycin Displays an Enhanced Toxicity to Cancer Stem Cells in Orthotopic Breast Tumors Molecular pharmaceutics (2014).
30. Lee, C., Levin, A., Branton, D., Copper staining: a five-minute protein stain for sodium dodecyl sulfate-polyacrylamide gels Analytical biochemistry (1987); 166, 308-312.
31. Frey, A., Di Canzio, J., Zurakowski, D., A statistically defined endpoint titer determination method for immunoassays J Immunol Methods (1998); 221, 35-41.
32. Shen, Z., Reznikoff, G., Dranoff, G., Rock, K. L., Cloned dendritic cells can present exogenous antigens on both 32. MHC class I and class II molecules The Journal of Immunology (1997); 158, 2723-2730.
33. Karttunen, J., Sanderson, S., Shastri, N., Detection of rare antigen-presenting cells by the lacZ T-cell activation assay suggests an expression cloning strategy for T-cell antigens Proceedings of the National Academy of Sciences (1992); 89, 6020-6024.
34. Bernard, A., Coitot, S., Bremont, A., Bernard, G., T and B cell cooperation: a dance of life and death Transplantation (2005); 79, S8-S11.
35. Parker, D. C., T cell-dependent B cell activation Annual review of immunology (1993); 11, 331-360.
36. Murphy, K., in *Janeway's Immunobiology* (Garland Science, 2012).
37. VanRegenmortel, M. H., in *Structure of Antigens*, M. H. VanRegenmortel, Ed. (CRC Press, 1992), pp. 1-28.
38. M., S., Antigenicity: some molecular aspects Science (1969); 166.
39. Murphy, K., in *Janeway's Immunobiology*. (Garland Science, 2012), pp. 888.
40. Liu, W., Peng, Z., Liu, Z., Lu, Y., Ding, J., Chen, Y. H., High epitope density in a single recombinant protein molecule of the extracellular domain of influenza A virus M2 protein significantly enhances protective immunity Vaccine (2004); 23, 366-371.
41. Kovacs-Nolan, J., Mine, Y., Tandem copies of a human rotavirus VP8 epitope can induce specific neutralizing antibodies in BALB/c mice Biochimica et biophysica acta (2006); 1760, 1884-1893.
42. Partidos, C., Stanley, C., Steward, M., The influence of orientation and number of copies of T and B cell epitopes on the specificity and affinity of antibodies induced by chimeric peptides European journal of immunology (1992); 22, 2675-2680.
43. Onda, M., Beers, R., Xiang, L., Nagata, S., Wang, Q. C., Pastan, I., An immunotoxin with greatly reduced immunogenicity by identification and removal of B cell epitopes Proc Natl Acad Sci USA (2008); 105, 11311-11316.
44. Onda, M., Nagata, S., FitzGerald, D. J., Beers, R., Fisher, R. J., Vincent, J. J. et al., Characterization of the B cell epitopes associated with a truncated form of *Pseudomonas* exotoxin (PE38) used to make immunotoxins for the treatment of cancer patients Journal of immunology (Baltimore, Md.: 1950) (2006); 177, 8822-8834.
45. MacEwan, S. R., Chilkoti, A., Elastin-like polypeptides: biomedical applications of tunable biopolymers Biopolymers (2010); 94, 60-77.
46. Smejkal, G. B., The Coomassie chronicles: past, present and future perspectives in polyacrylamide gel staining Expert review of proteomics (2004); 1, 381-387.
47. Creighton, T. E., *Proteins: Structures and Molecular Properties*. (W.H. Freeman Company, 1993).
48. Urry, D. W., Luan, C. H., Parker, T. M., Gowda, D. C., Prasad, K. U., Reid, M. C., Safavy, A., Temperature of Polypeptide Inverse Temperature Transition Depends on Mean Residue Hydrophobicity J. Am. chem. Soc. (1991); 113, 3.
49. Meyer, D. E., Chilkoti, A., Quantification of the effects of chain length and concentration on the thermal behavior of elastin-like polypeptides Biomacromolecules (2004); 5, 846-851.
50. Jefferis, R., Aggregation, immune complexes and immunogenicity mAbs (2011); 3, 503-504.
51. Rosenberg, A. S., Effects of protein aggregates: an immunologic perspective The AAPS journal (2006); 8, E501-507.
52. Zhou, L., Hoofring, S., Wu, Y., Vu, T., Ma, P., Swanson, S. et al., Stratification of Antibody-Positive Subjects by Antibody Level Reveals an Impact of Immunogenicity on Pharmacokinetics The AAPS journal (2013); 15, 30-40.
53. Kontos, S., Hubbell, J. A., Drug development: longer-lived proteins Chemical Society reviews (2012); 41, 2686-2695.
54. De Groot, A. S., Scott, D. W., Immunogenicity of protein therapeutics Trends in immunology (2007); 28, 482-490.
55. U.S. Department of Health and Human Services Food and Drug Administration, *Guidance for Industry Immunogenicity Assessment for Therapeutic Protein Products* (2013).
56. Shankar, G., Shores, E., Wagner, C., Mire-Sluis, A., Scientific and regulatory considerations on the immunogenicity of biologics Trends in biotechnology (2006); 24, 274-280.
57. Bachmann, M. F., Zinkernagel, R. M., Neutralizing Antiviral B Cell Responses Annual Review of Immunology (1997); 15, 235-270.
58. Feldmann, M., Basten, A., The Relationship Between Antigenic Structure And The Requirement For Thymus-Derived Cells In The Immune Response The Journal of Experimental Medicine (1971); 134, 103-119.
59. Urry, D. W., Physical Chemistry of Biological Free Energy Transduction As Demonstrated by Elastic Protein-Based Polymers Journal of Physical Chemistry B (1997); 101, 11007-11028.
60. Chilkoti, A., Dreher, M. R., Meyer, D. E., Raucher, D., Targeted drug delivery by thermally responsive polymers Adv Drug Deliv Rev (2002); 54, 613-630.
61. Liu, J., Bauer, H., Callahan, J., Kopeckova, P., Pan, H., Kopecek, J., Endocytic uptake of a large array of HPMA copolymers: Elucidation into the dependence on the physicochemical characteristics J Control Release (2010); 143, 71-79.
62. MacKay, J. A., Chen, M., McDaniel, J. R., Liu, W., Simnick, A. J., Chilkoti, A., Self-assembling chimeric polypeptide-doxorubicin conjugate nanoparticles that abolish tumours after a single injection Nat Mater (2009); 8, 993-999.
63. Shi, P., Aluri, S., Lin, Y. A., Shah, M., Edman, M., Dhandhukia, J. et al., Elastin-based protein polymer nanoparticles carrying drug at both corona and core suppress tumor growth in vivo Journal of controlled release: official journal of the Controlled Release Society (2013); 171, 330-338.
64. Bidwell, G. L., 3rd, Perkins, E., Hughes, J., Khan, M., James, J. R., Raucher, D., Thermally targeted delivery of a c-Myc inhibitory polypeptide inhibits tumor progression and extends survival in a rat glioma model PloS one (2013); 8, e55104.
65. Kaspar, A. A., Reichert, J. M., Future directions for peptide therapeutics development Drug discovery today (2013); 18, 807-817.
66. Le, D. H., Hanamura, R., Pham, D. H., Kato, M., Tirrell, D. A., Okubo, T. et al., Self-assembly of elastin-mimetic double hydrophobic polypeptides Biomacromolecules (2013); 14, 1028-1034.
67. Benitez, P. L., Sweet, J. A., Fink, H., Chennazhi, K. P., Nair, S. V., Enejder, A. et al., Sequence-specific cross-linking of electrospun, elastin-like protein preserves bioactivity and native-like mechanics Advanced healthcare materials (2013); 2, 114-118.
68. Garcia-Arevalo, C., Bermejo-Martin, J. F., Rico, L., Iglesias, V., Martin, L., Rodriguez-Cabello, J. C. et al., Immunomodulatory nanoparticles from elastin-like recombinamers: single-molecules for tuberculosis vaccine development Mol Pharm (2013); 10, 586-597.

What is claimed is:

1. A recombinant polypeptide comprising an homologous amino acid repeat sequence, wherein the homologous amino acid repeat sequence is Gly-Val-Leu-Pro-Gly-Val-Gly (SEQ ID NO: 1: iTEP$_A$), wherein the homologous amino acid repeat sequence is reiterated linearly.

2. A recombinant polypeptide comprising (SEQ ID NO: 23)
Gly-(Gly-Val-Leu-Pro-Gly-Val-Gly)$_{28}$-Gly-Gly;

(SEQ ID NO: 24)
Gly-(Gly-Ala-Gly-Val-Pro-Gly)$_{70}$-Gly-Gly;

(SEQ ID NO: 25)
Gly-(Val-Pro-Gly-Phe-Gly-Ala-Gly-Ala-Gly)$_{21}$-Gly-Gly; or (SEQ ID NO: 26)
Gly-(Val-Pro-Gly-Leu-Gly-Ala-Gly-Ala-Gly)$_{96}$-Gly-Gly.

3. The recombinant polypeptide of claim 1, further comprising two or more of the homologous amino acid repeat sequences reiterated linearly.

4. A pharmaceutical composition comprising the recombinant polypeptide of claim 1 and a pharmaceutically acceptable carrier.

5. A pharmaceutical composition comprising the recombinant polypeptide of claim 2 and a pharmaceutically acceptable carrier.

* * * * *

SEQUENCE LISTING

<160> NUMBER OF SEQ ID NOS: 62

<210> SEQ ID NO 1
<211> LENGTH: 7
<212> TYPE: PRT
<213> ORGANISM: Artificial sequence
<220> FEATURE:
<223> OTHER INFORMATION: Synthetic construct

<400> SEQUENCE: 1

Gly Val Leu Pro Gly Val Gly
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic construct

<400> SEQUENCE: 2

Gly Ala Gly Val Pro Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Val Pro Gly Phe Gly Ala Gly Ala Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Val Pro Gly Leu Gly Ala Gly Ala Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic construct

<400> SEQUENCE: 5

Val Pro Gly Leu Gly Val Gly Ala Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Gly Val Leu Pro Gly Val Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic construct

<400> SEQUENCE: 7

Gly Val Leu Pro Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic construct

<400> SEQUENCE: 8

Gly Leu Val Pro Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Gly Leu Val Pro Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic construct

<400> SEQUENCE: 10

Gly Val Pro Leu Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic construct

<400> SEQUENCE: 11

Gly Ile Pro Gly Val Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic construct

<400> SEQUENCE: 12

Gly Gly Val Leu Pro Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic construct

<400> SEQUENCE: 13

Gly Val Leu Pro Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic construct

<400> SEQUENCE: 14

Gly Val Gly Val Leu Pro Gly
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic construct

<400> SEQUENCE: 15

Gly Val Pro Gly
1

<210> SEQ ID NO 16
<211> LENGTH: 9
<212> TYPE: PRT
<213> ORGANISM: Artificial Sequence
<220> FEATURE:
<223> OTHER INFORMATION: Synthetic construct

<400> SEQUENCE: 16

Val Pro Gly Leu Gly Ala Gly Ala Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Val Pro Gly Phe Gly Ala Gly Ala Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic construct

<400> SEQUENCE: 18

Val Pro Gly Phe Gly Val Gly Ala Gly
1               5

```
<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Leu Val Val Gly Gly Gly Pro
1               5

<210> SEQ ID NO 20
<211> LENGTH: 18
<212> TYPE: PRT
<213> ORGANISM: Artificial Sequence
<220> FEATURE:
<223> OTHER INFORMATION: Synthetic construct

<400> SEQUENCE: 20

Ala Gly Gly Pro Gly Val Val Ala Gly Gly Pro Gly Val Ala Gly Gly
1               5                   10                  15

Pro Gly

<210> SEQ ID NO 21
<211> LENGTH: 8
<212> TYPE: PRT
<213> ORGANISM: Artificial Sequence
<220> FEATURE:
<223> OTHER INFORMATION: Synthetic construct

<400> SEQUENCE: 21

Ser Ile Ile Asn Phe Glu Lys Leu
1               5

<210> SEQ ID NO 22
<211> LENGTH: 193
<212> TYPE: PRT
<213> ORGANISM: Artificial Sequence
<220> FEATURE:
<223> OTHER INFORMATION: Synthetic construct

<400> SEQUENCE: 22

Gly Gly Val Leu Pro Gly Val Gly Gly Val Leu Pro Gly Val Gly Gly
1               5                   10                  15

Val Leu Pro Gly Val Gly Gly Val Leu Pro Gly Val Gly Gly Val Leu
                20                  25                  30

Pro Gly Val Gly Gly Val Leu Pro Gly Val Gly Gly Val Leu Pro Gly
            35                  40                  45

Val Gly Gly Val Leu Pro Gly Val Gly Gly Val Leu Pro Gly Val Gly
        50                  55                  60

Gly Val Leu Pro Gly Val Gly Gly Val Leu Pro Gly Val Gly Gly Val
65                  70                  75                  80

Leu Pro Gly Val Gly Gly Val Leu Pro Gly Val Gly Gly Val Leu Pro
                85                  90                  95

Gly Val Gly Gly Val Leu Pro Gly Val Gly Gly Val Leu Pro Gly Val
                100                 105                 110

Gly Gly Val Leu Pro Gly Val Gly Gly Val Leu Pro Gly Val Gly Gly
            115                 120                 125

Val Leu Pro Gly Val Gly Gly Val Leu Pro Gly Val Gly Gly Val Leu
        130                 135                 140

Pro Gly Val Gly Gly Val Leu Pro Gly Val Gly Gly Val Leu Pro Gly
145                 150                 155                 160
```

```
Val Gly Gly Val Leu Pro Gly Val Gly Val Leu Pro Gly Val Gly
            165                 170                 175

Gly Val Leu Pro Gly Val Gly Val Leu Pro Gly Val Gly Val Gly
            180                 185                 190

Gly
```

<210> SEQ ID NO 23
<211> LENGTH: 423
<212> TYPE: PRT
<213> ORGANISM: Artificial Sequence
<220> FEATURE:
<223> OTHER INFORMATION: Synthetic construct

<400> SEQUENCE: 23

```
Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
            20                  25                  30

Ala Gly Val Pro Gly Gly Ala Gly Val Pro Gly Gly Ala Gly Val Pro
            35                  40                  45

Gly Gly Ala Gly Val Pro Gly Gly Ala Gly Val Pro Gly Gly Ala Gly
    50                  55                  60

Val Pro Gly Gly Ala Gly Val Pro Gly Gly Ala Gly Val Pro Gly Gly
65                  70                  75                  80

Ala Gly Val Pro Gly Gly Ala Gly Val Pro Gly Gly Ala Gly Val Pro
                85                  90                  95

Gly Gly Ala Gly Val Pro Gly Gly Ala Gly Val Pro Gly Gly Ala Gly
            100                 105                 110

Val Pro Gly Gly Ala Gly Val Pro Gly Gly Ala Gly Val Pro Gly Gly
        115                 120                 125

Ala Gly Val Pro Gly Gly Ala Gly Val Pro Gly Gly Ala Gly Val Pro
    130                 135                 140

Gly Gly Ala Gly Val Pro Gly Gly Ala Gly Val Pro Gly Gly Ala Gly
145                 150                 155                 160

Val Pro Gly Gly Ala Gly Val Pro Gly Gly Ala Gly Val Pro Gly Gly
                165                 170                 175

Ala Gly Val Pro Gly Gly Ala Gly Val Pro Gly Gly Ala Gly Val Pro
            180                 185                 190

Gly Gly Ala Gly Val Pro Gly Gly Ala Gly Val Pro Gly Gly Ala Gly
        195                 200                 205

Val Pro Gly Gly Ala Gly Val Pro Gly Gly Ala Gly Val Pro Gly Gly
    210                 215                 220

Ala Gly Val Pro Gly Gly Ala Gly Val Pro Gly Gly Ala Gly Val Pro
225                 230                 235                 240

Gly Gly Ala Gly Val Pro Gly Gly Ala Gly Val Pro Gly Gly Ala Gly
                245                 250                 255

Val Pro Gly Gly Ala Gly Val Pro Gly Gly Ala Gly Val Pro Gly Gly
            260                 265                 270

Ala Gly Val Pro Gly Gly Ala Gly Val Pro Gly Gly Ala Gly Val Pro
        275                 280                 285

Gly Gly Ala Gly Val Pro Gly Gly Ala Gly Val Pro Gly Gly Ala Gly
    290                 295                 300

Val Pro Gly Gly Ala Gly Val Pro Gly Gly Ala Gly Val Pro Gly Gly
305                 310                 315                 320
```

Ala Gly Val Pro Gly Ala Gly Val Pro Gly Ala Gly Val Pro
                325                 330                 335

Gly Gly Ala Gly Val Pro Gly Ala Gly Val Pro Gly Gly Ala Gly
            340                 345                 350

Val Pro Gly Gly Ala Gly Val Pro Gly Gly Ala Gly Val Pro Gly Gly
        355                 360                 365

Ala Gly Val Pro Gly Gly Ala Gly Val Pro Gly Gly Ala Gly Val Pro
        370                 375                 380

Gly Gly Ala Gly Val Pro Gly Gly Ala Gly Val Pro Gly Gly Ala Gly
385                 390                 395                 400

Val Pro Gly Gly Ala Gly Val Pro Gly Gly Ala Gly Val Pro Gly Gly
        405                 410                 415

Ala Gly Val Pro Gly Gly Gly
        420

<210> SEQ ID NO 24
<211> LENGTH: 192
<212> TYPE: PRT
<213> ORGANISM: Artificial Sequence
<220> FEATURE:
<223> OTHER INFORMATION: Synthetic construct

<400> SEQUENCE: 24

Gly Val Pro Gly Phe Gly Ala Gly Ala Gly Val Pro Gly Phe Gly Ala
1               5                   10                  15

Gly Ala Gly Val Pro Gly Phe Gly Ala Gly Ala Gly Val Pro Gly Phe
            20                  25                  30

Gly Ala Gly Ala Gly Val Pro Gly Phe Gly Ala Gly Ala Gly Val Pro
        35                  40                  45

Gly Phe Gly Ala Gly Ala Gly Val Pro Gly Phe Gly Ala Gly Ala Gly
    50                  55                  60

Val Pro Gly Phe Gly Ala Gly Ala Gly Val Pro Gly Phe Gly Ala Gly
65                  70                  75                  80

Ala Gly Val Pro Gly Phe Gly Ala Gly Ala Gly Val Pro Gly Phe Gly
                85                  90                  95

Ala Gly Ala Gly Val Pro Gly Phe Gly Ala Gly Ala Gly Val Pro Gly
            100                 105                 110

Phe Gly Ala Gly Ala Gly Val Pro Gly Phe Gly Ala Gly Ala Gly Val
        115                 120                 125

Pro Gly Phe Gly Ala Gly Ala Gly Val Pro Gly Phe Gly Ala Gly Ala
    130                 135                 140

Gly Val Pro Gly Phe Gly Ala Gly Ala Gly Val Pro Gly Phe Gly Ala
145                 150                 155                 160

Gly Ala Gly Val Pro Gly Phe Gly Ala Gly Ala Gly Val Pro Gly Phe
                165                 170                 175

Gly Ala Gly Ala Gly Val Pro Gly Phe Gly Ala Gly Ala Gly Gly Gly
            180                 185                 190

<210> SEQ ID NO 25
<211> LENGTH: 867
<212> TYPE: PRT
<213> ORGANISM: Artificial Sequence
<220> FEATURE:
<223> OTHER INFORMATION: Synthetic construct

<400> SEQUENCE: 25

Gly Val Pro Gly Leu Gly Ala Gly Ala Gly Val Pro Gly Leu Gly Ala
1               5                   10                  15

-continued

Gly Ala Gly Val Pro Gly Leu Gly Ala Gly Ala Gly Val Pro Gly Leu
              20                  25                  30

Gly Ala Gly Ala Gly Val Pro Gly Leu Gly Ala Gly Ala Gly Val Pro
          35                  40                  45

Gly Leu Gly Ala Gly Ala Gly Val Pro Gly Leu Gly Ala Gly Ala Gly
     50                  55                  60

Val Pro Gly Leu Gly Ala Gly Ala Gly Val Pro Gly Leu Gly Ala Gly
 65                  70                  75                  80

Ala Gly Val Pro Gly Leu Gly Ala Gly Ala Gly Val Pro Gly Leu Gly
                 85                  90                  95

Ala Gly Ala Gly Val Pro Gly Leu Gly Ala Gly Ala Gly Val Pro Gly
            100                 105                 110

Leu Gly Ala Gly Ala Gly Val Pro Gly Leu Gly Ala Gly Ala Gly Val
        115                 120                 125

Pro Gly Leu Gly Ala Gly Ala Gly Val Pro Gly Leu Gly Ala Gly Ala
    130                 135                 140

Gly Val Pro Gly Leu Gly Ala Gly Ala Gly Val Pro Gly Leu Gly Ala
145                 150                 155                 160

Gly Ala Gly Val Pro Gly Leu Gly Ala Gly Ala Gly Val Pro Gly Leu
                165                 170                 175

Gly Ala Gly Ala Gly Val Pro Gly Leu Gly Ala Gly Ala Gly Val Pro
            180                 185                 190

Gly Leu Gly Ala Gly Ala Gly Val Pro Gly Leu Gly Ala Gly Ala Gly
        195                 200                 205

Val Pro Gly Leu Gly Ala Gly Ala Gly Val Pro Gly Leu Gly Ala Gly
    210                 215                 220

Ala Gly Val Pro Gly Leu Gly Ala Gly Ala Gly Val Pro Gly Leu Gly
225                 230                 235                 240

Ala Gly Ala Gly Val Pro Gly Leu Gly Ala Gly Ala Gly Val Pro Gly
                245                 250                 255

Leu Gly Ala Gly Ala Gly Val Pro Gly Leu Gly Ala Gly Ala Gly Val
            260                 265                 270

Pro Gly Leu Gly Ala Gly Ala Gly Val Pro Gly Leu Gly Ala Gly Ala
        275                 280                 285

Gly Val Pro Gly Leu Gly Ala Gly Ala Gly Val Pro Gly Leu Gly Ala
    290                 295                 300

Gly Ala Gly Val Pro Gly Leu Gly Ala Gly Ala Gly Val Pro Gly Leu
305                 310                 315                 320

Gly Ala Gly Ala Gly Val Pro Gly Leu Gly Ala Gly Ala Gly Val Pro
                325                 330                 335

Gly Leu Gly Ala Gly Ala Gly Val Pro Gly Leu Gly Ala Gly Ala Gly
            340                 345                 350

Val Pro Gly Leu Gly Ala Gly Ala Gly Val Pro Gly Leu Gly Ala Gly
        355                 360                 365

Ala Gly Val Pro Gly Leu Gly Ala Gly Ala Gly Val Pro Gly Leu Gly
    370                 375                 380

Ala Gly Ala Gly Val Pro Gly Leu Gly Ala Gly Ala Gly Val Pro Gly
385                 390                 395                 400

Leu Gly Ala Gly Ala Gly Val Pro Gly Leu Gly Ala Gly Ala Gly Val
                405                 410                 415

Pro Gly Leu Gly Ala Gly Ala Gly Val Pro Gly Leu Gly Ala Gly Ala
            420                 425                 430

Gly Val Pro Gly Leu Gly Ala Gly Ala Gly Val Pro Gly Leu Gly Ala
                435                 440                 445

Gly Ala Gly Val Pro Gly Leu Gly Ala Gly Ala Gly Val Pro Gly Leu
        450                 455                 460

Gly Ala Gly Ala Gly Val Pro Gly Leu Gly Ala Gly Ala Gly Val Pro
465                 470                 475                 480

Gly Leu Gly Ala Gly Ala Gly Val Pro Gly Leu Gly Ala Gly Ala Gly
            485                 490                 495

Val Pro Gly Leu Gly Ala Gly Ala Gly Val Pro Gly Leu Gly Ala Gly
                500                 505                 510

Ala Gly Val Pro Gly Leu Gly Ala Gly Ala Gly Val Pro Gly Leu Gly
        515                 520                 525

Ala Gly Ala Gly Val Pro Gly Leu Gly Ala Gly Ala Gly Val Pro Gly
530                 535                 540

Leu Gly Ala Gly Ala Gly Val Pro Gly Leu Gly Ala Gly Ala Gly Val
545                 550                 555                 560

Pro Gly Leu Gly Ala Gly Ala Gly Val Pro Gly Leu Gly Ala Gly Ala
            565                 570                 575

Gly Val Pro Gly Leu Gly Ala Gly Ala Gly Val Pro Gly Leu Gly Ala
                580                 585                 590

Gly Ala Gly Val Pro Gly Leu Gly Ala Gly Ala Gly Val Pro Gly Leu
        595                 600                 605

Gly Ala Gly Ala Gly Val Pro Gly Leu Gly Ala Gly Ala Gly Val Pro
610                 615                 620

Gly Leu Gly Ala Gly Ala Gly Val Pro Gly Leu Gly Ala Gly Ala Gly
625                 630                 635                 640

Val Pro Gly Leu Gly Ala Gly Ala Gly Val Pro Gly Leu Gly Ala Gly
            645                 650                 655

Ala Gly Val Pro Gly Leu Gly Ala Gly Ala Gly Val Pro Gly Leu Gly
                660                 665                 670

Ala Gly Ala Gly Val Pro Gly Leu Gly Ala Gly Ala Gly Val Pro Gly
        675                 680                 685

Leu Gly Ala Gly Ala Gly Val Pro Gly Leu Gly Ala Gly Ala Gly Val
690                 695                 700

Pro Gly Leu Gly Ala Gly Ala Gly Val Pro Gly Leu Gly Ala Gly Ala
705                 710                 715                 720

Gly Val Pro Gly Leu Gly Ala Gly Ala Gly Val Pro Gly Leu Gly Ala
            725                 730                 735

Gly Ala Gly Val Pro Gly Leu Gly Ala Gly Ala Gly Val Pro Gly Leu
                740                 745                 750

Gly Ala Gly Ala Gly Val Pro Gly Leu Gly Ala Gly Ala Gly Val Pro
        755                 760                 765

Gly Leu Gly Ala Gly Ala Gly Val Pro Gly Leu Gly Ala Gly Ala Gly
770                 775                 780

Val Pro Gly Leu Gly Ala Gly Ala Gly Val Pro Gly Leu Gly Ala Gly
785                 790                 795                 800

Ala Gly Val Pro Gly Leu Gly Ala Gly Ala Gly Val Pro Gly Leu Gly
            805                 810                 815

Ala Gly Ala Gly Val Pro Gly Leu Gly Ala Gly Ala Gly Val Pro Gly
                820                 825                 830

Leu Gly Ala Gly Ala Gly Val Pro Gly Leu Gly Ala Gly Ala Gly Val
        835                 840                 845

Pro Gly Leu Gly Ala Gly Ala Gly Val Pro Gly Leu Gly Ala Gly Ala

Gly Gly Gly
865

<210> SEQ ID NO 26
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 26

Xaa Val Pro Gly Leu Gly Val Gly Ala Gly Xaa
1               5                   10

<210> SEQ ID NO 27
<211> LENGTH: 4
<212> TYPE: PRT
<213> ORGANISM: Artificial sequence
<220> FEATURE:
<223> OTHER INFORMATION: Synthetic construct

<400> SEQUENCE: 27

Gly Val Pro Gly
1

<210> SEQ ID NO 28
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 28

Val Pro Gly Xaa Gly
1               5

<210> SEQ ID NO 29
<211> LENGTH: 28
<212> TYPE: PRT
<213> ORGANISM: Artificial sequence
<220> FEATURE:
<223> OTHER INFORMATION: Synthetic construct

<400> SEQUENCE: 29

Gly Val Leu Pro Gly Val Gly Gly Val Leu Pro Gly Val Gly Gly Val
1               5                   10                  15

Leu Pro Gly Val Gly Gly Val Leu Pro Gly Val Gly
            20                  25

<210> SEQ ID NO 30
<211> LENGTH: 30
<212> TYPE: PRT
<213> ORGANISM: Artificial sequence
<220> FEATURE:
<223> OTHER INFORMATION: Synthetic construct

```
<400> SEQUENCE: 30

Gly Ala Gly Val Pro Gly Gly Ala Gly Val Pro Gly Gly Ala Gly Val
1               5                   10                  15

Pro Gly Gly Ala Gly Val Pro Gly Gly Ala Gly Val Pro Gly
            20                  25                  30

<210> SEQ ID NO 31
<211> LENGTH: 27
<212> TYPE: PRT
<213> ORGANISM: Artificial sequence
<220> FEATURE:
<223> OTHER INFORMATION: Synthetic construct

<400> SEQUENCE: 31

Val Pro Gly Phe Gly Ala Gly Ala Gly Val Pro Gly Phe Gly Ala Gly
1               5                   10                  15

Ala Gly Val Pro Gly Phe Gly Ala Gly Ala Gly
            20                  25

<210> SEQ ID NO 32
<211> LENGTH: 27
<212> TYPE: PRT
<213> ORGANISM: Artificial sequence
<220> FEATURE:
<223> OTHER INFORMATION: Synthetic construct

<400> SEQUENCE: 32

Val Pro Gly Leu Gly Ala Gly Ala Gly Val Pro Gly Leu Gly Ala Gly
1               5                   10                  15

Ala Gly Val Pro Gly Leu Gly Ala Gly Ala Gly
            20                  25

<210> SEQ ID NO 33
<211> LENGTH: 66
<212> TYPE: DNA
<213> ORGANISM: Artificial sequence
<220> FEATURE:
<223> OTHER INFORMATION: Synthetic construct

<400> SEQUENCE: 33
ctagaaataa ttttgtttaa ctttaagaag gaggagtaca tatgggcggt tgataatgat      60
cttcag                                                                 66

<210> SEQ ID NO 34
<211> LENGTH: 66
<212> TYPE: DNA
<213> ORGANISM: Artificial sequence
<220> FEATURE:
<223> OTHER INFORMATION: Synthetic construct

<400> SEQUENCE: 34
gatcctgaag atcattatca accgcccata tgtactcctc cttcttaaag ttaaacaaaa      60
ttattt                                                                 66

<210> SEQ ID NO 35
<211> LENGTH: 90
<212> TYPE: DNA
<213> ORGANISM: Artificial sequence
<220> FEATURE:
<223> OTHER INFORMATION: Synthetic construct

<400> SEQUENCE: 35
```
cgcgggtgtg ccgggcggcg ccggtgttcc aggggcgcg ggtgtgccgg gaggcgcagg    60
tgtccctggg ggcgctggtg taccgggagg                                    90

<210> SEQ ID NO 36
<211> LENGTH: 90
<212> TYPE: DNA
<213> ORGANISM: Artificial sequence
<220> FEATURE:
<223> OTHER INFORMATION: Synthetic construct

<400> SEQUENCE: 36
tcccggtaca ccagcgcccc cagggacacc tgcgcctccc ggcacacccg cgcccctgg     60 aacaccggcg ccgcccggca cacccgcgcc                                    90

<210> SEQ ID NO 37
<211> LENGTH: 81
<212> TYPE: DNA
<213> ORGANISM: Artificial sequence
<220> FEATURE:
<223> OTHER INFORMATION: Synthetic construct

<400> SEQUENCE: 37
cgtgccgggc tttggtgcgg gcgccggggt tccaggcttc ggtgcaggcg cgggagtccc    60
gggttttggc gccggggctg g                                             81

<210> SEQ ID NO 38
<211> LENGTH: 81
<212> TYPE: DNA
<213> ORGANISM: Artificial sequence
<220> FEATURE:
<223> OTHER INFORMATION: Synthetic construct

<400> SEQUENCE: 38
agccccggcg ccaaaacccg ggactcccgc gcctgcaccg aagcctggaa ccccggcgcc    60
cgcaccaaag cccggcacgc c                                             81

<210> SEQ ID NO 39
<211> LENGTH: 81
<212> TYPE: DNA
<213> ORGANISM: Artificial sequence
<220> FEATURE:
<223> OTHER INFORMATION: Synthetic construct

<400> SEQUENCE: 39
cgtgccgggc tgggtgcgg gcgccggggt tccaggctta ggtgcaggcg cgggagtccc     60
gggtctgggc gccggggctg g                                             81

<210> SEQ ID NO 40
<211> LENGTH: 81
<212> TYPE: DNA
<213> ORGANISM: Artificial sequence
<220> FEATURE:
<223> OTHER INFORMATION: Synthetic construct

<400> SEQUENCE: 40
agccccggcg cccagacccg ggactcccgc gcctgcacct aagcctggaa ccccggcgcc    60
cgcacccagg cccggcacgc c                                             81

<210> SEQ ID NO 41
<211> LENGTH: 84
<212> TYPE: DNA
<213> ORGANISM: Artificial sequence
<220> FEATURE:
<223> OTHER INFORMATION: Synthetic construct

<400> SEQUENCE: 41
cgtgctgccg ggtgttggcg gtgtgttacc aggcgtcggg ggtgtgctgc cgggcgttgg    60
tggtgtcttg cctggcgtag gagg    84

<210> SEQ ID NO 42
<211> LENGTH: 84
<212> TYPE: DNA
<213> ORGANISM: Artificial sequence
<220> FEATURE:
<223> OTHER INFORMATION: Synthetic construct

<400> SEQUENCE: 42
tcctacgcca ggcaagacac caccaacgcc cggcagcaca ccccgacgc ctggtaacac    60 accgccaaca cccggcagca cgcc    84

<210> SEQ ID NO 43
<211> LENGTH: 63
<212> TYPE: DNA
<213> ORGANISM: Artificial sequence
<220> FEATURE:
<223> OTHER INFORMATION: Synthetic construct

<400> SEQUENCE: 43
ggagagtata atcaactttg aaaaactgac tgaaagcatc ataaatttcg aaaagctgac    60
cgg    63

<210> SEQ ID NO 44
<211> LENGTH: 63
<212> TYPE: DNA
<213> ORGANISM: Artificial sequence
<220> FEATURE:
<223> OTHER INFORMATION: Synthetic construct

<400> SEQUENCE: 44
ggtcagcttt tcgaaattta tgatgctttc agtcagtttt tcaaagttga ttatactctc    60
ccc    63

<210> SEQ ID NO 45
<211> LENGTH: 24
<212> TYPE: DNA
<213> ORGANISM: Artificial sequence
<220> FEATURE:
<223> OTHER INFORMATION: Synthetic construct

<400> SEQUENCE: 45
ctgtggttgc ggctgcgggt gtgg    24

<210> SEQ ID NO 46
<211> LENGTH: 24
<212> TYPE: DNA
<213> ORGANISM: Artificial sequence
<220> FEATURE:
<223> OTHER INFORMATION: Synthetic construct

<400> SEQUENCE: 46
acacccgcag ccgcaaccac agcc    24

<210> SEQ ID NO 47
<211> LENGTH: 108
<212> TYPE: DNA

<213> ORGANISM: Artificial sequence
<220> FEATURE:
<223> OTHER INFORMATION: Synthetic construct

<400> SEQUENCE: 47

```
cggtggaggt gggtgtggtg gcggcggagg tggcggtggc tgcggtggtg gcggcggggg    60
cggcggttgc ggcggcggtg gcggtggggg aggatgtggt gggggtgg                108
```

<210> SEQ ID NO 48
<211> LENGTH: 108
<212> TYPE: DNA
<213> ORGANISM: Artificial sequence
<220> FEATURE:
<223> OTHER INFORMATION: Synthetic construct

<400> SEQUENCE: 48

```
accccccacca catcctcccc caccgccacc gccgccgcaa ccgccgcccc cgccgccacc    60
accgcagcca ccgccacctc cgccgccacc acacccacct ccaccgcc                 108
```

<210> SEQ ID NO 49
<211> LENGTH: 196
<212> TYPE: PRT
<213> ORGANISM: Artificial sequence
<220> FEATURE:
<223> OTHER INFORMATION: Synthetic construct

<400> SEQUENCE: 49

```
Gly Val Leu Pro Gly Val Gly Gly Val Leu Pro Gly Val Gly Gly Val
1               5                   10                  15

Leu Pro Gly Val Gly Gly Val Leu Pro Gly Val Gly Gly Val Leu Pro
            20                  25                  30

Gly Val Gly Gly Val Leu Pro Gly Val Gly Gly Val Leu Pro Gly Val
        35                  40                  45

Gly Gly Val Leu Pro Gly Val Gly Gly Val Leu Pro Gly Val Gly Gly
    50                  55                  60

Val Leu Pro Gly Val Gly Gly Val Leu Pro Gly Val Gly Gly Val Leu
65                  70                  75                  80

Pro Gly Val Gly Gly Val Leu Pro Gly Val Gly Gly Val Leu Pro Gly
                85                  90                  95

Val Gly Gly Val Leu Pro Gly Val Gly Gly Val Leu Pro Gly Val Gly
            100                 105                 110

Gly Val Leu Pro Gly Val Gly Gly Val Leu Pro Gly Val Gly Gly Val
        115                 120                 125

Leu Pro Gly Val Gly Gly Val Leu Pro Gly Val Gly Gly Val Leu Pro
    130                 135                 140

Gly Val Gly Gly Val Leu Pro Gly Val Gly Gly Val Leu Pro Gly Val
145                 150                 155                 160

Gly Gly Val Leu Pro Gly Val Gly Gly Val Leu Pro Gly Val Gly Gly
                165                 170                 175

Val Leu Pro Gly Val Gly Gly Val Leu Pro Gly Val Gly Gly Val Leu
            180                 185                 190

Pro Gly Val Gly
        195
```

<210> SEQ ID NO 50
<211> LENGTH: 420
<212> TYPE: PRT
<213> ORGANISM: Artificial sequence
<220> FEATURE:

-continued

<223> OTHER INFORMATION: Synthetic construct

<400> SEQUENCE: 50

```
Gly Ala Gly Val Pro Gly Gly Ala Gly Val Pro Gly Gly Ala Gly Val
1               5                   10                  15
Pro Gly Gly Ala Gly Val Pro Gly Gly Ala Gly Val Pro Gly Gly Ala
            20                  25                  30
Gly Val Pro Gly Gly Ala Gly Val Pro Gly Gly Ala Gly Val Pro Gly
        35                  40                  45
Gly Ala Gly Val Pro Gly Gly Ala Gly Val Pro Gly Gly Ala Gly Val
    50                  55                  60
Pro Gly Gly Ala Gly Val Pro Gly Gly Ala Gly Val Pro Gly Gly Ala
65                  70                  75                  80
Gly Val Pro Gly Gly Ala Gly Val Pro Gly Gly Ala Gly Val Pro Gly
            85                  90                  95
Gly Ala Gly Val Pro Gly Gly Ala Gly Val Pro Gly Gly Ala Gly Val
            100                 105                 110
Pro Gly Gly Ala Gly Val Pro Gly Gly Ala Gly Val Pro Gly Gly Ala
            115                 120                 125
Gly Val Pro Gly Gly Ala Gly Val Pro Gly Gly Ala Gly Val Pro Gly
        130                 135                 140
Gly Ala Gly Val Pro Gly Gly Ala Gly Val Pro Gly Gly Ala Gly Val
145                 150                 155                 160
Pro Gly Gly Ala Gly Val Pro Gly Gly Ala Gly Val Pro Gly Gly Ala
            165                 170                 175
Gly Val Pro Gly Gly Ala Gly Val Pro Gly Gly Ala Gly Val Pro Gly
            180                 185                 190
Gly Ala Gly Val Pro Gly Gly Ala Gly Val Pro Gly Gly Ala Gly Val
            195                 200                 205
Pro Gly Gly Ala Gly Val Pro Gly Gly Ala Gly Val Pro Gly Gly Ala
            210                 215                 220
Gly Val Pro Gly Gly Ala Gly Val Pro Gly Gly Ala Gly Val Pro Gly
225                 230                 235                 240
Gly Ala Gly Val Pro Gly Gly Ala Gly Val Pro Gly Gly Ala Gly Val
            245                 250                 255
Pro Gly Gly Ala Gly Val Pro Gly Gly Ala Gly Val Pro Gly Gly Ala
            260                 265                 270
Gly Val Pro Gly Gly Ala Gly Val Pro Gly Gly Ala Gly Val Pro Gly
            275                 280                 285
Gly Ala Gly Val Pro Gly Gly Ala Gly Val Pro Gly Gly Ala Gly Val
            290                 295                 300
Pro Gly Gly Ala Gly Val Pro Gly Gly Ala Gly Val Pro Gly Gly Ala
305                 310                 315                 320
Gly Val Pro Gly Gly Ala Gly Val Pro Gly Gly Ala Gly Val Pro Gly
            325                 330                 335
Gly Ala Gly Val Pro Gly Gly Ala Gly Val Pro Gly Gly Ala Gly Val
            340                 345                 350
Pro Gly Gly Ala Gly Val Pro Gly Gly Ala Gly Val Pro Gly Gly Ala
            355                 360                 365
Gly Val Pro Gly Gly Ala Gly Val Pro Gly Gly Ala Gly Val Pro Gly
        370                 375                 380
Gly Ala Gly Val Pro Gly Gly Ala Gly Val Pro Gly Gly Ala Gly Val
385                 390                 395                 400
```

Pro Gly Gly Ala Gly Val Pro Gly Gly Ala Gly Val Pro Gly Gly Ala
            405                 410                 415

Gly Val Pro Gly
        420

<210> SEQ ID NO 51
<211> LENGTH: 189
<212> TYPE: PRT
<213> ORGANISM: Artificial sequence
<220> FEATURE:
<223> OTHER INFORMATION: Synthetic construct

<400> SEQUENCE: 51

Val Pro Gly Phe Gly Ala Gly Ala Gly Val Pro Gly Phe Gly Ala Gly
1               5                   10                  15

Ala Gly Val Pro Gly Phe Gly Ala Gly Ala Gly Val Pro Gly Phe Gly
            20                  25                  30

Ala Gly Ala Gly Val Pro Gly Phe Gly Ala Gly Ala Gly Val Pro Gly
        35                  40                  45

Phe Gly Ala Gly Ala Gly Val Pro Gly Phe Gly Ala Gly Ala Gly Val
    50                  55                  60

Pro Gly Phe Gly Ala Gly Ala Gly Val Pro Gly Phe Gly Ala Gly Ala
65                  70                  75                  80

Gly Val Pro Gly Phe Gly Ala Gly Ala Gly Val Pro Gly Phe Gly Ala
                85                  90                  95

Gly Ala Gly Val Pro Gly Phe Gly Ala Gly Ala Gly Val Pro Gly Phe
            100                 105                 110

Gly Ala Gly Ala Gly Val Pro Gly Phe Gly Ala Gly Ala Gly Val Pro
        115                 120                 125

Gly Phe Gly Ala Gly Ala Gly Val Pro Gly Phe Gly Ala Gly Ala Gly
    130                 135                 140

Val Pro Gly Phe Gly Ala Gly Ala Gly Val Pro Gly Phe Gly Ala Gly
145                 150                 155                 160

Ala Gly Val Pro Gly Phe Gly Ala Gly Ala Gly Val Pro Gly Phe Gly
                165                 170                 175

Ala Gly Ala Gly Val Pro Gly Phe Gly Ala Gly Ala Gly
            180                 185

<210> SEQ ID NO 52
<211> LENGTH: 864
<212> TYPE: PRT
<213> ORGANISM: Artificial sequence
<220> FEATURE:
<223> OTHER INFORMATION: Synthetic construct

<400> SEQUENCE: 52

Val Pro Gly Leu Gly Ala Gly Ala Gly Val Pro Gly Leu Gly Ala Gly
1               5                   10                  15

Ala Gly Val Pro Gly Leu Gly Ala Gly Ala Gly Val Pro Gly Leu Gly
            20                  25                  30

Ala Gly Ala Gly Val Pro Gly Leu Gly Ala Gly Ala Gly Val Pro Gly
        35                  40                  45

Leu Gly Ala Gly Ala Gly Val Pro Gly Leu Gly Ala Gly Ala Gly Val
    50                  55                  60

Pro Gly Leu Gly Ala Gly Ala Gly Val Pro Gly Leu Gly Ala Gly Ala
65                  70                  75                  80

Gly Val Pro Gly Leu Gly Ala Gly Ala Gly Val Pro Gly Leu Gly Ala
                85                  90                  95

-continued

Gly Ala Gly Val Pro Gly Leu Gly Ala Gly Ala Gly Val Pro Gly Leu
            100                 105                 110
Gly Ala Gly Ala Gly Val Pro Gly Leu Gly Ala Gly Ala Gly Val Pro
            115                 120                 125
Gly Leu Gly Ala Gly Ala Gly Val Pro Gly Leu Gly Ala Gly Ala Gly
            130                 135                 140
Val Pro Gly Leu Gly Ala Gly Ala Gly Val Pro Gly Leu Gly Ala Gly
145                 150                 155                 160
Ala Gly Val Pro Gly Leu Gly Ala Gly Ala Gly Val Pro Gly Leu Gly
                165                 170                 175
Ala Gly Ala Gly Val Pro Gly Leu Gly Ala Gly Ala Gly Val Pro Gly
            180                 185                 190
Leu Gly Ala Gly Ala Gly Val Pro Gly Leu Gly Ala Gly Ala Gly Val
            195                 200                 205
Pro Gly Leu Gly Ala Gly Ala Gly Val Pro Gly Leu Gly Ala Gly Ala
            210                 215                 220
Gly Val Pro Gly Leu Gly Ala Gly Ala Gly Val Pro Gly Leu Gly Ala
225                 230                 235                 240
Gly Ala Gly Val Pro Gly Leu Gly Ala Gly Ala Gly Val Pro Gly Leu
                245                 250                 255
Gly Ala Gly Ala Gly Val Pro Gly Leu Gly Ala Gly Ala Gly Val Pro
            260                 265                 270
Gly Leu Gly Ala Gly Ala Gly Val Pro Gly Leu Gly Ala Gly Ala Gly
            275                 280                 285
Val Pro Gly Leu Gly Ala Gly Ala Gly Val Pro Gly Leu Gly Ala Gly
            290                 295                 300
Ala Gly Val Pro Gly Leu Gly Ala Gly Ala Gly Val Pro Gly Leu Gly
305                 310                 315                 320
Ala Gly Ala Gly Val Pro Gly Leu Gly Ala Gly Ala Gly Val Pro Gly
                325                 330                 335
Leu Gly Ala Gly Ala Gly Val Pro Gly Leu Gly Ala Gly Ala Gly Val
            340                 345                 350
Pro Gly Leu Gly Ala Gly Ala Gly Val Pro Gly Leu Gly Ala Gly Ala
            355                 360                 365
Gly Val Pro Gly Leu Gly Ala Gly Ala Gly Val Pro Gly Leu Gly Ala
            370                 375                 380
Gly Ala Gly Val Pro Gly Leu Gly Ala Gly Ala Gly Val Pro Gly Leu
385                 390                 395                 400
Gly Ala Gly Ala Gly Val Pro Gly Leu Gly Ala Gly Ala Gly Val Pro
                405                 410                 415
Gly Leu Gly Ala Gly Ala Gly Val Pro Gly Leu Gly Ala Gly Ala Gly
            420                 425                 430
Val Pro Gly Leu Gly Ala Gly Ala Gly Val Pro Gly Leu Gly Ala Gly
            435                 440                 445
Ala Gly Val Pro Gly Leu Gly Ala Gly Ala Gly Val Pro Gly Leu Gly
            450                 455                 460
Ala Gly Ala Gly Val Pro Gly Leu Gly Ala Gly Ala Gly Val Pro Gly
465                 470                 475                 480
Leu Gly Ala Gly Ala Gly Val Pro Gly Leu Gly Ala Gly Ala Gly Val
                485                 490                 495
Pro Gly Leu Gly Ala Gly Ala Gly Val Pro Gly Leu Gly Ala Gly Ala
            500                 505                 510

Gly Val Pro Gly Leu Gly Ala Gly Ala Gly Val Pro Gly Leu Gly Ala
            515                 520                 525

Gly Ala Gly Val Pro Gly Leu Gly Ala Gly Ala Gly Val Pro Gly Leu
        530                 535                 540

Gly Ala Gly Ala Gly Val Pro Gly Leu Gly Ala Gly Ala Gly Val Pro
545                 550                 555                 560

Gly Leu Gly Ala Gly Ala Gly Val Pro Gly Leu Gly Ala Gly Ala Gly
                565                 570                 575

Val Pro Gly Leu Gly Ala Gly Ala Gly Val Pro Gly Leu Gly Ala Gly
            580                 585                 590

Ala Gly Val Pro Gly Leu Gly Ala Gly Ala Gly Val Pro Gly Leu Gly
        595                 600                 605

Ala Gly Ala Gly Val Pro Gly Leu Gly Ala Gly Ala Gly Val Pro Gly
    610                 615                 620

Leu Gly Ala Gly Ala Gly Val Pro Gly Leu Gly Ala Gly Ala Gly Val
625                 630                 635                 640

Pro Gly Leu Gly Ala Gly Ala Gly Val Pro Gly Leu Gly Ala Gly Ala
                645                 650                 655

Gly Val Pro Gly Leu Gly Ala Gly Ala Gly Val Pro Gly Leu Gly Ala
            660                 665                 670

Gly Ala Gly Val Pro Gly Leu Gly Ala Gly Ala Gly Val Pro Gly Leu
        675                 680                 685

Gly Ala Gly Ala Gly Val Pro Gly Leu Gly Ala Gly Ala Gly Val Pro
    690                 695                 700

Gly Leu Gly Ala Gly Ala Gly Val Pro Gly Leu Gly Ala Gly Ala Gly
705                 710                 715                 720

Val Pro Gly Leu Gly Ala Gly Ala Gly Val Pro Gly Leu Gly Ala Gly
                725                 730                 735

Ala Gly Val Pro Gly Leu Gly Ala Gly Ala Gly Val Pro Gly Leu Gly
            740                 745                 750

Ala Gly Ala Gly Val Pro Gly Leu Gly Ala Gly Ala Gly Val Pro Gly
        755                 760                 765

Leu Gly Ala Gly Ala Gly Val Pro Gly Leu Gly Ala Gly Ala Gly Val
    770                 775                 780

Pro Gly Leu Gly Ala Gly Ala Gly Val Pro Gly Leu Gly Ala Gly Ala
785                 790                 795                 800

Gly Val Pro Gly Leu Gly Ala Gly Ala Gly Val Pro Gly Leu Gly Ala
                805                 810                 815

Gly Ala Gly Val Pro Gly Leu Gly Ala Gly Ala Gly Val Pro Gly Leu
            820                 825                 830

Gly Ala Gly Ala Gly Val Pro Gly Leu Gly Ala Gly Ala Gly Val Pro
        835                 840                 845

Gly Leu Gly Ala Gly Ala Gly Val Pro Gly Leu Gly Ala Gly Ala Gly
    850                 855                 860

<210> SEQ ID NO 53
<211> LENGTH: 619
<212> TYPE: PRT
<213> ORGANISM: Artificial sequence
<220> FEATURE:
<223> OTHER INFORMATION: Synthetic construct

<400> SEQUENCE: 53

Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
            20                  25                  30

Ala Gly Val Pro Gly Gly Ala Gly Val Pro Gly Gly Ala Gly Val Pro
        35                  40                  45

Gly Gly Ala Gly Val Pro Gly Gly Ala Gly Val Pro Gly Gly Ala Gly
    50                  55                  60

Val Pro Gly Gly Ala Gly Val Pro Gly Gly Ala Gly Val Pro Gly Gly
65                  70                  75                  80

Ala Gly Val Pro Gly Gly Ala Gly Val Pro Gly Gly Ala Gly Val Pro
        85                  90                  95

Gly Gly Ala Gly Val Pro Gly Gly Ala Gly Val Pro Gly Gly Ala Gly
    100                 105                 110

Val Pro Gly Gly Ala Gly Val Pro Gly Gly Ala Gly Val Pro Gly Gly
        115                 120                 125

Ala Gly Val Pro Gly Gly Ala Gly Val Pro Gly Gly Ala Gly Val Pro
        130                 135                 140

Gly Gly Ala Gly Val Pro Gly Gly Ala Gly Val Pro Gly Gly Ala Gly
145                 150                 155                 160

Val Pro Gly Gly Ala Gly Val Pro Gly Gly Ala Gly Val Pro Gly Gly
        165                 170                 175

Ala Gly Val Pro Gly Gly Ala Gly Val Pro Gly Gly Ala Gly Val Pro
        180                 185                 190

Gly Gly Ala Gly Val Pro Gly Gly Ala Gly Val Pro Gly Gly Ala Gly
        195                 200                 205

Val Pro Gly Gly Ala Gly Val Pro Gly Gly Ala Gly Val Pro Gly Gly
        210                 215                 220

Ala Gly Val Pro Gly Gly Ala Gly Val Pro Gly Gly Ala Gly Val Pro
225                 230                 235                 240

Gly Gly Ala Gly Val Pro Gly Gly Ala Gly Val Pro Gly Gly Ala Gly
            245                 250                 255

Val Pro Gly Gly Ala Gly Val Pro Gly Gly Ala Gly Val Pro Gly Gly
        260                 265                 270

Ala Gly Val Pro Gly Gly Ala Gly Val Pro Gly Gly Ala Gly Val Pro
        275                 280                 285

Gly Gly Ala Gly Val Pro Gly Gly Ala Gly Val Pro Gly Gly Ala Gly
        290                 295                 300

Val Pro Gly Gly Ala Gly Val Pro Gly Gly Ala Gly Val Pro Gly Gly
305                 310                 315                 320

Ala Gly Val Pro Gly Gly Ala Gly Val Pro Gly Gly Ala Gly Val Pro
            325                 330                 335

Gly Gly Ala Gly Val Pro Gly Gly Ala Gly Val Pro Gly Gly Ala Gly
            340                 345                 350

Val Pro Gly Gly Ala Gly Val Pro Gly Gly Ala Gly Val Pro Gly Gly
        355                 360                 365

Ala Gly Val Pro Gly Gly Ala Gly Val Pro Gly Gly Ala Gly Val Pro
        370                 375                 380

Gly Gly Ala Gly Val Pro Gly Gly Ala Gly Val Pro Gly Gly Ala Gly
385                 390                 395                 400

Val Pro Gly Gly Ala Gly Val Pro Gly Gly Ala Gly Val Pro Gly Gly
            405                 410                 415

Ala Gly Val Pro Gly Gly Val Leu Pro Gly Val Gly Gly Val Leu
        420                 425                 430

Pro Gly Val Gly Gly Val Leu Pro Gly Val Gly Gly Val Leu Pro Gly

```
            435                 440                 445
Val Gly Gly Val Leu Pro Gly Val Gly Val Leu Pro Gly Val Gly
    450                 455                 460

Gly Val Leu Pro Gly Val Gly Val Leu Pro Gly Val Gly Val
465                 470                 475                 480

Leu Pro Gly Val Gly Gly Val Leu Pro Gly Val Gly Val Leu Pro
                485                 490                 495

Gly Val Gly Gly Val Leu Pro Gly Val Gly Val Leu Pro Gly Val
            500                 505                 510

Gly Gly Val Leu Pro Gly Val Gly Val Leu Pro Gly Val Gly Gly
        515                 520                 525

Val Leu Pro Gly Val Gly Gly Val Leu Pro Gly Val Gly Val Leu
    530                 535                 540

Pro Gly Val Gly Gly Val Leu Pro Gly Val Gly Gly Val Leu Pro Gly
545                 550                 555                 560

Val Gly Gly Val Leu Pro Gly Val Gly Gly Val Leu Pro Gly Val Gly
                565                 570                 575

Gly Val Leu Pro Gly Val Gly Gly Val Leu Pro Gly Val Gly Gly Val
            580                 585                 590

Leu Pro Gly Val Gly Gly Val Leu Pro Gly Val Gly Gly Val Leu Pro
        595                 600                 605

Gly Val Gly Gly Val Leu Pro Gly Val Gly Gly
    610                 615
```

<210> SEQ ID NO 54
<211> LENGTH: 20
<212> TYPE: PRT
<213> ORGANISM: Artificial sequence
<220> FEATURE:
<223> OTHER INFORMATION: Synthetic construct

<400> SEQUENCE: 54

```
Glu Ser Ile Ile Asn Phe Glu Lys Leu Thr Glu Ser Ile Ile Asn Phe
1               5                   10                  15

Glu Lys Leu Thr
            20
```

<210> SEQ ID NO 55
<211> LENGTH: 641
<212> TYPE: PRT
<213> ORGANISM: Artificial sequence
<220> FEATURE:
<223> OTHER INFORMATION: Synthetic construct

<400> SEQUENCE: 55

```
Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
            20                  25                  30

Ala Gly Val Pro Gly Gly Ala Gly Val Pro Gly Gly Ala Gly Val Pro
        35                  40                  45

Gly Gly Ala Gly Val Pro Gly Gly Ala Gly Val Pro Gly Gly Ala Gly
    50                  55                  60

Val Pro Gly Gly Ala Gly Val Pro Gly Gly Ala Gly Val Pro Gly Gly
65                  70                  75                  80

Ala Gly Val Pro Gly Gly Ala Gly Val Pro Gly Gly Ala Gly Val Pro
                85                  90                  95
```

Gly Gly Ala Gly Val Pro Gly Gly Ala Gly Val Pro Gly Gly Ala Gly
            100                 105                 110

Val Pro Gly Gly Ala Gly Val Pro Gly Gly Ala Gly Val Pro Gly Gly
        115                 120                 125

Ala Gly Val Pro Gly Gly Ala Gly Val Pro Gly Gly Ala Gly Val Pro
    130                 135                 140

Gly Gly Ala Gly Val Pro Gly Gly Ala Gly Val Pro Gly Gly Ala Gly
145                 150                 155                 160

Val Pro Gly Gly Ala Gly Val Pro Gly Gly Ala Gly Val Pro Gly Gly
            165                 170                 175

Ala Gly Val Pro Gly Gly Ala Gly Val Pro Gly Gly Ala Gly Val Pro
        180                 185                 190

Gly Gly Ala Gly Val Pro Gly Gly Ala Gly Val Pro Gly Gly Ala Gly
    195                 200                 205

Val Pro Gly Gly Ala Gly Val Pro Gly Gly Ala Gly Val Pro Gly Gly
210                 215                 220

Ala Gly Val Pro Gly Gly Ala Gly Val Pro Gly Gly Ala Gly Val Pro
225                 230                 235                 240

Gly Gly Ala Gly Val Pro Gly Gly Ala Gly Val Pro Gly Gly Ala Gly
            245                 250                 255

Val Pro Gly Gly Ala Gly Val Pro Gly Gly Ala Gly Val Pro Gly Gly
        260                 265                 270

Ala Gly Val Pro Gly Gly Ala Gly Val Pro Gly Gly Ala Gly Val Pro
    275                 280                 285

Gly Gly Ala Gly Val Pro Gly Gly Ala Gly Val Pro Gly Gly Ala Gly
    290                 295                 300

Val Pro Gly Gly Ala Gly Val Pro Gly Gly Ala Gly Val Pro Gly Gly
305                 310                 315                 320

Ala Gly Val Pro Gly Gly Ala Gly Val Pro Gly Gly Ala Gly Val Pro
            325                 330                 335

Gly Gly Ala Gly Val Pro Gly Gly Ala Gly Val Pro Gly Gly Ala Gly
        340                 345                 350

Val Pro Gly Gly Ala Gly Val Pro Gly Gly Ala Gly Val Pro Gly Gly
    355                 360                 365

Ala Gly Val Pro Gly Gly Ala Gly Val Pro Gly Gly Ala Gly Val Pro
    370                 375                 380

Gly Gly Ala Gly Val Pro Gly Gly Ala Gly Val Pro Gly Gly Ala Gly
385                 390                 395                 400

Val Pro Gly Gly Ala Gly Val Pro Gly Gly Ala Gly Val Pro Gly Gly
            405                 410                 415

Ala Gly Val Pro Gly Gly Gly Val Leu Pro Gly Val Gly Gly Val Leu
        420                 425                 430

Pro Gly Val Gly Gly Val Leu Pro Gly Val Gly Gly Val Leu Pro Gly
    435                 440                 445

Val Gly Gly Val Leu Pro Gly Val Gly Gly Val Leu Pro Gly Val Gly
    450                 455                 460

Gly Val Leu Pro Gly Val Gly Gly Val Leu Pro Gly Val Gly Gly Val
465                 470                 475                 480

Leu Pro Gly Val Gly Gly Val Leu Pro Gly Val Gly Gly Val Leu Pro
            485                 490                 495

Gly Val Gly Gly Val Leu Pro Gly Val Gly Gly Val Leu Pro Gly Val
        500                 505                 510

Gly Gly Val Leu Pro Gly Val Gly Gly Val Leu Pro Gly Val Gly Gly

```
                515                 520                 525
Val Leu Pro Gly Val Gly Gly Val Leu Pro Gly Val Gly Gly Val Leu
        530                 535                 540

Pro Gly Val Gly Gly Val Leu Pro Gly Val Gly Gly Val Leu Pro Gly
545                 550                 555                 560

Val Gly Gly Val Leu Pro Gly Val Gly Gly Val Leu Pro Gly Val Gly
                565                 570                 575

Gly Val Leu Pro Gly Val Gly Gly Val Leu Pro Gly Val Gly Gly Val
            580                 585                 590

Leu Pro Gly Val Gly Gly Val Leu Pro Gly Val Gly Gly Val Leu Pro
        595                 600                 605

Gly Val Gly Gly Val Leu Pro Gly Val Gly Glu Ser Ile Ile Asn
    610                 615                 620

Phe Glu Lys Leu Thr Glu Ser Ile Ile Asn Phe Glu Lys Leu Thr Gly
625                 630                 635                 640

Gly

<210> SEQ ID NO 56
<211> LENGTH: 444
<212> TYPE: PRT
<213> ORGANISM: Artificial sequence
<220> FEATURE:
<223> OTHER INFORMATION: Synthetic construct

<400> SEQUENCE: 56

Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
            20                  25                  30

Ala Gly Val Pro Gly Gly Ala Gly Val Pro Gly Gly Ala Gly Val Pro
        35                  40                  45

Gly Gly Ala Gly Val Pro Gly Gly Ala Gly Val Pro Gly Gly Ala Gly
    50                  55                  60

Val Pro Gly Gly Ala Gly Val Pro Gly Gly Ala Gly Val Pro Gly Gly
65                  70                  75                  80

Ala Gly Val Pro Gly Gly Ala Gly Val Pro Gly Gly Ala Gly Val Pro
                85                  90                  95

Gly Gly Ala Gly Val Pro Gly Gly Ala Gly Val Pro Gly Gly Ala Gly
            100                 105                 110

Val Pro Gly Gly Ala Gly Val Pro Gly Gly Ala Gly Val Pro Gly Gly
        115                 120                 125

Ala Gly Val Pro Gly Gly Ala Gly Val Pro Gly Gly Ala Gly Val Pro
    130                 135                 140

Gly Gly Ala Gly Val Pro Gly Gly Ala Gly Val Pro Gly Gly Ala Gly
145                 150                 155                 160

Val Pro Gly Gly Ala Gly Val Pro Gly Gly Ala Gly Val Pro Gly Gly
                165                 170                 175

Ala Gly Val Pro Gly Gly Ala Gly Val Pro Gly Gly Ala Gly Val Pro
            180                 185                 190

Gly Gly Ala Gly Val Pro Gly Gly Ala Gly Val Pro Gly Gly Ala Gly
        195                 200                 205

Val Pro Gly Gly Ala Gly Val Pro Gly Gly Ala Gly Val Pro Gly Gly
    210                 215                 220

Ala Gly Val Pro Gly Gly Ala Gly Val Pro Gly Gly Ala Gly Val Pro
225                 230                 235                 240
```

```
Gly Gly Ala Gly Val Pro Gly Gly Ala Gly Val Pro Gly Gly Ala Gly
                245                 250                 255

Val Pro Gly Gly Ala Gly Val Pro Gly Gly Ala Gly Val Pro Gly Gly
            260                 265                 270

Ala Gly Val Pro Gly Gly Ala Gly Val Pro Gly Gly Ala Gly Val Pro
        275                 280                 285

Gly Gly Ala Gly Val Pro Gly Gly Ala Gly Val Pro Gly Gly Ala Gly
    290                 295                 300

Val Pro Gly Gly Ala Gly Val Pro Gly Gly Ala Gly Val Pro Gly Gly
305                 310                 315                 320

Ala Gly Val Pro Gly Gly Ala Gly Val Pro Gly Gly Ala Gly Val Pro
            325                 330                 335

Gly Gly Ala Gly Val Pro Gly Gly Ala Gly Val Pro Gly Gly Ala Gly
        340                 345                 350

Val Pro Gly Gly Ala Gly Val Pro Gly Gly Ala Gly Val Pro Gly Gly
    355                 360                 365

Ala Gly Val Pro Gly Gly Ala Gly Val Pro Gly Gly Ala Gly Val Pro
370                 375                 380

Gly Gly Ala Gly Val Pro Gly Gly Ala Gly Val Pro Gly Gly Ala Gly
385                 390                 395                 400

Val Pro Gly Gly Ala Gly Val Pro Gly Gly Ala Gly Val Pro Gly Gly
            405                 410                 415

Ala Gly Val Pro Gly Gly Glu Ser Ile Ile Asn Phe Glu Lys Leu Thr
        420                 425                 430

Glu Ser Ile Ile Asn Phe Glu Lys Leu Thr Gly Gly
    435                 440

<210> SEQ ID NO 57
<211> LENGTH: 492
<212> TYPE: PRT
<213> ORGANISM: Artificial sequence
<220> FEATURE:
<223> OTHER INFORMATION: Synthetic construct

<400> SEQUENCE: 57

Gly Ala Gly Val Pro Gly Gly Ala Gly Val Pro Gly Gly Ala Gly Val
1               5                   10                  15

Pro Gly Gly Ala Gly Val Pro Gly Gly Ala Gly Val Pro Gly Gly Ala
            20                  25                  30

Gly Val Pro Gly Gly Ala Gly Val Pro Gly Gly Ala Gly Val Pro Gly
        35                  40                  45

Gly Ala Gly Val Pro Gly Gly Ala Gly Val Pro Gly Gly Ala Gly Val
    50                  55                  60

Pro Gly Gly Ala Gly Val Pro Gly Gly Ala Gly Val Pro Gly Gly Ala
65                  70                  75                  80

Gly Val Pro Gly Gly Ala Gly Val Pro Gly Gly Ala Gly Val Pro Gly
            85                  90                  95

Gly Ala Gly Val Pro Gly Gly Ala Gly Val Pro Gly Gly Ala Gly Val
        100                 105                 110

Pro Gly Gly Ala Gly Val Pro Gly Gly Ala Gly Val Pro Gly Gly Ala
    115                 120                 125

Gly Val Pro Gly Gly Ala Gly Val Pro Gly Gly Ala Gly Val Pro Gly
        130                 135                 140

Gly Ala Gly Val Pro Gly Gly Ala Gly Val Pro Gly Gly Ala Gly Val
145                 150                 155                 160
```

```
Pro Gly Gly Ala Gly Val Pro Gly Gly Ala Gly Val Pro Gly Gly Ala
            165                 170                 175

Gly Val Pro Gly Gly Ala Gly Val Pro Gly Gly Ala Gly Val Pro Gly
            180                 185                 190

Gly Ala Gly Val Pro Gly Gly Ala Gly Val Pro Gly Gly Ala Gly Val
            195                 200                 205

Pro Gly Gly Ala Gly Val Pro Gly Gly Ala Gly Val Pro Gly Gly Ala
            210                 215                 220

Gly Val Pro Gly Gly Ala Gly Val Pro Gly Gly Ala Gly Val Pro Gly
225                 230                 235                 240

Gly Ala Gly Val Pro Gly Gly Ala Gly Val Pro Gly Gly Ala Gly Val
            245                 250                 255

Pro Gly Gly Ala Gly Val Pro Gly Gly Ala Gly Val Pro Gly Gly Ala
            260                 265                 270

Gly Val Pro Gly Gly Ala Gly Val Pro Gly Gly Ala Gly Val Pro Gly
            275                 280                 285

Gly Ala Gly Val Pro Gly Gly Ala Gly Val Pro Gly Gly Ala Gly Val
            290                 295                 300

Pro Gly Gly Ala Gly Val Pro Gly Gly Ala Gly Val Pro Gly Gly Ala
305                 310                 315                 320

Gly Val Pro Gly Gly Ala Gly Val Pro Gly Gly Ala Gly Val Pro Gly
            325                 330                 335

Gly Ala Gly Val Pro Gly Gly Ala Gly Val Pro Gly Gly Ala Gly Val
            340                 345                 350

Pro Gly Gly Ala Gly Val Pro Gly Gly Ala Gly Val Pro Gly Gly Ala
            355                 360                 365

Gly Val Pro Gly Gly Ala Gly Val Pro Gly Gly Ala Gly Val Pro Gly
            370                 375                 380

Gly Ala Gly Val Pro Gly Gly Ala Gly Val Pro Gly Gly Ala Gly Val
385                 390                 395                 400

Pro Gly Gly Ala Gly Val Pro Gly Gly Ala Gly Val Pro Gly Gly Ala
            405                 410                 415

Gly Val Pro Gly Cys Gly Gly Gly Gly Gly Gly Gly Cys Gly Gly
            420                 425                 430

Gly Gly Gly Gly Gly Gly Cys Gly Gly Gly Gly Gly Gly Gly Cys
            435                 440                 445

Gly Gly Gly Gly Gly Gly Gly Cys Gly Gly Gly Gly Gly
            450                 455                 460

Gly Cys Gly Gly Gly Gly Gly Gly Gly Cys Gly Gly Gly Gly Gly
465                 470                 475                 480

Gly Gly Gly Cys Gly Gly Gly Gly Gly Gly Gly
            485                 490

<210> SEQ ID NO 58
<211> LENGTH: 815
<212> TYPE: PRT
<213> ORGANISM: Artificial sequence
<220> FEATURE:
<223> OTHER INFORMATION: Synthetic construct

<400> SEQUENCE: 58

Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
            20                  25                  30
```

-continued

```
Ala Gly Val Pro Gly Gly Ala Gly Val Pro Gly Gly Ala Gly Val Pro
         35                  40                  45
Gly Gly Ala Gly Val Pro Gly Gly Ala Gly Val Pro Gly Gly Ala Gly
 50                  55                  60
Val Pro Gly Gly Ala Gly Val Pro Gly Gly Ala Gly Val Pro Gly Gly
 65                  70                  75                  80
Ala Gly Val Pro Gly Gly Ala Gly Val Pro Gly Gly Ala Gly Val Pro
             85                  90                  95
Gly Gly Ala Gly Val Pro Gly Gly Ala Gly Val Pro Gly Gly Ala Gly
            100                 105                 110
Val Pro Gly Gly Ala Gly Val Pro Gly Gly Ala Gly Val Pro Gly Gly
            115                 120                 125
Ala Gly Val Pro Gly Gly Ala Gly Val Pro Gly Gly Ala Gly Val Pro
            130                 135                 140
Gly Gly Ala Gly Val Pro Gly Gly Ala Gly Val Pro Gly Gly Ala Gly
145                 150                 155                 160
Val Pro Gly Gly Ala Gly Val Pro Gly Gly Ala Gly Val Pro Gly Gly
            165                 170                 175
Ala Gly Val Pro Gly Gly Ala Gly Val Pro Gly Gly Ala Gly Val Pro
            180                 185                 190
Gly Gly Ala Gly Val Pro Gly Gly Ala Gly Val Pro Gly Gly Ala Gly
            195                 200                 205
Val Pro Gly Gly Ala Gly Val Pro Gly Gly Ala Gly Val Pro Gly Gly
            210                 215                 220
Ala Gly Val Pro Gly Gly Ala Gly Val Pro Gly Gly Ala Gly Val Pro
225                 230                 235                 240
Gly Gly Ala Gly Val Pro Gly Gly Ala Gly Val Pro Gly Gly Ala Gly
            245                 250                 255
Val Pro Gly Gly Ala Gly Val Pro Gly Gly Ala Gly Val Pro Gly Gly
            260                 265                 270
Ala Gly Val Pro Gly Gly Ala Gly Val Pro Gly Gly Ala Gly Val Pro
            275                 280                 285
Gly Gly Ala Gly Val Pro Gly Gly Ala Gly Val Pro Gly Gly Ala Gly
            290                 295                 300
Val Pro Gly Gly Ala Gly Val Pro Gly Gly Ala Gly Val Pro Gly Gly
305                 310                 315                 320
Ala Gly Val Pro Gly Gly Ala Gly Val Pro Gly Gly Ala Gly Val Pro
            325                 330                 335
Gly Gly Ala Gly Val Pro Gly Gly Ala Gly Val Pro Gly Gly Ala Gly
            340                 345                 350
Val Pro Gly Gly Ala Gly Val Pro Gly Gly Ala Gly Val Pro Gly Gly
            355                 360                 365
Ala Gly Val Pro Gly Gly Ala Gly Val Pro Gly Gly Ala Gly Val Pro
            370                 375                 380
Gly Gly Ala Gly Val Pro Gly Gly Ala Gly Val Pro Gly Gly Ala Gly
385                 390                 395                 400
Val Pro Gly Gly Ala Gly Val Pro Gly Gly Ala Gly Val Pro Gly Gly
            405                 410                 415
Ala Gly Val Pro Gly Gly Gly Val Leu Pro Gly Val Gly Gly Val Leu
            420                 425                 430
Pro Gly Val Gly Gly Val Leu Pro Gly Val Gly Gly Val Leu Pro Gly
            435                 440                 445
```

Val Gly Gly Val Leu Pro Gly Val Gly Val Leu Pro Gly Val Gly
450                 455                 460

Gly Val Leu Pro Gly Val Gly Val Leu Pro Gly Val Gly Gly Val
465                 470                 475                 480

Leu Pro Gly Val Gly Val Leu Pro Gly Val Gly Gly Val Leu Pro
                485                 490                 495

Gly Val Gly Gly Val Leu Pro Gly Val Gly Gly Val Leu Pro Gly Val
            500                 505                 510

Gly Gly Val Leu Pro Gly Val Gly Gly Val Leu Pro Gly Val Gly Gly
                515                 520                 525

Val Leu Pro Gly Val Gly Gly Val Leu Pro Gly Val Gly Gly Val Leu
530                 535                 540

Pro Gly Val Gly Gly Val Leu Pro Gly Val Gly Gly Val Leu Pro Gly
545                 550                 555                 560

Val Gly Gly Val Leu Pro Gly Val Gly Gly Val Leu Pro Gly Val Gly
                565                 570                 575

Gly Val Leu Pro Gly Val Gly Gly Val Leu Pro Gly Val Gly Gly Val
            580                 585                 590

Leu Pro Gly Val Gly Gly Val Leu Pro Gly Val Gly Gly Val Leu Pro
        595                 600                 605

Gly Val Gly Gly Val Leu Pro Gly Val Gly Gly Val Leu Pro Gly Val
    610                 615                 620

Gly Gly Val Leu Pro Gly Val Gly Gly Val Leu Pro Gly Val Gly Gly
625                 630                 635                 640

Val Leu Pro Gly Val Gly Gly Val Leu Pro Gly Val Gly Gly Val Leu
                645                 650                 655

Pro Gly Val Gly Gly Val Leu Pro Gly Val Gly Gly Val Leu Pro Gly
            660                 665                 670

Val Gly Gly Val Leu Pro Gly Val Gly Gly Val Leu Pro Gly Val Gly
        675                 680                 685

Gly Val Leu Pro Gly Val Gly Gly Val Leu Pro Gly Val Gly Gly Val
    690                 695                 700

Leu Pro Gly Val Gly Gly Val Leu Pro Gly Val Gly Gly Val Leu Pro
705                 710                 715                 720

Gly Val Gly Gly Val Leu Pro Gly Val Gly Gly Val Leu Pro Gly Val
                725                 730                 735

Gly Gly Val Leu Pro Gly Val Gly Gly Val Leu Pro Gly Val Gly Gly
            740                 745                 750

Val Leu Pro Gly Val Gly Gly Val Leu Pro Gly Val Gly Gly Val Leu
        755                 760                 765

Pro Gly Val Gly Gly Val Leu Pro Gly Val Gly Gly Val Leu Pro Gly
    770                 775                 780

Val Gly Gly Val Leu Pro Gly Val Gly Gly Val Leu Pro Gly Val Gly
785                 790                 795                 800

Gly Val Leu Pro Gly Val Gly Gly Val Leu Pro Gly Val Gly Gly
                805                 810                 815

<210> SEQ ID NO 59
<211> LENGTH: 837
<212> TYPE: PRT
<213> ORGANISM: Artificial sequence
<220> FEATURE:
<223> OTHER INFORMATION: Synthetic construct

<400> SEQUENCE: 59

-continued

```
Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
            20                  25                  30

Ala Gly Val Pro Gly Gly Ala Gly Val Pro Gly Gly Ala Gly Val Pro
        35                  40                  45

Gly Gly Ala Gly Val Pro Gly Gly Ala Gly Val Pro Gly Gly Ala Gly
    50                  55                  60

Val Pro Gly Gly Ala Gly Val Pro Gly Gly Ala Gly Val Pro Gly Gly
65                  70                  75                  80

Ala Gly Val Pro Gly Gly Ala Gly Val Pro Gly Gly Ala Gly Val Pro
            85                  90                  95

Gly Gly Ala Gly Val Pro Gly Gly Ala Gly Val Pro Gly Gly Ala Gly
        100                 105                 110

Val Pro Gly Gly Ala Gly Val Pro Gly Gly Ala Gly Val Pro Gly Gly
    115                 120                 125

Ala Gly Val Pro Gly Gly Ala Gly Val Pro Gly Gly Ala Gly Val Pro
    130                 135                 140

Gly Gly Ala Gly Val Pro Gly Gly Ala Gly Val Pro Gly Gly Ala Gly
145                 150                 155                 160

Val Pro Gly Gly Ala Gly Val Pro Gly Gly Ala Gly Val Pro Gly Gly
            165                 170                 175

Ala Gly Val Pro Gly Gly Ala Gly Val Pro Gly Gly Ala Gly Val Pro
        180                 185                 190

Gly Gly Ala Gly Val Pro Gly Gly Ala Gly Val Pro Gly Gly Ala Gly
    195                 200                 205

Val Pro Gly Gly Ala Gly Val Pro Gly Gly Ala Gly Val Pro Gly Gly
    210                 215                 220

Ala Gly Val Pro Gly Gly Ala Gly Val Pro Gly Gly Ala Gly Val Pro
225                 230                 235                 240

Gly Gly Ala Gly Val Pro Gly Gly Ala Gly Val Pro Gly Gly Ala Gly
            245                 250                 255

Val Pro Gly Gly Ala Gly Val Pro Gly Gly Ala Gly Val Pro Gly Gly
        260                 265                 270

Ala Gly Val Pro Gly Gly Ala Gly Val Pro Gly Gly Ala Gly Val Pro
    275                 280                 285

Gly Gly Ala Gly Val Pro Gly Gly Ala Gly Val Pro Gly Gly Ala Gly
    290                 295                 300

Val Pro Gly Gly Ala Gly Val Pro Gly Gly Ala Gly Val Pro Gly Gly
305                 310                 315                 320

Ala Gly Val Pro Gly Gly Ala Gly Val Pro Gly Gly Ala Gly Val Pro
            325                 330                 335

Gly Gly Ala Gly Val Pro Gly Gly Ala Gly Val Pro Gly Gly Ala Gly
        340                 345                 350

Val Pro Gly Gly Ala Gly Val Pro Gly Gly Ala Gly Val Pro Gly Gly
    355                 360                 365

Ala Gly Val Pro Gly Gly Ala Gly Val Pro Gly Gly Ala Gly Val Pro
    370                 375                 380

Gly Gly Ala Gly Val Pro Gly Gly Ala Gly Val Pro Gly Gly Ala Gly
385                 390                 395                 400

Val Pro Gly Gly Ala Gly Val Pro Gly Gly Ala Gly Val Pro Gly Gly
            405                 410                 415

Ala Gly Val Pro Gly Gly Gly Val Leu Pro Gly Val Gly Gly Val Leu
```

```
                420             425             430
Pro Gly Val Gly Gly Val Leu Pro Gly Val Gly Val Leu Pro Gly
        435             440             445
Val Gly Gly Val Leu Pro Gly Val Gly Val Leu Pro Gly Val Gly
        450             455             460
Gly Val Leu Pro Gly Val Gly Val Leu Pro Gly Val Gly Gly Val
465             470             475             480
Leu Pro Gly Val Gly Val Leu Pro Gly Val Gly Gly Val Leu Pro
            485             490             495
Gly Val Gly Val Leu Pro Gly Val Gly Gly Val Leu Pro Gly Val
        500             505             510
Gly Gly Val Leu Pro Gly Val Gly Val Leu Pro Gly Val Gly Gly
        515             520             525
Val Leu Pro Gly Val Gly Val Leu Pro Gly Val Gly Gly Val Leu
        530             535             540
Pro Gly Val Gly Gly Val Leu Pro Gly Val Gly Gly Val Leu Pro Gly
545             550             555             560
Val Gly Gly Val Leu Pro Gly Val Gly Val Leu Pro Gly Val Gly
            565             570             575
Gly Val Leu Pro Gly Val Gly Gly Val Leu Pro Gly Val Gly Val
            580             585             590
Leu Pro Gly Val Gly Gly Val Leu Pro Gly Val Gly Gly Val Leu Pro
            595             600             605
Gly Val Gly Gly Val Leu Pro Gly Val Gly Gly Val Leu Pro Gly Val
        610             615             620
Gly Gly Val Leu Pro Gly Val Gly Gly Val Leu Pro Gly Val Gly Gly
625             630             635             640
Val Leu Pro Gly Val Gly Gly Val Leu Pro Gly Val Gly Gly Val Leu
            645             650             655
Pro Gly Val Gly Gly Val Leu Pro Gly Val Gly Gly Val Leu Pro Gly
            660             665             670
Val Gly Gly Val Leu Pro Gly Val Gly Gly Val Leu Pro Gly Val Gly
        675             680             685
Gly Val Leu Pro Gly Val Gly Gly Val Leu Pro Gly Val Gly Gly Val
        690             695             700
Leu Pro Gly Val Gly Gly Val Leu Pro Gly Val Gly Gly Val Leu Pro
705             710             715             720
Gly Val Gly Gly Val Leu Pro Gly Val Gly Gly Val Leu Pro Gly Val
            725             730             735
Gly Gly Val Leu Pro Gly Val Gly Gly Val Leu Pro Gly Val Gly Gly
            740             745             750
Val Leu Pro Gly Val Gly Gly Val Leu Pro Gly Val Gly Gly Val Leu
            755             760             765
Pro Gly Val Gly Gly Val Leu Pro Gly Val Gly Gly Val Leu Pro Gly
            770             775             780
Val Gly Gly Val Leu Pro Gly Val Gly Gly Val Leu Pro Gly Val Gly
785             790             795             800
Gly Val Leu Pro Gly Val Gly Gly Val Leu Pro Gly Val Gly Gly Glu
            805             810             815
Ser Ile Ile Asn Phe Glu Lys Leu Thr Glu Ser Ile Ile Asn Phe Glu
            820             825             830
Lys Leu Thr Gly Gly
        835
```

<210> SEQ ID NO 60
<211> LENGTH: 677
<212> TYPE: PRT
<213> ORGANISM: Artificial sequence
<220> FEATURE:
<223> OTHER INFORMATION: Synthetic construct

<400> SEQUENCE: 60

```
Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
            20                  25                  30

Ala Gly Val Pro Gly Gly Ala Gly Val Pro Gly Gly Ala Gly Val Pro
        35                  40                  45

Gly Gly Ala Gly Val Pro Gly Gly Ala Gly Val Pro Gly Gly Ala Gly
    50                  55                  60

Val Pro Gly Gly Ala Gly Val Pro Gly Gly Ala Gly Val Pro Gly Gly
65                  70                  75                  80

Ala Gly Val Pro Gly Gly Ala Gly Val Pro Gly Gly Ala Gly Val Pro
                85                  90                  95

Gly Gly Ala Gly Val Pro Gly Gly Ala Gly Val Pro Gly Gly Ala Gly
            100                 105                 110

Val Pro Gly Gly Ala Gly Val Pro Gly Gly Ala Gly Val Pro Gly Gly
        115                 120                 125

Ala Gly Val Pro Gly Gly Ala Gly Val Pro Gly Gly Ala Gly Val Pro
    130                 135                 140

Gly Gly Ala Gly Val Pro Gly Gly Ala Gly Val Pro Gly Gly Ala Gly
145                 150                 155                 160

Val Pro Gly Gly Ala Gly Val Pro Gly Gly Ala Gly Val Pro Gly Gly
                165                 170                 175

Ala Gly Val Pro Gly Gly Ala Gly Val Pro Gly Gly Ala Gly Val Pro
            180                 185                 190

Gly Gly Ala Gly Val Pro Gly Gly Ala Gly Val Pro Gly Gly Ala Gly
        195                 200                 205

Val Pro Gly Gly Ala Gly Val Pro Gly Gly Ala Gly Val Pro Gly Gly
    210                 215                 220

Ala Gly Val Pro Gly Gly Ala Gly Val Pro Gly Gly Ala Gly Val Pro
225                 230                 235                 240

Gly Gly Ala Gly Val Pro Gly Gly Ala Gly Val Pro Gly Gly Ala Gly
                245                 250                 255

Val Pro Gly Gly Ala Gly Val Pro Gly Gly Ala Gly Val Pro Gly Gly
            260                 265                 270

Ala Gly Val Pro Gly Gly Ala Gly Val Pro Gly Gly Ala Gly Val Pro
        275                 280                 285

Gly Gly Ala Gly Val Pro Gly Gly Ala Gly Val Pro Gly Gly Ala Gly
    290                 295                 300

Val Pro Gly Gly Ala Gly Val Pro Gly Gly Ala Gly Val Pro Gly Gly
305                 310                 315                 320

Ala Gly Val Pro Gly Gly Ala Gly Val Pro Gly Gly Ala Gly Val Pro
                325                 330                 335

Gly Gly Ala Gly Val Pro Gly Gly Ala Gly Val Pro Gly Gly Ala Gly
            340                 345                 350

Val Pro Gly Gly Ala Gly Val Pro Gly Gly Ala Gly Val Pro Gly Gly
        355                 360                 365
```

```
Ala Gly Val Pro Gly Gly Ala Gly Val Pro Gly Gly Ala Gly Val Pro
        370                 375                 380

Gly Gly Ala Gly Val Pro Gly Gly Ala Gly Val Pro Gly Gly Ala Gly
385                 390                 395                 400

Val Pro Gly Gly Ala Gly Val Pro Gly Gly Ala Gly Val Pro Gly Gly
                405                 410                 415

Ala Gly Val Pro Gly Gly Val Leu Pro Gly Val Gly Gly Val Leu
        420                 425                 430

Pro Gly Val Gly Gly Val Leu Pro Gly Val Gly Gly Val Leu Pro Gly
        435                 440                 445

Val Gly Gly Val Leu Pro Gly Val Gly Gly Val Leu Pro Gly Val Gly
        450                 455                 460

Gly Val Leu Pro Gly Val Gly Gly Val Leu Pro Gly Val Gly Gly Val
465                 470                 475                 480

Leu Pro Gly Val Gly Gly Val Leu Pro Gly Val Gly Gly Val Leu Pro
                485                 490                 495

Gly Val Gly Gly Val Leu Pro Gly Val Gly Gly Val Leu Pro Gly Val
                500                 505                 510

Gly Gly Val Leu Pro Gly Val Gly Gly Val Leu Pro Gly Val Gly Gly
        515                 520                 525

Val Leu Pro Gly Val Gly Gly Val Leu Pro Gly Val Gly Gly Val Leu
        530                 535                 540

Pro Gly Val Gly Gly Val Leu Pro Gly Val Gly Gly Val Leu Pro Gly
545                 550                 555                 560

Val Gly Gly Val Leu Pro Gly Val Gly Gly Val Leu Pro Gly Val Gly
                565                 570                 575

Gly Val Leu Pro Gly Val Gly Gly Val Leu Pro Gly Val Gly Gly Val
                580                 585                 590

Leu Pro Gly Val Gly Gly Val Leu Pro Gly Val Gly Gly Val Leu Pro
        595                 600                 605

Gly Val Gly Gly Val Leu Pro Gly Val Gly Gly Gly Gly Gly Gly Gly
        610                 615                 620

Gly Gly Cys Gly Gly Gly Gly Gly Gly Gly Cys Gly Gly Gly Gly
625                 630                 635                 640

Gly Gly Gly Gly Cys Gly Gly Gly Gly Gly Gly Gly Cys Gly Glu
                645                 650                 655

Ser Ile Ile Asn Phe Glu Lys Leu Thr Glu Ser Ile Ile Asn Phe Glu
        660                 665                 670

Lys Leu Thr Gly Gly
        675

<210> SEQ ID NO 61
<211> LENGTH: 649
<212> TYPE: PRT
<213> ORGANISM: Artificial sequence
<220> FEATURE:
<223> OTHER INFORMATION: Synthetic construct

<400> SEQUENCE: 61

Gly Gly Ala Gly Val Pro Gly Gly Ala Gly Val Pro Gly Gly Ala Gly
1               5                   10                  15

Val Pro Gly Gly Ala Gly Val Pro Gly Gly Ala Gly Val Pro Gly Gly
                20                  25                  30

Ala Gly Val Pro Gly Gly Ala Gly Val Pro Gly Gly Ala Gly Val Pro
        35                  40                  45
```

-continued

```
Gly Gly Ala Gly Val Pro Gly Ala Gly Val Pro Gly Ala Gly
         50                  55                  60

Val Pro Gly Gly Ala Gly Val Pro Gly Gly Ala Gly Val Pro Gly Gly
 65                  70                  75                  80

Ala Gly Val Pro Gly Gly Ala Gly Val Pro Gly Gly Ala Gly Val Pro
                 85                  90                  95

Gly Gly Ala Gly Val Pro Gly Gly Ala Gly Val Pro Gly Gly Ala Gly
                100                 105                 110

Val Pro Gly Gly Ala Gly Val Pro Gly Gly Ala Gly Val Pro Gly Gly
        115                 120                 125

Ala Gly Val Pro Gly Gly Ala Gly Val Pro Gly Gly Ala Gly Val Pro
    130                 135                 140

Gly Gly Ala Gly Val Pro Gly Gly Ala Gly Val Pro Gly Gly Ala Gly
145                 150                 155                 160

Val Pro Gly Gly Ala Gly Val Pro Gly Gly Ala Gly Val Pro Gly Gly
            165                 170                 175

Ala Gly Val Pro Gly Gly Ala Gly Val Pro Gly Gly Ala Gly Val Pro
            180                 185                 190

Gly Gly Ala Gly Val Pro Gly Gly Ala Gly Val Pro Gly Gly Ala Gly
            195                 200                 205

Val Pro Gly Gly Ala Gly Val Pro Gly Gly Ala Gly Val Pro Gly Gly
    210                 215                 220

Ala Gly Val Pro Gly Gly Ala Gly Val Pro Gly Gly Ala Gly Val Pro
225                 230                 235                 240

Gly Gly Ala Gly Val Pro Gly Gly Ala Gly Val Pro Gly Gly Ala Gly
                245                 250                 255

Val Pro Gly Gly Ala Gly Val Pro Gly Gly Ala Gly Val Pro Gly Gly
            260                 265                 270

Ala Gly Val Pro Gly Gly Ala Gly Val Pro Gly Gly Ala Gly Val Pro
        275                 280                 285

Gly Gly Ala Gly Val Pro Gly Gly Ala Gly Val Pro Gly Gly Ala Gly
    290                 295                 300

Val Pro Gly Gly Ala Gly Val Pro Gly Gly Ala Gly Val Pro Gly Gly
305                 310                 315                 320

Ala Gly Val Pro Gly Gly Ala Gly Val Pro Gly Gly Ala Gly Val Pro
                325                 330                 335

Gly Gly Ala Gly Val Pro Gly Gly Ala Gly Val Pro Gly Gly Ala Gly
            340                 345                 350

Val Pro Gly Gly Ala Gly Val Pro Gly Gly Ala Gly Val Pro Gly Gly
        355                 360                 365

Ala Gly Val Pro Gly Gly Ala Gly Val Pro Gly Gly Ala Gly Val Pro
    370                 375                 380

Gly Gly Ala Gly Val Pro Gly Gly Ala Gly Val Pro Gly Gly Ala Gly
385                 390                 395                 400

Val Pro Gly Gly Ala Gly Val Pro Gly Gly Ala Gly Val Pro Gly Gly
                405                 410                 415

Ala Gly Val Pro Gly Gly Val Leu Pro Gly Val Gly Gly Val Leu
            420                 425                 430

Pro Gly Val Gly Gly Val Leu Pro Gly Val Gly Gly Val Leu Pro Gly
        435                 440                 445

Val Gly Gly Val Leu Pro Gly Val Gly Gly Val Leu Pro Gly Val Gly
    450                 455                 460
```

```
Gly Val Leu Pro Gly Val Gly Gly Val Leu Pro Gly Val Gly Gly Val
465                 470                 475                 480

Leu Pro Gly Val Gly Gly Val Leu Pro Gly Val Gly Gly Val Leu Pro
                485                 490                 495

Gly Val Gly Gly Val Leu Pro Gly Val Gly Gly Val Leu Pro Gly Val
            500                 505                 510

Gly Gly Val Leu Pro Gly Val Gly Gly Val Leu Pro Gly Val Gly Gly
        515                 520                 525

Val Leu Pro Gly Val Gly Gly Val Leu Pro Gly Val Gly Gly Val Leu
    530                 535                 540

Pro Gly Val Gly Gly Val Leu Pro Gly Val Gly Gly Val Leu Pro Gly
545                 550                 555                 560

Val Gly Gly Val Leu Pro Gly Val Gly Gly Val Leu Pro Gly Val Gly
                565                 570                 575

Gly Val Leu Pro Gly Val Gly Gly Val Leu Pro Gly Val Gly Gly Val
            580                 585                 590

Leu Pro Gly Val Gly Gly Val Leu Pro Gly Val Gly Gly Val Leu Pro
        595                 600                 605

Gly Val Gly Gly Val Leu Pro Gly Val Gly Gly Cys Gly Cys Gly Cys
    610                 615                 620

Gly Cys Gly Glu Ser Ile Ile Asn Phe Glu Lys Leu Thr Glu Ser Ile
625                 630                 635                 640

Ile Asn Phe Glu Lys Leu Thr Gly Gly
                645

<210> SEQ ID NO 62
<211> LENGTH: 9
<212> TYPE: PRT
<213> ORGANISM: Artificial sequence
<220> FEATURE:
<223> OTHER INFORMATION: Synthetic construct

<400> SEQUENCE: 62

Val Pro Gly Leu Gly Val Gly Ala Gly
1               5
```